(12) United States Patent
Raab et al.

(10) Patent No.: US 10,988,788 B2
(45) Date of Patent: Apr. 27, 2021

(54) PLANTS EXPRESSING CELL WALL DEGRADING ENZYMES AND EXPRESSION VECTORS

(71) Applicant: Agrivida, Inc., Medford, MA (US)

(72) Inventors: R. Michael Raab, Arlington, MA (US); Vlad Samoylov, Sudbury, MA (US); Oleg Bougri, Boise, ID (US); Nathan Ekborg, Beverly, MA (US)

(73) Assignee: AGRIVIDA, INC., Woburn, MA (US)

( * ) Notice: Subject to any disclaimer, the term of this patent is extended or adjusted under 35 U.S.C. 154(b) by 192 days.

(21) Appl. No.: 15/046,064

(22) Filed: Feb. 17, 2016

(65) Prior Publication Data

US 2016/0160254 A1 Jun. 9, 2016

Related U.S. Application Data

(63) Continuation of application No. 13/508,280, filed as application No. PCT/US2010/055746 on Nov. 5, 2010, now abandoned, and a continuation-in-part of application No. 12/590,444, filed on Nov. 6, 2009, now Pat. No. 8,420,387.

(60) Provisional application No. 61/280,635, filed on Nov. 6, 2009, provisional application No. 61/398,589, filed on Jun. 28, 2010.

(51) Int. Cl.
| | | |
|---|---|---|
| C12P 19/14 | (2006.01) | |
| C12N 9/24 | (2006.01) | |
| C12N 15/82 | (2006.01) | |
| C12N 9/42 | (2006.01) | |
| C12P 19/02 | (2006.01) | |

(52) U.S. Cl.
CPC .............. *C12P 19/14* (2013.01); *C12N 9/248* (2013.01); *C12N 9/2437* (2013.01); *C12N 15/8216* (2013.01); *C12N 15/8245* (2013.01); *C12N 15/8246* (2013.01); *C12N 15/8257* (2013.01); *C12N 15/8261* (2013.01); *C12N 15/8287* (2013.01); *C12P 19/02* (2013.01); *C12Y 302/01004* (2013.01); *C12Y 302/01008* (2013.01); *C12Y 302/01* (2013.01)

(58) Field of Classification Search
CPC .................................................. C12N 9/2482
See application file for complete search history.

(56) References Cited

U.S. PATENT DOCUMENTS

| | | | |
|---|---|---|---|
| 6,521,435 B1 | 2/2003 | Okubara et al. | |
| 6,607,902 B2 | 8/2003 | Schroder Glad et al. | |
| 7,049,485 B2 | 5/2006 | Sticklen et al. | |
| 7,186,898 B1 | 3/2007 | Kossmann et al. | |
| 7,361,806 B2 | 4/2008 | Lebel et al. | |
| 7,981,650 B2 | 7/2011 | Levasseur et al. | |
| 8,093,456 B2 | 1/2012 | Sticklen et al. | |
| 8,101,393 B2 | 1/2012 | Gray et al. | |
| 8,343,747 B2 | 1/2013 | Burke et al. | |
| 8,455,715 B2 | 6/2013 | Paul et al. | |
| 9,309,528 B2 * | 4/2016 | Dixon ............... | C12N 15/8245 |
| 9,388,422 B2 | 7/2016 | Shen et al. | |
| 2002/0138878 A1 | 9/2002 | Sticklen et al. | |
| 2003/0131376 A1 | 7/2003 | Okubara et al. | |
| 2003/0180895 A1 | 9/2003 | Sibbesen et al. | |
| 2003/0233675 A1 | 12/2003 | Cao et al. | |
| 2004/0096938 A1 | 5/2004 | Xu et al. | |
| 2005/0125860 A1 | 6/2005 | Raab | |
| 2007/0192900 A1 | 8/2007 | Sticklen | |
| 2007/0250961 A1 | 10/2007 | Blaylock et al. | |
| 2009/0119800 A1 | 5/2009 | Lanahan et al. | |
| 2009/0155238 A1 | 6/2009 | Weiner et al. | |
| 2009/0193541 A1 | 7/2009 | Miles | |
| 2009/0298149 A1 | 12/2009 | Wang et al. | |
| 2010/0159510 A1 | 6/2010 | Raab | |
| 2012/0040409 A1 | 2/2012 | Hau et al. | |
| 2012/0258503 A1 | 10/2012 | Raab et al. | |

FOREIGN PATENT DOCUMENTS

| | | | |
|---|---|---|---|
| CA | 2681662 | 9/2008 | |
| CN | 1954072 | 4/2007 | |
| CN | 101200734 A | 6/2008 | |
| CN | 101960011 A | 1/2011 | |
| EP | 1293573 A3 | 3/2003 | |
| WO | WO-9736995 A2 * | 10/1997 | ........... C12N 9/2482 |
| WO | 0234926 A2 | 5/2002 | |
| WO | 03/050265 A2 | 6/2003 | |
| WO | 03056904 A2 | 7/2003 | |
| WO | WO 2005/096804 A2 * | 10/2005 | |
| WO | WO-2005096804 A2 * | 10/2005 | ........... C12N 9/2445 |

(Continued)

OTHER PUBLICATIONS

Jensen et al (Proc. Natl. Acad. Sci. vol. 93 pp. 3487-3491 1996), (Year: 1996).*
Herbers et al (Molecular Breeding 2: 81-87, 1996) (Year: 1996).*
Somerville, Chris. "Biofuels." Current biology 17.4 (2007): R115-R119. (Year: 2007).*
Jensen et al (1996, "Transgenic Barley Expressing a Protein-Engineered, Thermostable (1,3-1,4)-β-Glucanase During Germination", PNAS 93:3487-3491).*
Perler, Francine, InBase: the Intein Database, Oxford University Press, Nucleic Acids Research, 2002, vol. 30, No. 1, pp. 383-384.
Morris et al., Cloning of the xynB Gene from Dictyoglomus thermophilum Rt46B.1 and Action of the Gene Product on Kraft Pulp, American Society of Mocrobiology, Applied and Environmental Mocrobiology, May 1998, vol. 64, No. 5, pp. 1759-1765.

(Continued)

*Primary Examiner* — Stuart F Baum
(74) *Attorney, Agent, or Firm* — Volpe Koenig

(57) ABSTRACT

Vectors for expression of proteins in plants are described. The proteins may be enzymes and the enzymes can be but are not limited to cell wall degrading enzymes. A number of plants designed to express specific cell wall degrading enzymes are provided. The plants may have industrial and/or agricultural applications. Methods and materials for making the expression vectors and for making the plants are provided. Processes for which the plants could be used in industrial and agricultural applications are also provided.

10 Claims, 31 Drawing Sheets

Specification includes a Sequence Listing.

(56) References Cited

FOREIGN PATENT DOCUMENTS

| WO | 2007/146944 A2 | 12/2007 |
| WO | 2007146944 A2 | 12/2007 |
| WO | 2008064314 A2 | 5/2008 |
| WO | 2009/155601 A2 | 12/2009 |
| WO | 2009155601 A2 | 12/2009 |
| WO | 2010060056 A2 | 5/2010 |
| WO | 2010096510 A2 | 8/2010 |

OTHER PUBLICATIONS

Canadian Office Action dated Oct. 26, 2017 for Application No. 2829207.
U.S. Office Action dated Sep. 27, 2017 for Application No. 15002280.
UniProtKB—P177853 (P77853_DICTH); Integrated into UniProtKB/TrEMBL: Feb. 1, 1997.
McMillan, "Pretreatment of Lignocellulosic Biomass," American Chemical Society 1994, 292-324.
Ritte et al., "The starch-related R1 protein is an α-glucan, water dikinase," PNAS, 2002, vol. 99, No. 10, 7166-7171.
Shen et al., "Engineering a thermoregulated intein-modified xylanase into maize for consolidated lignocellulosic biomass processing," Nature Biotechnology, vol. 30, No. 11, Nov. 2012 (8 pages).
Zeidler et al., "Temperature-sensitive control of protein activity by conditionally splicing inteins," Nature Biotechnology, vol. 22, No. 7, Jul. 2004, 871-876.
Xiao-ping Zhang, "Practical Self-help Manual Against Agricultural Disasters," Harbin Institute of Technology Press, pp. 179-182, Dec. 31, 2008.
Sticklen, "Plant genetic engineering for biofuel production: towards affordable cellulosic ethanol," Nature Reviews, Genetics, vol. 9, Jun. 2008, 433-443.
Caspers et al., "Synthesis, processing and export of cytoplasmic endo-β-1,4-xylanase from barley aleurone during germination," The Plant Journal (2001) 26(2), 191-204.
Belknap et al., "pBINPLUS/ARS: an improved plant transformation vector based on Bbinplus" BioTechniques 44: 753-756, May 2008*.
Chinese Office Action issued in Chinese Application No. 2012800213882 with English Translation.
Christian et al., "The yield and composition of switchgrass and coastal panic grass grown as a biofuel in Southern England" Bioresource Technology 83 (2002) 115-124*.
English Translation of First Notification of Office Action dated Jan. 28, 2013, Chinese Application No. 201080060542.8.
GenBank Accession No. BAA33708, "endo-b-1,4-glucanase [Nasutitermes takasagoensis]" First Available Oct. 8, 1999*.
Guo et al., "Protein tolerance to random amino acid change" PNAS 2004 (101) 25: 9205-9210*.
Office Action, Chinese Patent Application No. 201080060542.8, dated Jan. 28, 2013.
Sivamani et al., "Expression enhancement of a rice polyubiquitin gene promoter" Plant Molecular Biology, 2006, 60: 225-239*.
Streatfield et al., "Corn as a production system for human and animal vaccines" Vaccine 21 (2003) 812-815*.
Tokuda et al., "Metazoan cellulase genes from termites: intron/exon structures and sites of expression" Biochim. Biophys. Acta 1447 (2-3), 146-159, 1999*.
Tokuda et al., "Cellulose Digestion in the Wood-Eating Higher Termite, Nasutitermes takasagoensis (Shiraki): Distribution of Cellulases and Properties of Endo_Beta-1,4-glucanase" Zoological Science, 1997, 14: 83-93*.
Office Action issued in U.S. Appl. No. 13/414,627 dated Mar. 12, 2015.

* cited by examiner

2510

  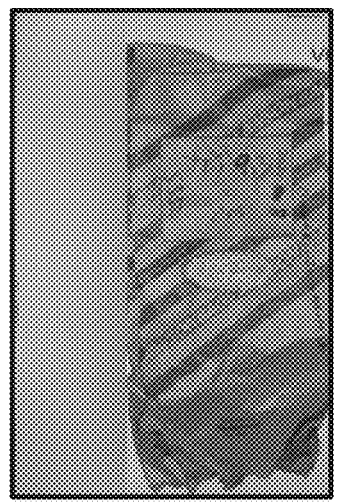
FIG. 27A  FIG. 27B  FIG. 27C
 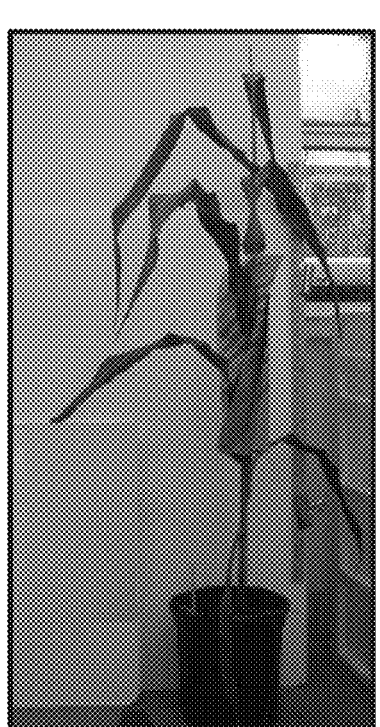 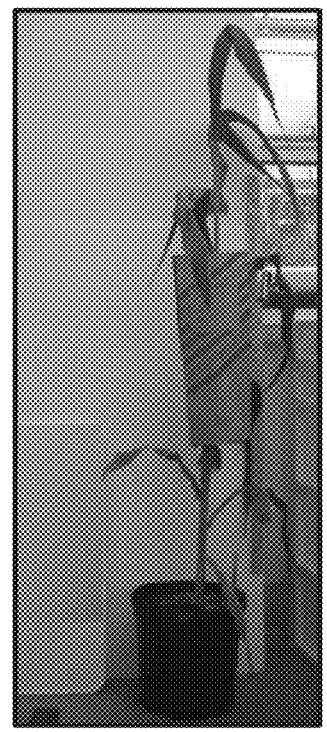
FIG. 28A  FIG. 28B  FIG. 28C ID NOS: 116-187 or the complement thereof.

PLANTS EXPRESSING CELL WALL DEGRADING ENZYMES AND EXPRESSION VECTORS

This application is a continuation of U.S. application Ser. No. 13/508,280 which was filed on Sep. 20, 2012 as a 35 U.S.C. § 371 national phase application of PCT/US10/55746 which was filed on Nov. 5, 2010 and claimed the benefit of U.S. provisional application No. 61/280,635 filed Nov. 6, 2009 and U.S. provisional application No. 61/398,589 filed Jun. 28, 2010. U.S. application Ser. No. 13/508,280 is a continuation-in-part of U.S. application Ser. No. 12/590,444 filed Nov. 6, 2009 and issued on Apr. 16, 2013 as U.S. Pat. No. 8,420,387 All of the above applications are incorporated herein by reference as if fully set forth.

The sequence listing electronically filed with this application titled "Sequence Listing," which was created on Feb. 17, 2016 and had a size of 2,226,296 bytes is incorporated by reference herein as if fully set forth.

FIELD OF INVENTION

The disclosure herein relates to plants expressing cell wall degrading enzymes, vectors, nucleic acids, proteins, related methods, and applications thereof.

BACKGROUND

Hydrolytic enzymes have important industrial and agricultural applications, but their expression and production may be associated with adverse phenotypic effects, depending upon the expression host. In particular, expression of cell wall degrading enzymes, such as cellulases, xylanases, ligninases, esterases, peroxidases, and other hydrolytic enzymes are often associated with detrimental effects on growth, physiological, and agronomic performance when expressed in plants. Some of these enzymes may also be poorly expressed in microbial hosts, due to their hydrolytic activity.

SUMMARY

In an aspect, the invention relates to a transgenic plant including a nucleic acid encoding an amino acid sequence with at least 90% identity to a sequence selected from SEQ ID NOS: 44-115.

In an aspect, the invention relates to a transgenic plant including a first nucleic acid that is capable of hybridizing under conditions of moderate stringency to a second nucleic acid consisting of a nucleotide sequence selected from SEQ ID NOS: 116-187 or the complement thereof.

In an aspect, the invention relates to a vector including a first nucleic acid capable of hybridizing under conditions of one of low, moderate or high stringency to a second nucleic acid consisting of the sequence of one of SEQ ID NOS: 116-187.

In an aspect, the invention relates to a vector including a nucleic acid having a sequence with at least 90% identity to a reference sequence selected from SEQ ID NOS: 188-283.

In an aspect, the invention relates to a method of processing plant biomass. The method includes pretreating a plant or part thereof through mixing the plant or part thereof with liquid to form a mixture having a liquid to solid ratio of less than or equal to 15. Pretreating also includes providing conditions to maintain the mixture at a temperature less than or equal to 100° C. The method also includes providing one or more enzyme for modification of at least one component of the plant or part thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 27A illustrates a transgenic plant made with pAG2020.

FIG. 27B illustrates a transgenic plant made with pAG2020.

FIG. 27C illustrates a cob from a transgenic plant made with pAG2020.

FIG. 28A illustrates a transgenic plant made with pAG2025.

FIG. 28B illustrates a transgenic plant made with pAG2025.

FIG. 28C illustrates a transgenic plant made with pAG2025.

DETAILED DESCRIPTION OF THE PREFERRED EMBODIMENTS

Figure 1:
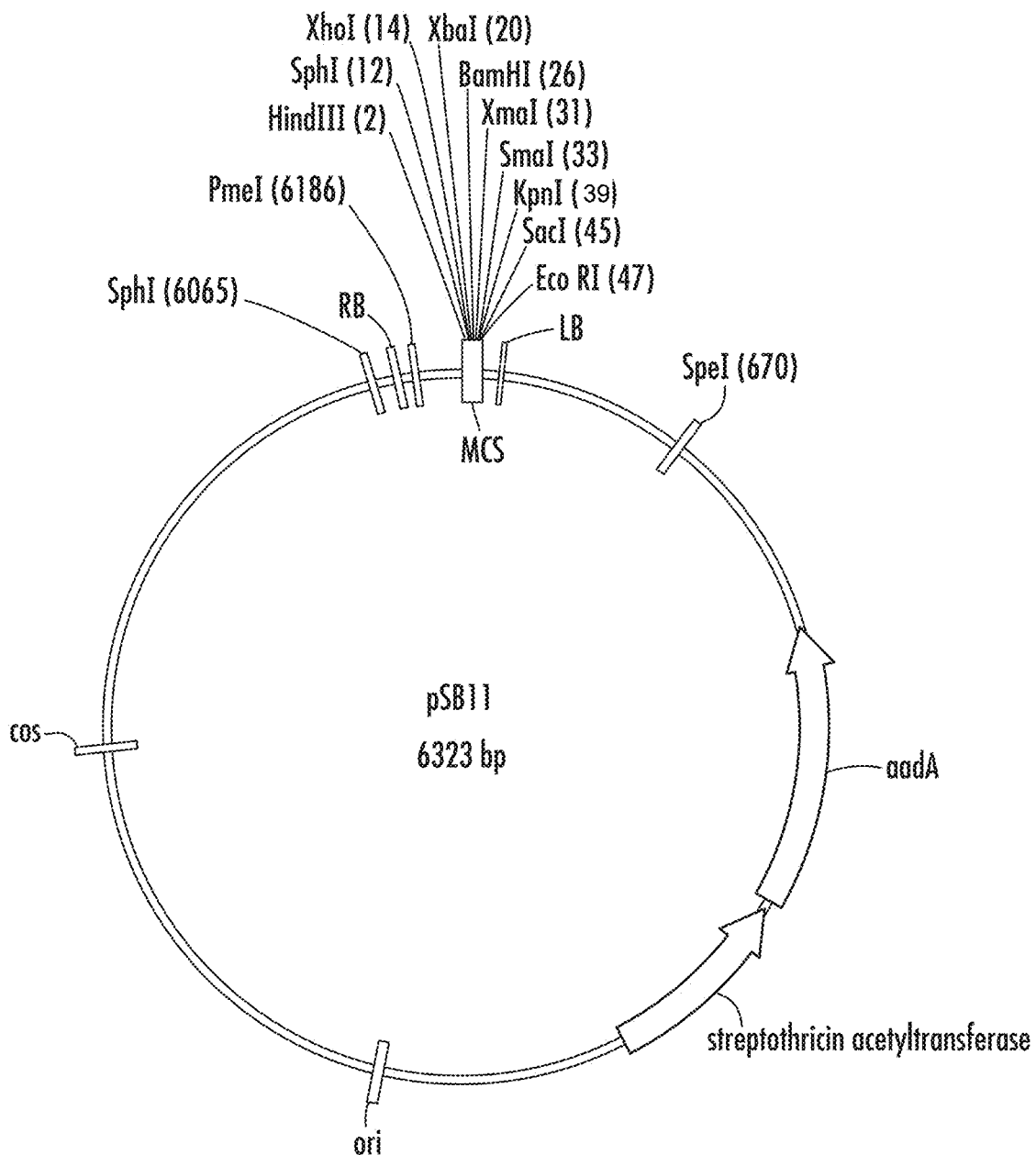
FIG. 1 illustrates a vector map of pSB11.

Certain terminology is used in the following description for convenience only and is not limiting. The words "right," "left," "top" and "bottom" designate directions in the drawings or specific examples to which reference is made.

The words "a" and "one," as used in the claims and in the corresponding portions of the specification, are defined as including one or more of the referenced item unless specifically stated otherwise. The phrase "at least one" followed by a list of two or more items, such as "A, B or C," means any individual one of A, B or C as well as any combination thereof.

Despite potential detrimental effects of enzymes on the expression host, producing enzymes in plants, microbes, and other organisms can create large economic benefits in the production of fuels, fiber, chemicals, sugars, textiles, pulp, paper, and animal feed. In some cases there are economic benefits to producing enzymes in plants, despite an agronomic or phenotypic effect. In addition, some phenotypic effects may be overcome using a variety of strategies that protect the plant from the enzyme activity. The embodiments herein include but are not limited to these strategies.

Strategies for plant-expressed enzymes may be crop dependent. A specific enzyme may have little or no value or benefits when expressed in one crop, but significant value or benefits when expressed in another crop. That is, the properties of the engineered plant may depend not only on the specific enzyme, but also on the specific plant that expresses the enzyme. For example, the expression of xylanase enzymes in plants can facilitate the hydrolysis of plant cell wall hemicellulose, and plant fiber, into fermentable sugars (for the production of fuels and chemicals) or digestible sugars (for animal feed and meat production). However, specific xylanase enzymes also decrease grain yield and may cause infertility when expressed in corn, preventing the use of that crop as a host for enzyme expression. Despite the negative effects on grain yield and fertility in corn, which may decrease the net economic value of the engineered plant versus the non-engineered plant, expression of the identical xylanases in another crop, such as switchgrass, *miscanthus*, sugarcane or *sorghum*, may actually be beneficial because infertility in these crops would prevent the outcrossing of the xylanase gene and commercially relevant amounts of plant propagules could be produced using tissue culture or vegetative propagation. While a decrease in fertility, grain yield, or dry matter biomass in corn might prevent, or decrease the value of, expression of specific xylanase enzymes that would otherwise be valuable in the chemical processing and animal feed industries, expression of the identical enzymes in switchgrass, *miscanthus*, *sorghum*, or sugarcane may not only provide the economic value created by the enzyme, but could be beneficial from a regulatory and safety perspective.

Likewise, the value of an enzyme expressed in one tissue of a crop may be different when expressed in a different tissue, or when expressed in the same tissue in a different crop. Different benefits result because specific crop tissues (such as grain, seed, leaves, stalks, roots, flowers, pollen, etc.) may have different values depending upon the crop and the new properties imparted by the expressed enzyme. Specific xylanase and cellulase enzymes have dramatic agronomic and phenotypic effects when expressed constitutively in corn. Constitutive expression of these enzymes, individually or in combination, often results in stunted plants, infertile plants, or plants with lower yields and agronomic performance. However, seed specific expression of specific xylanase and cellulase enzymes may decrease or eliminate any detrimental agronomic effect or yield decrease, while still providing high levels of enzyme. This may be a benefit in corn grain. Producing the same enzymes in switchgrass, *miscanthus*, forage or sweet *sorghum*, or sugarcane, where grain yields may be considerably lower on a per acre basis when compared to corn, may lead to a different profile for seed specific expression of a xylanase or cellulase. Embodiments include expression of a CWDE seed specifically in any kind of transgenic plant. Depending upon the application, such as animal feed production, meat or dairy production, poultry production, paper production, or the production of fermentable sugars, where the enzyme containing grain could be mixed with other harvested feedstock (pretreated or unpretreated), this may be a very effective way of providing beneficial doses of enzyme in corn grain or other grains and seeds.

The net economic value of a plant-expressed enzyme may differ, depending upon where the enzyme is designed to localize and accumulate, and where it is targeted. For example, specific xylanase and cellulase enzymes may have dramatic phenotypic and agronomic effects when targeted to the plant cell wall, but little or no effect when maintained intracellularly or targeted to the vacuole. This may create economic benefits by providing an intracellularly contained source of enzyme for applications where it is desired to mix the enzyme with a substrate. In contrast, while the same enzymes could provide value in an admix application such as in animal feed or the processing of pretreated biomass, these enzymes may provide little or no value in a self-processing application where plant cell wall targeting is preferred to generate fermentable or digestible sugars, but problematic because of the resulting phenotypic or agronomic effects.

As described above, an exogenous enzyme can be expressed in a particular plant, plant organ, plant tissue, plant cell, or plant sub-cellular region or compartment. Embodiments herein include expressing an exogenous enzyme in a plant, a region of a plant, a plant organ, a plant tissue, or a sub-cellular plant region or compartment. Embodiments also include a plant including an exogenous enzyme where the exogenous enzyme can be in the whole plant or localized in a region of the plant, in a plant organ, in plant tissues, or in a plant sub-cellular region or compartment. Transgenic plants adapted to or having cytoplasmic accumulation of an exogenous CWDE may be provided. The design of where in the plant and in what plant the exogenous enzyme is expressed can be but is not limited to a design that takes into account the phenotypic, safety, economic, or regulatory issues set forth above.

Vectors for expression of proteins in plants are provided in embodiments herein. The proteins may be enzymes and the enzymes can be but are not limited to cell wall degrading enzymes. A number of plants designed to express specific cell wall degrading enzymes are provided. The plants may have industrial and/or agricultural applications. Methods and materials for making the expression vectors and for making the plants are provided. Processes for which the plants could be used in industrial and agricultural applications are also provided.

Vectors for expressing in planta either a cell wall degrading enzyme (or CWDE) or a intein-modified CWDE variant are provided. In an embodiment, the vector is suitable for transformation of a dicotyledonous plant. In an embodiment, the vector is suitable for transformation of a monocotyledonous plant. The CWDEs from which the CWDE in a vector or plant may be selected from but are not limited to xylanases, cellulases, cellobiohydrolases, glucosidases, xylosidases, arabinofuranosidases, and ferulic acid esterases. In an embodiment, the CWDE encoding sequence is disrupted by the insertion of an intein sequence. The inserted intein sequence may inactivate the function of the corresponding CWDE. In an embodiment, the vector design permits insertion of at least three to four gene expression and/or gene silencing cassettes. Each cassette could include a CWDE or intein-modified CWDE.

In an embodiment, the genetic elements used in a vector herein or in the construction thereof can provide at least one of the following attributes: the ability to select transgenic events after plant transformation, the ability to affect an optimal level of the gene expression in cells or affect desired sub-cellular enzyme targeting. The vectors may contain a selectable marker, which can be but is not limited to a *E. coli* phosphomannose isomerase (PMI) gene. Other selectable markers that can be included, in addition to or in place of the PMI marker, are those known in the art (such as but not limited to EPSPS, BAR, npt-II, GUS, etc). The vectors may also include one or more promoters. The promoters may be constitutive or global, tissue specific, seed specific, leaf specific, organ specific, sub-cellular region or compartment specific, or developmental stage specific promoters. Preferred promoters include the rice Ubiquitin 3 gene promoter (OsUbi3P) with the first intron (Accession No. AY954394, SEQ ID NO: 1) or rice Actin 1 gene promoter (Accession No. 544221, SEQ ID NO: 2. Other constitutive promoters, such as but not limited to the maize ubiquitin promoter (SEQ ID NO: 3), could also be used and substituted for OsUbi3P or the rice Actin 1 promoter. The Ubiquitin 3 and rice Actin 1 gene promoters are constitutive and global promoters that can be used to provide gene expression in transgenic plants. The glutelin promoter from the rice GluB-4 gene (Accession No. AY427571, SEQ ID NO: 4) with its own signal sequence may also be provided in the vectors. The glutelin promoter is a seed-specific promoter. Other seed specific promoters (such as but not limited to the maize zein Zc2promoter SEQ ID NO: 5) could be provided in the vectors. In order to deliver the enzymes to their corresponding substrates or to places for high level of enzyme accumulation such as vacuoles, various targeting signal sequences can be provided in the vector. Targeting signal sequences that can be provided in a CWDE or vector encoding a CWDE include but are not limited to PR1a (SEQ ID NO: 6, encoded by the nucleic acid sequence of SEQ ID NO: 7), BAASS (SEQ ID NO: 8, encoded by the nucleic acid sequence of SEQ ID NO: 9), and barley aleurain (SEQ ID NO: 10, encoded by the nucleic acid of SEQ ID NO: 11). Other targeting sequences that can be included include but are not limited to the endoplasmic reticulum (ER) retention sequence SEKDEL (SEQ ID NO: 12, encoded by the nucleic acid of SEQ ID NO: 13), and the abridged sequence KDEL (SEQ ID NO: 10, encoded by the nucleic acid of SEQ ID NO: 16). The enzymes may be provided without a targeting sequence. The enzymes may be provided such that they accumulate in the cytoplasm. A transcription terminator may be provided. The efficient transcription terminator sequence from the nopaline synthase gene of *Agrobacterium tumefaciens* is used in gene expression cassette examples herein.

In an embodiment, a transgenic plant including a nucleic acid encoding a CWDE or a CWDE modified with at least one of a signal sequence or an intein is provided. The nucleic acid sequence encoding the CWDE may encode any CWDE amino acid sequence. The nucleic acid sequence encoding the CWDE modified with at least one of a signal sequence or an intein may encode any CWDE amino acid sequence and at least one of any signal sequence or any intein. The nucleic acid may encode a protein having at least 70, 72, 75, 80, 85, 90, 91, 92, 93, 94, 95, 96, 97, 98, 99 or 100% identity to a sequence selected from SEQ ID NOS: 44-115. The nucleic acid may encode a protein having at least 70, 72, 75, 80, 85, 90, 91, 92, 93, 94, 95, 96, 97, 98, 99 or 100% identity to a sequence selected from SEQ ID NOS: 44-45, 49-54, 57-59, 85-86, 94-96, 104-109 and 113-115. The nucleic acid may encode a protein having at least 70, 72, 75, 80, 85, 90, 91, 92, 93, 94, 95, 96, 97, 98, 99 or 100% identity to a sequence selected from SEQ ID NOS: 47 and 55. The nucleic acid may encode a protein having at least 70, 72, 75, 80, 85, 90, 91, 92, 93, 94, 95, 96, 97, 98, 99 or 100% identity to a sequence selected from SEQ ID NOS: 46, 48 and 56. The nucleic acid may encode a protein having at least 70, 72, 75, 80, 85, 90, 91, 92, 93, 94, 95, 96, 97, 98, 99 or 100% identity to a sequence selected from SEQ ID NOS: 60-67, 70 and 75. The nucleic acid may encode a protein at having least 70, 72, 75, 80, 85, 90, 91, 92, 93, 94, 95, 96, 97, 98, 99 or 100% identity to a sequence selected from SEQ ID NOS: 68-69, 71-74, 76-77 and 112. The nucleic acid may encode a protein having at least 70, 72, 75, 80, 85, 90, 91, 92, 93, 94, 95, 96, 97, 98, 99 or 100% identity to a sequence selected from SEQ ID NOS: 78-84. The nucleic acid may encode a protein having at least 70, 72, 75, 80, 85, 90, 91, 92, 93, 94, 95, 96, 97, 98, 99 or 100% identity to a sequence selected from SEQ ID NOS: 97-103. The nucleic acid may encode a protein having at least 70, 72, 75, 80, 85, 90, 91, 92, 93, 94, 95, 96, 97, 98, 99 or 100% identity to a sequence selected from SEQ ID NOS: 87-93 and 110-111. The nucleic acid may encode a protein having at least 70, 72, 75, 80, 85, 90, 91, 92, 93, 94, 95, 96, 97, 98, 99 or 100% identity to a sequence selected from SEQ ID NOS: 44, 45, 49 and 54. The nucleic acid may encode a protein having at least 70, 72, 75, 80, 85, 90, 91, 92, 93, 94, 95, 96, 97, 98, 99 or 100% identity to a sequence selected from SEQ ID NOS: 45, 87, 104-106 and 113. The nucleic acid may encode a protein having at least 70, 72, 75, 80, 85, 90, 91, 92, 93, 94, 95, 96, 97, 98, 99 or 100% identity to a sequence selected from SEQ ID NOS: 50-53, 57-59, 94-96, 104-109 and 113-115. The nucleic acid may encode a protein having at least 70, 72, 75, 80, 85, 90, 91, 92, 93, 94, 95, 96, 97, 98, 99 or 100% identity to a sequence selected from SEQ ID NOS: 54-56 and 60-65. Any of the nucleic acids set for the above that encode a protein having less than 100% identity to the cited reference sequence may encode a protein having the same or substantially the same activity as a protein having 100% identity to the cited reference sequence. Activity may be assessed by assays known in the art for any particular protein. Activity may be assessed by a method set forth in an example or portion thereof herein. Substantially the same activity would be known in the art. In an embodiment, substantially the same activity is within 20% of the activity of a protein having 100% identity to the cited reference sequence. In an embodiment, substantially the same activity is within 15% of the activity of a protein having 100% identity to the cited reference sequence. In an embodiment, substantially the same activity is within 10% of the activity of a protein having 100% identity to the cited reference sequence. In an embodiment, substantially the same activity is within 5% of the activity of a protein having 100% identity to the cited reference sequence. In an embodiment, substantially the same activity is within 1% of the activity of a protein having 100% identity to the cited reference sequence. The above mentioned nucleic acids may be provided in embodiments herein alone, as part of another nucleic acid, as part of a vector or as stated above as part of a transgenic plant. Identity can be measured by the Smith-Waterman algorithm (Smith T F, Waterman M S (1981), "Identification of Common Molecular Subsequences," *Journal of Molecular Biology* 147: 195-197, which is incorporated by reference in its entirety as if fully set forth). In an embodiment, the transgenic plant may be derived from one of corn, switchgrass, *miscanthus*, sugarcane or *sorghum*. The transgenic plant may be made by *agrobacterium* mediated transformation using a plasmid having a nucleotide sequence as set forth above. The plasmid have a sequence with at least 70, 72, 75, 80, 85, 90, 91, 92, 93, 94, 95, 96, 97, 98, 99 or 100% identity to a sequence selected from SEQ ID NOS: 188-283. The plasmid consist essentially of a sequence with at least 70, 72, 75, 80, 85, 90, 91, 92, 93, 94, 95, 96, 97, 98, 99 or 100% identity to a sequence selected from SEQ ID NOS: 188-283. The plasmid consist of a sequence with at least 70, 72, 75, 80, 85, 90, 91, 92, 93, 94, 95, 96, 97, 98, 99 or 100% identity to a sequence selected from SEQ ID NOS: 188-283.

In an embodiment, a transgenic plant including a nucleic acid hybridizing to a reference nucleic acid encoding a CWDE or a CWDE modified with at least one of a signal sequence or an intein is provided. The reference nucleic acid sequence encoding the CWDE may encode any CWDE amino acid sequence. The reference nucleic acid sequence encoding the CWDE modified with at least one of a signal sequence or an intein may encode any CWDE amino acid sequence and at least one of any signal sequence or any intein. The nucleic acid included in the transgenic plant may be referred to as a first nucleic acid. The first nucleic acid may be capable of hybridizing under conditions of low stringency to a second nucleic acid consisting of a nucleotide sequence selected from SEQ ID NOS: 116-187 or the complement thereof. The first nucleic acid may be capable of hybridizing under conditions of moderate stringency to a second nucleic acid consisting of a nucleotide sequence selected from SEQ ID NOS: 116-187 or the complement thereof. The first nucleic acid may be capable of hybridizing under conditions of high stringency to a second nucleic acid consisting of a nucleotide sequence selected from SEQ ID NOS: 116-187 or the complement thereof. The first nucleic acid may be capable of hybridizing under conditions of low, moderate or high stringency to a second nucleic acid consisting of a nucleotide sequence selected from SEQ ID NOS: 116-117, 121-126, 129-131, 157-158, 166-168, 176-181 and 185-187 or the complement thereof. The first nucleic acid may be capable of hybridizing under conditions of low, moderate or high stringency to a second nucleic acid consisting of a nucleotide sequence selected from SEQ ID NOS: 119 and 127 or the complement thereof. The first nucleic acid may be capable of hybridizing under conditions of low, moderate or high stringency to a second nucleic acid consisting of a nucleotide sequence selected from SEQ ID NOS: 118, 120 and 128 or the complement thereof. The first nucleic acid may be capable of hybridizing under conditions of low, moderate or high stringency to a second nucleic acid consisting of a nucleotide sequence selected from SEQ ID NOS: 132-139, 142 and 147 or the complement thereof. The first nucleic acid may be capable of hybridizing under conditions of low, moderate or high stringency to a second nucleic acid consisting of a nucleotide sequence selected from SEQ ID NOS: 140-141, 143-146, 148-149 and 184 or the complement thereof. The first nucleic acid may be capable of hybridizing under conditions of low, moderate or high stringency to a second nucleic acid consisting of a nucleotide sequence selected from SEQ ID NOS: 150-156 or the complement thereof. The first nucleic acid may be capable of hybridizing under conditions of low, moderate or high stringency to a second nucleic acid consisting of a nucleotide sequence selected from SEQ ID NOS: 169-175 or the complement thereof. The first nucleic acid may be capable of hybridizing under conditions of low, moderate or high stringency to a second nucleic acid consisting of a nucleotide sequence selected from SEQ ID NOS: 159-165 and 182-183 or the complement thereof. The first nucleic acid may be capable of hybridizing under conditions of low, moderate or high stringency to a second nucleic acid consisting of a nucleotide sequence selected from SEQ ID NOS: 116, 117, 121 and 126 or the complement thereof. The first nucleic acid may be capable of hybridizing under conditions of low, moderate or high stringency to a second nucleic acid consisting of a nucleotide sequence selected from SEQ ID NOS: 117, 159, 176-178 and 185 or the complement thereof. The first nucleic acid may be capable of hybridizing under conditions of low, moderate or high stringency to a second nucleic acid consisting of a nucleotide sequence selected from SEQ ID NOS: 122-125, 129-131, 166-168, 176-181 and 185-187 or the complement thereof. The first nucleic acid may be capable of hybridizing under conditions of low, moderate or high stringency to a second nucleic acid consisting of a nucleotide sequence selected from SEQ ID NOS: 126-128 and 132-137 or the complement thereof. Examples of hybridization protocols and methods for optimization of hybridization protocols are described in the following books: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated herein by reference as if fully set forth. By way of example, but not limitation, procedures for hybridization conditions of moderate stringency are as follows: filters containing DNA are pretreated for 2-4 h at 68° C. in a solution containing 6×SSC (Amresco, Inc., Solon, Ohio), 0.5% SDS (Amersco, Inc., Solon, Ohio), 5×Denhardt's solution (Amersco, Inc., Solon, Ohio), and 100 μg/mL denatured, salmon sperm DNA (Invitrogen Life Technologies, Inc., Carlsbad, Calif.). Approximately 0.2 mL of pretreatment solution are used per square centimeter of membrane used. Hybridizations are carried out in the same solution with the following modifications: 0.01 M EDTA (Amersco, Inc., Solon, Ohio), 100 μg/ml salmon sperm DNA, and 5-20×10$^6$ cpm $^{32}$P-labeled or fluorescently labeled probes can be used. Filters are incubated in hybridization mixture for 16-20 h at 68° C. and then washed for 15 minutes at room temperature (within five degrees of 25° C.) in a solution containing 2×SSC and 0.1% SDS, with gentle agitation. The wash solution is replaced with a solution containing 0.1×SSC and 0.5% SDS, and incubated an additional 2 h at 68° C., with gentle agitation. Filters are blotted dry and exposed for development in an imager or by autoradiography. If necessary, filters are washed for a third time and re-exposed for development. By way of example, but not limitation, low stringency refers to hybridizing conditions that employ low temperature for hybridization, for example, temperatures between 37° C. and 60° C. By way of example, but not limitation, high stringency refers to hybridizing conditions as set forth above but with modification to employ high temperatures, for example, hybridization temperatures over 68° C. Any of the nucleic acids set for the above that have less than 100% identity to the cited reference sequence may encode a protein having the same or substantially the same activity as a protein encoded by a nucleic acid sequence having 100% identity to the cited reference sequence. Activity may be assessed by assays known in the art for any particular protein. Activity may be assessed by a method set forth in an example or portion thereof herein. Substantially the same activity would be known in the art. In an embodiment, substantially the same activity is within 20% of the activity of a protein encoded by a nucleic acid sequence having 100% identity to the cited reference sequence. In an embodiment, substantially the same activity is within 15% of the activity of a protein encoded by a nucleic acid sequence having 100% identity to the cited reference sequence. In an embodiment, substantially the same activity is within 10% of the activity of a protein encoded by a nucleic acid sequence having 100% identity to the cited reference sequence. In an embodiment, substantially the same activity is within 5% of the activity of a protein encoded by a nucleic acid sequence having 100% identity to the cited reference sequence. In an embodiment, substantially the same activity is within 1% of the activity of a protein encoded by a nucleic acid sequence having 100% identity to the cited reference sequence. The transgenic plant may be derived from one of corn, switchgrass, *miscanthus*, sugarcane or *sorghum*. The transgenic plant may be made by *Agrobacterium* mediated transformation using a plasmid including any of the above nucleic acids.

In an embodiment, a vector including a nucleic acid encoding a CWDE or a CWDE modified with at least one of a signal sequence or an intein is provided. The nucleic acid sequence encoding the CWDE may encode any CWDE amino acid sequence. The nucleic acid sequence encoding the CWDE modified with at least one of a signal sequence or an intein may encode any CWDE amino acid sequence and at least one of any signal sequence or any intein. The nucleic acid may encode a protein having least 70, 72, 75, 80, 85, 90, 91, 92, 93, 94, 95, 96, 97, 98, 99 or 100% identity to a sequence selected from SEQ ID NOS: 44-115. The nucleic acid sequence may hybridize under conditions of low stringency to a reference nucleic acid consisting of the sequence of one of SEQ ID NOS: 116-187 or the complement thereof. The nucleic acid sequence may hybridize under conditions of moderate stringency to a reference nucleic acid consisting of the sequence of one of SEQ ID NOS: 116-187 or the complement thereof. The nucleic acid sequence may hybridize under conditions of high stringency to a reference nucleic acid consisting of the sequence of one of SEQ ID NOS: 116-187 or the complement thereof. The vector may include a sequence having 70, 72, 80, 85, 90, 91, 92, 93, 94, 95, 96, 97, 98, 99 or 100% identity to a sequence selected from SEQ ID NOS: 188-283. The vector may consist essentially of a sequence having 70, 72, 80, 85, 90, 91, 92, 93, 94, 95, 96, 97, 98, 99 or 100% identity to a sequence selected from SEQ ID NOS: 188-283. The vector may consist of a sequence having 70, 72, 80, 85, 90, 91, 92, 93, 94, 95, 96, 97, 98, 99 or 100% identity to a sequence selected from SEQ ID NOS: 188-283.

In an embodiment, an isolated nucleic acid, polynucleotide, or oligonucleotide encoding at least a portion of any of the amino acid sequences of SEQ ID NOS: 44-115 can be used as a hybridization probe or primer. In an embodiment, the complement of said isolated nucleic acid, polynucleotide or oligonucleotide may be used as a hybridization probe or primer. In an embodiment, an isolated nucleic acid having a sequence that hybridizes under conditions of low, moderate or high stringency to at least a portion of a nucleic acid having the sequence of any one of SEQ ID NOS: 116-187 and 188-283 or the complement thereof may be used as a hybridization probe or primer. These isolated nucleic acids, polynucleotides, or oligonucleotides are not limited to but may have a length in the range from 10 to 100, 10 to 90, 10 to 80, 10 to 70, 10 to 60, 10 to 50, 10 to 40, 10 to 35, 10 to 30, 10 to 25, 10 to 20 or 10 to 15 nucleotides, or from 20 to 30 nucleotides, or be 25 nucleotides in length. A range of nucleotide sequence lengths recited herein includes every length of nucleotide sequence within the range, endpoints inclusive. The recited length of nucleotides may start at any single position within a reference sequence where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a nucleic acid encoding one of the proteins of SEQ ID NOS: 44-115 or the complement of said nucleic acid. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a nucleic acid with the sequence of one of SEQ ID NOS: 116-283. In an embodiment, a hybridization probe or primer hybridizes along its length to a corresponding length of a nucleic acid encoding the sequence of one of SEQ ID NOS: 44-115 or the complement said nucleic acid. In an embodiment, a hybridization probe or primer hybridizes along its length to a corresponding length of a nucleic acid having the sequence of one of SEQ ID NOS: 116-187 or the complement thereof. In an embodiment, hybridization can occur under conditions of low stringency. In an embodiment, hybridization can occur under conditions of moderate stringency. In an embodiment, hybridization can occur under conditions of high stringency.

The isolated nucleic acids, polynucleotides, or oligonucleotides of embodiments herein may include natural nucleotides, natural nucleotide analogues, or synthetic nucleotide analogues. Nucleic acids, polynucleotides, or oligonucleotides of embodiments herein may be any kind of nucleic acid including deoxyribonucleic acid (DNA), ribonucleic acid (RNA), or peptide nucleic acid (PNA). The nucleic acid sequences listed herein are listed as DNA sequences but other nucleic acids are contemplated as embodiments herein, including RNA sequences where U replaces T.

Although non-labeled hybridization probes or primers can be used in the embodiments herein, the hybridization probes or primers may be detectably labeled and could be used to detect, sequence, or synthesize nucleic acids. Exemplary labels include, but are not limited to, radionuclides, light-absorbing chemical moieties, dyes, and fluorescent moieties. The label may be a fluorescent moiety, such as 6-carboxyfluorescein (FAM), 6-carboxy-4,7,2',7'-tetrachlorofluoroscein (TET), rhodamine, JOE (2,7-dimethoxy-4,5-dichloro-6-carboxyfluorescein), HEX (hexachloro-6-carboxyfluorescein), or VIC.

In an embodiment, a method of processing plant biomass is provided. The method may include pretreating a plant or part thereof through mixing the plant or part thereof with liquid to form a mixture having a liquid to solid ratio of less than or equal to 15. Pretreating may include providing conditions to maintain the mixture at a temperature less than or equal to 100° C. The method may include providing one or more enzyme. The plant biomass may be or be derived from any plant or part thereof. The plant biomass may be or be derived from any transgenic plant or part thereof described, illustrated or claimed herein. The method may include a plant or part thereof other than any transgenic plant or part thereof described, illustrated or claimed herein, and combining it with any transgenic plant or part thereof described, illustrated or claimed herein. The liquid to solid ratio in the mixture may be a value less than or equal to 25, 24, 23, 22, 21, 20, 19, 18, 17, 16, 15, 14, 13, 12, 11, 10, 9, 8, 7, 6, 5, 4, 3, 2 or 1. The liquid to solid ratio may be 8 or less. The liquid to solid ratio may be 8. The step of pretreating may include maintaining the temperature of less than or equal to 100° C. for at least four hours. The step of pretreating may include maintaining the temperature of 40° C. to 90° C. The liquid provided to make the mixture may be any liquid. In an embodiment, the liquid is water. In an embodiment, the liquid includes water, ammonium bisulfite and ammonium carbonate. The ammonium bisulfite may be at any suitable concentration. In an embodiment, the ammonium bisulfite concentration is a value within 8% to 38% (endpoints inclusive) on a wt./wt. basis with the plant or part thereof. The ammonium carbonate may be at any suitable pH. In an embodiment, the ammonium carbonate pH is a pH in the range of 7.6 to 8.5, enpoints inclusive. The ammonium carbonate concentration may be any suitable concentration. In an embodiment, the ammonium carbonate concentration is a value within 4% to 19% (endpoints inclusive) on a wt./wt. basis with the plant or part thereof. The step of providing one or more enzyme may include providing any enzyme suitable for processing plant biomass. In an embodiment, the one or more enzyme includes at least one enzyme capable hydrolyzing lignocellulosic material. In an embodiment, the one or more enzymes include at least one of an endoglucanase, a β-glucosidase, a cellobiohydrolase or a xylanase. In an embodiment, the one or more enzymes include at least one of a xylanase, a cellulase, a cellobiohydrolase, a glucosidase, a xylosidase, an arabinofuronosidase or a ferulic acid esterase. In an embodiment, the method includes a step of providing one or more enzyme where the one or more enzyme is not a xylanase, and then adding a xylanase as an additional step.

Any single embodiment herein may be supplemented with one or more element from any one or more other embodiment herein.

EXAMPLES

The following non-limiting examples are provided to illustrate particular embodiments. The embodiments throughout may be supplemented with one or more detail from any one or more example below.

Example 1—pSB11

Referring to FIG. 1, a vector of an embodiment herein may be based on the pSB11 intermediate plasmid (a derivative of pBR322). pSB11 is available from Japan Tobacco. The pSB11 plasmid is suitable for cloning and can be easily maintained in *E. coli*. The pSB11 conjugates with the pSB1 "super-binary" acceptor vector (a disarmed Ti plasmid), which can be maintained in the LB4404 strain of *Agrobacterium tumefaciens*, through homologous recombination using cos and on sites present in both vectors. The integration product represents a hybrid vector that can be subsequently used for plant transformation. pSB1 contains virulence genes such as virB, virC and virG required for T-DNA processing and delivering to the plant cell. pSB11 has a multiple cloning site containing unique restriction enzyme recognition sites for cloning expression cassettes with the target gene sequences.

Example 2—pAG1000

Figure 2A:
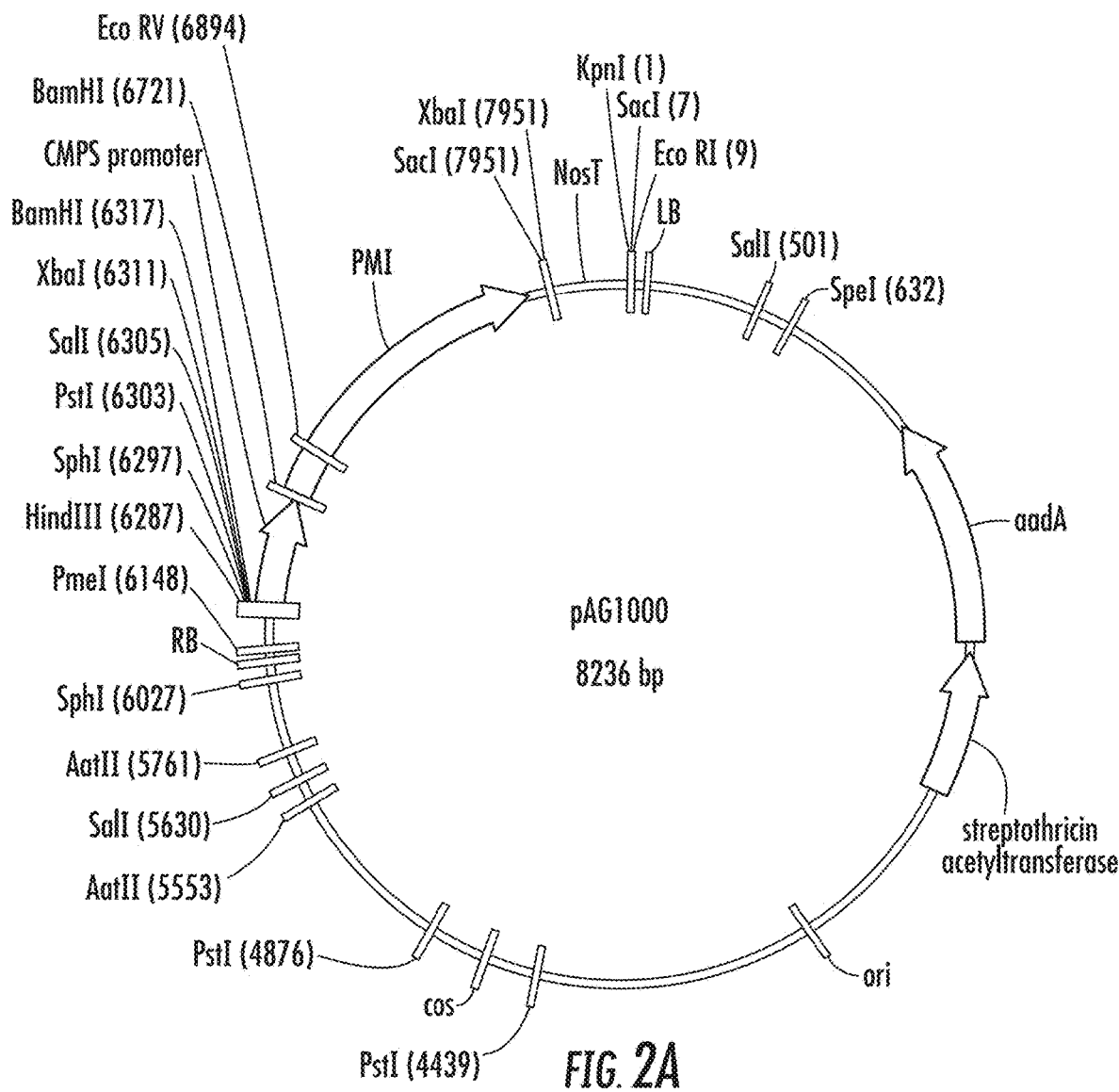
FIG. 2A illustrates a vector map of AG1000.

Referring to FIG. 2A, pAG1000 was created by modification of pSB11 in order to enable it to accept several gene expression cassettes. Initially, the original expression cassette containing a positive selectable marker gene manA encoding phosphomannose isomerase (PMI) driven by the Cestrum Yellow Leaf Curling Virus promoter (CMPS) was cloned from pNOV2819 plasmid (Syngenta Biotechnology) into pSB11 as HindIII-KpnI fragment to generate pAG1000.

Figure 2B:
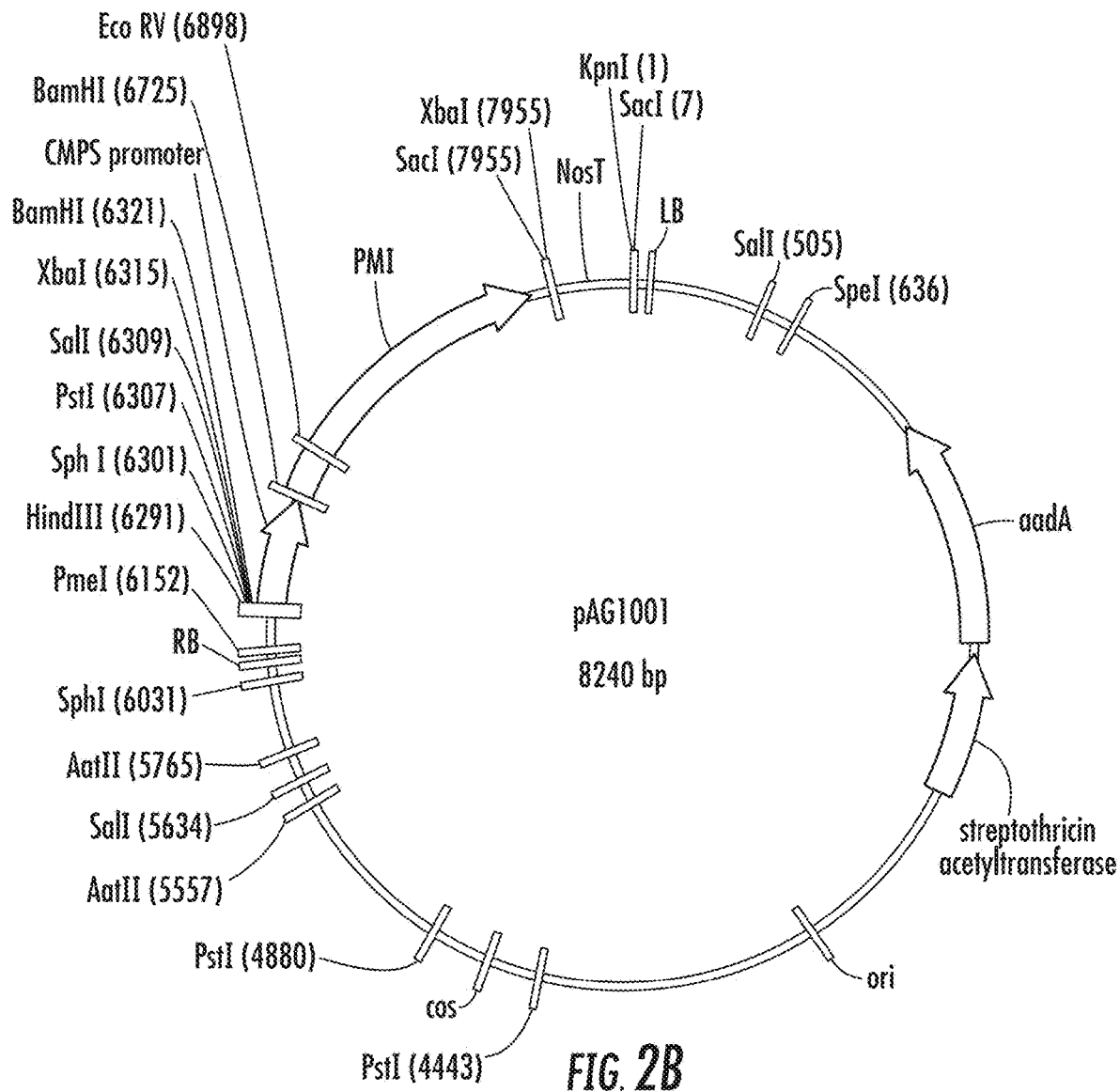
FIG. 2B illustrates a vector map of pAG1001.
Figure 2C:
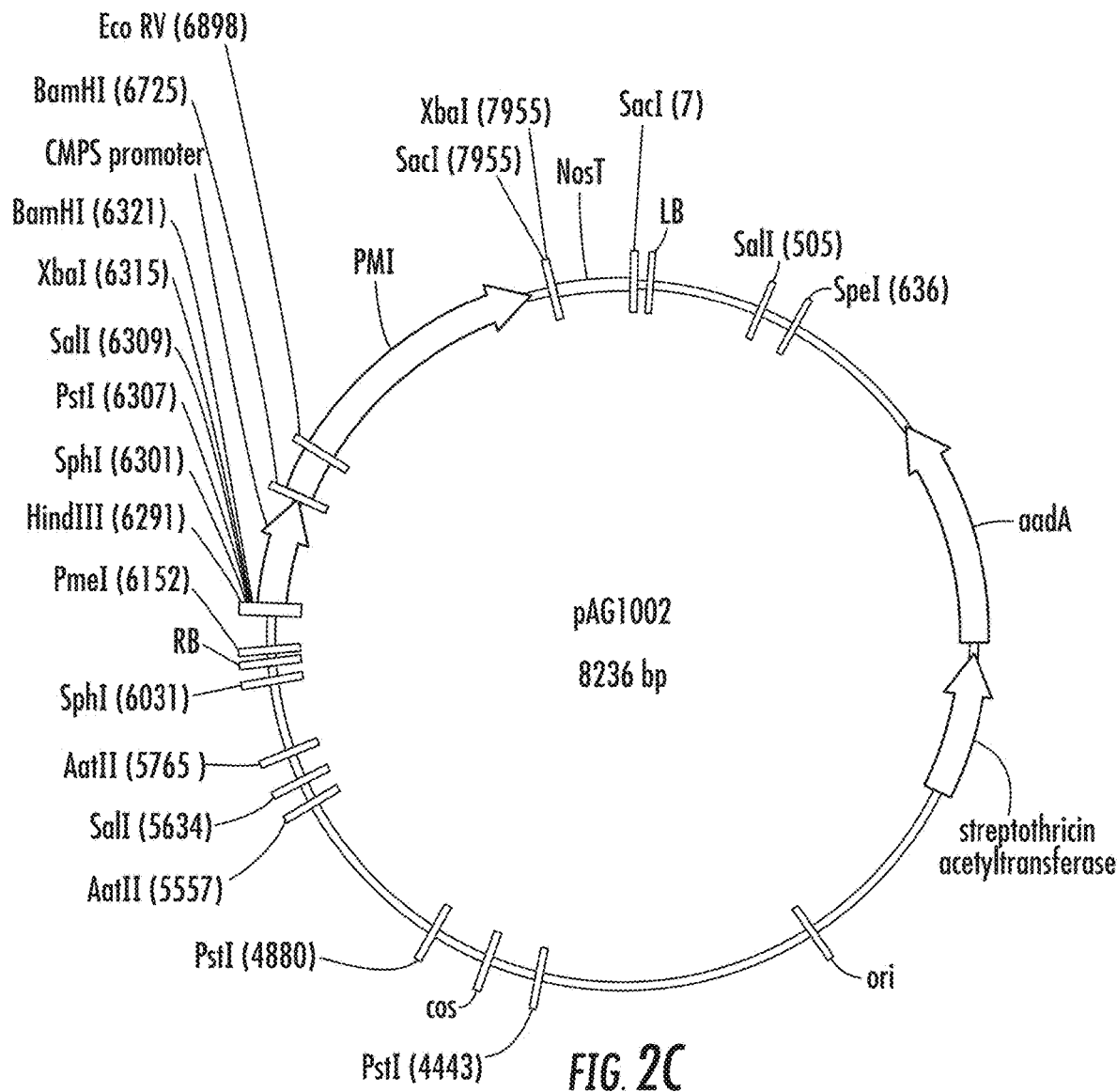
FIG. 2C illustrates a vector map of pAG1002.
Figure 3A:
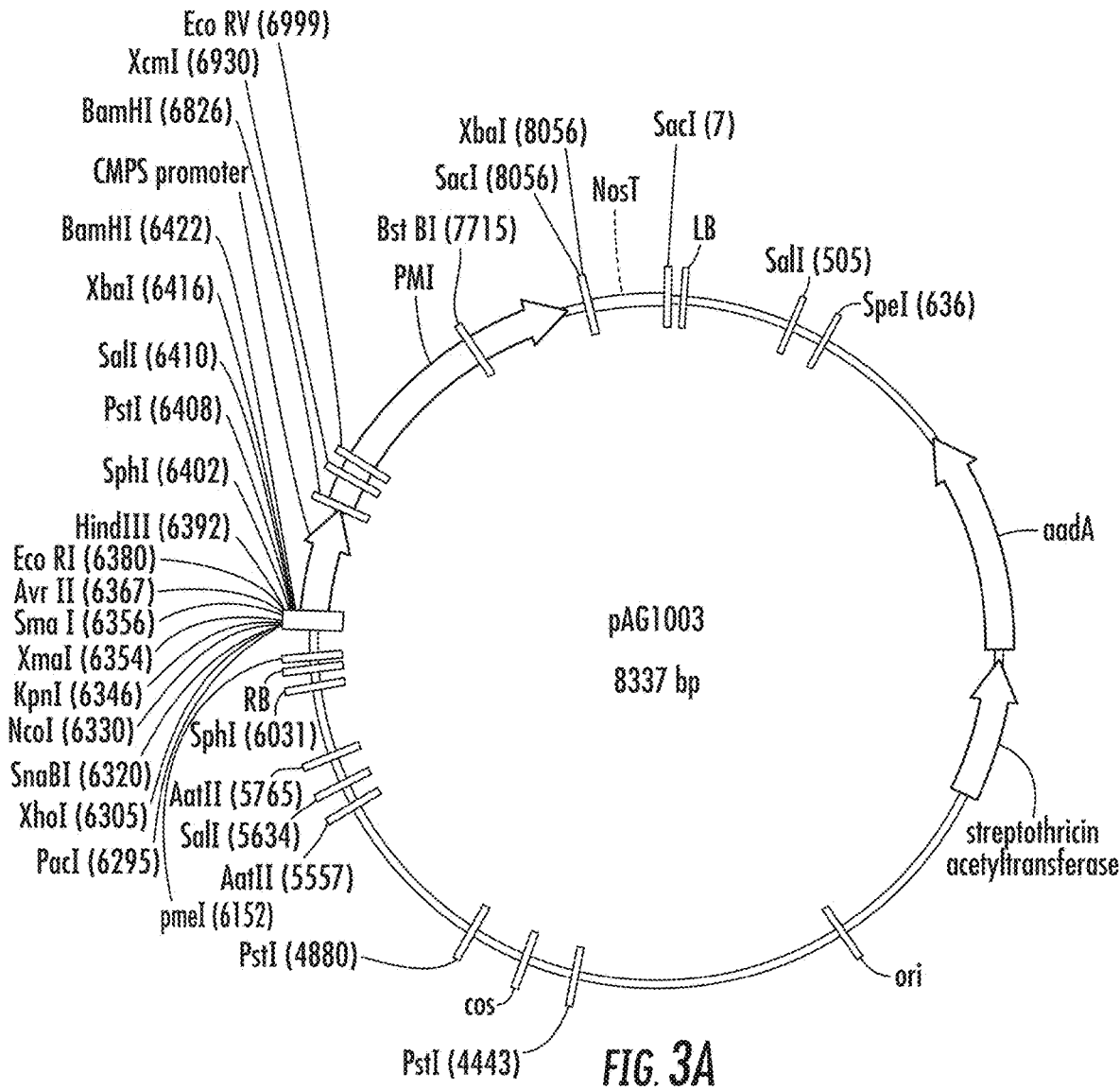
FIG. 3A illustrates a vector map of pAG1003.

Example 3—pAG1001, pAG1002 and pAG1003 pAG1000 was further modified by removal of EcoRI site (nucleotide position #7) to generate pAG1001 (FIG. 2B) and then KpnI site (nt position #1) to produce pAG1002 (FIG. 2C). These modifications made the EcoRI and KpnI sites available for subsequent cloning expression cassettes with the genes of interest (GOI). Referring to FIG. 3A, a new multiple cloning site (MCS) sequence, below, containing PacI, XhoI, SnaBI, NcoI, KpnI, XmaI, AvrII, EcoRI sites, was PCR synthesized as a 249 bp PmeI-HindIII fragment and cloned into PmeI-HindIII sites of pAG1002 to provide the pAG1003 vector.

>MCS
(SEQ ID NO: 17)
GTTTAAACTGAAGGCGGGAAACGACAACCTGATCATGAGCGGAGAATTAA

GGGAGTCACGTTATGACCCCCGCCGATGACGCGGGACAAGCCGTTTTACG

TTTGGAACTGACAGAACCGCAACGTTGAAGGAGCCACTCAGCTTAATTAA

GTCTAACTCGAGTTACTGGTACGTACCAAATCCATGGAATCAAGGTACCA

TCAATCCCGGGTATTCATCCTAGGTATCCAAGAATTCATACTAAAGCTT

Example 4—pAG2000

Figure 3B:
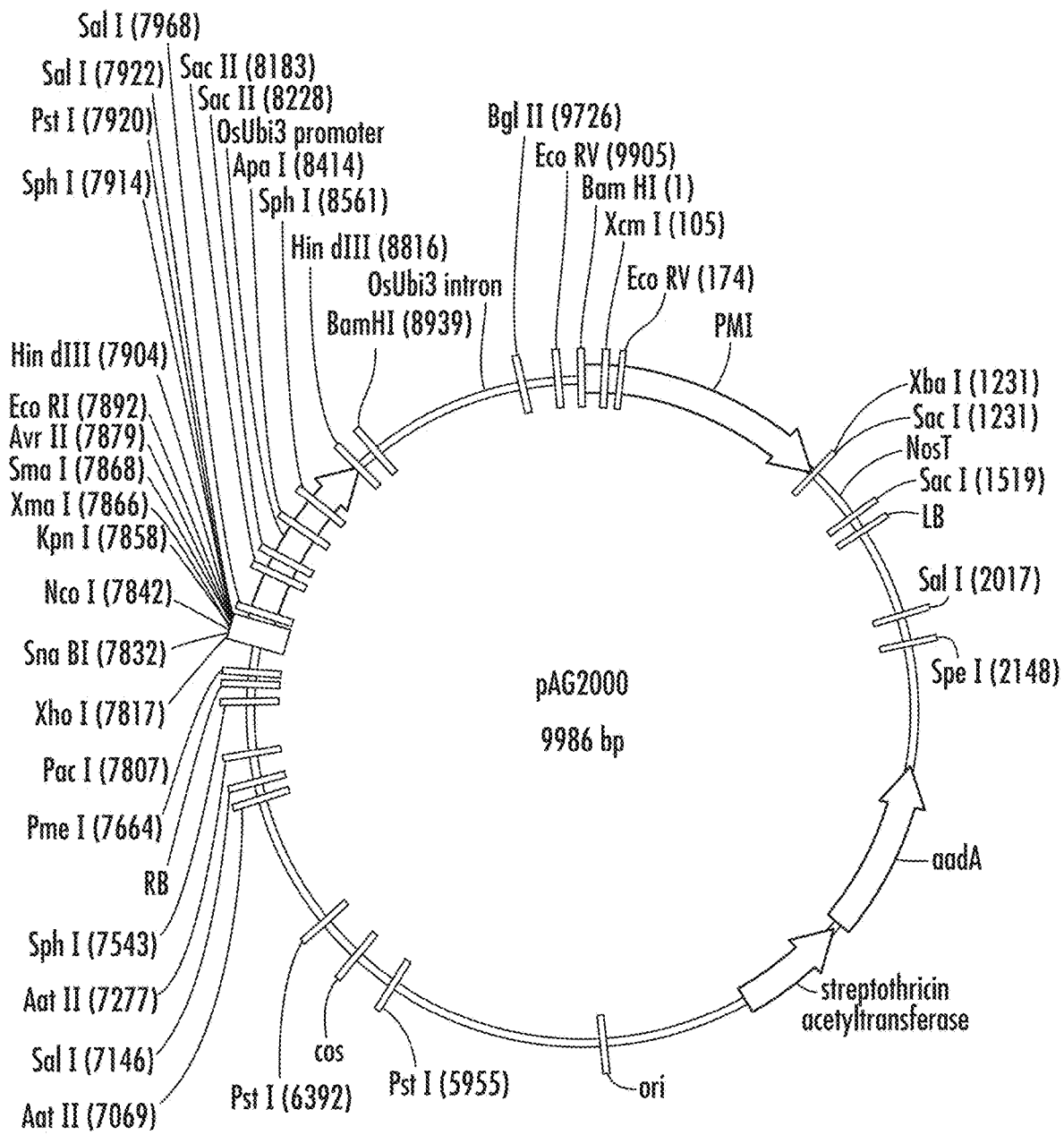
FIG. 3B illustrates a vector map of pAG2000.

Referring to FIG. 3B, higher expression levels may be provided by replacing the viral CMPS promoter in pAG1003 by the rice Ubiquitin 3 promoter (SEQ ID NO: 1), which is an extensively studied promoter with demonstrated efficacy for gene expression in monocots. The OsUbi3P has been cloned from the pRESQ101 plasmid. pRESQ101 was described by E. Sivamani, J. D. Starmer, R. Qu, "Sequence analysis of rice rubi3 promoter gene expression cassettes for improved transgene expression," Plant Science, 177(6): 549-556, 2009, which is incorporated herein by reference as if fully set forth. The following modifications were made to the OsUbi3P for the cloning purposes: 1) An EcoRI site was introduced at the 5' end via a PCR approach; 2) an XmaI site was removed, while a BamHI site was added to the 3' end. A partial sequence of OsUbi3P was assembled as an ApaI-BamHI fragment in pBluescript and then cloned as the HindIII-BamHI entire promoter region including the first Ubiquitin intron fused to PMI in pAG1003 digested with HindIII-SpeI. The latter cloning produced the pAG2000 vector.

Example 5—pAG2004 and pAG2005

The pAG2000 vector was further modified in order to develop a cloning vector amenable of accepting GOI expression cassettes while providing enhanced expression of the PMI selectable marker for plant transformation. The optimization of PMI expression included replacement of original junction sequence connecting the OsUbi3 intron with the start PMI gene codon in pAG2000 (shown in SEQ ID NO: 18, below) by a new 9 nt sequence. The original junction sequence is underlined and the start codon is in bold in the version of SEQ ID NO: 18 presented below. The new 9 nt sequence is shown as boxed in the version of SEQ ID NO: 19 presented below. The boxed sequence was validated as the efficacious sequence in providing a high level of transient GUS expression in pRESQ48 by E. Sivamani and R. Qu (2006), which is incorporated herein by reference as if fully set forth. This 9 nt sequence represents the three initial codons of the rice Ubiquitin 3 gene, where the start codon ATG has been modified to ATC in order to eliminate an additional translation initiation site. To achieve this modification, the BglII-XcmI fragment of pAG2000 (nucleotide positions 9726-105) was replaced by the PCR synthesized fragment, which contained the required 9 nt junction sequence and was generated in successive reactions using primers P64/P68, P64/P66, and P64/P67.

>BglII-XcmI (9726-105) of pAG2000

(SEQ ID NO: 18)

Agatctgttgtcctgtagttacttatgtcagttttgttattatctgaagatattttggttgttgcttgttgatgtggtgtgagctgtgagca gcgctcttatgattaatgatgctgtccaattgtagtgtagtatgatgtgattgatatgttcatctattttgagctgacagtaccgatatcgt aggatctggtgccaacttattctccagctgctttttttttacctatgttaattccaatcctttcttgcctcttccag<u>GGATCCCCGATC</u>

ATGCAAAAACTCATTAACTCAGTGCAAAACTATGCCTGGGGCAGCAAAACGGCGTTGACT

GAACTTTATGGTATGGAAAATCCGTCCAGCCAGCCGATGG

>BglII-XcmI PCR synthesized fragment for pAG2004 construction (SEQ ID NO: 19)

Agatctgttgtcctgtagttacttatgtcagttttgttattatctgaagatattttggttgttgcttgttgatgtggtgtgagctgtgagca gcgctcttatgattaatgatgctgtccaattgtagtgtagtatgatgtgattgatatgttcatctattttgagctgacagtaccgatatcgt aggatctggtgccaacttattaccagctgctttttttttacctatgttaattccaatcctttcttgcctcttccag ATCCAGATA ATG

CAGAAACTCATTAACTCAGTGCAAAACTATGCCTGGGGCAGCAAAACGGCGTTGACTGAA

CTTTATGGTATGGAAAATCCGTCCAGCCAGCCGATGG

| Primer | Sequence |
|---|---|
| P64 | AGATCTGTTGTCCTGTAGTTACTTATGTCA (SEQ ID NO: 20) |
| P66 | CCATCGGCTGGCTGGACGGATTTTCCATACCATAAAGTTCAGTC AACGCCGTTTTGCTGCCCCAGGCATA (SEQ ID NO: 21) |
| P67 | CCATCGGCTGGCTGGACGGATTTTC (SEQ ID NO: 22) |
| P68 | CGTTTTGCTGCCCCAGGCATAGTTTTGCACTGAGTTAATGAGTT TCTGCATTATCTGGATCTGGAAGAGGCAAGAAAGGATTGGA (SEQ ID NO: 23) |

Figure 3C:
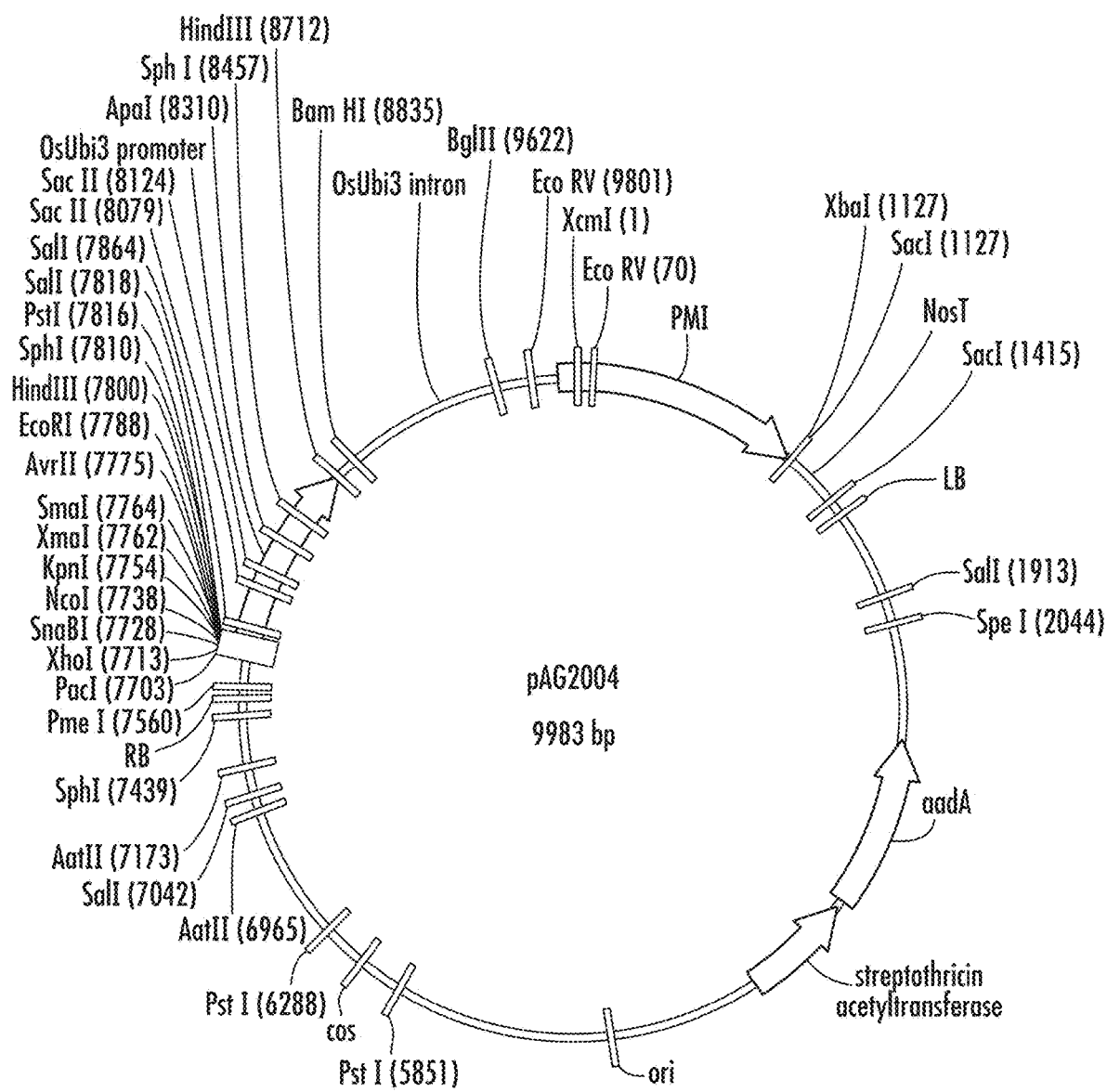
FIG. 3C illustrates a vector map of pAG2004.

Referring to FIG. 3C, the modifications above lead the pAG2004 vector, which is an embodiment herein. The pAG2004 vector was subsequently used to conjugate with pSB1 in LBA4404 strain of *Agrobacterium tumefaciens* and to transform immature maize embryos using Japan Tobacco transformation procedure (Japan Tobacco Operating Manual for plasmid pSB1, Version 3.1, Jun. 5, 2006; Komari, T., et. al., "Binary Vectors and Super-binary Vectors", Methods in Molecular Biology, Volume 343: *Agrobacterium* Protocols, pages 15-41, Humana Press, which is incorporated herein by reference as if fully set forth). The maize transformation efficiencies of the pAG2004 and its derivative pAG2005, which contain OsUbi3 promoter cloned as KpnI-XmaI into pAG2004 MCS, may be in the range of 20-60%, while the pAG1003 with the original PMI expression cassette from pNOV2819, where manA expression is driven by the CMPS viral promoter, may provide up to 15% transformation efficiency.

The sequence of pAG2005 is given in SEQ ID NO: 24, which is set forth below:

(SEQ ID NO: 24)

aattcatactaaagcttgcatgcctgcaggtcgactctagtaacggccgc cagtgtgctggaattaattcggcttgtcgaccacccaacccatatcgac agaggatgtgaagaacaggtaaatcacgcagaagaacccatctctgatag cagctatcgattagaacaacgaatccatattgggtccgtgggaaatactt actgcacaggaaggggggcgatctgacgaggccccgccaccggcctcgacc cgaggccgaggccgacgaagcgccggcgagtacgcgcgccgcggcggcctc tgcccgtgccctctgcgcgtgggagggagaggccgcggtggtgggggcgc gcgcgcgcgcgcgcgcagctggtgcggcggcgcgggggtcagccgccgag ccggcggcgacggaggagcagggcggcgtggacgcgaacttccgatcggt tggtcagagtgcgcgagttgggcttagccaattaggtctcaacaatctat tgggccgtaaaattcatgggccctggtttgtctaggcccaatatcccgtt catttcagcccacaaatatttccccagaggattattaaggcccacacgca gcttatagcagatcaagtacgatgtttcctgatcgttggatcggaaacgt acggtcttgatcaggcatgccgacttcgtcaaagagaggcggcatgacct gacgcggagttggttccgggcaccgtctggatggtcgtaccgggaccgga cacgtgtcgcgcctccaactacatggacacgtgtggtgctgccattgggc cgtacgcgtggcggtgaccgcaccggatgctgcctcgcaccgccttgccc acgctttatatagagaggttttctctccattaatcgcatagcgagtcgaa tcgaccgaaggggaggggggagcgaagctttgcgttctctaatcgcctcgt caaggtaactaatcaatcacctcgtcctaatcctcgaatctctcgtggtg cccgtctaatctcgcgattttgatgctcgtggtggaaagcgtaggaggat cccgtgcgagttagtctcaatctctcagggtttcgtgcgattttagggtg atccacctcttaatcgagttacggtttcgtgcgattttagggtaatcctc ttaatctctcattgatttagggtttcgtgagaatcgaggtagggatctgt gttatttatatcgatctaatagatggattggttttgagattgttctgtca gatggggattgtttcgatatattaccctaatgatgtgtcagatggggatt gtttcgatatattaccctaatgatgtgtcagatggggattgtttcgatat attaccctaatgatggataataagagtagttcacagttatgttttgatcc tgccacatagtttgagttttgtgatcagatttagttttacttatttgtgc ttagttcggatgggattgttctgatattgttccaatagatgaatagctcg ttaggttaaaatctttaggttgagttaggcgacacatagtttatttcctc tggatttggattggaattgtgttcttagttttttttcccctggatttggat tggaattgtgtggagctgggttagagaattacatctgtatcgtgtacacc

```
tacttgaactgtagagcttgggttctaaggtcaatttaatctgtattgta
tctggctctttgcctagttgaactgtagtgctgatgttgtactgtgtttt
tttacccgttttatttgctttactcgtgcaaatcaaatctgtcagatgct
agaactaggtggctttattctgtgttcttacatagatctgttgtcctgta
gttacttatgtcagttttgttattatctgaagatattttttggttgttgct
tgttgatgtggtgtgagctgtgagcagcgctcttatgattaatgatgctg
tccaattgtagtgtagtatgatgtgattgatatgttcatctattttgagc
tgacagtaccgatatcgtaggatctggtgccaacttattctccagctgct
tttttttacctatgttaattccaatccttcttgcctctccagatccaga
taatgcagaaactcattaactcagtgcaaaactatgcctggggcagcaaa
acggcgttgactgaactttatggtatggaaaatccgtccagccagccgat
ggccgagctgtggatgggcgcacatccgaaaagcagttcacgagtgcaga
atgccgccggagatatcgtttcactgcgtgatgtgattgagagtgataaa
tcgactctgctcggagaggccgttgccaaacgctttggcgaactgccttt
cctgttcaaagtattatgcgcagcacagccactctccattcaggttcatc
caaacaaacacaattctgaaatcggttttgccaaagaaaatgccgcaggt
atcccgatggatgccgccgagcgtaactataaagatcctaaccacaagcc
ggagctggttttttgcgctgacgcctttccttgcgatgaacgcgtttcgtg
aattttccgagattgtctccctactccagccggtcgcaggtgcacatccg
gcgattgctcacttttttacaacagcctgatgccgaacgtttaagcgaact
gttcgccagcctgttgaatatgcagggtgaagaaaaatcccgcgcgctgg
cgattttaaaatcggccctcgatagccagcagggtgaaccgtggcaaacg
attcgtttaatttctgaattttaccggaagacagcggtctgttctcccc
gctattgctgaatgtggtgaaattgaaccctggcgaagcgatgttcctgt
tcgctgaaacaccgcacgcttacctgcaaggcgtggcgctggaagtgatg
gcaaactccgataacgtgctgcgtgcgggtctgacgcctaaatacattga
tattccggaactggttgccaatgtgaaattcgaagccaaaccggctaacc
agttgttgaccagccggtgaaacaaggtgcagaactggacttcccgatt
ccagtggatgattttgccttctcgctgcatgaccttagtgataaagaaac
caccattagccagcagagtgccgccattttgttctgcgtcgaaggcgatg
caacgttgtggaaaggttctcagcagttacagcttaaaccgggtgaatca
gcgtttattgccgccaacgaatcaccggtgactgtcaaaggccacggccg
tttagcgcgtgtttacaacaagctgtaagagcttactgaaaaaattaaca
tctcttgctaagctgggagctctagatcccgaatttccccgatcgttca
aacatttggcaataaagtttcttaagattgaatcctgttgccggtcttgc
gatgattatcatataatttctgttgaattacgttaagcatgtaataatta
acatgtaatgcatgacgttatttatgagatgggtttttatgattagagtc
ccgcaattatacatttaatacgcgatagaaaacaaaatatagcgcgcaaa
ctaggataaaattatcgcgcgcggtgtcatctatgttactagatcgggaat
tggcgagctcgaattaattcagtacattaaaaacgtccgcaatgtgttat taagttgtctaagcgtcaatttgtttacaccacaatatatcctgccacca
gccagccaacagctccccgaccggcagctcggcacaaaatcaccactcga
tacaggcagcccatcagtccgggacggcgtcagcgggagagccgttgtaa
ggcggcagactttgctcatgttaccgatgctattcggaagaacggcaact
aagctgccgggtttgaaacacggatgatctcgcggagggtagcatgttga
ttgtaacgatgacagagcgttgctgcctgtgatcaaatatcatctccctc
gcagagatccgaattatcagccttcttattcatttctcgcttaaccgtga
caggctgtcgatcttgagaactatgccgacataataggaaatcgctggat
aaagccgctgaggaagctgagtggcgctatttctttagaagtgaacgttg
acgatcgtcgaccgtaccccgatgaattaattcggacgtacgttctgaac
acagctggatacttacttgggcgattgtcatacatgacatcaacaatgta
cccgtttgtgtaaccgtctcttggaggttcgtatgacactagtggttccc
ctcagcttgcgactagatgttgaggcctaacattttattagagagcaggc
tagttgcttagatacatgatcttcaggccgttatctgtcagggcaagcga
aaattggccatttatgacgaccaatgccccgcagaagctcccatctttgc
cgccatagacgccgcgcccccttttgggggtgtagaacatccttttgcca
gatgtgaaaagaagttcgttgtcccattgttggcaatgacgtagtagcc
ggcgaaagtgcgagacccatttgcgctatatataagcctacgatttccgt
tgcgactattgtcgtaattggatgaactattatcgtagttgctctcagag
ttgtcgtaatttgatggactattgtcgtaattgcttatggagttgtcgta
gttgcttggagaaatgtcgtagttggatggggagtagtcataggaagac
gagcttcatccactaaaacaattggcaggtcagcaagtgcctgccccgat
gccatcgcaagtacgaggcttagaaccaccttcaacagatcgcgcatagt
cttccccagctctctaacgcttgagttaagccgcgccgcgaagcggcgtc
ggcttgaacgaattgttagacattatttgccgactaccttggtgatctcg
cctttcacgtagtgaacaaattcttccaactgatctgcgcgcgaggccaa
gcgatcttcttgtccaagataagcctgcctagcttcaagtatgacgggct
gatactgggccggcaggcgctccattgcccagtcggcagcgacatccttc
ggcgcgattttgccggttactgcgctgtaccaaatgcgggacaacgtaag
cactacatttcgctcatcgccagcccagtcgggcggcgagttccatagcg
ttaaggtttcatttagcgcctcaaatagatcctgttcaggaaccggatca
aagagttcctccgccgctggacctaccaaggcaacgctatgttctcttgc
ttttgtcagcaagatagccagatcaatgtcgatcgtggctggctcgaaga
tacctgcaagaatgtcattgcgctgccattctccaaattgcagttcgcgc
ttagctggataacgccacggaatgatgtcgtcgtgcacaacaatggtgac
ttctacagcgcggagaatctcgctctctccagggggaagccgaagtttcca
aaaggtcgttgatcaaagctcgccgcgttgtttcatcaagccttacggtc
accgtaaccagcaaatcaatatcactgtgtggcttcaggccgccatccac
tgcggagccgtacaaatgtacggccagcaacgtcggttcgagatggcgct
cgatgacgccaactacctctgatagttgagtcgatacttcggcgatcacc
gcttccctcatgatgtttaactcctgaattaagccgcgccgcgaagcggt
```

-continued gtcggcttgaatgaattgttaggcgtcatcctgtgctcccgagaaccagt
accagtacatcgctgtttcgttcgagacttgaggtctagttttatacgtg
aacaggtcaatgccgccgagagtaaagccacattttgcgtacaaattgca
ggcaggtacattgttcgtttgtgtctctaatcgtatgccaaggagctgtc
tgcttagtgcccactttttcgcaaattcgatgagactgtgcgcgactcct
ttgcctcggtgcgtgtgcgacacaacaatgtgttcgatagaggctagatc
gttccatgttgagttgagttcaatcttcccgacaagctcttggtcgatga
atgcgccatagcaagcagagtcttcatcagagtcatcatccgagatgtaa
tccttccggtaggggctcacacttctggtagatagttcaaagccttggtc
ggataggtgcacatcgaacacttcacgaacaatgaaatggttctcagcat
ccaatgtttccgccacctgctcagggatcaccgaaatcttcatatgacgc
ctaacgcctggcacagcggatcgcaaacctggcgcggcttttggcacaaa
aggcgtgacaggtttgcgaatccgttgctgccacttgttaacccttttgc
cagatttggtaactataatttatgttagaggcgaagtcttgggtaaaaac
tggcctaaaattgctggggatttcaggaaagtaaacatcaccttccggct
cgatgtctattgtagatatgtagtgtatctacttgatcggggggatctg
ctgcctcgcgcgtttcggtgatgacggtgaaaacctctgacacatgcagc
tcccggagacggtcacagcttgtctgtaagcggatgccgggagcagacaa
gcccgtcagggcgcgtcagcgggtgttggcgggtgtcggggcgcagccat
gacccagtcacgtagcgatagcggagtgtatactggcttaactatgcggc
atcagagcagattgtactgagagtgcaccatatgcggtgtgaaataccgc
acagatgcgtaaggagaaaataccgcatcaggcgctcttccgcttcctcg
ctcactgactcgctgcgctcggtcgttcggctgcggcgagcggtatcagc
tcactcaaaggcggtaatacggttatccacagaatcaggggataacgcag
gaaagaacatgtgagcaaaaggccagcaaaaggccaggaaccgtaaaaag
gccgcgttgctggcgtttttccataggctccgcccccctgacgagcatca
caaaaatcgacgctcaagtcagaggtggcgaaacccgacaggactataaa
gataccaggcgtttccccctggaagctccctcgtgcgctctcctgttccg
accctgccgcttaccggatacctgtccgcctttctcccttcgggaagcgt
ggcgctttctcatagctcacgctgtaggtatctcagttcggtgtaggtcg
ttcgctccaagctgggctgtgtgcacgaaccccccgttcagcccgaccgc
tgcgccttatccggtaactatcgtcttgagtccaacccggtaagacacga
cttatcgccactggcagcagccactggtaacaggattagcagagcgaggt
atgtaggcggtgctacagagttcttgaagtggtggcctaactacggctac
actagaaggacagtatttggtatctgcgctctgctgaagccagttacctt
cggaaaaagagttggtagctcttgatccggcaaacaaaccaccgctggta
gcggtggtttttttgtttgcaagcagcagattacgcgcagaaaaaaagga
tctcaagaagatcctttgatcttttctacggggtctgacgctcagtggaa
cgaaaactcacgttaagggattttggtcatgagattatcaaaaaggatct
tcacctagatccttttaaattaaaaatgaagttttaaatcaatctaaagt -continued atatatgagtaaacttggtctgacagttaccaatgcttaatcagtgaggc
acctatctcagcgatctgtctatttcgttcatccatagttgcctgactcc
ccgtcgtgtagataactacgatacgggagggcttaccatctggccccagt
gctgcaatgataccgcgagacccacgctcaccggctccagatttatcagc
aataaaccagccagccggaagggccgagcgcagaagtggtcctgcaactt
tatccgcctccatccagtctattaattgttgccgggaagctagagtaagt
agttcgccagttaatagtttgcgcaacgttgttgccattgctgcaggggg
ggggggggggggttccattgttcattccacggacaaaaacagagaaagg
aaacgacagaggccaaaaagctcgctttcagcacctgtcgtttcctttct
tttcagagggtattttaaataaaaacattaagttatgacgaagaagaacg
gaaacgccttaaaccggaaaattttcataaatagcgaaaacccgcgaggt
cgccgccccgtaacctgtcggatcaccggaaaggacccgtaaagtgataa
tgattatcatctacatatcacaacgtgcgtggaggccatcaaaccacgtc
aaataatcaattatgacgcaggtatcgtattaattgatctgcatcaactt
aacgtaaaaacaacttcagacaatacaaatcagcgacactgaatacgggg
caacctcatgtccccccccccccccccctgcaggcatcgtggtgtcacgc
tcgtcgtttggtatggcttcattcagctccggttcccaacgatcaaggcg
agttacatgatccccatgttgtgcaaaaaagcggttagctccttcggtc
ctccgatcgttgtcagaagtaagttggccgcagtgttatcactcatggtt
atggcagcactgcataattctcttactgtcatgccatccgtaagatgctt
ttctgtgactggtgagtactcaaccaagtcattctgagaatagtgtatgc
ggcgaccgagttgctcttgcccggcgtcaacacgggataataccgcgcca
catagcagaactttaaaagtgctcatcattggaaaacgttcttcggggcg
aaaactctcaaggatcttaccgctgttgagatccagttcgatgtaaccca
ctcgtgcacccaactgatcttcagcatcttttactttcaccagcgtttct
gggtgagcaaaaacaggaaggcaaaatgccgcaaaaaagggaataagggc
gacacggaaatgttgaatactcatactcttcctttttcaatattattgaa
gcatttatcagggttattgtctcatgagcggatacatatttgaatgtatt
tagaaaaataaacaaatagggggttccgcgcacatttccccgaaaagtgcc
acctgacgtctaagaaaccattattatcatgacattaacctataaaaata
ggcgtatcacgaggccctttcgtcttcaagaattggtcgacgatcttgct
gcgttcggatattttcgtggagttcccgccacagacccggattgaaggcg
agatccagcaactcgcgccagatcatcctgtgacggaacttggcgcgtg
atgactggccaggacgtcggccgaaagagcgacaagcagatcacgctttt
cgacagcgtcggatttgcgatcgaggattttttcggcgctgcgctacgtcc
gcgaccgcgttgagggatcaagccacagcagcccactcgaccttctagcc
gacccagacgagccaagggatcttttggaatgctgctccgtcgtcaggc
tttccgacgtttgggtggttgaacagaagtcattatcgcacggaatgcca
agcactcccgagggggaaccctgtggttggcatgcacatacaaatggacga
acggataaaccttttcacgcccttttaaatatccgattattctaataaac
gctctttctcttaggttttacccgccaatatatcctgtcaaacactgatag

```
tttaaactgaaggcgggaaacgacaacctgatcatgagcggagaattaag ggagtcacgttatgaccccgccgatgacgcgggacaagccgttttacgt ttggaactgacagaaccgcaacgttgaaggagccactcagcttaattaag tctaactcgagttactggtacgtaccaaatccatggaatcaaggtaccgt cgactctagtaacggccgccagtgtgctggaattaattcggcttgtcgac cacccaaccccatatcgacagaggatgtgaagaacaggtaaatcacgca aagaacccatctctgatagcagctatcgattagaacaacgaatccatatt gggtccgtgggaaatacttactgcacaggaaggggcgatctgacgaggc cccgccaccggcctcgacccgaggccgaggccgacgaagcgccggcgagt acggcgccgcggcggcctctgcccgtgccctctgcgcgtgggagggagag gccgcggtggtggggcgcgcgcgcgcgcgcgcagctggtgcggcggc gcgggggtcagccgccgagccggcggcgacggaggagcagggcggcgtgg acgcgaacttccgatcggttggtcagagtgcgcgagttgggcttagccaa ttaggtctcaacaatctattgggccgtaaaattcatgggccctggtttgt ctaggcccaatatcccgttcatttcagcccacaaatatttccccagagga ttattaaggcccacacgcagcttatagcagatcaagtacgatgtttcctg atcgttggatcggaaacgtacggtcttgatcaggcatgccgacttcgtca aagagaggcggcatgacctgacgcggagttggttccgggcaccgtctgga tggtcgtaccgggaccggacacgtgtcgcgcctccaactacatggacacg tgtggtgctgccattgggccgtacgcgtggcggtgaccgcaccggatgct gcctcgcaccgccttgcccacgctttatatagagaggttttctctccatt aatcgcatagcgagtcgaatcgaccgaaggggaggggagcgaagctttg cgttctctaatcgcctcgtcaaggtaactaatcaatcacctcgtcctaat cctcgaatctctcgtggtgcccgtctaatctcgcgattttgatgctcgtg gtggaaagcgtaggaggatcccgtgcgagttagtctcaatctctcagggt ttcgtgcgattttagggtgatccacctcttaatcgagttacggtttcgtg cgatttagggtaatcctcttaatctctcattgatttagggtttcgtgag aatcgaggtagggatctgtgttatttatatcgatctaatagatggattgg ttttgagattgttctgtcagatggggattgtttcgatatattaccctaat gatgtgtcagatggggattgtttcgatatattaccctaatgatgtgtcag atggggattgtttcgatatattaccctaatgatggataataagagtagtt cacagttatgttttgatcctgccacatagtttgagtttgtgatcagatt tagttttacttatttgtgcttagttcggatgggattgttctgatattgtt ccaatagatgaatagctcgttaggttaaaatctttaggttgagttaggcg acacatagtttatttcctctggatttggattggaattgtgttcttagttt ttttcccctggatttggattggaattgtgtggagctgggttagagaatta catctgtatcgtgtacacctacttgaactgtagagcttgggttctaaggt caatttaatctgtattgtatctggctctttgcctagttgaactgtagtgc tgatgttgtactgtgttttttacccgttttatttgcttactcgtgcaaa tcaaatctgtcagatgctagaactaggtggctttattctgtgttcttaca tagatctgttgtcctgtagttacttatgtcagttttgttattatctgaag atatttttggttgttgcttgttgatgtggtgtgagctgtgagcagcgctc ttatgattaatgatgctgtccaattgtagtgtagtatgatgtgattgata tgttcatctattttgagctgacagtaccgatatcgtaggatctggtgcca acttattctccagctgctttttttttacctatgttaattccaatcctttct tgcctctccagcccgggtattcatcctaggtccccgaatttccccgatcg ttcaaacatttggcaataaagtttcttaagattgaatcctgttgccggtc ttgcgatgattatcatataatttctgttgaattacgttaagcatgtaata attaacatgtaatgcatgacgttatttatgagatgggttttttatgattag agtcccgcaattatacatttaatacgcgatagaaaacaaaatatagcgcg caaactaggataaattatcgcgcgcggtgtcatctatgttactagatcgg gaattgg
```

Example 5—Genetic Elements Used in Vector Development

Promoters

Vectors were made to include a 2014 bp sequence of rice Ubiquitin 3 gene promoter with the first intron (OsUbi3P, Accession # AY954394, SEQ ID NO: 1, shown below) for constitutive or "global" gene expression. The first intron sequence of OsUbi3P is shown as lower case letters in the presentation of SEQ ID NO: 1 below. Vectors herein can include different or additional promoters. Vectors were made including the rice Actin1 gene promoter with the first gene intron (OsAct1P, Accession No. 544221, SEQ ID NO: 2), which is a constitutive promoter. The rice Actin1 gene promoter may be utilized for PMI gene expression in vectors herein. For example, vectors pAG3000-pAG3003 include the rice Actin1 gene promoter with the first gene intron. Some vectors were made to include the 1474 bp rice Glutelin B-4 gene promoter (OsGluB4P, Accession # AY427571, SEQ ID NO: 4), which may be used for the seed specific gene expression and has been used to express enzymes and intein-modified enzymes.

```
>OsUbi3P
                                              (SEQ ID NO: 1)
CCACCCAACCCCATATCGACAGAGGATGTGAAGAACAGGTAAATCACGCA

GAAGAACCCATCTCTGATAGCAGCTATCGATTAGAACAACGAATCCATAT

TGGGTCCGTGGGAAATACTTACTGCACAGGAAGGGGCGATCTGACGAGG

CCCCGCCACCGGCCTCGACCCGAGGCCGAGGCCGACGAAGCGCCGGCGAG

TACGGCGCCGCGGCGGCCTCTGCCCGTGCCCTCTGCGCGTGGGAGGGAGA

GGCCGCGGTGGTGGGGCGCGCGCGCGCGCGCGCAGCTGGTGCGGCGG

CGCGGGGGTCAGCCGCCGAGCCGGCGGCGACGGAGGAGCAGGGCGGCGTG

GACGCGAACTTCCGATCGGTTGGTCAGAGTGCGCGAGTTGGGCTTAGCCA

ATTAGGTCTCAACAATCTATTGGGCCGTAAAATTCATGGGCCCTGGTTTG

TCTAGGCCCAATATCCCGTTCATTTCAGCCCACAAATATTTCCCCAGAGG

ATTATTAAGGCCCACACGCAGCTTATAGCAGATCAAGTACGATGTTTCCT

GATCGTTGGATCGGAAACGTACGGTCTTGATCAGGCATGCCGACTTCGTC
```

-continued

```
AAAGAGAGGCGGCATGACCTGACGCGGAGTTGGTTCCGGGCACCGTCTGG

ATGGTCGTACCGGGACCGGACACGTGTCGCGCCTCCAACTACATGGACAC

GTGTGGTGCTGCCATTGGGCCGTACGCGTGGCGGTGACCGCACCGGATGC

TGCCTCGCACCGCCTTGCCCACGCTTTATATAGAGAGGTTTTCTCTCCAT

TAATCGCATAGCGAGTCGAATCGACCGAAGGGGAGGGGGAGCGAAGCTTT

GCGTTCTCTAATCGCCTCGTCAAGgtaactaatcaatcacctcgtcctaa tcctcgaatctctcgtggtgcccgtctaatctcgcgattttgatgctcgt ggtggaaagcgtaggaggatcccgtgcgagttagtctcaatctctcaggg tttcgtgcgattttagggtgatccacctcttaatcgagttacggtttcgt gcgattttagggtaatcctcttaatctctcattgatttagggtttcgtga gaatcgaggtagggatctgtgttatttatatcgatctaatagatggattg gttttgagattgttctgtcagatggggattgtttcgatatattaccctaa tgatgtgtcagatggggattgtttcgatatattaccctaatgatgtgtca gatggggattgtttcgatatattaccctaatgatggataataagagtagt tcacagttatgttttgatcctgccacatagtttgagttttgtgatcagat ttagttttacttatttgtgcttagttcggatgggattgttctgatattgt tccaatagatgaatagctcgttaggttaaaatctttaggttgagttaggc gacacatagtttatttcctctggatttggattggaattgtgttcttagtt atttcccctggatttggattggaattgtgtggagctgggttagagaatta catctgtatcgtgtacacctacttgaactgtagagcttgggttctaaggt caatttaatctgtattgtatctggctcttgcctagttgaactgtagtgc tgatgttgtactgtgttttttacccgttttatttgctttactcgtgcaa atcaaatctgtcagatgctagaactaggtggctttattctgtgttcttac atagatctgttgtcctgtagttacttatgtcagttttgttattatctgaa gatattttggttgttgcttgttgatgtggtgtgagctgtgagcagcgct cttatgattaatgatgctgtccaattgtagtgtagtatgatgtgattgat atgttcatctattttgagctgacagtaccgatatcgtaggatctggtgcc aacttattctccagctgctttttttacctatgttaattccaatcctttc ttgcctcttccag,
```
promoter sequence in upper case letters
(SEQ ID NO: 25), first intron in lower case
letters (SEQ ID NO: 26)

>OsAct1P
(SEQ ID NO: 2)
```
TAGCTAGCATATTCGAGGTCATTCATATGCTTGAGAAGAGAGTCGGGATA

GTCCAAAATAAAACAAAGGTAAGATTACCTGGTCAAAAGTGAAAACATCA

GTTAAAAGGTGGTATAAGTAAAATATCGGTAATAAAAGGTGGCCCAAAGT

GAAATTTACTCTTTTCTACTATTATAAAAATTGAGGATGTTTTGTCGGTA

CTTTGATACGTCATTTTTGTATGAATTGGTTTTTAAGTTTATTCGCGATT

TGGAAATGCATATCTGTATTTGAGTCGGTTTTTAAGTTCGTTGCTTTTGT

AAATACAGAGGGATTTGTATAAGAAATATCTTTAAAAAACCCATATGCTA

ATTTGACATAATTTTTGAGAAAAATATATATTCAGGCCAATTCCACAATG

AACAATAATAAGATTAAAATAGCTTGCCCCCGTTGCAGCGATGGGTATTT
```

```
TTTCTAGTAAAATAAAAGATAAACTTAGACTCAAAACATTTACAAAAACA

ACCCCTAAAGTCCTAAAGCCCAAAGTGCTATGCACGATCCATAGCAAGCC

CAGCCCAACCCAACCCAACCCAACCCACCCCAGTGCAGCCAACTGGCAAA

TAGTCTCCACCCCCGGCACTATCACCGTGAGTTGTCCGCACCACCGCACG

TCTCGCAGCCAAAAAAAAAAAAAGAAAGAAAAAAAGAAAAAGAAAAACA

GCAGGTGGGTCCGGGTCGTGGGGGCCGGAAAAGCGAGGAGGATCGCGAGC

AGCGACGAGGCCCGGCCCTCCCTCCGCTTCCAAAGAAACGCCCCCCATCG

CCACTATATACATACCCCCCCTCTCCTCCCATCCCCCCAACCCTACCAC

CACCACCACCACCACCTCCTCCCCCCTCGCTGCCGGACGACGAGCTCCTC

CCCCCTCCCCCTCCGCCGCCGCCGGTAACCACCCCGCCCCTCTCCTCTTT

CTTTCTCCGTTTTTTTTTCGTCTCGGTCTCGATCTTTGGCCTTGGTAGT

TTGGGTGGGCGAGAGCGGCTTCGTCGCCCAGATCGGTGCGCGGGAGGGGC

GGGATCTCGCGGCTGGCGTCTCCGGGCGTGAGTCGGCCCGCATCCTCGCG

GGGAATGGGGCTCTCGGATGTAGATCTTCTTTCTTTCTTCTTTTTGTGGT

AGAATTTGAATCCCTCAGCATTGTTCATCGGTAGTTTTTCTTTTCATGAT

TTGTGACAAATGCAGCCTCGTGCGGAGCTTTTTTGTAG
```

>OsGluB4P
(SEQ ID NO: 4)
```
TACAGGGTTCCTTGCGTGAAGAAGGGTGGCCTGCGGTTCACCATTAACGG

TCACGACTACTTCCAGCTAGTACTGGTGACCAACGTCGCGGCGGCAGGGT

CAATCAAGTCCATGGAGGTTATGGGTTCCAACACAGCGGATTGGATGCCG

ATGGCACGTAACTGGGGCGCCCAATGGCACTCACTGGCCTACCTCACCGG

TCAAGGTCTATCCTTTAGGGTCACCAACACAGATGACCAAACGCTCGTCT

TCACCAACGTCGTGCCACCAGGATGGAAGTTTGGCCAGACATTTGCAAGC

AAGCTGCAGTTCAAGTGAGAGGAGAAGCCTGAATTGATACCGGAGCGTTT

CTTTTGGGAGTAACATCTCTGGTTGCCTAGCAAACATATGATTGTATATA

AGTTTCGTTGTGCGTTTATTCTTTCGGTGTGTAAAATAACATACATGCTT

TCCTGATATTTTCTTGTATATATGTACACACACGACAAATCCTTCCAT

TTCTATTATTATTGAACAATTTAATTGCGAGGGCGAGTACTTGTCTGTTT

ACCTTTTTTTTTCAGATGGCATTTTATAGTTTAACCTTTCATGGACCGG

CAGTAGTTCTAACCATGAATGAAAAGAAATCATAGTCCACACCACGCAGG

GACATTGTGGTCATTTTAGACAAGACGATTTGATTAATGTCTTGTATGAT

ATGGTCGACAGTGAGGACTAACAAACATATGGCATATTTTATTACCGGCG

AGTTAAATAAATTTATGTCACAGTAATAAACTGCCTAATAAATGCACGCC

AGAAAATATAATGATAAAAAAAGAAAAGATACATAAGTCCATTGCTTCT

ACTTTTTTAAAAATTAAATCCAACATTTTCTATTTTTTGGTATAAACTTG

GAAGTACTAGTTGGATATGCAAAATCATCTAACCTCCATATATTTCATCA

ATTTGTTTACTTTACATATGGGAGAGGATAGTATGTCAAAGAAAATGACA

ACAAGCTTACAAGTTTCTTATTTTAAAAGTTCCGCTAACTTATCAAGCAT

AGTGTGCCACGCAAAACTGACAACAAACCAACAAATTTAAGGAGCGCCTA

ACTTATCATCTATGACATACCGCACAAAATGATAACATACTAGAGAAACT

TTATTGCACAAAAGGAAATTTATCCATAAGGCAAAGGAACATCTTAAGGC
```

-continued

TTTGGATATACATTTACCAACAAGCATTGTTTGTATTACCCCTAAAGCGC

AAGACATGTCATCCATGAGTCATAGTGTGTATATCTCAACATTGCAAAGC

TACCTTTTTTCTATTATACTTTTCGCATTATAGGCTAGATATTATCTATA

CATGTCAACAAACTCTATCCCTACGTCATATCTGAAGATTCTTTTCTTCA

CTATATAAGTTGGCTTCCCTGTCATTGAACTCACATCAACCAGCCCAAGT

TTCCAATAACATCCTCAAATAGCT

The rice Ubiquitin 3 gene promoter was cloned from the pRESQ101, as it is described above, while the rice Act1 and GluB-4 gene promoters were synthesized. With rice Act1 gene promoter is fused to PMI selectable marker, up to 23% transformation efficiency was observed in stable transformation of maize using mannose selection medium during plant tissue culture.

Signal Sequences

Signal sequences can be included with a CWDE sequence (with or without further modification; e.g., with an intein) or in a vector to direct enzymes expressed in planta to specific locations within, or external to, the plant cell. In some examples, described below, the tobacco PR1a (amyloplast targeting) and barley alpha amylase BAASS [SEQ ID NO: 8] (cell wall targeting) signal sequences were included in CWDEs or vectors herein. These signal sequences can direct enzymes to their respective targeting locations. In some examples, described below, the barley aleurain HvAleSP (vacuole targeting), rice GluB4 (seed expression) and ER retaining (SEKDEL) signal sequences were included, and these sequences can localize protein to the respective cellular compartments or specific tissues. A goal of such targeting may be achieving high levels of protein accumulation while avoiding potential detrimental effects on plant growth and development. Signal sequences used in examples herein and their corresponding encoding nucleotide sequences are presented below:

PR1a protein sequence
(SEQ ID NO: 6)
M G F V L F S Q L P S F L L V S T L L L F L V I S
H S C R A PR1a nucleotide sequence
(SEQ ID NO: 7)
ATGGGCTTCGTGCTCTTCTCCCAGCTGCCTTCCTTCCTTCTTGTCTCCAC

CCTGCTCTTGTTCCTCGTGATCTCCCACTCCTGCCGCGCC

BAASS protein sequence
(SEQ ID NO: 8)
M A N K H L S L S L F L V L L G L S A S L A S G Q V BAASS nucleotide sequence
(SEQ ID NO: 9)
ATGGCGAACAAACATTTGTCCCTCTCCCTCTTCCTCGTCCTCCTTGGCCT

GTCGGCCAGCTTGGCCTCCGGGCAAGTC

HvAle protein sequence
(SEQ ID NO: 10)
M A H A R V L L L A L A V L A T A A V A V A S S S
S F A D S N P I R P V T D R A A S T HvAle nucleotide sequence
(SEQ ID NO: 11)
ATGGCCCACGCCCGCGTCCTCCTCCTGGCGCTCGCCGTCCTGGCCACCGC

CGCCGTCGCCGTCGCCTCCTCCTCCTCCTTCGCCGACTCCAACCCGATCC

GCCCGGTGACCGACCGCGCCGCCTCCACC

SEKDEL
(SEQ ID NO: 12)

(SEQ ID NO: 13)
AGCGAGAAGGACGAGCTG

KDEL
(SEQ ID NO: 14)

(SEQ ID NO: 15)
AAGGACGAGCTG

GluB4SP protein sequence
(SEQ ID NO: 27)
M A T I A F S R L S I Y F C V L L L C H G S M A GluB4SP nucleotide sequence
(SEQ ID NO: 28)
ATGGCCACCATCGCTTTCTCCCGCTTGTCCATCTACTTCTGCGTGCTTCT

CCTGTGCCACGGCTCCATGGCC

Targeting sequences can be modified from their original versions to reflect the codon usage frequencies for optimal gene expression in monocot plants. In an embodiment, the host codon usage frequencies are from maize. Each signal sequence can be synthesized by PCR using specific primers and connected to the 3' ends of a sequence; for example, either the OsUbi3 or OsGluB4 promoter, using a fusion PCR approach.

Transcription Terminator

A transcription terminator can be included in the vectors herein. In an embodiment, the efficient transcription terminator sequence (NosT) from the nopaline synthase gene of *Agrobacterium tumefaciens* is used in gene expression cassettes cloned in plant transformation vectors. The sequence is presented below:

NosT
(SEQ ID NO: 29)
TCCCCGAATTTCCCCGATCGTTCAAACATTTGGCAATAAAGTTTCTT

AAGATTGAATCCTGTTGCCGGTCTTGCGATGATTATCATATAATTTCT

GTTGAATTACGTTAAGCATGTAATAATTAACATGTAATGCATGACGTT

ATTTATGAGATGGGTTTTTATGATTAGAGTCCCGCAATTATACATTTAA

TACGCGATAGAAAACAAAATATAGCGCGCAAACTAGGATAAATTAT

CGCGCGCGGTGTCATCTATGTTACTAGATCGGGAATTG

This sequence appears twice in pAG2005 (SEQ ID NO: 24). The second appearance at positions 12034 to 12288 follows the second OsUbi3 promoter plus intron sequence and XmaI site, and is followed with an EcoRI restriction site (GAATTC, positions 12310 to 5 of SEQ ID NO: 24). The Nos terminator sequence can be PCR amplified from pNOV2819 as 276 bp fragment. Other transcription terminators known in the art could be substituted and used in place of the Nos terminator. One other terminator that could be used in place of the Nos terminator is the 35S terminator.

Example 6—Vector Development for Overexpression of Wild Type P77853 Xylanase

Figure 4:
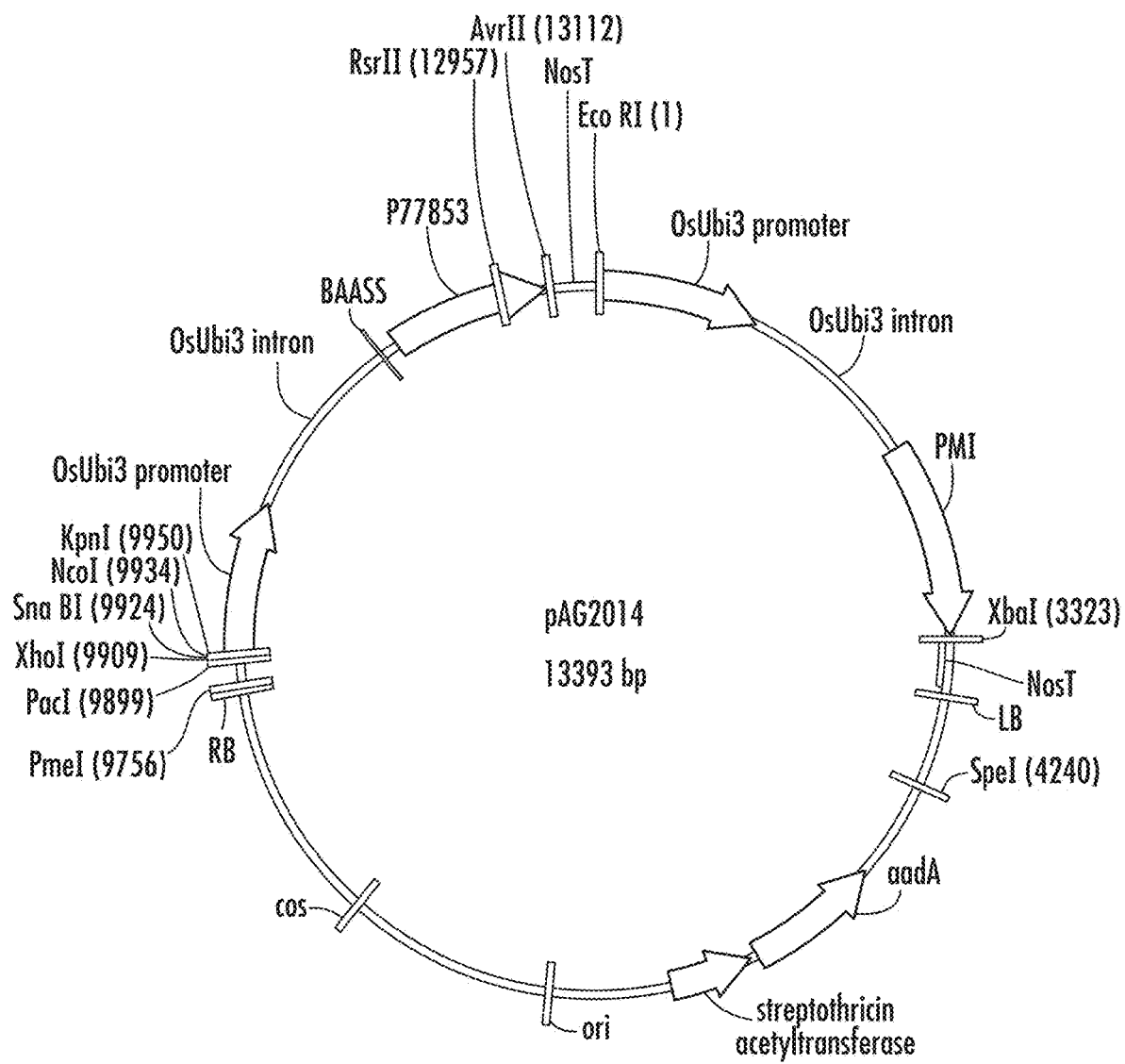
FIG. 4 illustrates a vector map of pAG2014.

Referring to FIG. 4, vector pAG2014 construction provides and example of a representative approach to clone genes encoding CWDEs such as xylanases, cellulases and any other genes of specific interest for development of transgenic monocotyledonous plants including, but not limited to maize, switchgrass, *sorghum, miscanthus* and sugarcane.

Connection of Signal Sequence to a Coding Region of Mature Enzyme

A signal sequence protein of interest junction can be determined experimentally or through models. For this example, the SignalP 3.0 server publically available through the Center for Biological Sequence Analysis of the Technical University of Denmark was used to predict the best junction between the signal peptide and the wild type P77853 xylanase enzyme. The method utilized in SignalP 3.0 incorporates a prediction of cleavage sites and a signal peptide/non-signal peptide prediction based on a combination of several artificial neural networks and hidden Markov models. The program output provides a confidence score for the cleavage of signal peptide from the mature protein. Three variant junctions were evaluated; a first with a direct connection between BAASS [SEQ ID NO: 8] and P77853 ( . . . GQV QTS . . . ), a second with removal of one amino acid from the carboxy terminus of BAASS ( . . . GQ QTS . . . ), and a third with the removal of one amino acid from the carboxy terminus of BAASS [SEQ ID NO: 8] and removal of one amino acid from the amino terminus of P77853 ( . . . GQ TS . . . ). The variant with the highest score was advanced to molecular cloning. The sequences of BASS, P77853, and the first, second and third junctions are below with the junction underlined:

BAASS from barley alpha amylase (Acc. #X15226) 78 bp (SEQ ID NO: 8)
M A N K H L S L S L F L V L L G L S A S L A S G Q V (SEQ ID NO: 9)
ATGGCGAACAAACATTTGTCCCTCTCCCTCTTCCTCGTCCTCCTTGG
CCTGTCGGCCAGCTTGGCCTCCGGG<u>CAAGTC</u>//

(SEQ ID NO: 30)
QTSITLTSNASGTFDGYYYELWKDTGNTTMTVYTQGRFSCQWSNINNALF
RTGKKYNQNWQSLGTIRITYSATYNPNGNSYLCIYGWSTNPLVEFYIVES
WGNWRPPGATSLGQVTIDGGTYDIYRTTRVNQPSIVGTATFDQYWSVRTS
KRTSGTVTVTDHFRAWANRGLNLGTIDQITLCVEGYQSSGSANITQNTFS
QGSSSGSSGGSSGSTTTTRIECENMSLSGPYVSRITNPFNGIALYANGDT
ARATVNFPASRNYNFRLRGCGNNNNLARVDLRIDGRTVGTFYYQGTYPWE
APIDNVYVSAGSHTVEITVTADNGTWDVYADYLVIQ

BAASS:P77853 1$^{st}$ connection variant (SEQ ID NO: 31)
MANKHLSLSLFLVLLGLSASLASG<u>QV</u>QTSITLTSNASGTFDGYYYELWKD
TGNTTMTVYTQGRFSCQWSNINNALFRTGKKYNQNWQSLGTIRITYSATY
NPNGNSYLCIYGWSTNPLVEFYIVESWGNWRPPGATSLGQVTIDGGTYDI
YRTTRVNQPSIVGTATFDQYWSVRTSKRTSGTVTVTDHFRAWANRGLNLG
TIDQITLCVEGYQSSGSANITQNTFSQGSSSGSSGGSSGSTTTTRIECEN
MSLSGPYVSRITNPFNGIALYANGDTARATVNFPASRNYNFRLRGCGNNN
NLARVDLRIDGRTVGTFYYQGTYPWEAPIDNVYVSAGSHTVEITVTADNG
TWDVYADYLVIQ SignalP3.0 Server Prediction: Signal peptide
Most likely cleavage site between pos. 24 and 25: ASG-QV
Signal peptide probability: 1.000
Max cleavage site probability: 0.740 between pos. 24 and 25
BAASS:P77853 2$^{nd}$ connection variant (SEQ ID NO: 32)
MANKHLSLSLFLVLLGLSASLASG<u>QQ</u>TSITLTSNASGTFDGYYYELWKDT
GNTTMTVYTQGRFSCQWSNINNALFRTGKKYNQNWQSLGTIRITYSATYN
PNGNSYLCIYGWSTNPLVEFYIVESWGNWRPPGATSLGQVTIDGGTYDIY
RTTRVNQPSIVGTATFDQYWSVRTSKRTSGTVTVTDHFRAWANRGLNLGT
IDQITLCVEGYQSSGSANITQNTFSQGSSSGSSGGSSGSTTTTRIECENM
SLSGPYVSRITNPFNGIALYANGDTARATVNFPASRNYNFRLRGCGNNNN
LARVDLRIDGRTVGTFYYQGTYPWEAPIDNVYVSAGSHTVEITVTADNGT
WDVYADYLVIQ SignalP3.0 Server Prediction: Signal peptide
Most likely cleavage site between pos. 24 and 25: ASG-QQ
Signal peptide probability: 1.000
Max cleavage site probability: 0.768 between pos. 24 and 25
BAASS:P77853 3$^{rd}$ connection variant (SEQ ID NO: 33)
MANKHLSLSLFLVLLGLSASLASG<u>QT</u>SITLTSNASGTFDGYYYELWKDTG
NTTMTVYTQGRFSCQWSNINNALFRTGKKYNQNWQSLGTIRITYSATYNP
NGNSYLCIYGWSTNPLVEFYIVESWGNWRPPGATSLGQVTIDGGTYDIYR
TTRVNQPSIVGTATFDQYWSVRTSKRTSGTVTVTDHFRAWANRGLNLGTI
DQITLCVEGYQSSGSANITQNTFSQGSSSGSSGGSSGSTTTTRIECENMS
LSGPYVSRITNPFNGIALYANGDTARATVNFPASRNYNFRLRGCGNNNNL
ARVDLRIDGRTVGTFYYQGTYPWEAPIDNVYVSAGSHTVEITVTADNGTW
DVYADYLVIQ SignalP3.0 Server Prediction: Signal peptide
Most likely cleavage site between pos. 24 and 25: ASG-QT
Signal peptide probability: 1.000
Max cleavage site probability: 0.582 between pos. 24 and 25

In this example, the 2$^{nd}$ variant of connection between BAASS [SEQ ID NO:8] and P77853 ( . . . GQ QTS . . . ), was selected for pAG2014 vector development based on the maximum cleavage site probability output results from the ServerP 3.0.

The individual genetic elements for pAG2014 construction were assembled in primary PCR reactions as depicted below. The first PCR reaction (PCR-1) was used to amplify 372 bp of the 3' end of the rice Ubiquitin 3 gene first intron (shown in low case letters) starting from its own BglII site (underlined). The fragment was linked to the 9nt sequence (presented as Italics capital letters) representing modified three initial codons of the rice Ubiquitin 3 gene (detailed description is provided above), BAASS (shown in capital letters) and 27 nt sequence (boxed) of the 5' end of the coding region of P77853 mature protein. The second PCR reaction (PCR-2) was performed to amplify the entire coding region of P77853 mature protein fused to the TAG stop codon followed by the AvrII restriction site (underlined).

1. PCR-1 to amplify 372 bp 3' end of the rice Ubiquitin 3 gene first intron, 9 bp junction sequence, BAASS and 5' end of P77853:
PCR-1 Product (SEQ ID NO: 34)
Agatctgttgtcctgtagttacttatgtcagttttgttattatctgaagatattttggttgttgcttgttgatgtggtgtgagct gtgagcagcgctcttatgattaatgatgctgtccaattgtagtgtagtatgatgtgattgatatgttcatctattttgagctga cagtaccgatatcgtaggatctggtgccaacttattctccagctgcttttttttacctatgttaattccaatcctttcttgcctcttc cagATCCAGATAATGGCGAACAAACATTTGTCCCTCTCCCTCTTCCTCGTCCTCCTT

GGCCTGTCGGCCAGCTTGGCCTCCGGGCAACAAACAAGCATTACTCTGACATCCA

AC

Primers ovb79:
(SEQ ID NO: 35)
agatctgttgtcctgtagttacttatgtc ovb86:
(SEQ ID NO: 36)
CCGACAGGCCAAGGAGGACGAGGAAGAGGGAGAGGGACAAATGTTTGTTC GCCATTATCTGGATctggaagaggcaagaaaggattggaa ovb101:

(SEQ ID NO: 37)
GTTGGATGTCAGAGTAATGCTTGTTTGTTGCCCGGAGGCCAAGCTGGCCG

ACAGGCCAAGGAGGAC

2. PCR-2 to amplify 1017 bp coding region of mature P77853 protein:
PCR-2 Product (SEQ ID NO: 38)
CAAACAAGCATTACTCTGACATCCAACGCATCCGGTACGTTTGACGGTTA

CTATTACGAACTCTGGAAGGATACTGGCAATACAACAATGACGGTCTACA

CTCAAGGTCGCTTTTCCTGCCAGTGGTCGAACATCAATAACGCGTTGTTT

AGGACCGGGAAGAAATACAACCAGAATTGGCAGTCTCTTGGCACAATCCG

GATCACGTACTCTGCGACTTACAACCCAAACGGGAACTCCTACTTGTGTA

TCTATGGCTGGTCTACCAACCCATTGGTCGAGTTCTACATCGTTGAGTCC

TGGGGGAACTGGAGACCGCCTGGTGCCACGTCCCTGGGCCAAGTGACAAT

CGATGGCGGGACCTACGACATCTATAGGACGACACGCGTCAACCAGCCTT

CCATTGTGGGGACAGCCACGTTCGATCAGTACTGGAGCGTGCGCACCTCT

AAGCGGACTTCAGGAACAGTGACCGTGACCGATCACTTCCGCGCCTGGGC

GAACCGGGGCCTGAACCTCGGCACAATAGACCAAATTACATTGTGCGTGG

AGGGTTACCAAAGCTCTGGATCAGCCAACATCACCCAGAACACCTTCTCT

CAGGGCTCTTCTTCCGGCAGTTCGGGTGGCTCATCCGGCTCCACAACGAC

TACTCGCATCGAGTGTGAGAACATGTCCTTGTCCGGACCCTACGTTAGCA

GGATCACCAATCCCTTTAATGGTATTGCGCTGTACGCCAACGGAGACACA

GCCCGCGCTACCGTTAACTTCCCCGCAAGTCGCAACTACAATTTCCGCCT

GCGGGGTTGCGGCAACAACAATAATCTTGCCCGTGTGGACCTGAGGATCG

ACGGACGGACCGTCGGGACCTTTTATTACCAGGGCACATACCCCTGGGAG

GCCCCAATTGACAATGTTTATGTCAGTGCGGGGAGTCATACAGTCGAAAT

CACTGTTACTGCGGATAACGGCACATGGGACGTGTATGCCGACTACCTGG

TGATACAGTGACCTAGG

Primers ovb93:
(SEQ ID NO: 39)
CAAACAAGCATTACTCTGACATCCAAC ovb95:
(SEQ ID NO: 40)
CCTAGGTCACTGTATCACCAGGTAGTCGGCAT The subsequent "fusion PCR" approach (Yon and Fried, 1989) was utilized to "stitch" together genetic elements prepared in PCR-1 and PCR-2. This approach generated the expected 1362 bp BglII-AvrII sequence consisting of 261 bp of the 3' end of rice Ubiquitin 3 gene first intron with its native 3' end BglII site, 9 nt connecting sequence between the intron and the ATG codon of the 75 bp BAASS signal sequence, and 1011 bp mature P77853 xylanase coding region terminating in TGA stop codon that is flanked by the AvrII restriction site:

3'OsUbi3Pint:BAASS:P77853 as BglII-AvrII (SEQ ID NO: 41)

agatctgttgtcctgtagttacttatgtcagttttgttattatctgaagatattttggttgttgcttgttgatgtggtgtgagctg tgagcagcgctcttatgattaatgatgctgtccaattgtagtgtagtatgatgtgattgatatgttcatctattttgagctgac agtaccgatatcgtaggatctggtgccaacttattctccagctgcttttttttacctatgttaattccaatcctttcttgcctcttcc agATCCAGATAATGGCGAACAAACATTTGTCCCTCTCCCTCTTCCTCGTCCTCCTT

GGCCTGTCGGCCAGCTTGGCCTCCGGGCAACAAACAAGCATTACTCTGACATCCA

ACGCATCCGGTACGTTTGACGGTTACTATTACGAACTCTGGAAGGATACTGGCAA

TACAACAATGACGGTCTACACTCAAGGTCGCTTTTCCTGCCAGTGGTCGAACATC

AATAACGCGTTGTTTAGGACCGGGAAGAAATACAACCAGAATTGGCAGTCTCTTG

GCACAATCCGGATCACGTACTCTGCGACTTACAACCCAAACGGGAACTCCTACTT

GTGTATCTATGGCTGGTCTACCAACCCATTGGTCGAGTTCTACATCGTTGAGTCC

TGGGGGAACTGGAGACCGCCTGGTGCCACGTCCCTGGGCCAAGTGACAATCGAT

GGCGGGACCTACGACATCTATAGGACGACACGCGTCAACCAGCCTTCCATTGTGG

GGACAGCCACGTTCGATCAGTACTGGAGCGTGCGCACCTCTAAGCGGACTTCAG

GAACAGTGACCGTGACCGATCACTTCCGCGCCTGGGCGAACCGGGGCCTGAACC

TCGGCACAATAGACCAAATTACATTGTGCGTGGAGGGTTACCAAAGCTCTGGATC

AGCCAACATCACCCAGAACACCTTCTCTCAGGGCTCTTCTTCCGGCAGTTCGGGT

GGCTCATCCGGCTCCACAACGACTACTCGCATCGAGTGTGAGAACATGTCCTTGT

CCGGACCCTACGTTAGCAGGATCACCAATCCCTTTAATGGTATTGCGCTGTACGC

CAACGGAGACACAGCCCGCGCTACCGTTAACTTCCCCGCAAGTCGCAACTACAAT

TTCCGCCTGCGGGGTTGCGGCAACAACAATAATCTTGCCCGTGTGGACCTGAGGA

TCGACGGACGGACCGTCGGGACCTTTTATTACCAGGGCACATACCCCTGGGAGG

CCCCAATTGACAATGTTTATGTCAGTGCGGGGAGTCATACAGTCGAAATCACTGT

TACTGCGGATAACGGCACATGGGACGTGTATGCCGACTACCTGGTGATACAGTGA

CCTAGG

Figure 5:
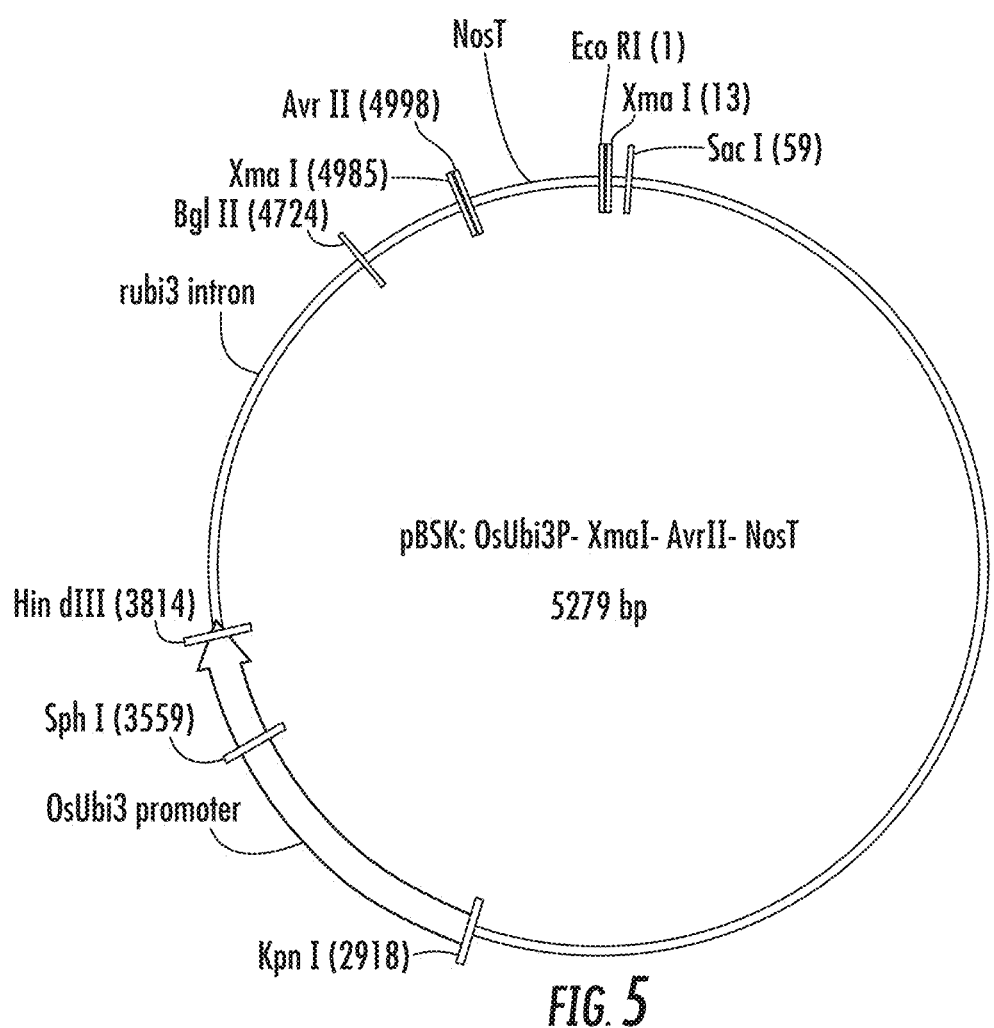
FIG. 5 illustrates a vector map of pBSK:OsUbi3P:XmaI:AvrII:NosT.
Figure 6:
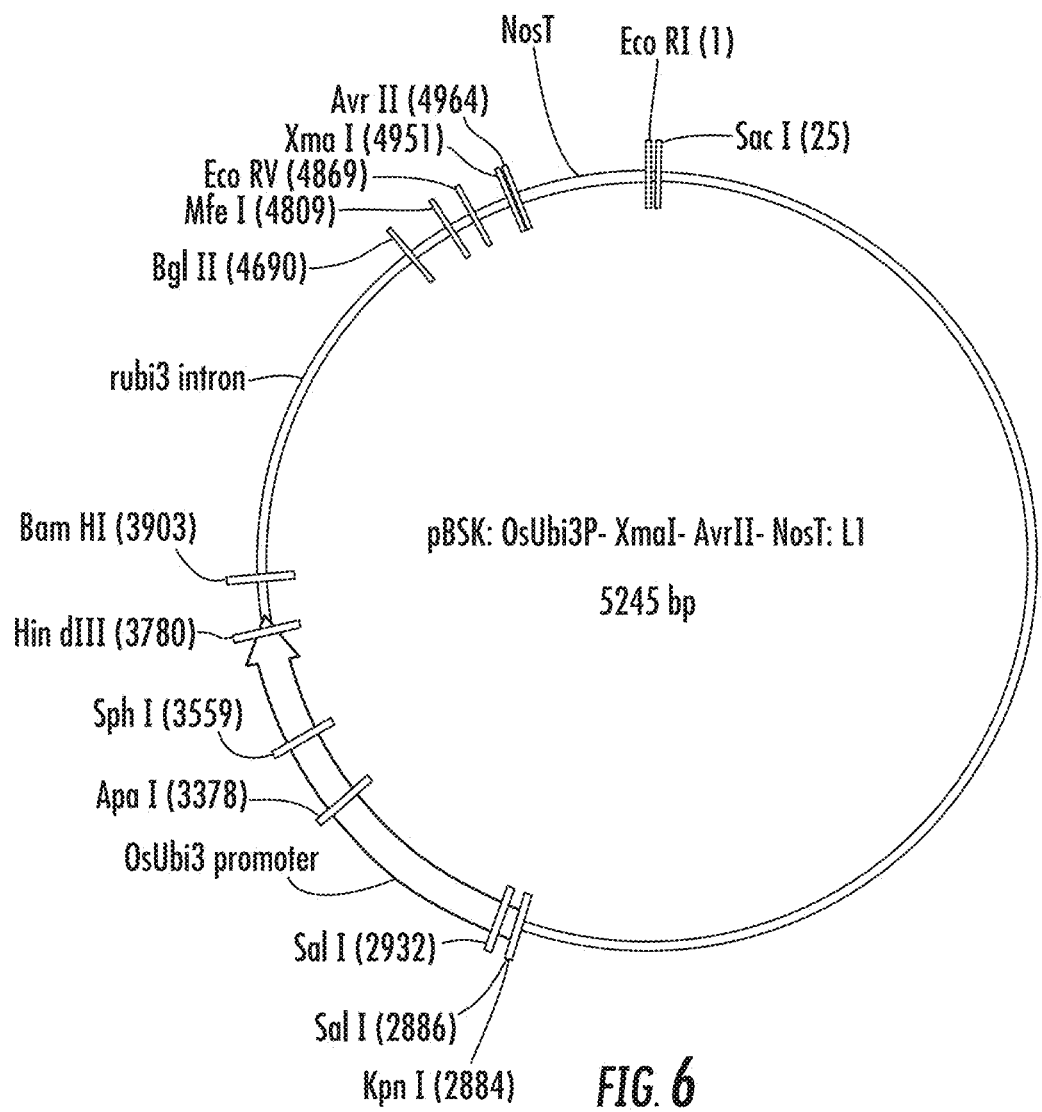
FIG. 6 illustrates a vector map of pBSK:OsUbi3P:XmaI:AvrII:NosT:L1.

The fusion PCR product was subsequently excised from the gel, gel purified using QIAquick Gel Extraction Kit (Cat. #28706) and ligated to the pPCR-Blunt II TOPO vector. The fusion PCR product was completely sequenced using vector specific and gene specific primers. The sequence verified fusion PCR fragment was released from the pPCR-Blunt II TOPO vector with BglII-AvrII digestion and cloned into pBluescript that was prepared in the following manipulations:

1. Referring to FIG. 5, the 2362 bp KpnI-EcoRI fragment of pAG2005, which includes OsUbi3 promoter fused to the sequence CCCGGGTATTCATCCTAGG (SEQ ID NO: 42) with XmaI (underlined) and AvrII (boxed) sites and a Nos terminator, was initially cloned into pBluescript to give the pBSK:OsUbi3P:XmaI:AvrII:NosT vector.
2. Referring to FIG. 6, cloning of the L1 linker GAATTCTTACATTAGCACTAGAGCTC (SEQ ID NO: 43) into EcoRI-SacI sites of pBSK:OsUbi3P:XmaI:AvrII:NosT removed an extra XmaI site and produced the "shuttle" vector pBSK:OsUbi3P:XmaI:AvrII:NosT:L1: pBSK:OsUbi3P:XmaI:AvrII:NosT:L1 readily accepts BglII-AvrII digested DNA fragments. In this manner, cloning fusion PCR products similar to that described in the above example, would lead to reconstruction of the entire expression cassette for the gene of interest. For example, the 1362 bp BglII-AvrII digested fusion PCR product described above for P77853 was inserted in the BglII-AvrII digested pBSK:OsUbi3P:XmaI:AvrII:NosT:L1 to create the OsUbi3P:BAASS:P77853:NosT expression cassette.

The entire expression cassette OsUbi3P:BAASS:P77853:NosT was further excised as a KpnI-EcoRI fragment using restriction enzymes and cloned into pAG2005 to generate the pAG2014. The pAG2014 vector can be used for expressing the wild type P77853 xylanase in transgenic plants from the rice Ubiquitin 3 gene promoter, and targeting expressed enzyme to the plant cell wall by the barley alpha amylase signal sequence (BAASS). Using the same process, vectors in the following list were generated. The list below also includes pAG1000, 1002, 1003, 1004, 1005, 2000, 2004. The vectors below may be utilized for plant transformation and expression of the transgenes.

1. pAG1000-pAG1002 (SEQ ID NOS: 188-190, respectively) are CMPSP:PMI in pSB11 with various restriction sites removed.
2. pAG1003 (SEQ ID NO: 191) is pAG1002 with an MCS.

3. pAG1004 is pAG1003 with GUS-int in the MCS.
4. pAG1005 (SEQ ID NO: 192) is pAG1003 with CPMSP:PMI, where PMI is codon and expression optimized for maize.
5. pAG2000 (SEQ ID NO: 193) is pAG1003 with one connection of the rice Ubi3 promoter and PMI in HindIII-SpeI replacing CMPSP:PMI.
6. pAG2001 (SEQ ID NO: 194) is pAG2000 with the rice Ubi3 promoter in the MCS.
7. pAG2002 (SEQ ID NO: 195) is pAG2001 with the rice Ubi3 promoter and the Nos terminator in the MCS.
8. pAG2003 (SEQ ID NO: 196) is pAG2000 with second connection between the rice Ubi3 promoter and PMI.
9. pAG2004 (SEQ ID NO: 197) is pAG2000 with third connection between rice Ubi3 promoter and PMI.
10. pAG2005 (SEQ ID NO: 198) is pAG2004 with the added rice Ubi3 promoter and Nos terminator from pAG2002 in the MCS.
11. pAG2006 (SEQ ID NO: 199) is pAG2005 with GUS between the rice Ubi3 promoter and the Nos terminator, using one connection between the OsUbi3P and GUS.
12. pAG2007 (SEQ ID NO: 200) is pAG2005 with GUS between the rice Ubi3 promoter and the Nos terminator, using a second connection between OsUbi3P and GUS.
13. pAG2009 (SEQ ID NO: 201) is pAG2005 with GUS fused to the PR1a intracellular space localization signal sequence (using one connection) and between the rice Ubi3 promoter and the Nos terminator.
14. pAG2010 (SEQ ID NO: 202) is pAG2005 with GUS fused to the PR1a intracellular space localization signal sequence (using second connection) and between the rice Ubi3 promoter and the Nos terminator.
15. pAG2011 (SEQ ID NO: 203) is pAG2005 with GUS fused to the BAASS cell wall targeting signal sequence and between the rice Ubi3 promoter and the Nos terminator.
16. pAG2012 (SEQ ID NO: 204) is pAG2007 with GUS between the rice glutelin GluB-4 promoter and the Nos terminator.
17. pAG2013 (SEQ ID NO: 205) is pAG2005 with GUS fused to the HvExoI cell wall targeting signal sequence and between the rice the Ubi3 promoter and the Nos terminator.
18. pAG2014 (SEQ ID NO: 206) is pAG2005 with WT P77853 fused to the BAASS cell wall targeting signal sequence and between the rice Ubi3 promoter and the Nos terminator.
19. pAG2015 (SEQ ID NO: 207) is pAG2005 with WT P77853 between rice Ubi3 promoter and Nos terminator.
20. pAG2016 (SEQ ID NO: 208) is pAG2005 with GUS fused to the PR1a (maize expression optimized) intracellular space localization signal and between the rice Ubi3 promoter sequence and the Nos terminator.
21. pAG2017 (SEQ ID NO: 209) is pAG2005 with WT P40942 fused to the PR1a (maize expression optimized) intracellular space localization signal and between the rice Ubi3 promoter sequence and the Nos terminator.
22. pAG2018 (SEQ ID NO: 210) is pAG2005 with WT O30700 fused to the BAASS cell wall targeting signal sequence and between the rice Ubi3 promoter and the Nos terminator.
23. pAG2019 (SEQ ID NO: 211) is pAG2005 with WT P40942 fused to the BAASS cell wall targeting signal sequence and between the rice Ubi3 promoter and the Nos terminator
24. pAG2020 (SEQ ID NO: 212) is pAG2005 with WT P77853 fused to the PR1a (maize expression optimized) intracellular space localization signal and between the rice Ubi3 promoter sequence and the Nos terminator.
25. pAG2021 (SEQ ID NO: 213) is pAG2005 with P77853m3 fused to the PR1a (maize expression optimized) intracellular space localization signal and between the rice Ubi3 promoter sequence and the Nos terminator.
26. pAG2022 (SEQ ID NO: 214) is pAG2005 with P77853m3:SEKDEL fused to the PR1a (maize expression optimized) intracellular space localization signal sequence and between the rice Ubi3 promoter and the Nos terminator.
27. pAG2023 (SEQ ID NO: 215) is pAG2005 with P77853m3 fused to the BAASS cell wall targeting signal sequence and between the rice Ubi3 promoter and the Nos terminator.
28. pAG2024 (SEQ ID NO: 216) is pAG2005 with P77853m3:SEKDEL fused to the BAASS cell wall targeting signal sequence and between the rice Ubi3 promoter and the Nos terminator.
29. pAG2025 (SEQ ID NO: 217) is pAG2012 with WT P77853 fused to GluB-4 signal sequence and between the rice glutelin GluB-4 promoter and the Nos terminator.
30. pAG2026 (SEQ ID NO: 218) is pAG2012 with WT O30700 fused to GluB-4 signal sequence and between the rice glutelin GluB-4 promoter and the Nos terminator.
31. pAG2027 (SEQ ID NO: 219) is pAG2012 with WT P40942 fused to GluB-4 signal sequence and between the rice glutelin GluB-4 promoter and the Nos terminator.
32. pAG2028 (SEQ ID NO: 220) is pAG2005 with P77853T134-195 fused to the PR1a (maize expression optimized) intracellular space localization signal sequence and between the rice Ubi3 promoter and the Nos terminator.
33. pAG2029 (SEQ ID NO: 221) is pAG2005 with P77853T134-195 fused to the BAASS cell wall targeting signal sequence and between the rice Ubi3 promoter and the Nos terminator.
34. pAG2030 (SEQ ID NO: 222) is pAG2005 with P77853m3 between the rice Ubi3 promoter and the Nos terminator.
35. pAG2031 (SEQ ID NO: 223) is pAG2012 with WT P54583 fused to GluB-4 signal sequence and between the rice glutelin GluB-4 promoter and the Nos terminator.
36. pAG2032 (SEQ ID NO: 224) is pAG2012 with WT P54583:SEKDEL fused to GluB-4 signal sequence and between the rice glutelin GluB-4 promoter and the Nos terminator.
37. pAG2033 (SEQ ID NO: 225) is pAG2005 with WT P54583 between the rice Ubi3 promoter and the Nos terminator.
38. pAG2034 (SEQ ID NO: 226) is pAG2005 with WT P54583:SEKDEL between the rice Ubi3 promoter and the Nos terminator.
39. pAG2035 (SEQ ID NO: 227) is pAG2005 with WT P54583 fused to PR1a (maize expression optimized) intracellular space localization signal and between the rice Ubi3 promoter sequence and the Nos terminator.
40. pAG2036 (SEQ ID NO: 228) is pAG2005 with WT P54583:SEKDEL fused to the PR1a (maize expression optimized) intracellular space localization signal sequence between the rice Ubi3 promoter and the Nos terminator.

41. pAG2037 (SEQ ID NO: 229) is pAG2005 with WT P54583 fused to the BAASS cell wall targeting signal sequence and between the rice Ubi3 promoter and the Nos terminator.
42. pAG2038 (SEQ ID NO: 230) is pAG2005 with WT P54583:SEKDEL fused to the BAASS cell wall targeting signal sequence and between the rice Ubi3 promoter and the Nos terminator.
43. pAG2039 (SEQ ID NO: 231) is pAG2005 with GUS fused to HvAleSP and between the rice Ubi3 promoter and the Nos terminator.
44. pAG2040 (SEQ ID NO: 232) is pAG2005 with WT NtEGm fused to the BAASS cell wall targeting signal sequence and between the rice Ubi3 promoter and the Nos terminator.
45. pAG2042 (SEQ ID NO: 234) is pAG2005 with WT P54583 fused to the HvAleSP vacuole targeting signal sequence and between the rice Ubi3 promoter and the Nos terminator.
46. pAG2043 (SEQ ID NO: 235) is pAG2005 with WT NtEGm between the rice Ubi3 promoter and the Nos terminator.
47. pAG2044 (SEQ ID NO: 236) is pAG2005 with WT NtEGm fused to the PR1a (maize expression optimized) intracellular space localization signal sequence and between the rice Ubi3 promoter and the Nos terminator.
48. pAG2045 (SEQ ID NO: 237) is pAG2005 with WT NtEGm:SEKDEL fused to the PR1a (maize expression optimized) intracellular space localization signal sequence and between the rice Ubi3 promoter and the Nos terminator.
49. pAG2046 (SEQ ID NO: 238) is pAG2005 with WT NtEGm:SEKDEL fused to the BAASS cell wall targeting signal sequence and between the rice Ubi3 promoter and the Nos terminator.
50. pAG2047 (SEQ ID NO: 239) is pAG2005 with WT P54583:SEKDEL fused to the HvAleSP vacuole targeting signal sequence and between the rice Ubi3 promoter and the Nos terminator.
51. pAG2048 (SEQ ID NO: 240) is pAG2005 with WT NtEGm between the rice Ubi3 promoter fused to HvAleSP vacuole targeting signal sequence and the Nos terminator.
52. pAG2049 (SEQ ID NO: 241) is pAG2005 with WT NtEGm:SEKDEL fused to the HvAleSP vacuole targeting signal sequence and between the rice Ubi3 promoter and the Nos terminator.
53. pAG2050 (SEQ ID NO: 242) is pAG2005 with WT P26222 between the rice Ubi3 promoter and the Nos terminator.
54. pAG2051 (SEQ ID NO: 243) is pAG2005 with WT P26222 fused to the PR1a (maize expression optimized) intracellular space localization signal sequence and between the rice Ubi3 promoter and the Nos terminator.
55. pAG2052 (SEQ ID NO: 244) is pAG2005 with WT P26222:SEKDEL fused to the PR1a (maize expression optimized) intracellular space localization signal sequence and between rice Ubi3 promoter and Nos terminator.
56. pAG2053 (SEQ ID NO: 245) is pAG2005 with WT P26222 fused to the BAASS cell wall targeting signal sequence and between the rice Ubi3 promoter and the Nos terminator.
57. pAG2054 (SEQ ID NO: 246) is pAG2005 with WT P26222:SEKDEL fused to the BAASS cell wall targeting signal sequence and between the rice Ubi3 promoter and the Nos terminator.
58. pAG2055 (SEQ ID NO: 247) is pAG2005 with WT P26222 fused to the HvAleSP vacuole targeting signal sequence and between the rice Ubi3 promoter and the Nos terminator.
59. pAG2056 (SEQ ID NO: 248) is pAG2005 with WT P26222:SEKDEL fused to the HvAleSP vacuole targeting signal sequence and between the rice Ubi3 promoter and the Nos terminator.
60. pAG2057 (SEQ ID NO: 249) is pAG2005 with WT P77853:SEKDEL fused to the BAASS cell wall targeting signal sequence and between the rice Ubi3 promoter and the Nos terminator.
61. pAG2058 (SEQ ID NO: 250) is pAG2005 with WT P77853:SEKDEL fused to the PR1a (maize expression optimized) intracellular space localization signal sequence and between the rice Ubi3 promoter and the Nos terminator.
62. pAG2059 (SEQ ID NO: 251) is pAG2005 with WT 043097 between the rice Ubi3 promoter and the Nos terminator.
63. pAG2060 (SEQ ID NO: 252) is pAG2005 with WT 043097 fused to the PR1a (maize expression optimized) intracellular space localization signal sequence and between the rice Ubi3 promoter and the Nos terminator.
64. pAG2061 (SEQ ID NO: 253) is pAG2005 with WT 043097:SEKDEL fused to the PR1a (maize expression optimized) intracellular space localization signal sequence and between the rice Ubi3 promoter and the Nos terminator.
65. pAG2062 (SEQ ID NO: 254) is pAG2005 with WT 043097 fused to the BAASS cell wall targeting signal sequence and between the rice Ubi3 promoter and the Nos terminator.
66. pAG2063 (SEQ ID NO: 255) is pAG2005 with WT 043097:SEKDEL fused to the BAASS cell wall targeting signal sequence and between the rice Ubi3 promoter and the Nos terminator.
67. pAG2064 (SEQ ID NO: 256) is pAG2005 with WT 043097 fused to the HvAleSP vacuole targeting signal sequence and between the rice Ubi3 promoter and the Nos terminator.
68. pAG2065 (SEQ ID NO: 257) is pAG2005 with WT 043097:SEKDEL fused to the HvAleSP vacuole targeting signal sequence and between the rice Ubi3 promoter and the Nos terminator.
69. pAG2066 (SEQ ID NO: 258) is pAG2005 with P77853-S158-2 intein modified xylanase fused to the BAASS cell wall targeting signal sequence and between the rice Ubi3 promoter and the Nos terminator.
70. pAG2067 (SEQ ID NO: 259) is pAG2005 with P77853-S158-19 intein modified xylanase fused to the BAASS cell wall targeting signal sequence and between the rice Ubi3 promoter and the Nos terminator.
71. pAG2068 (SEQ ID NO: 260) is pAG2005 with P77853-T134-1 intein modified xylanase fused to the BAASS cell wall targeting signal sequence and between the rice Ubi3 promoter and the Nos terminator.

72. pAG2069 (SEQ ID NO: 261) is pAG2005 with WT 068438 between the rice Ubi3 promoter and the Nos terminator.
73. pAG2070 (SEQ ID NO: 262) is pAG2005 with WT 068438 fused to the PR1a (maize expression optimized) intracellular space localization signal and between the rice Ubi3 promoter sequence and the Nos terminator.
74. pAG2071 (SEQ ID NO: 263) is pAG2005 with WT 068438:SEKDEL fused to the PR1a (maize expression optimized) intracellular space localization signal sequence and between the rice Ubi3 promoter and the Nos terminator.
75. pAG2072 (SEQ ID NO: 264) is pAG2005 with WT 068438 fused to the BAASS cell wall targeting signal sequence and between the rice Ubi3 promoter and the Nos terminator.
76. pAG2073 (SEQ ID NO: 265) is pAG2005 with WT 068438:SEKDEL fused to the BAASS cell wall targeting signal sequence and between the rice Ubi3 promoter and the Nos terminator.
77. pAG2074 (SEQ ID NO: 266) is pAG2005 with WT 068438 fused to the HvAleSP vacuole targeting signal sequence and between the rice Ubi3 promoter and the Nos terminator.
78. pAG2075 (SEQ ID NO: 267) is pAG2005 with WT 068438:SEKDEL fused to the HvAleSP vacuole targeting signal sequence and between the rice Ubi3 promoter and the Nos terminator.
79. pAG2076 (SEQ ID NO: 268) is pAG2005 with P77853-S158-2 intein modified xylanase between the rice Ubi3 promoter and the Nos terminator.
80. pAG2077 (SEQ ID NO: 269) is pAG2005 with P77853-S158-19 intein modified xylanase between the rice Ubi3 promoter and the Nos terminator.
81. pAG2078 (SEQ ID NO: 270) is pAG2005 with P77853-T134-1 intein modified xylanase between the rice Ubi3 promoter and the Nos terminator.
82. pAG2079 (SEQ ID NO: 271) is pAG2005 with P77853-S158-2:SEKDEL intein modified xylanase fused to BAASS cell wall targeting signal sequence and between the rice Ubi3 promoter and the Nos terminator.
83. pAG2080 (SEQ ID NO: 272) is pAG2005 with P77853-S158-19:SEKDEL intein modified xylanase fused to the BAASS cell wall targeting signal sequence and between the rice Ubi3 promoter and the Nos terminator.
84. pAG2081 (SEQ ID NO: 273) is pAG2005 with P77853-T134-1:SEKDEL intein modified xylanase fused to the BAASS cell wall targeting signal sequence and between the rice Ubi3 promoter and the Nos terminator.
85. pAG3000 (SEQ ID NO: 280) is pAG1003 with rice Act1 promoter driving PMI in place of CMPSP:PMI using one connection between OsAct1P and PMI (partial eukaryotic translation initiation site consensus sequence).
86. pAG3001 (SEQ ID NO: 281) is pAG1003 with rice Act1 promoter driving PMI in place of CMPS-PMI using second connection between OsAct1P and PMI (complete eukaryotic translation initiation site consensus sequence).
87. pAG3002 (SEQ ID NO: 282) is pAG3000 with GUS between the rice Ubi3 promoter fused to BAASS cell wall targeting signal sequence and the Nos terminator.
88. pAG3003 (SEQ ID NO: 283) is pAG3001 with GUS fused to the BAASS cell wall targeting signal sequence and between the rice Ubi3 promoter and the Nos terminator.
89. pAG2041 (SEQ ID NO: 233) is pAG2004 with NosT cloned into the AvrII-EcoRI sites.
90. pAG2082 (SEQ ID NO: 274) is pAG2005 with WT 043097 fused to Glutelin B-4 signal peptide and between rice the Glutelin B-4 promoter and the Nos terminator.
91. pAG2083 (SEQ ID NO: 275) is pAG2005 with WT 043097:SEKDEL fused to Glutelin B-4 signal peptide and between the rice Glutelin B-4 promoter and the Nos terminator.
92. pAG2084 (SEQ ID NO: 276) is pAG2005 with WT NtEGm fused to Glutelin B-4 signal peptide and between the rice Glutelin B-4 promoter and the Nos terminator.
93. pAG2085 (SEQ ID NO: 275) is pAG2005 with P77853-T145-307 intein modified xylanase between the rice Ubi3 promoter and the Nos terminator.
94. pAG2086 (SEQ ID NO: 278) is pAG2005 with P77853-T145-307 intein modified xylanase fused to BAASS cell wall targeting signal sequence and between the rice Ubi3 promoter and Nos terminator.
95. pAG2087 (SEQ ID NO: 279) is pAG2005 with P77853-T145-307:SEKDEL intein modified xylanase fused to BAASS cell wall targeting signal sequence and between the rice Ubi3 promoter and the Nos terminator.

The amino acid sequence of the protein encoded in each of the above listed vectors 18-19, 21-84 and 89-95 and the nucleic acid encoding the protein is provided in Table 1, below.

Embodiments herein include but are not limited to the gene sequences under the heading "Nucleotide sequence" in Table 1, below, the amino acid sequences under the heading "Protein sequence" in Table 1, plants including the gene sequences in Table 1, vectors including the gene sequences in Table 1, the vectors under the heading "pAG vector" in Table 1, plants including the vectors in Table 1, plants including proteins encoded by the Nucleotide sequences in Table 1 and plants including the Protein sequences in Table 1. For the vectors in Table 1, each entry under the "pAG vector" heading includes a number. The number is added to "pAG" to complete the vector name. For example, the listing "2014" is for the vector pAG2014.

TABLE 1

Sequences of CWDEs and their fusions in vectors

| pAG Sequence vector annotation | Protein sequence | Nucleotide sequence |
|---|---|---|
| 2014 BAASS:P77853 | MANKHLSLSLFLVLLG LSASLASGQQTSITLT SNASGTFDGYYYELWK DTGNTTMTVYTQGRFS CQWSNINNALFRTGKK | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC |

TABLE 1-continued

Sequences of CWDEs and their fusions in vectors

| pAG vector | Sequence annotation | Protein sequence | Nucleotide sequence |
|---|---|---|---|
| | | YNQNWQSLGTIRITYS ATYNPNGNSYLCIYGW STNPLVEFYIVESWGN WRPPGATSLGQVTIDG GTYDIYRTTRVNQPSI VGTATFDQYWSVRTSK RTSGTVTVTDHFRAWA NRGLNLGTIDQITLCV EGYQSSGSANITQNTF SQGSSSGSSGGSSGST TTTRIECENMSLSGPY VSRITNPFNGIALYAN GDTARATVNFPASRNY NFRLRGCGNNNNLARV DLRIDGRTVGTFYYQG TYPWEAPIDNVYVSAG SHTVEITVTADNGTWD VYADYLVIQ* (SEQ ID NO: 44) | CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATGATGGCGGGACCTACGACATCTATAGGACGACAC GCGTCAACCAGCCTTCCATTGTGGGGACAGCCACGTTCGATCAGTA CTGGAGCGTGCGCACCTCTAAGCGGACTTCAGGAACAGTGACCGTG ACCGATCACTTCCGCGCCTGGGCGAACCGGGGCCTGAACCTCGGCA CAATAGACCAAATTACATTGTGCGTGGAGGGTTACCAAAGCTCTGG ATCAGCCAACATCACCCAGAACACCTTCTCTCAGGGCTCTTCTTCC GGCAGTTCGGGTGGCTCATCCGGCTCCACAACGACTACTCGCATCG AGTGTGAGAACATGTCCTTGTCCGGACCCTACGTTAGCAGGATCAC CAATCCCTTTAATGGTATTGCGCTGTACGCCAACGGAGACACAGCC CGCGCTACCGTTAACTTCCCCGCAAGTCGCAACTACAATTTCCGCC TGCGGGGTTGCGGCAACAACAATAATCTTGCCCGTGTGGACCTGAG GATCGACGGACGGACCGTCGGGACCTTTTATTACCAGGGCACATAC CCCTGGGAGGCCCCAATTGACAATGTTTATGTCAGTGCGGGGAGTC ATACAGTCGAAATCACTGTTACTGCGGATAACGGCACATGGGACGT GTATGCCGACTACCTGGTGATACAGTGA (SEQ ID NO: 116) |
| 2015 | P77853 | MQTSITLTSNASGTFD GYYYELWKDTGNTTMT VYTQGRFSCQWSNINN ALFRTGKKYNQNWQSL GTIRITYSATYNPNGN SYLCIYGWSTNPLVEF YIVESWGNWRPPGATS LGQVTIDGGTYDIYRT TRVNQPSIVGTATFDQ YWSVRTSKRTSGTVTV TDHFRAWANRGLNLGT IDQITLCVEGYQSSGS ANITQNTFSQGSSSGS SGGSSGSTTTTRIECE NMSLSGPYVSRITNPF NGIALYANGDTARATV NFPASRNYNFRLRGCG NNNNLARVDLRIDGRT VGTFYYQGTYPWEAPI DNVYVSAGSHTVEITV TADNGTWDVYADYLVI Q* (SEQ ID NO: 45) | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGCTTTTCCTGCCAGTGGTCGAACATC AATAACGCGTTGTTTAGGACCGGGAAGAAATACAACCAGAATTGGC AGTCTCTTGGCACAATCCGGATCACGTACTCTGCGACTTACAACCC AAACGGGAACTCCTACTTGTGTATCTATGGCTGGTCTACCAACCCA TTGGTCGAGTTCTACATCGTTGAGTCCTGGGGGAACTGGAGACCGC CTGGTGCCACGTCCCTGGGCCAAGTGACAATGATGGCGGGACCTA CGACATCTATAGGACGACACGCGTCAACCAGCCTTCCATTGTGGGG ACAGCCACGTTCGATCAGTACTGGAGCGTGCGCACCTCTAAGCGGA CTTCAGGAACAGTGACCGTGACCGATCACTTCCGCGCCTGGGCGAA CCGGGGCCTGAACCTCGGCACAATAGACCAAATTACATTGTGCGTG GAGGGTTACCAAAGCTCTGGATCAGCCAACATCACCCAGAACACCT TCTCTCAGGGCTCTTCTTCCGGCAGTTCGGGTGGCTCATCCGGCTC CACAACGACTACTCGCATCGAGTGTGAGAACATGTCCTTGTCCGGA CCCTACGTTAGCAGGATCACCAATCCCTTTAATGGTATTGCGCTGT ACGCCAACGGAGACACAGCCCGCGCTACCGTTAACTTCCCCGCAAG TCGCAACTACAATTTCCGCCTGCGGGGTTGCGGCAACAACAATAAT CTTGCCCGTGTGGACCTGAGGATCGACGGACGGACCGTCGGGACCT TTTATTACCAGGGCACATACCCCTGGGAGGCCCCAATTGACAATGT TTATGTCAGTGCGGGGAGTCATACAGTCGAAATCACTGTTACTGCG GATAACGGCACATGGGACGTGTATGCCGACTACCTGGTGATACAGT GA (SEQ ID NO: 117) |
| 2017 | PR1a:040942 | MGFVLFSQLPSFLLVS TLLLFLVISHSCRAFN DQTSAEDIPSLAEAFR DYFPIGAAIEPGYTTG QIAELYKKHVNMLVAE NAMKPASLQPTEGNFQ WADADRIVQFAKENGM ELRFHTLVWHNQTPTG FSLDKEGKPMVEETDP QKREENRKLLLQRLEN YIRAVVLRYKDDIKSW DVVNEVIEPNDPGGMR NSPWYQITGTEYIEVA FRATREAGGSDIKLYI NDYNTDDPVKRDILYE LVKNLLEKGVPIDGVG HQTHIDIYNPPVERII ESIKKFAGLGLDNIIT ELDMSIYSWNDRSDYG DSIPDYILTLQAKRYQ ELFDALKENKDIVSAV VFWGISDKYSWLNGFP VKRTNAPLLFDRNFMP KPAFWAIVDPSRLRE* (SEQ ID NO: 46) | ATGGGCTTCGTGCTCTTCTCCCAGCTGCCTTCCTTCCTTCTTGTCT CCACCCTGCTCTTGTTCCTCGTGATCTCCCACTCCTGCCGCGCCTT CAACGACCAGACAAGTGCAGAGGATATTCCGTCACTTGCCGAAGCG TTCAGGGACTATTTCCCTATCGGAGCTGCCATTGAGCCGGGCTATA CCACGGGTCAGATTGCCGAATTGTACAAGAAACACGTGAATATGCT GGTCGCGGAGAACGCCATGAAGCCCGCCTCGCTCCAGCCGACGGAG GGTAATTTTCAGTGGGCCGACGCGGACCGCATTGTTCAGTTCGCTA AGGAAAACGGAATGGAGCTTCGGTTTCACACGTTGGTGTGGCACAA TCAAACCCCAACTGGCTTCAGCCTGGATAAGGAAGGGAAACCTATG GTCGAGGAAACGGACCCTCAAAAGAGAGAAGAGAACAGGAAACTCC TTTTGCAGCGCCTCGAAAACTATATCCGGGCCGTTGTGTTGAGATA CAAGGATGACATCAAGTCCTGGGATGTTGTCAATGAGGTTATAGAA CCAAACGACCCAGGGGGTATGCGTAATTCTCCCTGGTATCAAATCA CAGGAACCGAATATATTGAGGTCGCATTTCGCGCGACACGTGAAGC TGGCGGGTCAGATATAAAGCTGTATATTAATGATTACAATACGGAC GATCCTGTTAAACGGGATATACTCTACGAGCTTGTGAAGAACTTGC TGGAGAAAGGTGTCCCGATTGATGGCGTGGAGCATCAGACACATAT CGACATCTACAACCCACCCGTTGAAAGGATTATCGAGTCGATTAAG AAGTTCGCCGGACTCGGGCTTGATAATATCATTACCGAACTGGACA TGAGCATCTATTCCTGGAATGATCGCTCTGACTACGGTGATTCAAT CCCTGACTATATTCTCACCTTGCAGGCCAAAAGATACCAGGAGCTT TTCGATGCGCTGAAGGAGAATAAGGACATAGTCTCGGCTGTGGTCT TTTGGGGAATTAGCGACAAATACTCCTGGCTGAATGCTTCCCGGT CAAGAGGACTAATGCCCCATTGCTGTTTGATCGCAACTTTATGCCT AAACCAGCATTTTGGGCAATCGTGGACCCGAGTAGACTCAGGGAAT AA (SEQ ID NO: 118) |
| 2018 | BAASS:030700 | MANKHLSLSLFLVLLG LSASLASGQVQPFAWQ VASLADRYEESFDIGA | ATGGCGAACAAACATTTGTCCCTCTCCCTCTTCCTCGTCCTCCTTG GCCTGTCGGCCAGCTTGGCCTCCGGGCAAGTTCAGCCGTTCGCATG GCAGGTGGCATCCCTGGCTGACCGCTACGAAGAGAGCTTCGATATT |

TABLE 1-continued

Sequences of CWDEs and their fusions in vectors

| pAG vector | Sequence annotation | Protein sequence | Nucleotide sequence |
|---|---|---|---|
| | | AVEPHQLNGRQGKVLK HHYNSIVAENAMKPIS LQPEEGVFTWDGADAI VEFARKNNMNLRFHTL VWHNQVPDWFFLDEEG NPMVEETNEAKRQANK ELLLERLETHIKTVVE RYKDDVTAWDVVNEVV DDGTPNERGLRESVWY QITGDEYIRVAFETAR KYAGEDAKLFINDYNT EVTPKRDHLYNLVQDL LADGVPIDGVGHQAHI QIDWPTIDEIRTSMEM FAGLGLDNQVTELDVS LYGWPPRPAFPTYDAI PQERFQAQADRYNQLF ELYEELDADLSSVTFW GIADNHTWLDDRAREY NDGVGKDAPFVFDPNY RVKPAFWRIID* (SEQ ID NO: 47) | GGAGCGGCGGTGGAACCCTCACCAATTGAACGGTCGCCAGGGGAAGG TCCTGAAGCATCACTATAACTCAATCGTGGCCGAGAATGCTATGAA GCCGATCTCCCTCCAACCGGAAGAAGGAGTTTTCACGTGGGATGGA GCTGATGCAATAGTGGAGTTCGCGCGGAAAAATAACATGAACCTGC GCTTTCACACGCTCGTGTGGCATAACCAAGTGCCCGACTGGTTCTT CCTGGACGAAGAGGGTAACCCTATGGTCGAGGAGACTAACGAAGCG AAAAGGCAAGCGAATAAAGAGCTTTTGCTTGAGAGACTTGAGACTC ATATCAAAACTGTGGTCGAAAGGTACAAGGATGACGTTACGGCCTG GGATGTGGTGAATGAGGTTGTGGACGATGGCACCCCAAATGAAAGG GGACTGCGCGAGAGCGTTTGGTATCAGATTACAGGCGATGAATACA TTAGAGTGGCATTCGAGACTGCGCGCAAGTACGCTGGCGAAGACGC TAAGCTGTTCATCAACGACTACAACACGGAGGTGACACCCAAGCGC GATCACCTCTACAACTTGGTTCAAGACCTGCTCGCGGACGGGGTCC CGATCGATGGAGTGGGACATCAAGCCCATATCCAGATCGATTGGCC CACCATCGATGAGATCAGGACCTCGATGGAGATGTTTGCCGGCCTT GGGCTCGACAACCAAGTTACCGAACTGATGTTTCTTGTACGGTT GGCCGCCTCGCCCGGCATTCCCGACCTACGATGCAATCCCTCAAGA GAGGTTTCAGGCGCAGGCGGATAGATACAATCAGCTCTTCGAGCTT TACGAGGAACTCGACGCTGACCTCTCAAGCGTGACCTTCTGGGGGA TCGCGGACAACCATACCTGGCTCGACGACAGGGCCAGAGAATACAA TGACGGGGTCGGCAAAGATGCCCCGTTCGTCTTCGATCCGAACTAC AGGGTTAAACCTGCCTTCTGGCGCATCATTGACTGA (SEQ ID NO: 119) |
| 2019 | BAASS:P40942 | MANKHLSLSLFLVLLG LSASLASGQVFNDQTS AEDIPSLAEAFRDYFP IGAAIEPGYTTGQIAE LYKKHVNMLVAENAMK PASLQPTEGNFQWADA DRIVQFAKENGMELRF HTLVWHNQTPTGFSLD KEGKPMVEETDPQKRE ENRKLLLQRLENYIRA VVLRYKDDIKSWDVVN EVIEPNDPGGMRNSPW YQITGTEYIEVAFRAT REAGGSDIKLYINDYN TDDPVKRDILYELVKN LLEKGVPIDGVGHQTH IDIYNPPVERIIESIK KFAGLGLDNIITELDM SIYSWNDRSDYGDSIP DYILTLQAKRYQELFD ALKENKDIVSAVVFWG ISDKYSWLNGFPVKRT NAPLLFDRNFMPKPAF WAIVDPSRLRE* (SEQ ID NO: 48) | ATGGCGAACAAACATTTGTCCCTCTCCCTCTTCCTCGTCCTCCTTG GCCTGTCGGCCAGCTTGGCCTCCGGGCAAGTCTTCAACGACCAGAC AAGTGCAGAGGATATTCCGTCACTTGCCGAAGCGTTCAGGGACTAT TTCCCTATCGGAGCTGCCATTGAGCCGGGCTATACCACGGGTCAGA TTGCCGAATTGTACAAGAAACACGTGAATATGCTGGTCGCGGAGAA CGCTATGAAGCCCGCCTCGCTCCAGCCGACGGAGGGTAATTTTCAG TGGGCCGACGCGGACCGCATTGTTCAGTTCGCTAAGGAAAACGGAA TGGAGCTTCGGTTTCACACGTTGGTGTGGCACAATCAAACCCCAAC CGGCTTCAGCCTGGATAAGGAAGGGAAACCTATGGTCGAGGAAACG GACCCTCAAAAGAGAGAAGAGAACAGGAAACTCCTTTTGCAGCGCC TCGAAAACTATATCCGGGCCGTTGTGTTGAGATACAAGGATGACAT CAAGTCCTGGGATGTTGTCAATGAGGTTATAGAACCAAACGACCCA GGGGGTATGCGTAATTCTCCCTGGTATCAAATCACAGGAACCGAAT ATATTGAGGTCGCATTTCGCGCGACACGTGAAGCTGGCGGGTCAGA TATAAAGCTGTATATTAATGATTACAATACGGACGATCCTGTTAAA CGGGATATACTCTACGAGCTTGTGAAGAACTTGCTGGAGAAAGGTG TCCCGATTGATGGCGTGGGACATCAGACACATATCGACATCTACAA CCCACCCGTTGAAAGGATTATCGAGTCGATTAAGAAGTTCGCCGGA CTCGGGCTTGATAATATCATTACCGAACTGGACATGAGCATCTATT CCTGGAATGATCGCTCTGACTACGGTGATTCAATCCCTGACTATAT TCTCACCTTGCAGGCCAAAAGATACCAGGAGCTTTTCGATGCGCTG AAGGAGAATAAGGATATAGTCTCGGCTGTGGTCTTTTGGGGAATTA GCGACAAATACTCCTGGCTGAATGGCTTCCCGGTCAAGAGGACTAA TGCCCCATTGCTGTTTGATCGCAACTTTATGCCTAAACCAGCATTT TGGGCAATCGTGGACCCGAGTAGACTCAGGGAATAA (SEQ ID NO: 120) |
| 2020 | PR1a:P77853 | MGFVLFSQLPSFLLVS TLLLFLVISHSCRAQQ TSITLTSNASGTFDGY YYELWKDTGNTTMTVY TQGRFSCQWSNINNAL FRTGKKYNQNWQSLGT IRITYSATYNPNGNSY LCIYGWSTNPLVEFYI VESWGNWRPPGATSLG QVTIDGGTYDIYRTTR VNQPSIVGTATFDQYW SVRTSKRTSGTVTVTD HFRAWANRGLNLGTID QITLCVEGYQSSGSAN ITQNTFSQGSSSGSSG GSSGSTTTTRIECENM SLSGPYVSRITNPFNG IALYANGDTARATVNF PASRNYNFRLRGCGNN NNLARVDLRIDGRTVG | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GCAAACAAGCATTACTCTGACATCCAACGCATCCGGTACGTTTGAC GGTTACTATTACGAACTCTGGAAGGATACTGGCAATACAACAATGA CGGTCTACACTCAAGGTCGCTTTTCCTGCCAGTGGTCGAACATCAA TAACGCGTTGTTTAGGACCGGGAAGAAATACAACCAGAATTGGCAG TCTCTTGGCACAATCCGGATCACGTACTCTGCGACTTACAACCCAA ACGGGAACTCCTACTTGTGTATCTATGGCTGGTCTACCAACCCATT GGTCGAGTTCTACATCGTTGAGTCCTGGGGGAACTGGAGACCGCCT GGTGCCACGTCCCTGGGCCAAGTGACAATCGATGGCGGGACCTACG ACATCTATAGGACGACACGCGTCAACCAGCCTTCCATTGTGGGAC AGCCACGTTCGATCAGTACTGGAGCGTGCGCACCTCTAAGCGGACT TCAGGAACAGTGACCGTGACCGATCACTTCCGCGCCTGGGCGAACC GGGGCCTGAACCTCGGCACAATAGACCAAATTACATTGTGCGTGGA GGGTTACCAAAGCTCTGGATCAGCCAACATCACCCAGAACACCTTC TCTCAGGGCTCTTCTTCCGGCAGTTCGGGTGGCTCATCCGGCTCCA CAACGACTACTCGCATCGAGTGTGAGAACATGTCCTTGTCCGGACC CTACGTTAGCAGGATCACCAATCCCTTTAATGGTATTGCGCTGTAC GCCAACGGAGACACAGCCCGCGCTACCGTTAACTTCCCCGCAAGTC GCAACTACAATTTCCGCCTGCGGGGTTGCGGCAACAACAATAATCT |

TABLE 1-continued

Sequences of CWDEs and their fusions in vectors

| pAG vector | Sequence annotation | Protein sequence | Nucleotide sequence |
|---|---|---|---|
| | | TFYYQGTYPWEAPIDN VYVSAGSHTVEITVTA DNGTWDVYADYLVIQ* (SEQ ID NO: 49) | TGCCCGTGTGGACCTGAGGATCGACGGACGGACCGTCGGGACCTTT TATTACCAGGGCACATACCCCTGGGAGGCCCCAATTGACAATGTTT ATGTCAGTGCGGGGAGTCATACAGTCGAAATCACTGTTACTGCGGA TAACGGCACATGGGACGTGTATGCCGACTACCTGGTGATACAGTGA (SEQ ID NO: 121) |
| 2021 | PR1a:P77853m3 | MGFVLFSQLPSFLLVS TLLLFLVISHSCRAQQ TSITLTSNASGTFDGY YYELWKDTGNTTMTVY TQGRFSCQWSNLPEEW VPLTKNGKSKTFRIGG FVDGLMKANQGKVKKT GDTEVLEVAGIHANSF DRKSKKSRTMAVKAVI RHRYSGNVYRIVLNSG RKITITEGHSLFVYRN GDLVEATGEDVKIGDN LAVPRSDGSGDITEDR VVEIKREYYDGYVYDL SLDEDENFLAGHGYLM AHNSNINNALFRTGKK YNQNWQSLGTIRITYS ATYNPNGNSYLCIYGW STNPLVEFYIVESWGN WRPPGATSLGQVTIDG GTYDIYRTTRVNQPSI VGTATFDQYWSVRTSK RTSGTVTVTDHFRAWA NRGLNLGTIDQITLCV EGYQSSGSANITQNTF SQGSSSGSSGGSSGST TTTRIECENMSLSGPY VSRITNPFNGIALYAN GDTARATVNFPASCNY NFRLRGCGNNNNLARV DLRIDGRTVGTFYYQG TYPWEAPIDNVYVSAG SHTVEITVTADNGTWD VYADYLVIQ* (SEQ ID NO: 50) | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GCAAACAAGCATTACTCTGACATCCAACGCATCCGGTACGTTTGAC GGTTACTATTACGAACTCTGGAAGGATACTGGCAATACAACAATGA CGGTCTACACTCAAGGTCGCTTTTCCTGCCAGTGGTCTAATTTGCC AGAAGAGTGGGTTCCTTTAACTAAGAATGGTAAGTCAAAGACCTTT AGAATTGGAGGCTTCGTAGACGGTTTGATGAAGGCTAACCAAGGAA AGGTCAAGAAGACCGGTGACACCGAAGTATTAGAGGTTGCAGGTAT CCATGCCAATTCCTTTGACAGAAAGTCAAAGAAGTCCAGAACCATG GCTGTAAAAGCAGTCATTAGACACAGATATTCCGGAAACGTGTACA GAATAGTTTTGAACTCCGGAAGAAAGATCACCATTACTGAGGGACA TTCCTTATTCGTCTATAGAAACGGTGACTTGGTGGAAGCCACAGGT GAGGATGTAAAGATAGGTGATAACTTAGCTGTTCCAAGAAGCGACG GATCCGGAGACATTACTGAGGATAGAGTTGTAGAAATTAAGAGAGA GTACTACGACGGTTATGTCTATGACTTGTCATTGGATGAAGATGAA AATTTCTTGGCAGGACACGGTTACTTGATGGCCCATAACTCGAACA TCAATAACGCGTTGTTTAGGACCGGGAAGAAATACAACCAGAATTG GCAGTCTCTTGGCACAATCCGGATCACGTACTCTGCGACTTACAAC CCAAACGGGAACTCCTACTTGTGTATCTATGGCTGGTCTACCAACC CATTGGTCGAGTTCTACATCGTTGAGTCCTGGGGGAACTGGAGACC GCCTGGTGCCACGTCCCTGGGCCAAGTGACAATCGATGGCGGGACC TACGACATCTATAGGACGACACGCGTCAACCAGCCTTCCATTGTGG GGACAGCCACGTTCGATCAGTACTGGAGCGTGCGCACCTCTAAGCG GACTTCAGGAACAGTGACCGTGACCGATCACTTCCGCGCCTGGGCG AACCGGGGCCTGAACCTCGGCACAATAGACCAAATTACATTGTGCG TGGAGGGTTACCAAAGCTCTGGATCAGCCAACATCACCCAGAACAC CTTCTCTCAGGGGCTCTTCTTCCGGCAGTTCGGGTGGCTCATCCGGC TCCACAACGACTACTCGCATCGAGTGTGAGAACATGTCCTTGTCCG GACCCTACGTTAGCAGGATCACCAATCCCTTTAATGGTATTGCGCT GTACGCCAACGGAGACACAGCCCGCGCTACCGTTAACTTCCCCGCA AGTTGCAACTACAATTTCCGCCTGCGGGGTTGCGGCAACAACAATA ATCTTGCCCGTGTGGACCTGAGGATCGACGGACGGACCGTCGGGAC CTTTTATTACCAGGGCACATACCCCTGGGAGGCCCCAATTGACAAT GTTTATGTCAGTGCGGGGAGTCATACAGTCGAAATCACTGTTACTG CGGATAACGGCACATGGGACGTGTATGCCGACTACCTGGTGATACA GTGA (SEQ ID NO: 122) |
| 2022 | PR1a:P77853m3: SEKDEL | MGFVLFSQLPSFLLVS TLLLFLVISHSCRAQQ TSITLTSNASGTFDGY YYELWKDTGNTTMTVY TQGRFSCQWSNLPEEW VPLTKNGKSKTFRIGG FVDGLMKANQGKVKKT GDTEVLEVAGIHANSF DRKSKKSRTMAVKAVI RHRYSGNVYRIVLNSG RKITITEGHSLFVYRN GDLVEATGEDVKIGDN LAVPRSDGSGDITEDR VVEIKREYYDGYVYDL SLDEDENFLAGHGYLM AHNSNINNALFRTGKK YNQNWQSLGTIRITYS ATYNPNGNSYLCIYGW STNPLVEFYIVESWGN WRPPGATSLGQVTIDG GTYDIYRTTRVNQPSI VGTATFDQYWSVRTSK RTSGTVTVTDHFRAWA NRGLNLGTIDQITLCV EGYQSSGSANITQNTF SQGSSSGSSGGSSGST TTTRIECENMSLSGPY VSRITNPFNGIALYAN GDTARATVNFPASCNY NFRLRGCGNNNNLARV DLRIDGRTVGTFYYQG TYPWEAPIDNVYVSAG | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GCAAACAAGCATTACTCTGACATCCAACGCATCCGGTACGTTTGAC GGTTACTATTACGAACTCTGGAAGGATACTGGCAATACAACAATGA CGGTCTACACTCAAGGTCGCTTTTCCTGCCAGTGGTCTAATTTGCC AGAAGAGTGGGTTCCTTTAACTAAGAATGGTAAGTCAAAGACCTTT AGAATTGGAGGCTTCGTAGACGGTTTGATGAAGGCTAACCAAGGAA AGGTCAAGAAGACCGGTGACACCGAAGTATTAGAGGTTGCAGGTAT CCATGCCAATTCCTTTGACAGAAAGTCAAAGAAGTCCAGAACCATG GCTGTAAAAGCAGTCATTAGACACAGATATTCCGGAAACGTGTACA GAATAGTTTTGAACTCCGGAAGAAAGATCACCATTACTGAGGGACA TTCCTTATTCGTCTATAGAAACGGTGACTTGGTGGAAGCCACAGGT GAGGATGTAAAGATAGGTGATAACTTAGCTGTTCCAAGAAGCGACG GATCCGGAGACATTACTGAGGATAGAGTTGTAGAAATTAAGAGAGA GTACTACGACGGTTATGTCTATGACTTGTCATTGGATGAAGATGAA AATTTCTTGGCAGGACACGGTTACTTGATGGCCCATAACTCGAACA TCAATAACGCGTTGTTTAGGACCGGGAAGAAATACAACCAGAATTG GCAGTCTCTTGGCACAATCCGGATCACGTACTCTGCGACTTACAAC CCAAACGGGAACTCCTACTTGTATCTATGGCTGGTCTACCAACC CATTGGTCGAGTTCTACATCGTTGAGTCCTGGGGGAACTGGAGACC GCCTGGTGCCACGTCCCTGGGCCAAGTGACAATCGATGGCGGGACC TACGACATCTATAGGACGACACGCGTCAACCAGCCTTCCATTGTGG GGACAGCCACGTTCGATCAGTACTGGAGCGTGCGCACCTCTAAGCG GACTTCAGGAACAGTGACCGTGACCGATCACTTCCGCGCCTGGGCG AACCGGGGCCTGAACCTCGGCACAATAGACCAAATTACATTGTGCG TGGAGGGTTACCAAAGCTCTGGATCAGCCAACATCACCCAGAACAC CTTCTCTCAGGGGCTCTTCTTCCGGCAGTTCGGGTGGCTCATCCGGC TCCACAACGACTACTCGCATCGAGTGTGAGAACATGTCCTTGTCCG GACCCTACGTTAGCAGGATCACCAATCCCTTTAATGGTATTGCGCT GTACGCCAACGGAGACACAGCCCGCGCTACCGTTAACTTCCCCGCA AGTTGCAACTACAATTTCCGCCTGCGGGGTTGCGGCAACAACAATA ATCTTGCCCGTGTGGACCTGAGGATCGACGGACGGACCGTCGGGAC |

TABLE 1-continued

Sequences of CWDEs and their fusions in vectors

| pAG vector | Sequence annotation | Protein sequence | Nucleotide sequence |
|---|---|---|---|
| | | SHTVEITVTADNGTWD VYADYLVIQSEKDEL* (SEQ ID NO: 51) | CTTTTATTACCAGGGCACATACCCCTGGGAGGCCCCAATTGACAAT GTTTATGTCAGTGCGGGGAGTCATACAGTCGAAATCACTGTTACTG CGGATAACGGCACATGGGACGTGTATGCCGACTACCTGGTGATACA GAGCGAGAAGGACGAGCTGTGA (SEQ ID NO: 123) |
| 2023 | BAASS:P77853m3 | MANKHLSLSLFLVLLG LSASLASGQQTSITLT SNASGTFDGYYYELWK DTGNTTMTVYTQGRFS CQWSNLPEEWVPLTKN GKSKTFRIGGFVDGLM KANQGKVKKTGDTEVL EVAGIHANSFDRKSKK SRTMAVKAVIRHRYSG NVYRIVLNSGRKITIT EGHSLFVYRNGDLVEA TGEDVKIGDNLAVPRS DGSGDITEDRVVEIKR EYYDGYVYDLSLDEDE NFLAGHGYLMAHNSNI NNALFRTGKKYNQNWQ SLGTIRITYSATYNPN GNSYLCIYGWSTNPLV EFYIVESWGNWRPPGA TSLGQVTIDGGTYDIY RTTRVNQPSIVGTATF DQYWSVRTSKRTSGTV TVTDHFRAWANRGLNL GTIDQITLCVEGYQSS GSANITQNTFSQGSSS GSSGGSSGSTTTTRIE CENMSLSGPYVSRITN PFNGIALYANGDTARA TVNFPASCNYNFRLRG CGNNNNLARVDLRIDG RTVGTFYYQGTYPWEA PIDNVYVSAGSHTVEI TVTADNGTWDVYADYL VIQ* (SEQ ID NO: 52) | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCTAATTTGCCAGAAGAGTGGGTTCCTTT AACTAAGAATGGTAAGTCAAAGACCTTTAGAATTGGAGGCTTCGTA GACGGTTTGATGAAGGCTAACCAAGGAAAGGTCAAGAAGACCGGTG ACACCGAAGTATTAGAGGTTGCAGGTATCCATGCCAATTCCTTTGA CAGAAAGTCAAAGAAGTCCAGAACCATGGCTGTAAAAGCAGTCATT AGACACAGATATTCCGGAAACGTGTACAGAATAGTTTTGAACTCCG GAAGAAAGATCACCATTACTGAGGGACATTCCTTATTCGTCTATAG AAACGGTGACTTGGTGGAAGCCACAGGTGAGGATGTAAAGATAGGT GATAACTTAGCTGTTCCAAGAAGCGACGGATCCGGAGACATTACTG AGGATAGAGTTGTAGAAATTAAGAGAGAGTACTACGACGGTTATGT CTATGACTTGTCATTGGATGAAGATGAAAATTTCTTGGCAGGACAC GGTTACTTGATGGCCCATAACTCGAACATCAATAACGCGTTGTTTA GGACCGGGAAGAAATACAACCAGAATTGGCAGTCTCTTGGCACAAT CCGGATCACGTACTCTGCGACTTACAACCCAAACGGGAACTCCTAC TTGTGTATCTATGGCTGGTCTACCAACCCATTGGTCGAGTTCTACA TCGTTGAGTCCTGGGGGAACTGGAGACCGCCTGGTGCCACGTCCCT GGGCCAAGTGACAATCGATGGCGGGACCTACGACATCTATAGGACG ACACGCGTCAACCAGCCTTCCATTGTGGGGACAGCCACGTTCGATC AGTACTGGAGCGTGCGCACCTCTAAGCGGACTTCAGGAACAGTGAC CGTGACCGATCACTTCCGCGCCTGGGCGAACCGGGGCCTGAACCTC GGCACAATAGACCAAATTACATTGTGCGTGGAGGGTTACCAAAGCT CTGGATCAGCCAACATCACCCAGAACACCTTCTCTCAGGGCTCTTC TTCCGGCAGTTCGGGTGGCTCATCCGGCTCCACAACGACTACTCGC ATCGAGTGTGAGAACATGTCCTTGTCCGGACCCTACGTTAGCAGGA TCACCAATCCCTTTAATGGTATTGCGCTGTACGCCAACGGAGACAC AGCCCGCGCTACCGTTAACTTCCCCGCAAGTTGCAACTACAATTTC CGCCTGCGGGGTTGCGGCAACAACAATAATCTTGCCCGTGTGGACC TGAGGATCGACGGACGACCGTCGGGACCTTTTATTACCAGGGCAC ATACCCCTGGGAGGCCCCAATTGACAATGTTTATGTCAGTGCGGGG AGTCATACAGTCGAAATCACTGTTACTGCGGATAACGGCACATGGG ACGTGTATGCCGACTACCTGGTGATACAGTGA (SEQ ID NO: 124) |
| 2024 | BAASS:P77853m3: SEKDEL | MANKHLSLSLFLVLLG LSASLASGQQTSITLT SNASGTFDGYYYELWK DTGNTTMTVYTQGRFS CQWSNLPEEWVPLTKN GKSKTFRIGGFVDGLM KANQGKVKKTGDTEVL EVAGIHANSFDRKSKK SRTMAVKAVIRHRYSG NVYRIVLNSGRKITIT EGHSLFVYRNGDLVEA TGEDVKIGDNLAVPRS DGSGDITEDRVVEIKR EYYDGYVYDLSLDEDE NFLAGHGYLMAHNSNI NNALFRTGKKYNQNWQ SLGTIRITYSATYNPN GNSYLCIYGWSTNPLV EFYIVESWGNWRPPGA TSLGQVTIDGGTYDIY RTTRVNQPSIVGTATF DQYWSVRTSKRTSGTV TVTDHFRAWANRGLNL GTIDQITLCVEGYQSS GSANITQNTFSQGSSS GSSGGSSGSTTTTRIE CENMSLSGPYVSRITN PFNGIALYANGDTARA TVNFPASCNYNFRLRG CGNNNNLARVDLRIDG RTVGTFYYQGTYPWEA PIDNVYVSAGSHTVEI TVTADNGTWDVYADYL | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCTAATTTGCCAGAAGAGTGGGTTCCTTT AACTAAGAATGGTAAGTCAAAGACCTTTAGAATTGGAGGCTTCGTA GACGGTTTGATGAAGGCTAACCAAGGAAAGGTCAAGAAGACCGGTG ACACCGAAGTATTAGAGGTTGCAGGTATCCATGCCAATTCCTTTGA CAGAAAGTCAAAGAAGTCCAGAACCATGGCTGTAAAAGCAGTCATT AGACACAGATATTCCGGAAACGTGTACAGAATAGTTTTGAACTCCG GAAGAAAGATCACCATTACTGAGGGACATTCCTTATTCGTCTATAG AAACGGTGACTTGGTGGAAGCCACAGGTGAGGATGTAAAGATAGGT GATAACTTAGCTGTTCCAAGAAGCGACGGATCCGGAGACATTACTG AGGATAGAGTTGTAGAAATTAAGAGAGAGTACTACGACGGTTATGT CTATGACTTGTCATTGGATGAAGATGAAAATTTCTTGGCAGGACAC GGTTACTTGATGGCCCATAACTCGAACATCAATAACGCGTTGTTTA GGACCGGGAAGAAATACAACCAGAATTGGCAGTCTCTTGGCACAAT CCGGATCACGTACTCTGCGACTTACAACCCAAACGGGAACTCCTAC TTGTGTATCTATGGCTGGTCTACCAACCCATTGGTCGAGTTCTACA TCGTTGAGTCCTGGGGGAACTGGAGACCGCCTGGTGCCACGTCCCT GGGCCAAGTGACAATCGATGGCGGGACCTACGACATCTATAGGACG ACACGCGTCAACCAGCCTTCCATTGTGGGGACAGCCACGTTCGATC AGTACTGGAGCGTGCGCACCTCTAAGCGGACTTCAGGAACAGTGAC CGTGACCGATCACTTCCGCGCCTGGGCGAACCGGGGCCTGAACCTC GGCACAATAGACCAAATTACATTGTGCGTGGAGGGTTACCAAAGCT CTGGATCAGCCAACATCACCCAGAACACCTTCTCTCAGGGCTCTTC TTCCGGCAGTTCGGGTGGCTCATCCGGCTCCACAACGACTACTCGC ATCGAGTGTGAGAACATGTCCTTGTCCGGACCCTACGTTAGCAGGA TCACCAATCCCTTTAATGGTATTGCGCTGTACGCCAACGGAGACAC AGCCCGCGCTACCGTTAACTTCCCCGCAAGTTGCAACTACAATTTC CGCCTGCGGGGTTGCGGCAACAACAATAATCTTGCCCGTGTGGACC TGAGGATCGACGGACGACCGTCGGGACCTTTTATTACCAGGGCAC ATACCCCTGGGAGGCCCCAATTGACAATGTTTATGTCAGTGCGGGG |

TABLE 1-continued

Sequences of CWDEs and their fusions in vectors

| pAG vector | Sequence annotation | Protein sequence | Nucleotide sequence |
|---|---|---|---|
| | | VIQSEKDEL* (SEQ ID NO: 53) | AGTCATACAGTCGAAATCACTGTTACTGCGGATAACGGCACATGGG ACGTGTATGCCGACTACCTGGTGATACAGAGCGAGAAGGACGAGCT GTGA (SEQ ID NO: 125) |
| 2025 | GluB4SP:P77853 | MATIAFSRLSIYFCVL LLCHGSMAQTSITLTS NASGTFDGYYYELWKD TGNTTMTVYTQGRFSC QWSNINNALFRTGKKY NQNWQSLGTIRITYSA TYNPNGNSYLCIYGWS TNPLVEFYIVESWGNW RPPGATSLGQVTIDGG TYDIYRTTRVNQPSIV GTATFDQYWSVRTSKR TSGTVTVTDHFRAWAN RGLNLGTIDQITLCVE GYQSSGSANITQNTFS QGSSSGSSGGSSGSTT TTRIECENMSLSGPYV SRITNPFNGIALYANG DTARATVNFPASRNYN FRLRGCGNNNNLARVD LRIDGRTVGTFYYQGT YPWEAPIDNVYSAGS HTVEITVTADNGTWDV YADYLVIQ* (SEQ ID NO: 54) | ATGGCCACCATCGCTTTCTCCCGCTTGTCCATCTACTTCTGCGTGC TTCTCCTGTGCCACGGCTCCATGGCCCAAACAAGCATTACTCTGAC ATCCAACGCCATCCGGTACGTTTGACGGTTACTATTACGAACTCTGG AAGGATACTGGCAATACAACAATGACGGTCTACACTCAAGGTCGCT TTTCCTGCCAGTGGTCGAACATCAATAACGCGTTGTTTAGGACCGG GAAGAAATACAACCAGAATTGGCAGTCTCTTGGCACAATCCGGATC ACGTACTCTGCGACTTACAACCCAAACGGGAACTCCTACTTGTGTA TCTATGGCTGGTCTACCAACCCATTGGTCGAGTTCTACATCGTTGA GTCCTGGGGAACTGGAGACCGCCTGGTGCCACGTCCCTGGGCCAA GTGACAATCGATGGCGGGACCTACGACATCTATAGGACGACACGCG TCAACCAGCCTTCCATTGTGGGGACAGCCACGTTCGATCAGTACTG GAGCGTGCGCACCTCTAAGCGGACTTCAGGAACAGTGACCGTGACC GATCACTTCCGCGCCTGGGCGAACCGGGGCCTGAACCTCGGCACAA TAGACCAAATTACATTGTGCGTGGAGGGTTACCAAAGCTCTGGATC AGCCAACATCACCCAGAACACCTTCTCTCAGGGCTCTTCTTCCGGC AGTTCGGGTGGCTCATCGGGCTCCACAACGACTACTCGCATCGAGT GTGAGAACATGTCCTTGTCCGGACCCTACGTTAGCAGGATCACCAA TCCCTTTAATGGTATTGCGCTGTACGCCAACGGAGACACAGCCCGC GCTACCGTTAACTTCCCCGCAAGTCGCAACTACAATTTCCGCCTGC GGGGTTGCGGCAACAACAATAATCTTGCCCGTGTGGACCTGAGGAT CGACGGACGGACCGTCGGGACCTTTTATTACCAGGGCACATACCCC TGGGAGGCCCCAATTGACAATGTTTATGTCAGTGCGGGGAGTCATA CAGTCGAAATCACTGTTACTGCGGATAACGGCACATGGGACGTGTA TGCCGACTACCTGGTGATACAGTGA (SEQ ID NO: 126) |
| 2026 | GluB4SP:O30700 | MATIAFSRLSIYFCVL LLCHGSMAVQPFAWQV ASLADRYEESFDIGAA VEPHQLNGRQGKVLKH HYNSIVAENAMKPISL QPEEGVFTWDGADAIV EFARKNNMNLRFHTLV WHNQVPDWFFLDEEGN PMVEETNEAKRQANKE LLLERLETHIKTVVER YKDDVTAWDVVNEVVD DGTPNERGLRESVWYQ ITGDEYIRVAFETARK YAGEDAKLFINDYNTE VTPKRDHLYNLVQDLL ADGVPIDGVGHQAHIQ IDWPTIDEIRTSMEMF AGLGLDNQVTELDVSL YGWPPRPAFPTYDAIP QERFQAQADRYNQLFE LYEELDADLSSVTFWG IADNHTWLDDRAREYN DGVGKDAPFVFDPNYR VKPAFWRIID* (SEQ ID NO: 55) | ATGGCCACCATCGCTTTCTCCCGCTTGTCCATCTACTTCTGCGTGC TTCTCCTGTGCCACGGCTCCATGGCCGTTCAGCCGTTCGCATGGCA GGTGGCATCCCTGGCTGACCGCTACGAAGAGAGCTTCGATATTGGA GCGGCGGTGGAACCTCACCAATTGAACGGTCGCCAGGGGAAGGTCC TGAAGCATCACTATAACTCAATCGTGGCCGAGAATGCTATGAAGCC GATCTCCCTCCAACCGGAAGAAGGAGTTTTCACGTGGGATGGAGCT GATGCAATAGTGGAGTTCGCGCGGAAAAATAACATGAACCTGCGCT TTCACACGCTCGTGTGGCATAACCAAGTGCCCGACTGGTTCTTCCT GGACGAAGAGGGTAACCCTATGGTCGAGGAGACTAACGAAGCGAAA AGGCAAGCGAATAAAGAGCTTTTGCTTGAGAGACTTGAGACTCATA TCAAAACTGTGGTCGAAAGGTACAAGGATGACGTTACGGCCTGGGA TGTGGTGAATGAGGTTGTGGACGATGGACACCCCAAATGAAAGGGGA CTGCGCGAGAGCGTTTGGTATCAGATTACAGGCGATGAATACATTA GAGTGGCATTCGAGACTGCGCGCAAGTACGCTGGCGAAGACGCTAA GCTGTTCATCAACGACTACAACACGGAGGTGACACCCAAGCGCGAT CACCTCTACAACTTGGTTCAAGACCTGCTCGCGGACGGGGTCCCGA TCGATGGAGTGGGACATCAAGCCCATATCCAGATCGATTGGCCCAC CATCGATGAGATCAGGACCTCGATGGAGATGTTTGCCGGCCTTGGG CTCGACAACCAAGTTACCGAACTCGATGTTTCCTTGTACGGTTGGC CGCCTCGCCCGGCATTCCCGACCTACGATGCAATCCCTCAAGAGAG GTTTCAGGCGCAGGCGGATAGATACAATCAGCTCTTCGAGCTTTAC GAGGAACTCGACGCTGACCTCTCAAGCGTGACCTTCTGGGGGATCG CGGACAACCATACCTGGCTCGACGACAGGGCCAGAGAATACAATGA CGGGGTCGGCAAAGATGCCCCGTTCGTCTTCGATCCGAACTACAGG GTTAAACCTGCCTTCTGGCGCATCATTGACTGA (SEQ ID NO: 127) |
| 2027 | GluB4SP:P40942 | MATIAFSRLSIYFCVL LLCHGSMAFNDQTSAE DIPSLAEAFRDYFPIG AAIEPGYTTGQIAELY KKHVNMLVAENAMKPA SLQPTEGNFQWADADR IVQFAKENGMELRFHT LVWHNQTPTGFSLDKE GKPMVEETDPQKREEN RKLLLQRLENYIRAVV LRYKDDIKSWDVVNEV IEPNDPGGMRNSPWYQ ITGTEYIEVAFRATRE AGGSDIKLYINDYNTD DPVKRDILYELVKNLL EKGVPIDGVGHQTHID IYNPPVERIIESIKKF AGLGLDNIITELDMSI YSWNDRSDYGDSIPDY | ATGGCCACCATCGCTTTCTCCCGCTTGTCCATCTACTTCTGCGTGC TTCTCCTGTGCCACGGCTCCATGGCCTTCAACGACCAGACAAGTGC AGAGGATATTCCGTCACTTGCCGAAGCGTTCAGGGACTATTTCCCT ATCGGAGCTGCCATTGAGCCGGGCTATACCACGGGTCAGATTGCCG AATTGTACAAGAAACACGTGAATATGCTGGTCGCGGAGAACGCTAT GAAGCCCGCCTCGCTCCAGCCGACGGAGGGTAATTTTCAGTGGGCC GACGCGGACCGCATTGTTCAGTTCGCTAAGGAAAACGGAATGGAGC TTCGGTTTCACACGTTGGTGTGGCACAATCAAACCCCAACTGGCTT CAGCCTGGATAAGGAAGGGAAACCTATGGTCGAGGAAACGGACCCT CAAAAGAGAGAAGAGAACAGGAAACTCCTTTTGCAGCGCCTCGAAA ACTATATCCGGGCCGTTGTGTTGAGATACAAGGATGACATCAAGTC CTGGGATGTTGTCAATGAGGTTATAGAACCAAACGACCCAGGGGGT ATGCGTAATTCTCCCTGGTATCAAATCACAGGAACCGAATATATTG AGGTCGCATTTCGCGCGACACTCGAGGCCGGGTCAGATATAAA GCTGTATATTAATGATTACAATACGGACGATCCTGTTAAACGGGAT ATACTCTACGAGCTTGTGAAGAACTTGCTGGAGAAAGGTGTCCCGA TTGATGGCGTGGACATCAGACACATATCGACATCTACAACCCACC CGTTGAAAGGATTATCGAGTCGATTAAGAAGTTCGCCGGACTCGGG CTTGATAATATCATTACCGAACTGGACATGAGCATCTATTCCTGGA |

TABLE 1-continued

Sequences of CWDEs and their fusions in vectors

| pAG vector | Sequence annotation | Protein sequence | Nucleotide sequence |
|---|---|---|---|
| | | ILTLQAKRYQELFDAL KENKDIVSAVVFWGIS DKYSWLNGFPVKRTNA PLLFDRNFMPKPAFWA IVDPSRLRE* (SEQ ID NO: 56) | ATGATCGCTCTGACTACGGTGATTCAATCCCTGACTATATTCTCAC CTTGCAGGCCAAAAGATACCAGGAGCTTTTCGATGCGCTGAAGGAG AATAAGGATATAGTCTCGGCTGTGGTCTTTTGGGGAATTAGCGACA AATACTCCTGGCTGAATGGCTTCCCGGTCAAGAGGACTAATGCCCC ATTGCTGTTTGATCGCAACTTTATGCCTAAACCAGCATTTTGGGCA ATCGTGGACCCGAGTAGACTCAGGGAATAA (SEQ ID NO: 128) |
| 2028 | PR1a:P77853T134-195 | MGFVLFSQLPSFLLVS TLLLFLVISHSCRAQQ TSITLTSNASGTFDGY YYELWKDTGNTTMTVY TQGRFSCQWSNINNAL FRTGKKYNQNWQSLGT IRITYSATYNPNGNSY LCIYGWSTNPLVEFYI VESWGNWRPPGACLAE GSLVLDAATGQRVPIE KVRPGMEVFSLGPDYR LYRVPVLEVLESGVRE VVRLRTRSGRTLVLTP DHPLLTPEGWKPLCDL PLGTPIAVPAELPVAG HLAPPEERVTLLALLL GDGNTKLSGRRGTRPN ASFYSKDPELLAAYRR CAEALGAKVKAYVHPT TGVVTLATLAPRPGAQ DPVKRLVVEAGMVAKA EEKRVPEEVFRYRREA LALFLGRLFSTDGSVE KKRISYSSASLGLAQD VAHLLLRLGIRSQLRS RGPRAHEVLISGREDI LRFAELIGPYLLGAKR ERLAALEAEARRRLPG QGWHLRLVLPAVAYRV SEAKRRSGFSWSEAGR RVAVAGSCLSSGLNLK LPRRYLSRHRLSLLGE AFADPGLEALAEGQVL WDPIVAVEPAGKARTF DLRVPPFANFVSEDLV VHNTSLGQVTIDGGTY DIYRTTRVNQPSIVGT ATFDQYWSVRTSKRTS GTVTVTDHFRAWANRG LNLGTIDQITLCVEGY QSSGSANITQNTFSQG SSSGSSGGSSGSTTTT RIECENMSLSGPYVSR ITNPFNGIALYANGDT ARATVNFPASRNYNFR LRGCGNNNNLARVDLR IDGRTVGTFYYQGTYP WEAPIDNVYSAGSHT VEITVTADNGTWDVYA DYLVIQ* (SEQ ID NO: 57) | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GCAAACAAGCATTACTCTGACATCCAACGCATCCGGTACGTTTGAC GGTTACTATTACGAACTCTGGAAGGATACTGGCAATACAACAATGA CGGTCTACACTCAAGGTCGCTTTTCCTGCCAGTGGTCGAACATCAA TAACGCGTTGTTTAGGACCGGGAAGAAATACAACCAGAATTGGCAG TCTCTTGGCACAATCCGGATCACGTACTCTGCGACTTACAACCCAA ACGGGAACTCCTACTTGTGTATCTATGGCTGGTCTACCAACCCATT GGTCGAGTTCTACATCGTTGAGTCCTGGGGGAACTGGAGACCGCCT GGTGCCTGCCTGGCCGAGGGCTCGCTCGTCTTGGACGCGGCTACCG GGCAGAGGGTCCCTATCGAAAAGGTGCGTCCGGGGATGGAAGTTTT CTCCTTGGGACCTGATTACAGACTGTATCGGGTGCCCGTTTTGGAG GTCCTTGAGAGCGGGGTTAGGGAAGTTGTGCGCCTCAGAACTCGGT CAGGGAGAACGCTGGTGTTGACACCAGATCACCCGCTTTTGACCCC CGAAGGTTGGAAACCTCTTTGTGACCTCCCGCTTGGAACTCCAATT GCAGTCCCCGCAGAACTGCCTGTGGCGGCCACTTGGCCCCACCTG AAGAACGTGTTACGCTCCTGGCTCTTCTGTTGGGGGATGGGAACAC AAAGCTGTCGGGTCGGAGAGGTACACGTCCTAATGCCTCCTTCTAC AGCAAAGACCCCGAATTGCTCGCGGCTTATCGCCGGTGTGCAGAAG CCTTGGGTGCAAAGGTGAAAGCATACGTCCACCCGACTACGGGGGT GGTTACACTCGCAACCCTCGCTCCACGTCCTGGAGCTCAAGATCCT GTCAAACGCCTCGTTGTCGAGGCGGGAATGGTTGCTAAAGCCGAAG AGAAGAGGGTCCCGGAGGAGGTGTTTCGTTACCGGCGTGAGGCGTT GGCCCTTTTTCTTGGGCGTTTGTTCTCGACAGACGGCTCTGTTGAA AAGAAGAGGATCTCTTATTCAAGTGCCAGTTTGGGACTGGCCCAGG ATGTCGCACATCTCTTGCTGCGCCTTGGAATTAGATCTCAACTCCG TTCGAGAGGCCACGGGCTCACGAGGTTCTTATATCGGGCCGCGAG GATATTTTGCGATTTGCTGAACTTATCGGACCCTACCTCTTGGGGG CCAAGAGGGAGAGACTTGCAGCGCTGGAAGCTGAGGCCCGCAGGCG TTTGCCTGGACAGGGATGGCACTTGCGGCTTGTTCTTCCTGCCGTG GCGTACAGAGTGAGCGAGGCTAAAAGGCGCTCGGGATTTTCGTGGA GTGAAGCCGGTCGGCGCGTCGCAGTTGCGGGATCGTGTTTGTCATC TGGACTCAACCTCAAATTGCCCAGACGCTACCTTTCTCGGCACCGG TTGTCGCTGCTCGGTGAGGCTTTTGCCGACCCTGGGCTGGAAGCGC TCGCGGAAGGCCAAGTGCTCTGGGACCCTATTGTTGCTGTCGAACC GGCCGGTAAGGCGAGAACATTCGACTTGCGCGTTCCACCCTTTGCA AACTTCGTGAGCGAGGACCTGGTGGTGCATAACACGTCCCTGGGCC AAGTGACAATCGATGGCGGGACCTACGACATCTATAGGACGACACG CGTCAACCAGCCTTCCATTGTGGGACAGCCACGTTCGATCAGTAC TGGAGCGTGCGCACCTCTAAGCGGACTTCAGGAACAGTGACCGTGA CCGATCACTTCCGCGCCTGGGCGAACATGGGACCCTGAACCTCGGCAC AATAGACCAAATTACATTGTGCGTGGAGGGTTACCAAAGCTCTGGA TCAGCCAACATCACCCAGAACACCTTCTCTCAGGGCTCTTCTTCCG GCAGTTCGGGTGGCTCATCCGGCTCCACAACGACTACTCGCATCGA GTGTGAGAACATGTCCTTGTCCGGACCCTACGTTAGCAGGATCACC AATCCCTTTAATGGTATTGCGCTGTACGCCAACGGAGACACAGCCC GCGCTACCGTTAACTTCCCCGCAAGTCGCAACTACAATTTCCGGCT GCGGGGTTGCGGCAACAACAATAATCTTGCCCGTGTGGACCTGAGG ATCGACGGACGGACCGTCGGGACCTTTTATTACCAGGGCACATACC CCTGGGAGGCCCCAATTGACAATGTTTATGTCAGTGCGGGGAGTCA TACAGTCGAAATCACTGTTACTGCGGATAACGGCACATGGGACGTG TATGCCGACTACCTGGTGATACAGTGA (SEQ ID NO: 129) |
| 2029 | BAASS:P77853T134-195 | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGACLAEGSLVLD AATGQRVPIEKVRPGM EVFSLGPDYRLYRVPV LEVLESGVREVVRLRT RSGRTLVLTPDHPLLT PEGWKPLCDLPLGTPI | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCTGCCTGGCCGAG GGCTCGCTCGTCTTGGACGCGGCTACCGGGCAGAGGGTCCCTATCG AAAAGGTGCGTCCGGGGATGGAAGTTTTCTCCTTGGGACCTGATTA CAGACTGTATCGGGTGCCCGTTTTGGAGGTCCTTGAGAGCGGGGTT AGGGAAGTTGTGCGCCTCAGAACTCGGTCAGGGAGAACGCTGGTGT TGACACCAGATCACCCGCTTTTGACCCCCGAAGGTTGGAAACCTCT |

TABLE 1-continued

Sequences of CWDEs and their fusions in vectors

| pAG vector | Sequence annotation | Protein sequence | Nucleotide sequence |
|---|---|---|---|
| | | AVPAELPVAGHLAPPE ERVTLLALLLGDGNTK LSGRRGTRPNASFYSK DPELLAAYRRCAEALG AKVKAYVHPTTGVVTL ATLAPRPGAQDPVKRL VVEAGMVAKAEEKRVP EEVFRYRREALALFLG RLFSTDGSVEKKRISY SSASLGLAQDVAHLLL RLGIRSQLRSRGPRAH EVLISGREDILRFAEL IGPYLLGAKRERLAAL EAEARRRLPGQGWHLR LVLPAVAYRVSEAKRR SGFSWSEAGRRVAVAG SCLSSGLNLKLPRRYL SRHRLSLLGEAFADPG LEALAEGQVLWDPIVA VEPAGKARTFDLRVPP FANFVSEDLVVHNTSL GQVTIDGGTYDIYRTT RVNQPSIVGTATFDQY WSVRTSKRTSGTVTVT DHFRAWANRGLNLGTI DQITLCVEGYQSSGSA NITQNTFSQGSSSGSS GGSSGSTTTTRIECEN MSLSGPYVSRITNPFN GIALYANGDTARATVN FPASRNYNFRLRGCGN NNNLARVDLRIDGRTV GTFYYQGTYPWEAPID NVYVSAGSHTVEITVT ADNGTWDVYADYLVIQ * (SEQ ID NO: 58) | TTGTGACCTCCCGCTTGGAACTCCAATTGCAGTCCCCGCAGAACTG CCTGTGGCGGGCCACTTGGCCCCACCTGAAGAACGTGTTACGCTCC TGGCTCTTCTGTTGGGGGATGGGAACACAAAGCTGTCGGGTCGGAG AGGTACACGTCCTAATGCCTCCTTCTACAGCAAAGACCCCGAATTG CTCGCGGCTTATCGCCGGTGTGCAGAAGCCTTGGGTGCAAAGGTGA AAGCATACGTCCACCCGACTACGGGGGTGGTTACACTCGCAACCCT CGCTCCACGTCCTGGAGCTCAAGATCCTGTCAAACGCCTCGTTGTC GAGGCGGGAATGGTTGCTAAAGCCGAAGAGAAGAGGGTCCCGGAGG AGGTGTTCGTTACCGGCGTGAGGCGTTGGCCCTTTTCTTGGGCCG TTTGTTCTCGACAGACGGCTCTGTTGAAAAGAAGAGGATCTCTTAT TCAAGTGCCAGTTTGGGACTGGCCCAGGATGTCGCACATCTCTTGC TGCGCCTTGGAATTAGATCTCAACTCCGTTCGAGAGGGCCACGGGC TCACGAGGTTCTTATATCGGGCCGCGAGGATATTTTGCGATTTGCT GAACTTATCGGACCCTACCTCTTGGGGGCCAAGAGGGAGAGACTTG CAGCGCTGGAAGCTGAGGCCCGCAGGCGTTTGCCTGGACAGGGATG GCACTTGCGGCTTGTTCTTCCTGCCGTGGCGTACAGAGTGAGCGAG GCTAAAAGGCGCTCGGGATTTTCGTGGAGTGAAGCCGGTCGGCGCG TCGCAGTTGCGGGATCGTGTTTGTCATCTGGACTCAACCTCAAATT GCCCAGACGCTACCTTTCTCGGCACCGGTTGTCGCTGCTCGGTGAG GCTTTTGCCGACCCTGGCTGGAAGCGCTCGCGGAAGGCCAAGTGC TCTGGGACCCTATTGTTGCTGTCGAACCGGCCGGTAAGGCGAGAAC ATTCGACTTGCGCGTTCCACCCTTTGCAAACTTCGTGAGCGAGGAC CTGGTGGTGCATAACACGTCCCTGGGCCAAGTGACAATCGATGGCG GGACCTACGACATCTATAGGACGACACGCGTCAACCAGCCTTCCAT TGTGGGGACAGCCACGTTCGATCAGTACTGGAGCGTGCGCACCTCT AAGCGGACTTCAGGAACAGTGACCGTGACCGATCACTTCCGCGCCT GGGCGAACCGGGGCCTGAACCTCGGCACAATAGACCAAATTACATT GTGCGTGGAGGGTTACCAAAGCTCTGGATCAGCCAACATCACCCAG AACACCTTCTCTCAGGGCTCTTCTTCCGGCAGTTCGGGTGGCTCAT CCGGCTCCACAACGACTACTCGCATCGAGTGTGAGAACATGTCCTT GTCCGGACCCTACGTTAGCAGGATCACCAATCCCTTTAATGGTATT GCGCTGTACGCCAACGGAGACACAGCCCGCGCTACCGTTAACTTCC CCGCAAGTCGCAACTACAATTTCCGCCTGCGGGGTTGCGGCAACAA CAATAATCTTGCCCGTGTGGACCTGAGGATCGACGGACGGACCGTC GGGACCTTTTATTACCAGGGCACATACCCCTGGGAGGCCCCAATTG ACAATGTTTATGTCAGTGCGGGGAGTCATACAGTCGAAATCACTGT TACTGCGGATAACGGCACATGGGACGTGTATGCCGACTACCTGGTG ATACAGTGA (SEQ ID NO: 130) |
| 2030 | P77853m3 | MQTSITLTSNASGTFD GYYYELWKDTGNTTMT VYTQGRFSCQWSNLPE EWVPLTKNGKSKTFRI GGFVDGLMKANQGKVK KTGDTEVLEVAGIHAN SFDRKSKKSRTMAVKA VIRHRYSGNVYRIVLN SGRKITITEGHSLFVY RNGDLVEATGEDVKIG DNLAVPRSDGSGDITE DRVVEIKREYYDGYVY DLSLDEDENFLAGHGY LMAHNSNINNALFRTG KKYNQNWQSLGTIRIT YSATYNPNGNSYLCIY GWSTNPLVEFYIVESW GNWRPPGATSLGQVTI DGGTYDIYRTTRVNQP SIVGTATFDQYWSVRT SKRTSGTVTVTDHFRA WANRGLNLGTIDQITL CVEGYQSSGSANITQN TFSQGSSSGSSGGSSG STTTTRIECENMSLSG PYVSRITNPFNGIALY ANGDTARATVNFPASC NYNFRLRGCGNNNNLA RVDLRIDGRTVGTFYY QGTYPWEAPIDNVYVS AGSHTVEITVTADNGT WDVYADYLVIQ* (SEQ ID NO: 59) | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGCTTTTCCTGCCAGTGGTCTAATTTG CCAGAAGAGTGGGTTCCTTTAACTAAGAATGGTAAGTCAAAGACCT TTAGAATTGGAGGCTTCGTAGACGGTTTGATGAAGGCTAACCAAGG AAAGGTCAAGAAGACCGGTGACACCGAAGTATTAGAGGTTGCAGGT ATCCATGCCAATTCCTTTGACAGAAAGTCAAAGAAGTCCAGAACCA TGGCTGTAAAAGCAGTCATTAGACACAGATATTCCGGAAACGTGTA CAGAATAGTTTTGAACTCCGGAAGAAAGATCACCATTACTGAGGGA CATTCCTTATTCGTCTATAGAAACGGTGACTTGGTGGAAGCCACAG GTGAGGATGTAAAGATAGGTGATAACTTAGCTGTTCCAAGAAGCGA CGGATCCGGAGACATTACTGAGGATAGAGTTGTAGAAATTAAGAGA GAGTACTACGACGGTTATGTCTATGACTTGTCATTGGATGAAGATG AAAATTTCTTGGCAGGACACGGTTACTTGATGGCCCATAACTCGAA CATCAATAACGCGTTGTTTAGGACCGGGAAGAAATACAACCAGAAT TGGCAGTCTCTTGGCACAATCCGGATCACGTACTCTGCGACTTACA ACCCAAACGGGAACTCCTACTTGTGTATCTATGGCTGGTCTACCAA CCCATTGGTCGAGTTCTACATCGTTGAGTCCTGGGGGAACTGGAGA CCGCCTGGTGCCACGTCCCTGGGCCAAGTGACAATCGATGGCGGA CCTACGACATCTATAGGACGACACGCGTCAACCAGCCTTCCATTGT GGGGACAGCCACGTTCGATCAGTACTGGAGCGTGCGCACCTCTAAG CGGACTTCAGGAACAGTGACCGTGACCGATCACTTCCGCGCCTGGG CGAACCGGGGCCTGAACCTCGGCACAATAGACCAAATTACATTGTG CGTGGAGGGTTACCAAAGCTCTGGATCAGCCAACATCACCCAGAAC ACCTTCTCTCAGGGCTCTTCTTCCGGCAGTTCGGGTGGCTCATCCG GCTCCACAACGACTACTCGCATCGAGTGTGAGAACATGTCCTTGTC CGGACCCTACGTTAGCAGGATCACCAATCCCTTTAATGGTATTGCG CTGTACGCCAACGGAGACACAGCCCGCGCTACCGTTAACTTCCCCG CAAGTTGCAACTACAATTTCCGCCTGCGGGGTTGCGGCAACAACAA CAATCTTGCCCGTGTGGACCTGAGGATCGACGGACGGACCGTCGGG ACCTTTTATTACCAGGGCACATACCCCTGGGAGGCCCCAATTGACA ATGTTTATGTCAGTGCGGGGAGTCATACAGTCGAAATCACTGTTAC TGCGGATAACGGCACATGGGACGTGTATGCCGACTACCTGGTGATA CAGTGA (SEQ ID NO: 131) |

TABLE 1-continued

Sequences of CWDEs and their fusions in vectors

| pAG vector | Sequence annotation | Protein sequence | Nucleotide sequence |
|---|---|---|---|
| 2031 | GluB4SP:P54583 | MATIAFSRLSIYFCVL LLCHGSMAAGGGYWHT SGREILDANNVPVRIA GINWFGFETCNYVVHG LWSRDYRSMLDQIKSL GYNTIRLPYSDDILKP GTMPNSINFYQMNQDL QGLTSLQVMDKIVAYA GQIGLRIILDRHRPDC SGQSALWYTSSVSEAT WISDLQALAQRYKGNP TVVGFDLHNEPHDPAC WGCGDPSIDWRLAAER AGNAVLSVNPNLLIFV EGVQSYNGDSYWWGGN LQGAGQYPVVLNVPNR LVYSAHDYATSVYPQT WFSDPTFPNNMPGIWN KNWGYLFNQNIAPVWL GEFGTTLQSTTDQTWL KTLVQYLRPTAQYGAD SFQWTFWSWNPDSGDT GGILKDDWQTVDTVKD GYLAPIKSSIFDPVGA SASPSSQPSPSVSPSP SPSPSASRTPTPTPTP TASPTPTLTPTATPTP TASPTPSPTAASGARC TASYQVNSDWGNGFTV TVAVTNSGSVATKTWT VSWTFGGNQTITNSWN AAVTQNGQSVTARNMS YNNVIQPGQNTTFGFQ ASYTGSNAAPTVACAA S* (SEQ ID NO: 60) | ATGGCCACCATCGCTTTCTCCCGCTTGTCCATCTACTTCTGCGTGC TTCTCCTGTGCCACGGCTCCATGGCCGCTGGAGGAGGATACTGGCA CACTTCCGGCAGGGAGATCCTCGACGCAAATAACGTTCCAGTCAGA ATCGCCGGGATTAATTGGTTTGGCTTCGAAACGTGTAACTACGTGG TTCACGGCCTGTGGTCTCGGGATTACAGATCAATGCTCGACCAGAT CAAATCCTTGGGGTATAATACAATTAGGCTGCCCTACAGCGATGAC ATTCTTAAGCCTGGAACCATGCCGAACTCGATTAATTTCTACCAAA TGAACCAGGATCTGCAGGGATTGACTTCTCTGCAGGTTATGGACAA GATCGTGGCGTACGCCGGCCAAATCGGGCTCAGAATTATTTTGGAT CGGCACAGGCCAGACTGCTCAGGTCAGTCGGCCCTGTGGTACACAA GCTCCGTGTCAGAGGCAACATGGATTTCAGATCTTCAAGCCCTCGC ACAACGCTATAAAGGCAACCCCACGGTTGTGGGATTCGACCTTCAC AACGAACCTCACGATCCGGCCTGTTGGGGCTGCGGGGACCCTTCGA TCGACTGGAGACTGGCAGCGGAGAGGGCTGGTAACGCCGTTCTCAG CGTCAATCCCAACTTGCTGATCTTTGTGGAGGGAGTTCAGTCCTAC AACGGCGATTCTTACTGGTGGGGCGGAAATCTCCAAGGCGCAGGGC AGTATCCTGTCGTGCTTAACGTTCCGAATCGCCTGGTCTACTCAGC ACACGACTACGCGACTAGCGTGTACCCACAGACGTGGTTCTCCGAT CCCACATTTCCTAACAATATGCCGGGAATCTGGAACAAGAATTGGG GTTACTTGTTTAACCAAACATTGCTTCCAGTTTGGTTGGGTGAATT TGGCACCACTCTTCAGTCGACGACAGACCAAACCTGGCTGAAAACC CTCGTCCAGTATTTGCGGCCAACTGCTCAGTACGGAGCAGATTCTT TTCAATGGACGTTCTGGTCTTGGAATCCTGACTCCGGGGATACAGG CGGTATCCTGAAAGACGATTGGCAGACCGTGGACACTGTTAAGGAC GGGTACTTGGCGCCGATTAAAAGCTCGATCTTTGACCCAGTCGGCG CTAGCGCTTCCCCATCTTCACAACCTTCGCCGAGCGTCAGCCCCAG CCCAAGCCCAAGCCCGTCTGCCAGCAGAACCCCCACTCCCACACCT ACCCCCACGGCTCACCAACTCCGACGCTCACTCCTACGGCGACGC CAACACCAACTGCTTCACCCACTCCTAGCCCCACCGCAGCGAGCGG GGCTAGGTGCACCGCTTCTTACCAGGTCAACTCTGACTGGGGTAAT GGCTTCACCGTGACTGTGGCGGTCACTAACTCAGGAAGCGTCGCGA CGAAAACCTGGACTGTGTCCTGGACGTTCGGGGGCAACCAAACAAT CACCAACAGCTGGAACGCTGCAGTTACGCAGAATGGGCAAAGCGTC ACGGCGCGCAATATGAGCTACAACAACGTGATTCAACCAGGCCAGA ATACCACATTCGGTTTTCAAGCAAGCTATACCGGGTCAAACGCTGC CCCAACTGTCGCTTGTGCTGCCTCATGA (SEQ ID NO: 132) |
| 2032 | GluB4SP:P54583: SEKDEL | MATIAFSRLSIYFCVL LLCHGSMAAGGGYWHT SGREILDANNVPVRIA GINWFGFETCNYVVHG LWSRDYRSMLDQIKSL GYNTIRLPYSDDILKP GTMPNSINFYQMNQDL QGLTSLQVMDKIVAYA GQIGLRIILDRHRPDC SGQSALWYTSSVSEAT WISDLQALAQRYKGNP TVVGFDLHNEPHDPAC WGCGDPSIDWRLAAER AGNAVLSVNPNLLIFV EGVQSYNGDSYWWGGN LQGAGQYPVVLNVPNR LVYSAHDYATSVYPQT WFSDPTFPNNMPGIWN KNWGYLFNQNIAPVWL GEFGTTLQSTTDQTWL KTLVQYLRPTAQYGAD SFQWTFWSWNPDSGDT GGILKDDWQTVDTVKD GYLAPIKSSIFDPVGA SASPSSQPSPSVSPSP SPSPSASRTPTPTPTP TASPTPTLTPTATPTP TASPTPSPTAASGARC TASYQVNSDWGNGFTV | ATGGCCACCATCGCTTTCTCCCGCTTGTCCATCTACTTCTGCGTGC TTCTCCTGTGCCACGGCTCCATGGCCGCTGGAGGAGGATACTGGCA CACTTCCGGCAGGGAGATCCTCGACGCAAATAACGTTCCAGTCAGA ATCGCCGGGATTAATTGGTTTGGCTTCGAAACGTGTAACTACGTGG TTCACGGCCTGTGGTCTCGGGATTACAGATCAATGCTCGACCAGAT CAAATCCTTGGGGTATAATACAATTAGGCTGCCCTACAGCGATGAC ATTCTTAAGCCTGGAACCATGCCGAACTCGATTAATTTCTACCAAA TGAACCAGGATCTGCAGGGATTGACTTCTCTGCAGGTTATGGACAA GATCGTGGCGTACGCCGGCCAAATCGGGCTCAGAATTATTTTGGAT CGGCACAGGCCAGACTGCTCAGGTCAGTCGGCCCTGTGGTACACAA GCTCCGTGTCAGAGGCAACATGGATTTCAGATCTTCAAGCCCTCGC ACAACGCTATAAAGGCAACCCCACGGTTGTGGGATTCGACCTTCAC AACGAACCTCACGATCCGGCCTGTTGGGGCTGCGGGGACCCTTCGA TCGACTGGAGACTGGCAGCGGAGAGGGCTGGTAACGCCGTTCTCAG CGTCAATCCCAACTTGCTGATCTTTGTGGAGGGAGTTCAGTCCTAC AACGGCGATTCTTACTGGTGGGGCGGAAATCTCCAAGGCGCAGGGC AGTATCCTGTCGTGCTTAACGTTCCGAATCGCCTGGTCTACTCAGC ACACGACTACGCGACTAGCGTGTACCCACAGACGTGGTTCTCCGAT CCCACATTTCCTAACAATATGCCGGGAATCTGGAACAAGAATTGGG GTTACTTGTTTAACCAAACATTGCTTCCAGTTTGGTTGGGTGAATT TGGCACCACTCTTCAGTCGACGACAGACCAAACCTGGCTGAAAACC CTCGTCCAGTATTTGCGGCCAACTGCTCAGTACGGAGCAGATTCTT TTCAATGGACGTTCTGGTCTTGGAATCCTGACTCCGGGGATACAGG CGGTATCCTGAAAGACGATTGGCAGACCGTGGACACTGTTAAGGAC GGGTACTTGGCGCCGATTAAAAGCTCGATCTTTGACCCAGTCGGCG CTAGCGCTTCCCCATCTTCACAACCTTCGCCGAGCGTCAGCCCCAG CCCAAGCCCAAGCCCGTCTGCCAGCAGAACCCCCACTCCCACACCT ACCCCCACGGCTCACCAACTCCGACGCTCACTCCTACGGCGACGC CAACACCAACTGCTTCACCCACTCCTAGCCCCACCGCAGCGAGCGG |

TABLE 1-continued

Sequences of CWDEs and their fusions in vectors

| pAG vector | Sequence annotation | Protein sequence | Nucleotide sequence |
|---|---|---|---|
| | | TVAVTNSGSVATKTWT VSWTFGGNQTITNSWN AAVTQNGQSVTARNMS YNNVIQPGQNTTFGFQ ASYTGSNAAPTVACAA SSEKDEL* (SEQ ID NO: 61) | GGCTAGGTGCACCGCTTCTTACCAGGTCAACTCTGACTGGGGTAAT GGCTTCACCGTGACTGTGGCGGTCACTAACTCAGGAAGCGTCGCGA CGAAAACCTGGACTGTGTCCTGGACGTTCGGGGGCAACCAAACAAT CACCAACAGCTGGAACGCTGCAGTTACGCAGAATGGGCAAAGCGTC ACGGCGCGCAATATGAGCTACAACAACGTGATTCAACCAGGCCAGA ATACCACATTCGGTTTTCAAGCAAGCTATACCGGGTCAAACGCTGC CCCAACTGTCGCTTGTGCTGCCTCAAGCGAGAAGGACGAGCTGTGA (SEQ ID NO: 133) |
| 2033 | P54583 | MAGGGYWHTSGREILD ANNVPVRIAGINWFGF ETCNYVVHGLWSRDYR SMLDQIKSLGYNTIRL PYSDDILKPGTMPNSI NFYQMNQDLQGLTSLQ VMDKIVAYAGQIGLRI ILDRHRPDCSGQSALW YTSSVSEATWISDLQA LAQRYKGNPTVVGFDL HNEPHDPACWGCGDPS IDWRLAAERAGNAVLS VNPNLLIFVEGVQSYN GDSYWWGGNLQGAGQY PVVLNVPNRLVYSAHD YATSVYPQTWFSDPTF PNNMPGIWNKNWGYLF NQNIAPVWLGEFGTTL QSTTDQTWLKTLVQYL RPTAQYGADSFQWTFW SWNPDSGDTGGILKDD WQTVDTVKDGYLAPIK SSIFDPVGASASPSSQ PSPSVSPSPSPSPSAS RTPTPTPTPTASPTPT LTPTATPTPTASPTPS PTAASGARCTASYQVN SDWGNGFTVTVAVTNS GSVATKTWTVSWTFGG NQTITNSWNAAVTQNG QSVTARNMSYNNVIQP GQNTTFGFQASYTGSN AAPTVACAAS* (SEQ ID NO: 62) | ATGGCTGGAGGAGGATACTGGCACACTTCCGGCAGGGAGATCCTCG ACGCAAATAACGTTCCAGTCAGAATCGCCGGGATTAATTGGTTTGG CTTCGAAACGTGTAACTACGTGGTTCACGGCCTGTGGTCTCGGGAT TACAGATCAATGCTCGACCAGATCAAATCCTTGGGGTATAATACAA TTAGGCTGCCCTACAGCGATGACATTCTTAAGCCTGGAACCATGCC GAACTCGATTAATTTCTACCAAATGAACCAGGATCTGCAGGGATTG ACTTCTCTGCAGGTTATGGACAAGATCGTGGCGTACGCCGGCCAAA TCGGGCTCAGAATTATTTTGGATCGGCACAGGCCAGACTGCTCAGG TCAGTCGGCCCTGTGGTACACAAGCTCCGTGTCAGAGGCAACATGG ATTTCAGATCTTCAAGCCCTCGCACAACGCTATAAAGGCAACCCCA CGGTTGTGGGATTCGACCTTCACAACGAACCTCACGATCCGGCCTG TTGGGGCTGCGGGGACCCTTCGATCGACTGGAGACTGGCAGCGGAG AGGGCTGGTAACGCCGTTCTCAGCGTCAATCCCAACTTGCTGATCT TTGTGGAGGGAGTTCAGTCCTACAACGGCGATTCTTACTGGTGGGG CGGAAATCTCCAAGGCGCAGGGCAGTATCCTGTCGTGCTTAACGTT CCGAATCGCCTGGTCTACTCAGCACACGACTACGCGACTAGCGTGT ACCCACAGACGTGGTTCTCCGATCCCACATTTCCTAACAATATGCC GGGAATCTGGAACAAGAATTGGGGTTACTTGTTTAACCAAAACATT GCTCCAGTTTGGTTGGGTGAATTTGGCACCACTCTTCAGTCGACGA CAGACCAAACCTGGCTGAAAACCCTCGTCCAGTATTTGCGGCCAAC TGCTCAGTACGGAGCAGATTCTTTTCAATGGACGTTCTGGTCTTGG AATCCTGACTCCGGGGATACAGGCGGTATCCTGAAAGACGATTGGC AGACCGTGGACACTGTTAAGGACGGGTACTTGGCGCCGATTAAAG CTCGATCTTTGACCCAGTCGGCGCTAGCGCTTCCCCATCTTCACAA CCTTCGCCGAGCGTCAGCCCCAGCCCAAGCCCAAGCCCGTCTGCCA GCAGAACCCCCACTCCCACACCTACCCCCACGGCCTCACCAACTCC GACGCTCACTCCTACGGCGACGCCAACACCAACTGCTTCACCCACT CCTAGCCCCACCGCAGCGAGCGGGGCTAGGTGCACCGCTTCTTACC AGGTCAACTCTGACTGGGGTAATGGCTTCACCGTGACTGTGGCGGT CACTAACTCAGGAAGCGTCGCGACGAAAACCTGGACTGTGTCCTGG ACGTTCGGGGGCAACCAAACAATCACCAACAGCTGGAACGCTGCAG TTACGCAGAATGGGCAAAGCGTCACGGCGCGCAATATGAGCTACAA CAACGTGATTCAACCAGGCCAGAATACCACATTCGGTTTTCAAGCA AGCTATACCGGGTCAAACGCTGCCCCAACTGTCGCTTGTGCTGCCT CATGA (SEQ ID NO: 134) |
| 2034 | P54583:SEKDEL | MAGGGYWHTSGREILD ANNVPVRIAGINWFGF ETCNYVVHGLWSRDYR SMLDQIKSLGYNTIRL PYSDDILKPGTMPNSI NFYQMNQDLQGLTSLQ VMDKIVAYAGQIGLRI ILDRHRPDCSGQSALW YTSSVSEATWISDLQA LAQRYKGNPTVVGFDL HNEPHDPACWGCGDPS IDWRLAAERAGNAVLS VNPNLLIFVEGVQSYN GDSYWWGGNLQGAGQY PVVLNVPNRLVYSAHD YATSVYPQTWFSDPTF PNNMPGIWNKNWGYLF NQNIAPVWLGEFGTTL QSTTDQTWLKTLVQYL RPTAQYGADSFQWTFW SWNPDSGDTGGILKDD WQTVDTVKDGYLAPIK SSIFDPVGASASPSSQ PSPSVSPSPSPSPSAS RTPTPTPTPTASPTPT LTPTATPTPTASPTPS PTAASGARCTASYQVN SDWGNGFTVTVAVTNS GSVATKTWTVSWTFGG NQTITNSWNAAVTQNG | ATGGCTGGAGGAGGATACTGGCACACTTCCGGCAGGGAGATCCTCG ACGCAAATAACGTTCCAGTCAGAATCGCCGGGATTAATTGGTTTGG CTTCGAAACGTGTAACTACGTGGTTCACGGCCTGTGGTCTCGGGAT TACAGATCAATGCTCGACCAGATCAAATCCTTGGGGTATAATACAA TTAGGCTGCCCTACAGCGATGACATTCTTAAGCCTGGAACCATGCC GAACTCGATTAATTTCTACCAAATGAACCAGGATCTGCAGGGATTG ACTTCTCTGCAGGTTATGGACAAGATCGTGGCGTACGCCGGCCAAA TCGGGCTCAGAATTATTTTGGATCGGCACAGGCCAGACTGCTCAGG TCAGTCGGCCCTGTGGTACACAAGCTCCGTGTCAGAGGCAACATGG ATTTCAGATCTTCAAGCCCTCGCACAACGCTATAAAGGCAACCCCA CGGTTGTGGGATTCGACCTTCACAACGAACCTCACGATCCGGCCTG TTGGGGCTGCGGGGACCCTTCGATCGACTGGAGACTGGCAGCGGAG AGGGCTGGTAACGCCGTTCTCAGCGTCAATCCCAACTTGCTGATCT TTGTGGAGGGAGTTCAGTCCTACAACGGCGATTCTTACTGGTGGGG CGGAAATCTCCAAGGCGCAGGGCAGTATCCTGTCGTGCTTAACGTT CCGAATCGCCTGGTCTACTCAGCACACGACTACGCGACTAGCGTGT ACCCACAGACGTGGTTCTCCGATCCCACATTTCCTAACAATATGCC GGGAATCTGGAACAAGAATTGGGGTTACTTGTTTAACCAAAACATT GCTCCAGTTTGGTTGGGTGAATTTGGCACCACTCTTCAGTCGACGA CAGACCAAACCTGGCTGAAAACCCTCGTCCAGTATTTGCGGCCAAC TGCTCAGTACGGAGCAGATTCTTTTCAATGGACGTTCTGGTCTTGG AATCCTGACTCCGGGGATACAGGCGGTATCCTGAAAGACGATTGGC AGACCGTGGACACTGTTAAGGACGGGTACTTGGCGCCGATTAAAG CTCGATCTTTGACCCAGTCGGCGCTAGCGCTTCCCCATCTTCACAA CCTTCGCCGAGCGTCAGCCCCAGCCCAAGCCCAAGCCCGTCTGCCA GCAGAACCCCCACTCCCACACCTACCCCCACGGCCTCACCAACTCC GACGCTCACTCCTACGGCGACGCCAACACCAACTGCTTCACCCACT CCTAGCCCCACCGCAGCGAGCGGGGCTAGGTGCACCGCTTCTTACC AGGTCAACTCTGACTGGGGTAATGGCTTCACCGTGACTGTGGCGGT CACTAACTCAGGAAGCGTCGCGACGAAAACCTGGACTGTGTCCTGG |

TABLE 1-continued

Sequences of CWDEs and their fusions in vectors

| pAG vector | Sequence annotation | Protein sequence | Nucleotide sequence |
|---|---|---|---|
| | | QSVTARNMSYNNVIQP GQNTTFGFQASYTGSN AAPTVACAASSEKDEL * (SEQ ID NO: 63) | ACGTTCGGGGGCAACCAAACAATCACCAACAGCTGGAACGCTGCAG TTACGCAGAATGGGCAAAGCGTCACGGCGCGCAATATGAGCTACAA CAACGTGATTCAACCAGGCCAGAATACCACATTCGGTTTTCAAGCA AGCTATACCGGGTCAAACGCTGCCCCAACTGTCGCTTGTGCTGCCT CAAGCGAGAAGGACGAGCTGTGA (SEQ ID NO: 135) |
| 2035 | PR1a:P54583 | MGFVLFSQLPSFLLVS TLLLFLVISHSCRAQN AGGGYWHTSGREILDA NNVPVRIAGINWFGFE TCNYVVHGLWSRDYRS MLDQIKSLGYNTIRLP YSDDILKPGTMPNSIN FYQMNQDLQGLTSLQV MDKIVAYAGQIGLRII LDRHRPDCSGQSALWY TSSVSEATWISDLQAL AQRYKGNPTVVGFDLH NEPHDPACWGCGDPSI DWRLAAERAGNAVLSV NPNLLIFVEGVQSYNG DSYWWGGNLQGAGQYP VVLNVPNRLVYSAHDY ATSVYPQTWFSDPTFP NNMPGIWNKNWGYLFN QNIAPVWLGEFGTTLQ STTDQTWLKTLVQYLR PTAQYGADSFQWTFWS WNPDSGDTGGILKDDW QTVDTVKDGYLAPIKS SIFDPVGASASPSSQP SPSVSPSPSPSPSASR TPTPTPTPTASPTPTL TPTATPTPTASPTPSP TAASGARCTASYQVNS DWGNGFTVTVAVTNSG SVATKTWTVSWTFGGN QTITNSWNAAVTQNGQ SVTARNMSYNNVIQPG QNTTFGFQASYTGSNA APTVACAAS* (SEQ ID NO: 64) | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GAACGCTGGAGGAGGATACTGGCACACTTCCGGCAGGGAGATCCTC GACGCAAATAACGTTCCAGTCAGAATCGCCGGGATTAATTGGTTTG GCTTCGAAACGTGTAACTACGTGGTTCACGGCCTGTGGTCTCGGGA TTACAGATCAATGCTCGACCAGATCAAATCCTTGGGGTATAATACA ATTAGGCTGCCCTACAGCGATGACATTCTTAAGCCTGGAACCATGC CGAACTCGATTAATTTCTACCAAATGAACCAGGATCTGCAGGGATT GACTTCTCTGCAGGTTATGGACAAGATCGTGGCGTACGCCGGCCAA ATCGGGCTCAGAATTATTTTGGATCGGCACAGGCCAGACTGCTCAG GTCAGTCGGCCCTGTGGTACACAAGCTCCGTGTCAGAGGCAACATG GATTTCAGATCTTCAAGCCCTCGCACAACGCTATAAAGGCAACCCC ACGGTTGTGGGATTCGACCTTCACAACGAACCTCACGATCCGGCCT GTTGGGGCTGCGGGGACCCTTCGATCGACTGGAGACTGGCAGCGGA GAGGGCTGGTAACGCCGTTCTCAGCGTCAATCCCAACTTGCTGATC TTTGTGGAGGGAGTTCAGTCCTACAACGGCGATTCTTACTGGTGGG GCGGAAATCTCCAAGGCGCAGGGCAGTATCCTGTCGTGCTTAACGT TCCGAATCGCCTGGTCTACTCAGCACACGACTACGCGACTAGCGTG TACCACAGACGTGGTTCTCCGATCCCACATTTCCTAACAATATGC CGGGAATCTGGAACAAGAATTGGGGTTACTTGTTTAACCAAAACAT TGCTCCAGTTTGGTTGGGTGAATTTGGCACCACTCTTCAGTCGACG ACAGACCAAACCTGGCTGAAAACCCTCGTCCAGTATTTGCGGCCAA CTGCTCAGTACGGAGCAGATTCTTTTCAATGGACGTTCTGGTCTTG GAATCCTGACTCCGGGGATACAGGCGGTATCCTGAAAGACGATTGG CAGACCGTGGACACTGTTAAGGACGGGTACTTGGCGCCGATTAAA GCTCGATCTTTGACCCAGTCGGCGCTAGCGCTTCCCCATCTTCACA ACCTTCGCCGAGCGTCAGCCCCAGCCCAAGCCCAAGCCCGTCTGCC AGCAGAACCCCACTCCCACACCTACCCCCACGGCCTCACCAACTC CGACGCTCACTCCTACGGCGACGCCAACACCAACTGCTTCACCCAC TCCTAGCCCCACCGCAGCGAGCGGGCTAGGTGCACCGCTTCTTAC CAGGTCAACTCTGACTGGGGTAATGGCTTCACCGTGACTGTGGCGG TCACTAACTCAGGAAGCGTCGCGACGAAAACCTGGACTGTGTCCTG GACGTTCGGGGGCAACCAAACAATCACCAACAGCTGGAACGCTGCA GTTACGCAGAATGGGCAAAGCGTCACGGCGCGCAATATGAGCTACA ACAACGTGATTCAACCAGGCCAGAATACCACATTCGGTTTTCAAGC AAGCTATACCGGGTCAAACGCTGCCCCAACTGTCGCTTGTGCTGCC TCATGA (SEQ ID NO: 136) |
| 2036 | PR1a:P54583:SEKDEL | MGFVLFSQLPSFLLVS TLLLFLVISHSCRAQN AGGGYWHTSGREILDA NNVPVRIAGINWFGFE TCNYVVHGLWSRDYRS MLDQIKSLGYNTIRLP YSDDILKPGTMPNSIN FYQMNQDLQGLTSLQV MDKIVAYAGQIGLRII LDRHRPDCSGQSALWY TSSVSEATWISDLQAL AQRYKGNPTVVGFDLH NEPHDPACWGCGDPSI DWRLAAERAGNAVLSV NPNLLIFVEGVQSYNG DSYWWGGNLQGAGQYP VVLNVPNRLVYSAHDY ATSVYPQTWFSDPTFP NNMPGIWNKNWGYLFN QNIAPVWLGEFGTTLQ STTDQTWLKTLVQYLR PTAQYGADSFQWTFWS WNPDSGDTGGILKDDW QTVDTVKDGYLAPIKS SIFDPVGASASPSSQP SPSVSPSPSPSPSASR TPTPTPTPTASPTPTL TPTATPTPTASPTPSP TAASGARCTASYQVNS DWGNGFTVTVAVTNSG SVATKTWTVSWTFGGN | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GAACGCTGGAGGAGGATACTGGCACACTTCCGGCAGGGAGATCCTC GACGCAAATAACGTTCCAGTCAGAATCGCCGGGATTAATTGGTTTG GCTTCGAAACGTGTAACTACGTGGTTCACGGCCTGTGGTCTCGGGA TTACAGATCAATGCTCGACCAGATCAAATCCTTGGGGTATAATACA ATTAGGCTGCCCTACAGCGATGACATTCTTAAGCCTGGAACCATGC CGAACTCGATTAATTTCTACCAAATGAACCAGGATCTGCAGGGATT GACTTCTCTGCAGGTTATGGACAAGATCGTGGCGTACGCCGGCCAA ATCGGGCTCAGAATTATTTTGGATCGGCACAGGCCAGACTGCTCAG GTCAGTCGGCCCTGTGGTACACAAGCTCCGTGTCAGAGGCAACATG GATTTCAGATCTTCAAGCCCTCGCACAACGCTATAAAGGCAACCCC ACGGTTGTGGGATTCGACCTTCACAACGAACCTCACGATCCGGCCT GTTGGGGCTGCGGGGACCCTTCGATCGACTGGAGACTGGCAGCGGA GAGGGCTGGTAACGCCGTTCTCAGCGTCAATCCCAACTTGCTGATC TTTGTGGAGGGAGTTCAGTCCTACAACGGCGATTCTTACTGGTGGG GCGGAAATCTCCAAGGCGCAGGGCAGTATCCTGTCGTGCTTAACGT TCCGAATCGCCTGGTCTACTCAGCACACGACTACGCGACTAGCGTG TACCACAGACGTGGTTCTCCGATCCCACATTTCCTAACAATATGC CGGGAATCTGGAACAAGAATTGGGGTTACTTGTTTAACCAAAACAT TGCTCCAGTTTGGTTGGGTGAATTTGGCACCACTCTTCAGTCGACG ACAGACCAAACCTGGCTGAAAACCCTCGTCCAGTATTTGCGGCCAA CTGCTCAGTACGGAGCAGATTCTTTTCAATGGACGTTCTGGTCTTG GAATCCTGACTCCGGGGATACAGGCGGTATCCTGAAAGACGATTGG CAGACCGTGGACACTGTTAAGGACGGGTACTTGGCGCCGATTAAA GCTCGATCTTTGACCCAGTCGGCGCTAGCGCTTCCCCATCTTCACA ACCTTCGCCGAGCGTCAGCCCCAGCCCAAGCCCAAGCCCGTCTGCC AGCAGAACCCCACTCCCACACCTACCCCCACGGCCTCACCAACTC CGACGCTCACTCCTACGGCGACGCCAACACCAACTGCTTCACCCAC TCCTAGCCCCACCGCAGCGAGCGGGCTAGGTGCACCGCTTCTTAC CAGGTCAACTCTGACTGGGGTAATGGCTTCACCGTGACTGTGGCGG |

TABLE 1-continued

Sequences of CWDEs and their fusions in vectors

| pAG vector | Sequence annotation | Protein sequence | Nucleotide sequence |
|---|---|---|---|
| | | QTITNSWNAAVTQNGQ SVTARNMSYNNVIQPG QNTTFGFQASYTGSNA APTVACAASSEKDEL* (SEQ ID NO: 65) | TCACTAACTCAGGAAGCGTCGCGACGAAAACCTGGACTGTGTCCTG GACGTTCGGGGCAACCAAACAATCACCAACAGCTGGAACGCTGCA GTTACGCAGAATGGGCAAAGCGTCACGGCGCGCAATATGAGCTACA ACAACGTGATTCAACCAGGCCAGAATACCACATTCGGTTTTCAAGC AAGCTATACCGGGTCAAACGCTGCCCCAACTGTCGCTTGTGCTGCC TCAAGCGAGAAGGACGAGCTGTGA (SEQ ID NO: 137) |
| 2037 | BAASS:P54583 | MANKHLSLSLFLVLLG LSASLASGQVAGGGYW HTSGREILDANNVPVR IAGINWFGPETCNYVV HGLWSRDYRSMLDQIK SLGYNTIRLPYSDDIL KPGTMPNSINFYQMNQ DLQGLTSLQVMDKIVA YAGQIGLRIILDRHRP DCSGQSALWYTSSVSE ATWISDLQALAQRYKG NPTVVGFDLHNEPHDP ACWGCGDPSIDWRLAA ERAGNAVLSVNPNLLI FVEGVQSYNGDSYWWG GNLQGAGQYPVVLNVP NRLVYSAHDYATSVYP QTWFSDPTFPNNMPGI WNKNWGYLFNQNIAPV WLGEFGTTLQSTTDQT WLKTLVQYLRPTAQYG ADSFQWTFWSWNPDSG DTGGILKDDWQTVDTV KDGYLAPIKSSIFDPV GASASPSSQPSPSVSP SPSPSPSASRTPTPTP TPTASPTPTLTPTATP TPTASPTPSPTAASGA RCTASYQVNSDWGNGF TVTVAVTNSGSVATKT WTVSWTFGGNQTITNS WNAAVTQNGQSVTARN MSYNNVIQPGQNTTFG FQASYTGSNAAPTVAC AAS* (SEQ ID NO: 66) | ATGGCGAACAAACATTTGTCCCTCTCCCTCTTCCTCGTCCTCCTTG GCCTGTCGGCCAGCTTGGCCTCCGGGCAAGTCGCTGGAGGAGGATA CTGGCACACTTCCGGCAGGGAGATCCTCGACGCAAATAACGTTCCA GTCAGAATCGCCGGGATTAATTGGTTTGGCTTCGAAACGTGTAACT ACGTGGTTCACGGCCTGTGGTCTCGGGATTACAGATCAATGCTCGA CCAGATCAAATCCTTGGGTATAATACAATTAGGCTGCCCTACAGC GATGACATTCTTAAGCCTGGAACCATGCCGAACTCGATTAATTTCT ACCAAATGAACCAGGATCTGCAGGGATTGACTTCTCTGCAGGTTAT GGACAAGATCGTGGCGTACGCCGGCCAAATCGGGCTCAGAATTATT TTGGATCGGCACAGGCCAGACTGCTCAGGTCAGTCGGCCCTGTGGT ACACAAGCTCCGTGTCAGAGGCAACATGGATTTCAGATCTTCAAGC CCTCGCACAACGCTATAAAGGCAACCCCACGGTTGTGGGATTCGAC CTTCACAACGAACCTCACGATCCGGCCTGTTGGGGCTGCGGGGACC CTTCGATCGACTGGAGACTGGCAGCGGAGAGGGCTGGTAACGCCGT TCTCAGCGTCAATCCCAACTTGCTGATCTTTGTGGAGGGAGTTCAG TCCTACAACGGCGATTCTTACTGGTGGGGCGGAAATCTCCAAGGCG CAGGGCAGTATCCTGTCGTGCTTAACGTTCCGAATCGCCTGGTCTA CTCAGCACACGACTACGCGACTAGCGTGTACCCACAGACGTGGTTC TCCGATCCCACATTTCCTAACAATATGCCGGGAATCTGGAACAAGA ATTGGGGTTACTTGTTTAACCAAAACATTGCTCCAGTTTGGTTGGG TGAATTTGGCACCACTCTTCAGTCGACGACAGACCAAACCTGGCTG AAAACCCTCGTCCAGTATTTGCGGCCAACTGCTCAGTACGGAGCAG ATTCTTTTCAATGGACGTTCTGGTCTTGGAATCCTGACTCCGGGGA TACAGGCGGTATCCTGAAAGACGATTGGCAGACCGTGGACACTGTT AAGGACGGGTACTTGGCGCCGATTAAAAGCTCGATCTTTGACCCAG TCGGCGCTAGCGCTTCCCCATCTTCACAACCTTCGCCGAGCGTCAG CCCCAGCCCAAGCCCAAGCCCGTCTGCCAGCAGAACCCCCACTCCC ACACCTACCCCACGGCCTCACCAACTCCGACGCTCACTCCTACGG CGACGCCAACACCAACTGCTTCACCCACTCCTAGCCCCACCGCAGC GAGCGGGGCTAGGTGCACCGCTTCTTACCAGGTCAACTCTGACTGG GGTAATGGCTTCACCGTGACTGTGGCGGTCACTAACTCAGGAAGCG TCGCGACGAAAACCTGGACTGTGTCCTGGACGTTCGGGGGCAACCA AACAATCACCAACAGCTGGAACGCTGCAGTTACGCAGAATGGGCAA AGCGTCACGGCGCGCAATATGAGCTACAACAACGTGATTCAACCAG GCCAGAATACCACATTCGGTTTTCAAGCAAGCTATACCGGGTCAAA CGCTGCCCCAACTGTCGCTTGTGCTGCCTCATGA (SEQ ID NO: 138) |
| 2038 | BAASS:P54583:SEKDEL | MANKHLSLSLFLVLLG LSASLASGQVAGGGYW HTSGREILDANNVPVR IAGINWFGPETCNYVV HGLWSRDYRSMLDQIK SLGYNTIRLPYSDDIL KPGTMPNSINFYQMNQ DLQGLTSLQVMDKIVA YAGQIGLRIILDRHRP DCSGQSALWYTSSVSE ATWISDLQALAQRYKG NPTVVGFDLHNEPHDP ACWGCGDPSIDWRLAA ERAGNAVLSVNPNLLI FVEGVQSYNGDSYWWG GNLQGAGQYPVVLNVP NRLVYSAHDYATSVYP QTWFSDPTFPNNMPGI WNKNWGYLFNQNIAPV WLGEFGTTLQSTTDQT WLKTLVQYLRPTAQYG ADSFQWTFWSWNPDSG DTGGILKDDWQTVDTV KDGYLAPIKSSIFDPV GASASPSSQPSPSVSP SPSPSPSASRTPTPTP TPTASPTPTLTPTATP TPTASPTPSPTAASGA RCTASYQVNSDWGNGF TVTVAVTNSGSVATKT | ATGGCGAACAAACATTTGTCCCTCTCCCTCTTCCTCGTCCTCCTTG GCCTGTCGGCCAGCTTGGCCTCCGGGCAAGTCGCTGGAGGAGGATA CTGGCACACTTCCGGCAGGGAGATCCTCGACGCAAATAACGTTCCA GTCAGAATCGCCGGGATTAATTGGTTTGGCTTCGAAACGTGTAACT ACGTGGTTCACGGCCTGTGGTCTCGGGATTACAGATCAATGCTCGA CCAGATCAAATCCTTGGGTATAATACAATTAGGCTGCCCTACAGC GATGACATTCTTAAGCCTGGAACCATGCCGAACTCGATTAATTTCT ACCAAATGAACCAGGATCTGCAGGGATTGACTTCTCTGCAGGTTAT GGACAAGATCGTGGCGTACGCCGGCCAAATCGGGCTCAGAATTATT TTGGATCGGCACAGGCCAGACTGCTCAGGTCAGTCGGCCCTGTGGT ACACAAGCTCCGTGTCAGAGGCAACATGGATTTCAGATCTTCAAGC CCTCGCACAACGCTATAAAGGCAACCCCACGGTTGTGGGATTCGAC CTTCACAACGAACCTCACGATCCGGCCTGTTGGGGCTGCGGGGACC CTTCGATCGACTGGAGACTGGCAGCGGAGAGGGCTGGTAACGCCGT TCTCAGCGTCAATCCCAACTTGCTGATCTTTGTGGAGGGAGTTCAG TCCTACAACGGCGATTCTTACTGGTGGGGCGGAAATCTCCAAGGCG CAGGGCAGTATCCTGTCGTGCTTAACGTTCCGAATCGCCTGGTCTA CTCAGCACACGACTACGCGACTAGCGTGTACCCACAGACGTGGTTC TCCGATCCCACATTTCCTAACAATATGCCGGGAATCTGGAACAAGA ATTGGGGTTACTTGTTTAACCAAAACATTGCTCCAGTTTGGTTGGG TGAATTTGGCACCACTCTTCAGTCGACGACAGACCAAACCTGGCTG AAAACCCTCGTCCAGTATTTGCGGCCAACTGCTCAGTACGGAGCAG ATTCTTTTCAATGGACGTTCTGGTCTTGGAATCCTGACTCCGGGGA TACAGGCGGTATCCTGAAAGACGATTGGCAGACCGTGGACACTGTT AAGGACGGGTACTTGGCGCCGATTAAAAGCTCGATCTTTGACCCAG TCGGCGCTAGCGCTTCCCCATCTTCACAACCTTCGCCGAGCGTCAG CCCCAGCCCAAGCCCAAGCCCGTCTGCCAGCAGAACCCCCACTCCC ACACCTACCCCACGGCCTCACCAACTCCGACGCTCACTCCTACGG CGACGCCAACACCAACTGCTTCACCCACTCCTAGCCCCACCGCAGC GAGCGGGGCTAGGTGCACCGCTTCTTACCAGGTCAACTCTGACTGG |

TABLE 1-continued

Sequences of CWDEs and their fusions in vectors

| pAG vector | Sequence annotation | Protein sequence | Nucleotide sequence |
|---|---|---|---|
| | | WTVSWTFGGNQTITNS WNAAVTQNGQSVTARN MSYNNVIQPGQNTTFG FQASYTGSNAAPTVAC AASSEKDEL* (SEQ ID NO: 67) | GGTAATGGCTTCACCGTGACTGTGGCGGTCACTAACTCAGGAAGCG TCGCGACGAAAACCTGGACTGTGTCCTGGACGTTCGGGGGCAACCA AACAATCACCAACAGCTGGAACGCTGCAGTTACGCAGAATGGGCAA AGCGTCACGGCGCGCAATATGAGCTACAACAACGTGATTCAACCAG GCCAGAATACCACATTCGGTTTTCAAGCAAGCTATACCGGGTCAAA CGCTGCCCCAACTGTCGCTTGTGCTGCCTCAAGCGAGAAGGACGAG CTGTGA (SEQ ID NO: 139) |
| 2040 | PR1a:NtEGm | MGFVLFSQLPSFLLVS TLLLFLVISHSCRAAY DYKQVLRDSLLFYEAQ RSGRLPADQKVTWRKD SALNDQGDQGQDLTGG YFDAGDFVKFGFPMAY TATVLAWGLIDFEAGY SSAGALDDGRKAVKWA TDYFIKAHTSQNEFYG QVGQGDADHAFWGRPE DMTMARPAYKIDTSRP GSDLAGETAAALAAAS IVFRNVDGTYSNNLLT HARQLFDFANNYRGKY SDSITDARNFYASADY RDELVWAAAWLYRATN DNTYLNTAESLYDEFG LQNWGGGLNWDSKVSG VQVLLAKLTNKQAYKD TVQSYVNYLINNQQKT PKGLLYIDMWGTLRHA ANAAFIMLEAAELGLS ASSYRQFAQTQIDYAL GDGGRSFVCGFGSNPP TRPHHRSSSCPPAPAT CDWNTFNSPDPNYHVL SGALVGGPDQNDNYVD DRSDYVHNEVATDYNA GFQSALAALVALGY* (SEQ ID NO: 68) | ATGGGCTTCGTGCTCTTCTCCCAGCTGCCTTCCTTCCTTCTTGTCT CCACCCTGCTCTTGTTCCTCGTGATCTCCCACTCCTGCCGCGCCGC TTACGACTACAAGCAGGTGTTGCGGGACTCGCTACTATTCTATGAG GCCCAGAGATCCGGCCGGCTCCCAGCCGACCAGAAGGTCACGTGGA GGAAGGATAGCGCGCTGAATGACCAGGGTGACCAGGGACAAGACTT GACCGGCGGCTACTTTGACGCTGGGGACTTCGTCAAGTTCGGGTTC CCCATGGCTTATACCGCAACCGTGCTGGCATGGGGCCTCATAGATT TTGAGGCCGGCTACAGCAGTGCCGGGGCCTTGGATGATGGACGGAA GGCTGTCAAATGGGCCACCGACTATTTCATAAAGGCCCACACAAGT CAAAATGAGTTCTATGGTCAGGTCGGCCAGGGTGACGCCGATCACG CTTTCTGGGGAAGACCAGAGGATATGACGATGGCGCGCCCGGCGTA CAAGATAGACACCTCAAGGCCTGGCTCTGATCTGGCAGGCGAGACA GCGGCTGCTCTTGCCGCTGCTTCAATCGTGTTCCGGAACGTCGATG GCACTTACTCAAATAACCTGTTAACACACGCTCGCCAGCTATTCGA CTTCGCGAACAACTACCGGGGAAAGTATAGTGACTCTATTACTGAC GCAAGAAATTTCTACGCAAGCGCAGACTACAGAGACGAGTTGGTTT GGGCTGCTGCGTGGTTATACAGAGCGACCAACGACAACACCTACCT CAACACTGCTGAGTCACTGTACGATGAGTTTGGGCTACAGAACTGG GGGGGGGGCCTGAACTGGGATAGCAAGGTGTCTGGCGTGCAGGTGT TGTTGGCCAAGCTTACCAATAAGCAGGCCTACAAGGACACGGTGCA GTCTTACGTCAATTACCTAATTAATAACCAGCAGAAGACTCCCAAG CCCAAAGGCCTCCTCTACATCGACATGTGGGGCACCCTTCGCCACG CTGCCAACGCCGCATTCATCATGCTCGAAGCCGCCGAGCTGGGCTT GTCCGCCTCCTCTTATAGACAGTTCGCGCAAACGCAAATCGACTAC GCCCTGGGCGATGGTGGCCGCTCCTTTGTGTGCGGGTTCGGGAGTA ATCCTCCTACGAGACCGCACCACAGATCCTCGTCGTGCCCGCCAGC TCCCGCTACTTGCGACTGGAATACATTCAACTCACCTGACCCAAAC TACCACGTCCTCTCTGGGGCCCTAGTGGGCGGACCTGATCAGAATG ACAACTACGTCGATGACCGTTCAGACTATGTTCACAACGAAGTCGC CACTGATTACAACGCGGGTTTCCAGTCCGCGTTAGCTGCTTTGGTG GCCCTTGGTTACTGA (SEQ ID NO: 140) |
| 2041 | GluB4SP:NtEGm | MATIAFSRLSIYFCVL LLCHGSMAAYDYKQVL RDSLLFYEAQRSGRLP ADQKVTWRKDSALNDQ GDQGQDLTGGYFDAGD FVKFGFPMAYTATVLA WGLIDFEAGYSSAGAL DDGRKAVKWATDYFIK AHTSQNEFYGQVGQGD ADHAFWGRPEDMTMAR PAYKIDTSRPGSDLAG ETAAALAAASIVFRNV DGTYSNNLLTHARQLF DFANNYRGKYSDSITD ARNFYASADYRDELVW AAAWLYRATNDNTYLN TAESLYDEFGLQNWGG GLNWDSKVSGVQVLLA KLTNKQAYKDTVQSYV NYLINNQQKTPKGLLY IDMWGTLRHAANAAFI MLEAAELGLSASSYRQ FAQTQIDYALGDGGRS FVCGFGSNPPTRPHHR SSSCPPAPATCDWNTF NSPDPNYHVLSGALVG GPDQNDNYVDDRSDYV HNEVATDYNAGFQSAL AALVALGY* (SEQ ID NO: 69) | ATGGCCACCATCGCTTTCTCCCGCTTGTCCATCTACTTCTGCGTGC TTCTCCTGTGCCACGGCTCCATGGCCGCTTACGACTACAAGCAGGT GTTGCGGGACTCGCTACTATTCTATGAGGCCCAGAGATCCGGCCGG CTCCCAGCCGACCAGAAGGTCACGTGGAGGAAGGATAGCGCGCTGA ATGACCAGGGTGACCAGGGACAAGACTTGACCGGCGGCTACTTTGA CGCTGGGGACTTCGTCAAGTTCGGGTTCCCCATGGCTTATACCGCA ACCGTGCTGGCATGGGGCCTCATAGATTTTGAGGCCGGCTACAGCA GTGCCGGGGCCTTGGATGATGGACGGAAGGCTGTCAAATGGGCCAC CGACTATTTCATAAAGGCCCACACAAGTCAAAATGAGTTCTATGGT CAGGTCGGCCAGGGTGACGCCGATCACGCTTTCTGGGGAAGACCAG AGGATATGACGATGGCGCGCCCGGCGTACAAGATAGACACCTCAAG GCCTGGCTCTGATCTGGCAGGCGAGACAGCGGCTGCTCTTGCCGCT GCTTCAATCGTGTTCCGGAACGTCGATGGCACTTACTCAAATAACC TGTTAACACACGCTCGCCAGCTATTCGACTTCGCGAACAACTACCG GGGAAAGTATAGTGACTCTATTACTGACGCAAGAAATTTCTACGCA AGCGCAGACTACAGAGACGAGTTGGTTTGGGCTGCTGCGTGGTTAT ACAGAGCGACCAACGACAACACCTACCTCAACACTGCTGAGTCACT GTACGATGAGTTTGGGCTACAGAACTGGGGGGGGGGCCTGAACTGG GATAGCAAGGTGTCTGGCGTGCAGGTGTTGTTGGCCAAGCTTACCA ATAAGCAGGCCTACAAGGACACGGTGCAGTCTTACGTCAATTACCT AATTAATAACCAGCAGAAGACTCCCAAGGGCCTCCTCTACATCGAC ATGTGGGGCACCCTTCGCCACGCTGCCAACGCCGCATTCATCATGC TCGAAGCCGCCGAGCTGGGCTTGTCCGCCTCCTCTTATAGACAGTT CGCGCAAACGCAAATCGACTACGCCCTGGGCGATGGTGGCCGCTCC TTTGTGTGCGGGTTCGGGAGTAATCCTCCTACGAGACCGCACCACA GATCCTCGTCGTGCCCGCCAGCTCCCGCTACTTGCGACTGGAATAC ATTCAACTCACCTGACCCAAACTACCACGTCCTCTCTGGGGCCCTA GTGGGCGGACCTGATCAGAATGACAACTACGTCGATGACCGTTCAG ACTATGTTCACAACGAAGTCGCCACTGATTACAACGCGGGTTTCCA GTCCGCGTTAGCTGCTTTGGTGGCCCTTGGTTACTGA (SEQ ID NO: 141) |
| 2042 | HvAleSP:P54583 | MAHARVLLLALAVLAT AAVAVASSSSFADSNP IRPVTDRAASTAGGGY | ATGGCCCACGCCCGCGTCCTCCTCCTGGCGCTCGCCGTCCTGGCCA CCGCCGCCGTCGCCGTCGCCTCCTCCTCCTCCTTCGCCGACTCCAA CCCCGATCCGCCCGGTGACCGACCGCGCCGCCTCCACCGCTGGAGGA |

TABLE 1-continued

Sequences of CWDEs and their fusions in vectors

| pAG vector | Sequence annotation | Protein sequence | Nucleotide sequence |
|---|---|---|---|
| | | WHTSGREILDANNVPV RIAGINWFGFETCNYV VHGLWSRDYRSMLDQI KSLGYNTIRLPYSDDI LKPGTMPNSINFYQMN QDLQGLTSLQVMDKIV AYAGQIGLRIILDRHR PDCSGQSALWYTSSVS EATWISDLQALAQRYK GNPTVVGFDLHNEPHD PACWGCGDPSIDWRLA AERAGNAVLSVNPNLL IFVEGVQSYNGDSYWW GGNLQGAGQYPVVLNV PNRLVYSAHDYATSVY PQTWFSDPTFPNNMPG IWNKNWGYLFNQNIAP VWLGEFGTTLQSTTDQ TWLKTLVQYLRPTAQY GADSFQWTFWSWNPDS GDTGGILKDDWQTVDT VKDGYLAPIKSSIFDP VGASASPSSQPSPSVS PSPSPSPSASRTPTPT PTPTASPTPTLTPTAT PTPTASPTPSPTAASG ARCTASYQVNSDWGNG FTVTVAVTNSGSVATK TWTVSWTFGGNQTITN SWNAAVTQNGQSVTAR NMSYNNVIQPGQNTTF GFQASYTGSNAAPTVA CAAS* (SEQ ID NO: 70) | GGATACTGGCACACTTCCGGCAGGGAGATCCTCGACGCAAATAACG TTCCAGTCAGAATCGCCGGGATTAATTGGTTTGGCTTCGAAACGTG TAACTACGTGGTTCACGGCCTGTGGTCTCGGGATTACAGATCAATG CTCGACCAGATCAAATCCTTGGGGTATAATACAATTAGGCTGCCCT ACAGCGATGACATTCTTAAGCCTGGAACCATGCCGAACTCGATTAA TTTCTACCAAATGAACCAGGATCTGCAGGGATTGACTTCTCTGCAG GTTATGGACAAGATCGTGGCGTACGCCGGCCAAATCGGGCTCAGAA TTATTTTGGATCGGCACAGGCCAGACTGCTCAGGTCAGTCGGCCCT GTGGTACACAAGCTCCGTGTCAGAGGCAACATGGATTTCAGATCTT CAAGCCCTCGCACAACGCTATAAAGGCAACCCCACGGTTGTGGGAT TCGACCTTCACAACGAACCTCACGATCCGGCCTGTTGGGGCTGCGG GGACCCTTCGATCGACTGGAGACTGGCAGCGGAGAGGGCTGGTAAC GCCGTTCTCAGCGTCAATCCCAACTTGCTGATCTTTGTGGAGGGAG TTCAGTCCTACAACGGCGATTCTTACTGGTGGGGCGGAAATCTCCA AGGCGCAGGGCAGTATCCTGTCGTGCTTAACGTTCCGAATCGCCTG GTCTACTCAGCACACGACTACGCGACTAGCGTGTACCCACAGACGT GGTTCTCCGATCCCACATTTCCTAACAATATGCCGGGAATCTGGAA CAAGAATTGGGGTTACTTGTTTAACCAAAACATTGCTCCAGTTTGG TTGGGTGAATTTGGCACCACTCTTCAGTCGACGACAGACCAAACCT GGCTGAAAACCCTCGTCCAGTATTTGCGGCCAACTGCTCAGTACGG AGCAGATTCTTTTCAATGGACGTTCTGGTCTTGGAATCCTGACTCC GGGGATACAGGCGGTATCCTGAAAGACGATTGGCAGACCGTGGACA CTGTTAAGGACGGGTACTTGGCGCCGATTAAAAGCTCGATCTTTGA CCCCAGTCGGCGCTAGCGCTTCCCCATCTTCACAACCTTCGCCGAGC GTCAGCCCCAGCCCAAGCCCAAGCCCGTCTGCCAGCAGAACCCCCA CTCCCACACCTACCCCCACGGCCTCACCAACTCCGACGCTCACTCC TACGGCGACGCCAACACCAACTGCTTCACCCACTCCTAGCCCCACC GCAGCGAGCGGGGCTAGGTGCACCGCTTCTTACCAGGTCAACTCTG ACTGGGGTAATGGCTTCACCGTGACTGTGGCGGTCACTAACTCAGG AAGCGTCGCGACGAAAACCTGGACTGTGTCCTGGACGTTCGGGGGC AACCAAACAATCACCAACAGCTGGAACGCTGCAGTTACGCAGAATG GGCAAAGCGTCACGGCGCGCAATATGAGCTACAACAACGTGATTCA ACCAGGCCAGAATACCACATTCGGTTTTCAAGCAAGCTATACCGGG TCAAACGCTGCCCCAACTGTCGCTTGTGCTGCCTCATGA (SEQ ID NO: 142) |
| 2043 | NtEGm | MAYDYKQVLRDSLLFY EAQRSGRLPADQKVTW RKDSALNDQGDQGQDL TGGYFDAGDFVKFGFP MAYTATVLAWGLIDFE AGYSSAGALDDGRKAV KWATDYFIKAHTSQNE FYGQVGQGDADHAFWG RPEDMTMARPAYKIDT SRPGSDLAGETAAALA AASIVFRNVDGTYSNN LLTHARQLFDFANNYR GKYSDSITDARNFYAS ADYRDELVWAAAWLYR ATNDNTYLNTAESLYD EFGLQNWGGGLNWDSK VSGVQVLLAKLTNKQA YKDTVQSYVNYLINNQ QKTPKGLLYIDMWGTL RHAANAAFIMLEAAEL GLSASSYRQFAQTQID YALGDGGRSFVCGFGS NPPTRPHHRSSSCPPA PATCDWNTFNSPDPNY HVLSGALVGGPDQNDN YVDDRSDYVHNEVATD YNAGFQSALAALVALG Y* (SEQ ID NO: 71) | ATGGCTTACGACTACAAGCAGGTGTTGCGGGACTCGCTACTATTCT ATGAGGCCCAGAGATCCGGCCGGCTCCCAGCCGACCAGAAGGTCAC GTGGAGGAAGGATAGCGCGCTGAATGACCAGGGTGACCAGGGACAA GACTTGACCGGCGGCTACTTTGACGCTGGGGACTTCGTCAAGTTCG GGTTCCCCATGGCTTATACCGCAACCGTGCTGGCATGGGGCCTCAT AGATTTTGAGGCCGGCTACAGCAGTGCCGGGGCCTTGGATGATGGA CGGAAGGCTGTCAAATGGGCCACCGACTATTTCATAAAGGCCCACA CAAGTCAAAATGAGTTCTATGGTCAGGTCGGCCAGGGTGACGCCGA TCACGCTTTCTGGGGAAGACCAGAGGATATGACGATGGCGCGCCG GCGTACAAGATAGACACCTCAAGGCCTGGCTCTGATCTGGCAGGCG AGACAGCGGCTGCTCTTGCCGCTGCTTCAATCGTGTTCCGGAACGT CGATGGCACTTACTCAAATAACCTGTTAACACACGCTCGCCAGCTA TTCGACTTCGCGAACAACTACCGGGGAAAGTATAGTGACTCTATTA CTGACGCAAGAAATTTCTACGCAAGCGCAGACTACAGAGACGAGTT GGTTTGGGCTGCTGCGTGGTTATACAGAGCGACCAACGACAACACC TACCTCAACACTGCTGAGTCACTGTACGATGAGTTTGGGCTACAGA ACTGGGGGGGGGGGCCTGAACTGGGATAGCAAGGTGTCTGGCGTGCA GGTGTTGTTGGCCAAGCTTACCAATAAGCAGGCCTACAAGGACACG CAGTCTTACGTCAATTACCTAATTAATAACCAGCAGAAGACTC CCAAGGGCCTCCTCTACATCGACATGTGGGGCACCCTTCGCCACGC TGCCAACGCCGCATTCATCATGCTCGAAGCCGCCGAGCTGGGCTTG TCCGCCTCCTCTTATAGACAGTTCGCGCAAACGCAAATCGACTACG CCCTGGGCGATGGTGGCCGCTCCTTCGTGTGCGGGTTCGGGAGTAA TCCTCCTACGAGACCGCACCACAGATCCTCGTCGTGCCCGCCAGCT CCCGCTACTTGCGACTGGAATACATTCAACTCACCTGACCCAAACT ACCACGTCCTCTCTGGGGCCCTAGTGGGCGGACCTGATCAGAATGA CAACTACGTCGATGACCGTTCAGATATGTTCACAACGAAGTCGCC ACTGATTACAACGCGGGTTTCCAGTCCGCGTTAGCTGCTTTGGTGG CCCTTGGTTACTGA (SEQ ID NO: 143) |
| 2044 | PR1a:NtEGm | MGFVLFSQLPSFLLVS TLLLFLVISHSCRAAY DYKQVLRDSLLFYEAQ RSGRLPADQKVTWRKD SALNDQGDQGQDLTGG YFDAGDFVKFGFPMAY TATVLAWGLIDFEAGY SSAGALDDGRKAVKWA TDYFIKAHTSQNEFYG | ATGGGCTTCGTGCTCTTCTCCCAGCTGCCTTCCTTCCTTCTTGTCT CCACCCTGCTCTTGTTCCTCGTGATCTCCCACTCCTGCCGCGCCGC TTACGACTACAAGCAGGTGTTGCGGGACTCGCTACTATTCTATGAG GCCCAGAGATCCGGCCGGCTCCCAGCCGACCAGAAGGTCACGTGGA GGAAGGATAGCGCGCTGAATGACCAGGGTGACCAGGGACAAGACTT GACCGGCGGCTACTTTGACGCTGGGGACTTCGTCAAGTTCGGGTTC CCCATGGCTTATACCGCAACCGTGCTGGCATGGGGCCTCATAGATT TTGAGGCCGGCTACAGCAGTGCCGGGGCCTTGGATGATGGACGGAA GGCTGTCAAATGGGCCACCGACTATTTCATAAAGGCCCACACAAGT |

TABLE 1-continued

Sequences of CWDEs and their fusions in vectors

| pAG vector | Sequence annotation | Protein sequence | Nucleotide sequence |
|---|---|---|---|
| | | QVGQGDADHAFWGRPE DMTMARPAYKIDTSRP GSDLAGETAAALAAAS IVFRNVDGTYSNNLLT HARQLFDFANNYRGKY SDSITDARNFYASADY RDELVWAAAWLYRATN DNTYLNTAESLYDEFG LQNWGGGLNWDSKVSG VQVLLAKLTNKQAYKD TVQSYVNYLINNQQKT PKGLLYIDMWGTLRHA ANAAFIMLEAAELGLS ASSYRQFAQTQIDYAL GDGGRSFVCGFGSNPP TRPHHRSSSCPPAPAT CDWNTFNSPDPNYHVL SGALVGGPDQNDNYVD DRSDYVHNEVATDYNA GFQSALAALVALGY* (SEQ ID NO: 72) | CAAAATGAGTTCTATGGTCAGGTCGGCCAGGGTGACGCCGATCACG CTTTCTGGGGAAGACCAGAGGATATGACGATGGCGCGCCCGGCGTA CAAGATAGACACCTCAAGGCCTGGCTCTGATCTGGCAGGCGAGACA GCGGCTGCTCTTGCCGCTGCTTCAATCGTGTTCCGGAACGTCGATG GCACTTACTCAAATAACCTGTTAACACACGCTCGCCAGCTATTCGA CTTCGCGAACAACTACCGGGGAAAGTATAGTGACTCTATTACTGAC GCAAGAAATTTCTACGCAAGCGCAGACTACAGAGACGAGTTGGTTT GGGCTGCTGCGTGGTTATACAGAGCGACCAACGACAACACCTACCT CAACACTGCTGAGTCACTGTACGATGAGTTTGGGCTACAGAACTGG GGGGGGGGCCTGAACTGGGATAGCAAGGTGTCTGGCGTGCAGGTGT TGTTGGCCAAGCTTACCAATAAGCAGGCCTACAAGGACACGGTGCA GTCTTACGTCAATTACCTAATTAATAACCAGCAGAAGACTCCCAAG GGCCTCCTCTACATCGACATGTGGGGCACCCTTCGCCACGCTGCCA ACGCCGCATTCATCATGCTCGAAGCCGCCGAGCTGGGCTTGTCCGC CTCCTCTTATAGACAGTTCGCGCAAACGCAAATCGACTACGCCCTG GGCGATGGTGGCCGCTCCTTTGTGTGCGGGTTCGGGAGTAATCCTC CTACGAGACCGCACCACAGATCCTCGTCGTGCCCGCCAGCTCCCGC TACTTGCGACTGGAATACATTCAACTCACCTGACCCAAACTACCAC GTCCTCTCTGGGGCCCTAGTGGGCGGACCTGATCAGAATGACAACT ACGTCGATGACCGTTCAGACTATGTTCACAACGAAGTCGCCACTGA TTACAACGCGGGTTTCCAGTCCGCGTTAGCTGCTTTGGTGGCCCTT GGTTACTGA (SEQ ID NO: 144) |
| 2045 | PR1a:NtEGm:SEKDEL | MGFVLFSQLPSFLLVS TLLLFLVISHSCRAAY DYKQVLRDSLLFYEAQ RSGRLPADQKVTWRKD SALNDQGDQGQDLTGG YFDAGDFVKFGFPMAY TATVLAWGLIDFEAGY SSAGALDDGRKAVKWA TDYFIKAHTSQNEFYG QVGQGDADHAFWGRPE DMTMARPAYKIDTSRP GSDLAGETAAALAAAS IVFRNVDGTYSNNLLT HARQLFDFANNYRGKY SDSITDARNFYASADY RDELVWAAAWLYRATN DNTYLNTAESLYDEFG LQNWGGGLNWDSKVSG VQVLLAKLTNKQAYKD TVQSYVNYLINNQQKT PKGLLYIDMWGTLRHA ANAAFIMLEAAELGLS ASSYRQFAQTQIDYAL GDGGRSFVCGFGSNPP TRPHHRSSSCPPAPAT CDWNTFNSPDPNYHVL SGALVGGPDQNDNYVD DRSDYVHNEVATDYNA GFQSALAALVALGYSE KDEL* (SEQ ID NO: 73) | ATGGGCTTCGTGCTCTTCTCCCAGCTGCCTTCCTTCCTTCTTGTCT CCACCCTGCTCTTGTTCCTCGTGATCTCCCACTCCTGCCGCGCCGC TTACGACTACAAGGAGGTGTTGCGGGACTCGCTACTATTCTATGAG GCCCAGAGATCCGGCCGGCTCCCAGCCGACCAGAAGGTCACGTGGA GGAAGGATAGCGCGCTGAATGACCAGGGTGACCAGGGACAAGACTT GACCGGCGGCTACTTTGACGCTGGGGACTTCGTCAAGTTCGGGTTC CCCATGGCTTATACCGCAACCGTGCTGGCATGGGGCCTCATAGATT TTGAGGCCGGCTACAGCAGTGCCGGGGCCTTGGATGATGGACGGAA GGCTGTCAAATGGGCCACCGACTATTTCATAAAGGCCCACACAAGT CAAAATGAGTTCTATGGTCAGGTCGGCCAGGGTGACGCCGATCACG CTTTCTGGGGAAGACCAGAGGATATGACGATGGCGCGCCCGGCGTA CAAGATAGACACCTCAAGGCCTGGCTCTGATCTGGCAGGCGAGACA GCGGCTGCTCTTGCCGCTGCTTCAATCGTGTTCCGGAACGTCGATG GCACTTACTCAAATAACCTGTTAACACACGCTCGCCAGCTATTCGA CTTCGCGAACAACTACCGGGGAAAGTATAGTGACTCTATTACTGAC GCAAGAAATTTCTACGCAAGCGCAGACTACAGAGACGAGTTGGTTT GGGCTGCTGCGTGGTTATACAGAGCGACCAACGACAACACCTACCT CAACACTGCTGAGTCACTGTACGATGAGTTTGGGCTACAGAACTGG GGGGGGGGCCTGAACTGGGATAGCAAGGTGTCTGGCGTGCAGGTGT TGTTGGCCAAGCTTACCAATAAGCAGGCCTACAAGGACACGGTGCA GTCTTACGTCAATTACCTAATTAATAACCAGCAGAAGACTCCCAAG GGCCTCCTCTACATCGACATGTGGGGCACCCTTCGCCACGCTGCCA ACGCCGCATTCATCATGCTCGAAGCCGCCGAGCTGGGCTTGTCCGC CTCCTCTTATAGACAGTTCGCGCAAACGCAAATCGACTACGCCCTG GGCGATGGTGGCCGCTCCTTTGTGTGCGGGTTCGGGAGTAATCCTC CTACGAGACCGCACCACAGATCCTCGTCGTGCCCGCCAGCTCCCGC TACTTGCGACTGGAATACATTCAACTCACCTGACCCAAACTACCAC GTCCTCTCTGGGGCCCTAGTGGGCGGACCTGATCAGAATGACAACT ACGTCGATGACCGTTCAGACTATGTTCACAACGAAGTCGCCACTGA TTACAACGCGGGTTTCCAGTCCGCGTTAGCTGCTTTGGTGGCCCTT GGTTACAGCGAGAAGGACGAGCTGTGA (SEQ ID NO: 145) |
| 2046 | BAASS:NtEGm:SEKDEL | MANKHLSLSLFLVLLG LSASLASGQVAYDYKQ VLRDSLLFYEAQRSGR LPADQKVTWRKDSALN DQGDQGQDLTGGYFDA GDFVKFGFPMAYTATV LAWGLIDFEAGYSSAG ALDDGRKAVKWATDYF IKAHTSQNEFYGQVGQ GDADHAFWGRPEDMTM ARPAYKIDTSRPGSDL AGETAAALAAASIVFR NVDGTYSNNLLTHARQ LFDFANNYRGKYSDSI TDARNFYASADYRDEL VWAAAWLYRATNDNTY LNTAESLYDEFGLQNW GGGLNWDSKVSGVQVL LAKLTNKQAYKDTVQS YVNYLINNQQKTPKGL | ATGGCGAACAAACATTTGTCCCTCTCCCTCTTCCTCGTCCTCCTTG GCCTGTCGGCCAGCTTGGCCTCCGGGCAAGTCGCTTACGACTACAA GCAGGTGTTGCGGGACTCGCTACTATTCTATGAGGCCCAGAGATCC GGCCGGCTCCCAGCCGACCAGAAGGTCACGTGGAGGAAGGATAGCG CGCTGAATGACCAGGGTGACCAGGGACAAGACTTGACCGGCGGCTA CTTTGACGCTGGGGACTTCGTCAAGTTCGGGTTCCCCATGGCTTAT ACCGCAACCGTGCTGGCATGGGGCCTCATAGATTTTGAGGCCGGCT ACAGCAGTGCCGGGGCCTTGGATGATGGACGGAAGGCTGTCAAATG GGCCACCGACTATTTCATAAAGGCCCACACAAGTCAAATGAGTTC TATGGTCAGGTCGGCCAGGGTGACGCCGATCACGCTTTCTGGGGAA GACCAGAGGATATGACGATGGCGCGCCCGGCGTACAAGATAGACAC CTCAAGGCCTGGCTCTGATCTGGCAGGCGAGACAGCGGCTGCTCTT GCCGCTGCTTCAATCGTGTTCCGGAACGTCGATGGCACTTACTCAA ATAACCTGTTAACACACGCTCGCCAGCTATTCGACTTCGCGAACAA CTACCGGGGAAAGTATAGTGACTCTATTACTGACGCAAGAAATTTC TACGCAAGCGCAGACTACAGAGACGAGTTGGTTTGGGCTGCTGCGT GGTTATACAGAGCGACCAACGACAACACCTACCTCAACACTGCTGA GTCACTGTACGATGAGTTTGGGCTACAGAACTGGGGGGGGGGCCTG AACTGGGATAGCAAGGTGTCTGGCGTGCAGGTGTTGTTGGCCAAGC TTACCAATAAGCAGGCCTACAAGGACACGGTGCAGTCTTACGTCAA |

TABLE 1-continued

Sequences of CWDEs and their fusions in vectors

| pAG vector | Sequence annotation | Protein sequence | Nucleotide sequence |
|---|---|---|---|
| | | LYIDMWGTLRHAANAA FIMLEAAELGLSASSY RQFAQTQIDYALGDGG RSFVCGFGSNPPTRPH HRSSSCPPAPATCDWN TFNSPDPNYHVLSGAL VGGPDQNDNYVDDRSD YVHNEVATDYNAGFQS ALAALVALGYSEKDEL* (SEQ ID NO: 74) | TTACCTAATTAATAACCAGCAGAAGACTCCCAAGGGCCTCCTCTAC ATCGACATGTGGGGCACCCTTCGCCACGCTGCCAACGCCGCATTCA TCATGCTCGAAGCCGCCGAGCTGGGCTTGTCCGCCTCCTCTTATAG ACAGTTCGCGCAAACGCAAATCGACTACGCCCTGGGCGATGGTGGC CGCTCCTTTGTGTGCGGGTTCGGGAGTAATCCTCCTACGAGACCGC ACCACAGATCCTCGTCGTGCCCGCCAGCTCCCGCTACTTGCGACTG GAATACATTCAACTCACCTGACCCAAACTACCACGTCCTCTCTGGG GCCCTAGTGGGCGGACCTGATCAGAATGACAACTACGTCGATGACC GTTCAGACTATGTTCACAACGAAGTCGCCACTGATTACAACGCGGG TTTCCAGTCCGCGTTAGCTGCTTTGGTGGCCCTTGGTTACAGCGAG AAGGACGAGCTGTGA (SEQ ID NO: 146) |
| 2047 | HvAleSP:P54583: SEKDEL | MAHARVLLLALAVLAT AAVAVASSSSFADSNP IRPVTDRAASTAGGGY WHTSGREILDANNVPV RIAGINWFGFETCNYV VHGLWSRDYRSMLDQI KSLGYNTIRLPYSDDI LKPGTMPNSINFYQMN QDLQGLTSLQVMDKIV AYAGQIGLRIILDRHR PDCSGQSALWYTSSVS EATWISDLQALAQRYK GNPTVVGFDLHNEPHD PACWGCGDPSIDWRLA AERAGNAVLSVNPNLL IFVEGVQSYNGDSYWW GGNLQGAGQYPVVLNV PNRLVYSAHDYATSVY PQTWFSDPTFPNNMPG IWNKNWGYLFNQNIAP VWLGEFGTTLQSTTDQ TWLKTLVQYLRPTAQY GADSFQWTFWSWNPDS GDTGGILKDDWQTVDT VKDGYLAPIKSSIFDP VGASASPSSQPSPSVS PSPSPSPSASRTPTPT PTPTASPTPTLTPTAT PTPTASPTPSPTAASG ARCTASYQVNSDWGNG FTVTVAVTNSGSVATK TWTVSWTFGGNQTITN SWNAAVTQNGQSVTAR NMSYNNVIQPGQNTTF GFQASYTGSNAAPTVA CAASSEKDEL* (SEQ ID NO: 75) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCGCTGGAGGA GGATACTGGCACACTTCCGGCAGGGAGATCCTCGACGCAAATAACG TTCCAGTCAGAATCGCCGGGATTAATTGGTTTGGCTTCGAAACGTG TAACTACGTGGTTCACGGCCTGTGGTCTCGGGATTACAGATCAATG CTCGACCAGATCAAATCCTTGGGGTATAATACAATTAGGCTGCCCT ACAGCGATGACATTCTTAAGCCTGGAACCATGCCGAACTCGATTAA TTTCTACCAAATGAACCAGGATCTGCAGGGATTGACTTCTCTGCAG GTTATGGACAAGATCGTGGCGTACGCCGGCCAAATCGGGCTCAGAA TTATTTTGGATCGGCACAGGCCAGACTGCTCAGGTCAGTCGGCCCT GTGGTACACAAGCTCCGTGTCAGAGGCAACATGGATTTCAGATCTT CAAGCCCTCGCACAACGCTATAAAGGCAACCCCACGGTTGTGGGAT TCGACCTTCACAACGAACCTCACGATCCGGCCTGTTGGGGCTGCGG GGACCCTTCGATCGACTGGAGACTGGCAGCGGAGAGGGCTGGTAAC GCCGTTCTCAGCGTCAATCCCAACTTGCTGATCTTTGTGGAGGGAG TTCAGTCCTACAACGGCGATTCTTACTGGTGGGGCGGAAATCTCCA AGGCGCAGGGCAGTATCCTGTCGTGCTTAACGTTCCGAATCGCCTG GTCTACTCAGCACACGACTACGCGACTAGCGTGTACCCACAGACGT GGTTCTCCGATCCCACATTTCCTAACAATATGCCGGGAATCTGGAA CAAGAATTGGGGTTACTTGTTTAACCAAAACATTGCTCCAGTTTGG TTGGGTGAATTTGGCACCACTCTTCAGTCGACGACAGACCAAACCT GGCTGAAAACCCTCGTCCAGTATTTGCGGCCAACTGCTCAGTACGG AGCAGATTCTTTTCAATGGACGTTCTGGTCTTGGAATCCTGACTCC GGGGATACAGGCGGTATCCTGAAAGACGATTGGCAGACCGTGGACA CTGTTAAGGACGGGTACTTGGCGCCGATTAAAAGCTCGATCTTTGA CCCAGTCGGCGCTAGCGCTTCCCCATCTTCACAACCTTCGCCGAGC CCTCCCACACCTACCCCCACGGCCTCAACTCCGACGCTCACTCC TACGGCGACGCCAACACCAACTGCTTCACCCACTCCTAGCCCCACC GCAGCGAGCGGGGCTAGGTGCACCGCTTCTTACCAGGTCAACTCTG ACTGGGGTAATGGCTTCACCGTGACTGTGGCGGTCACTAACTCAGG AAGCGTCGCGACGAAAACCTGGACTGTGTCCTGGACGTTCGGGGGC AACCAAACAATCACCAACAGCTGGAACGCTGCAGTTACGCAGAATG GGCAAAGCGTCACGGCGCGCAATATGAGCTACAACAACGTGATTCA ACCAGGCCAGAATACCACATTCGGTTTTCAAGCAAGCTATACCGGG TCAAACGCTGCCCCAACTGTCGCTTGTGCTGCCTCAAGCGAGAAGG ACGAGCTGTGA (SEQ ID NO: 147) |
| 2048 | HvAleSP:NtEGm | MAHARVLLLALAVLAT AAVAVASSSSFADSNP IRPVTDRAASTAYDYK QVLRDSLLFYEAQRSG RLPADQKVTWRKDSAL NDQGDQGQDLTGGYFD AGDFVKFGFPMAYTAT VLAWGLIDPEAGYSSA GALDDGRKAVKWATDY FIKAHTSQNEFYGQVG QGDADHAFWGRPEDMT MARPAYKIDTSRPGSD LAGETAAALAAASIVF RNVDGTYSNNLLTHAR QLFDFANNYRGKYSDS ITDARNFYASADYRDE LVWAAAWLYRATNDNT YLNTAESLYDEFGLQN WGGGLNWDSKVSGVQV LLAKLTNKQAYKDTVQ SYVNYLINNQQKTPKG LLYIDMWGTLRHAANA AFIMLEAAELGLSASS YRQFAQTQIDYALGDG | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCGCTTACGAC TACAAGCAGGTGTTGCGGGACTCGCTACTATTCTATGAGGCCCAGA GATCCGGCCGGCTCCCAGCCGACCAGAAGGTCACGTGGAGGAAGGA TAGCGCGCTGAATGACCAGGGTGACCAGGGACAAGACTTGACCGGC GGCTACTTTGACGCTGGAGACTTCGTCAAGTTCGGGTTCCCCATGG CTTATACCGCAACCGTGCTGGCATGGGGCCTCATAGATTTTGAGGC CGGCTACAGCAGTGCCGGGGCCTTGGATGATGGACGGAAGGCTGTC AAATGGGCCACCGACTATTTCATAAAGGCCCACACAAGTCAAAATG AGTTCTATGGTCAGGTCGGCCAGGATGCCGATCACGCTTTCTG GGGAAGACCAGAGGATATGACGATGGCGCGCCCGGCGTACAAGATA GACACCTCAAGGCCTGGCTCTGATCTGGCAGGCGAGACAGCGGCTG CTCTTGCCGCTGCTTCAATCGTGTTCCGGAACGTCGATGGCACTTA CTCAAATAACCTGTTAACACACGCTCGCCAGCTATTCGACTTCGCG AACAACTACCGGGGAAAGTATAGTGACTCTATTACTGACGCAAGAA ATTTCTACGCAAGCGCAGACTACAGAGACGAGTTGGTTTGGGCTGC TGCGTGGTTATACAGAGCGACCAACGACAACACCTACCTCAACACT GCTGAGTCACTGTACGATGAGTTTGGGCTACAGAACTGGGGGGGAG GCCTGAACTGGGATAGCAAGGTGTCTGGCGTGCAGGTGTTGTTGGC CAAGCTTACCAATAAGCAGGCCTACAAGGACACGGTGCAGTCTTAC GTCAATTACCTAATTAATAACCAGCAGAAGACTCCCAAGGGCCTCC TCTACATCGACATGTGGGGCACCCTTCGCCACGCTGCCAACGCCGC ATTCATCATGCTCGAAGCCGCCGAGCTGGGCTTGTCCGCCTCCTCT |

TABLE 1-continued

Sequences of CWDEs and their fusions in vectors

| pAG vector | Sequence annotation | Protein sequence | Nucleotide sequence |
|---|---|---|---|
| | | GRSFVCGFGSNPPTRP HHRSSSCPPAPATCDW NTFNSPDPNYHVLSGA LVGGPDQNDNYVDDRS DYVHNEVATDYNAGFQ SALAALVALGY* (SEQ ID NO: 76) | TATAGACAGTTCGCGCAAACGCAAATCGACTACGCCCTGGGCGATG GTGGCCGCTCCTTTGTGTGCGGGTTCGGGAGTAATCCTCCTACGAG ACCGCACCACAGATCCTCGTCGTGCCCGCCAGCTCCCGCTACTTGC GACTGGAATACATTCAACTCACCTGACCCAAACTACCACGTCCTCT CTGGGGCCCAGTGGGCGGACCTGATCAGAATGACAACTACGTCGA TGACCGTTCAGACTATGTTCACAACGAAGTCGCCACTGATTACAAC GCGGGTTTCCAGTCCGCGTTAGCTGCTTTGGTGGCCCTTGGTTACT GA (SEQ ID NO: 148) |
| 2049 | HvAleSP:NtEGm:SEKDEL | MAHARVLLLALAVLAT AAVAVASSSSFADSNP IRPVTDRAASTAYDYK QVLRDSLLFYEAQRSG RLPADQKVTWRKDSAL NDQGDQGQDLTGGYFD AGDFVKFGFPMAYTAT VLAWGLIDFEAGYSSA GALDDGRKAVKWATDY FIKAHTSQNEFYGQVG QGDADHAFWGRPEDMT MARPAYKIDTSRPGSD LAGETAAALAAASIVF RNVDGTYSNNLLTHAR QLFDFANNYRGKYSDS ITDARNFYASADYRDE LVWAAAWLYRATNDNT YLNTAESLYDEFGLQN WGGGLNWDSKVSGVQV LLAKLTNKQAYKDTVQ SYVNYLINNQQKTPKG LLYIDMWGTLRHAANA AFIMLEAAELGLSASS YRQFAQTQIDYALGDG GRSFVCGFGSNPPTRP HHRSSSCPPAPATCDW NTFNSPDPNYHVLSGA LVGGPDQNDNYVDDRS DYVHNEVATDYNAGFQ SALAALVALGYSEKDE L* (SEQ ID NO: 77) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCGCTTACGAC TACAAGCAGGTGTTGCGGGACTCGCTACTATTCTATGAGGCCCAGA GATCCGGCCGGCTCCCAGCCGACCAGAAGGTCACGTGGAGGAAGGA TAGCGCGCTGAATGACCAGGGTGACCAGGGACAAGACTTGACCGGC GGCTACTTTGACGGTGGGGACTTCGTCAAGTTCGGGTTCCCCATGG CTTATACCGCAACCGTGCTGGCATGGGGCCTCATAGATTTTGAGGC CGGCTACAGGAGTGCCGGGGCCTTGGATGATGGACGGAAGGCTGTC AAATGGGCCACCGACTATTTCATAAAGGCCCACACAAGTCAAATGG AGTTCTATGGTCAGGTCGGCCAGGGTGACGCGATCACGCTTTCTG GGGAAGACCAGAGGATATGACGATGGCGCGCCCGGCGTACAAGATA GACACCTCAAGGCCTGGCTCTGATCTGGCAGGCGAGACAGCGGCTG CTCTTGCCGCTGCTTCAATCGTGTTCCGGAACGTCGATGGCACTTA CTCAAATAACCTGTTAACACACGCTCGCCAGCTATTCGACTTCGCG AACAACTACCGGGGAAAGTATAGTGACTCTATTACTGACGCAAGAA ATTTCTACGCAAGCGCAGACTACAGAGACGAGTTGGTTTGGGCTGC TGCGTGGTTATACAGAGCGACCAACGACAACACCTACCTCAACACT TGGGGCGGACTGTACGATGAGTTTGGGCTACAGAACTGGGGGGGGG GCCTGAACTGGGATAGCAAGGTGTCTGGCGTGCAGGTGTTGTTGGC CAAGCTTACCAATAAGCAGGCCTACAAGGACACGGTGCAGTCTTAC GTCAATTACCTAATTAATAACCAGCAGAAGACTCCCAAGGGCCTCC TCTACATCGACATGTGGGGCACCCTTCGCCACGCTGCCAACGCCGC ATTCATCATGCTCGAAGCCGCCGAGCTGGGCTTGTCCGCCTCCTCT TATAGACAGTTCGCGCAAACGCAAATCGACTACGCCCTGGGCGATG GTGGCCGCTCCTTTGTGTGCGGGTTCGGGAGTAATCCTCCTACGAG ACCGCACCACAGATCCTCGTCGTGCCCGCCAGCTCCCGCTACTTGC GACTGGAATACATTCAACTCACCTGACCCAAACTACCACGTCCTCT CTGGGGCCCAGTGGGCGGACCTGATCAGAATGACAACTACGTCGA TGACCGTTCAGACTATGTTCACAACGAAGTCGCCACTGATTACAAC GCGGGTTTCCAGTCCGCGTTAGCTGCTTTGGTGGCCCTTGGTTACA GCGAGAAGGACGAGCTGTGA (SEQ ID NO: 149) |
| 2050 | P26222 | MNDSPFYVNPNMSSAE WVRNNPNDPRTPVIRD RIASVPQGTWFAHHNP GQITGQVDALMSAAQA AGKIPILVVYNAPGRD CGNHSSGGAPSHSAYR SWIDEFAAGLKNRPAY IIVEPDLISLMSSCMQ HVQQEVLETMAYAGKA LKAGSSQARIYFDAGH SAWHSPAQMASWLQQA DISNSAHGIATNTSNY RWTADEVAYAKAVLSA IGNPSLRAVIDTSRNG NGPAGNEWCDPSGRAI GTPSTTNTGDPMIDAF LWIKLPGEADGCIAGA GQFVPQAAYEMAIAAG GTNPNPNPNPTPTPTP TPTPPPGSSGACTATY TIANEWNDGFQATVTV TANQNITGWTVTWTFT DGQTITNAWNADVSTS GSSVTARNVGHNGTLS QGASTEFGFVGSKGNS NSVPTLTCAAS* (SEQ ID NO: 78) | ATGAACGATAGTCCATTCTACGTGAACCCGAATATGTCATCAGCTG AGTGGGTGCGTAACAACCCCAATGACCCTCGCACACCAGTCATTAG GGATCGTATTGCCTCGGTGCCCCAAGGAACGTGGTTCGCCCACCAT AACCCTGGCCAGATTACAGGGCAAGTTGATGCTCTGATGTCCGCCG CTCAAGCCGCGGGTAAGATCCCTATTCTCGTGGTGTACAACGCACC AGGACGCGACTGCGGGAATCATAGTTCGGGTGGGGCTCCTTCCCAC AGCGCTTATCGGTCTTGGATCGACGAGTTTGCTGCTGGCCTCAAGA ACCGTCCCGCTTACATCATTGTGGAGCCTGACCTGATAAGCCTTAT GTCGTCGTATGCAGCACGTTCAACAGGAGGTGCTCGAGACTATG GCCTACGCAGGGAAGGCCTTGAAGGCCGGCTCATCCCAGGCCCGTA TCTATTTCGACGCGGGGCATTCGGCGTGGCATTCACCAGCGCAGAT GGCTTCTTGGCTCCAGCAGGCTGATATCTCAAACTCTGCACATGGT ATCGCCACGAATACTTCTAACTACCGTTGGACCGCTGATGAAGTCG CGTACGCCAAGGCCGTGCTGTCCGCCATAGGAAATCCCTCCCTCAG AGCCGTCATAGATACGTCCCGCAACGGAAATGGCCCTGCTGGAAAT GAGTGGTGCGACCCAAGCGGACGCGCTATCGGAACCCCGAGTACCA CAAATACTGGCGACCCAATGATCGATGCTTTCCTCTGGATTAAGCT TCCGGGAGAAGCAGACGGTTGCATCGCCGGAGCTGGCCAATTCGTT CCACAAGCAGCATACGAGATGGCTATTGCGGCGGGTGGTACGAATC CTAATCCCAACCCCAACCCTACGCCCAACGCCCACGACTCCCAC TCCACCTCCGGGGAGCAGCGGCCGCTGCACAGCCACCTATACAATC GCAAACGAATGGAATGATGGCTTCCAAGCGACGGTGACGGTGACCG CGAACCAGAACATCACTGGGTGGACTGTCACTTGGACTTTCACGGA TGGACAGACTATTACTAACGCCTGGAATGCTGACGTTTCGACGTCA GGTTCGTCTGTGACGGCGCGCAACGTCGGGCATAATGGTACTCTCT CCCAGGGCGCCAGCACAGAGTTTGGCTTTGTCGGCTCAAAGGGAAA TTCAAATAGCGTCCCCACTCTCACGTGCGCCGCCTCGTGA (SEQ ID NO: 150) |
| 2051 | PR1a:P26222 | MGFVLFSQLPSFLLVS TLLLFLVISHSCRAND SPFYVNPNMSSAEWVR NNPNDPRTPVIRDRIA | ATGGGCTTCGTGCTCTTCTCCCAGCTGCCTTCCTTCCTTCTTGTCT CCACCCTGCTCTTGTTCCTCGTGATCTCCCACTCCTGCCGCGCCAA CGATAGTCCATTCTACGTGAACCCGAATATGTCATCAGCTGAGTGG GTGCGTAACAACCCCAATGACCCTCGCACACCAGTCATTAGGGATC |

TABLE 1-continued

Sequences of CWDEs and their fusions in vectors

| pAG vector | Sequence annotation | Protein sequence | Nucleotide sequence |
|---|---|---|---|
| | | SVPQGTWFAHHNPGQI TGQVDALMSAAQAAGK IPILVVYNAPGRDCGN HSSGGAPSHSAYRSWI DEFAAGLKNRPAYIIV EPDLISLMSSCMQHVQ QEVLETMAYAGKALKA GSSQARIYFDAGHSAW HSPAQMASWLQQADIS NSAHGIATNTSNYRWT ADEVAYAKAVLSAIGN PSLRAVIDTSRNGNGP AGNEWCDPSGRAIGTP STTNTGDPMIDAFLWI KLPGEADGCIAGAGQF VPQAAYEMAIAAGGTN PNPNPNPTPTPTPTPT PPPGSSGACTATYTIA NEWNDGFQATVTVTAN QNITGWTVTWTFTDGQ TITNAWNADVSTSGSS VTARNVGHNGTLSQGA STEFGFVGSKGNSNSV PTLTCAAS* (SEQ ID NO: 79) | GTATTGCCTCGGTGCCCCAAGGAACGTGGTTCGCCCACCATAACCC TGGCCAGATTACAGGGCAAGTTGATGCTCTGATGTCCGCCGCTCAA GCCGCGGGTAAGATCCCTATTCTCGTGGTGTACAACGCACCAGGAC GCGACTGCGGGAATCATAGTTCGGGTGGGGCTCCTTCCCACAGCGC TTATCGGTCTTGGATCGACGAGTTTGCTGCTGGCCTCAAGAACCGT CCCGCTTACATCATTGTGGAGCCTGACCTGATAAGCCTTATGTCGT CGTGTATGCAGCACGTTCAACAGGAGGTGCTCGAGACTATGGCCTA CGCAGGGAAGGCCTTGAAGGCCGGCTCATCCCAGGCCCGTATCTAT TTCGACGCGGGGCATTCGGCGTGGCATTCACCAGCGCAGATGGCTT CTTGGCTCCAGCAGGCTGATATCTCAAACTCTGCACATGGTATCGC CACGAATACTTCTAACTACCGTTGGACCGCTGATGAAGTCGCGTAC GCCAAGGCCGTGCTGTCCGCCATAGGAAATCCCTCCCTCAGAGCCG TCATAGATACGTCCCGAACGGAAATGGCCCTGCTGGAAATGAGTG GTGCGACCCAAGCGGACGCGCTATCGGAACCCCGAGTACCACAAAT ACTGGCGACCCAATGATCGATGCTTTCCTCTGGATTAAGCTTCCGG GAGAAGCAGACGGTTGCATCGCCGGAGCTGGCCAATTCGTTCCACA AGCAGCATACGAGATGGCTATTGCGGCGGGTGGTACGAATCCTAAT CCCAACCCCAACCCTACGCCAACGCCCACACCGACTCCCACTCCAC CTCCGGGGAGCAGCGGCGCCTGCACAGCCACCTATACAATCGCAAA CGAATGGAATGATGGCTTCCAAGCGACGGTGACGGTGACCGCGAAC CAGAACATCACTGGGTGGACTGTCACTTGGACTTTCACGGATGGAC AGACTATTACTAACGCCTGGAATGCTGACGTTTCGACGTCAGGTTC GTCTGTGACGGCGCGCAACGTCGGGCATAATGGTACTCTCTCCCAG GGCGCCAGCACAGAGTTTGGCTTTGTCGGCTCAAAGGGAAATTCAA ATAGCGTCCCCACTCTCACGTGCGCCGCCTCGTGA (SEQ ID NO: 151) |
| 2052 | PR1a:P26222:SEKDEL | MGFVLFSQLPSFLLVS TLLLFLVISHSCRAND SPFYVNPNMSSAEWVR NNPNDPRTPVIRDRIA SVPQGTWFAHHNPGQI TGQVDALMSAAQAAGK IPILVVYNAPGRDCGN HSSGGAPSHSAYRSWI DEFAAGLKNRPAYIIV EPDLISLMSSCMQHVQ QEVLETMAYAGKALKA GSSQARIYFDAGHSAW HSPAQMASWLQQADIS NSAHGIATNTSNYRWT ADEVAYAKAVLSAIGN PSLRAVIDTSRNGNGP AGNEWCDPSGRAIGTP STTNTGDPMIDAFLWI KLPGEADGCIAGAGQF VPQAAYEMAIAAGGTN PNPNPNPTPTPTPTPT PPPGSSGACTATYTIA NEWNDGFQATVTVTAN QNITGWTVTWTFTDGQ TITNAWNADVSTSGSS VTARNVGHNGTLSQGA STEFGFVGSKGNSNSV PTLTCAASSEKDEL* (SEQ ID NO: 80) | ATGGGCTTCGTGCTCTTCTCCCAGCTGCCTTCCTTCCTTCTTGTCT CCACCCTGCTCTTGTTCCTCGTGATCTCCCACTCCTGCCGCGCCAA CGATAGTCCATTCTACGTGAACCCGAATATGTCATCAGCTGAGTGG CGTAACAACCCCAATGACCCTCGCACACCAGTCATTAGGGATC GTATTGCCTCGGTGCCCCAAGGAACGTGGTTCGCCCACCATAACCC TGGCCAGATTACAGGGCAAGTTGATGCTCTGATGTCCGCCGCTCAA GCCGCGGGTAAGATCCCTATTCTCGTGGTGTACAACGCACCAGGAC GCGACTGCGGGAATCATAGTTCGGGTGGGGCTCCTTCCCACAGCGC TTATCGGTCTTGGATCGACGAGTTTGCTGCTGGCCTCAAGAACCGT CCCGCTTACATCATTGTGGAGCCTGACCTGATAAGCCTTATGTCGT CGTGTATGCAGCACGTTCAACAGGAGGTGCTCGAGACTATGGCCTA CGCAGGGAAGGCCTTGAAGGCCGGCTCATCCCAGGCCCGTATCTAT TTCGACGCGGGGCATTCGGCGTGGCATTCACCAGCGCAGATGGCTT CTTGGCTCCAGCAGGCTGATATCTCAAACTCTGCACATGGTATCGC CACGAATACTTCTAACTACCGTTGGACCGCTGATGAAGTCGCGTAC GCCAAGGCCGTGCTGTCCGCCATAGGAAATCCCTCCCTCAGAGCCG TCATAGATACGTCCCGAACGGAAATGGCCCTGCTGGAAATGAGTG GTGCGACCCAAGCGGACGCGCTATCGGAACCCCGAGTACCACAAAT ACTGGCGACCCAATGATCGATGCTTTCCTCTGGATTAAGCTTCCGG GAGAAGCAGACGGTTGCATCGCCGGAGCTGGCCAATTCGTTCCACA AGCAGCATACGAGATGGCTATTGCGGCGGGTGGTACGAATCCTAAT CCCAACCCCAACCCTACGCCAACGCCCACACCGACTCCCACTCCAC CTCCGGGGAGCAGCGGCGCCTGCACAGCCACCTATACAATCGCAAA CGAATGGAATGATGGCTTCCAAGCGACGGTGACGGTGACCGCGAAC CAGAACATCACTGGGTGGACTGTCACTTGGACTTTCACGGATGGAC AGACTATTACTAACGCCTGGAATGCTGACGTTTCGACGTCAGGTTC GTCTGTGACGGCGCGCAACGTCGGGCATAATGGTACTCTCTCCCAG GGCGCCAGCACAGAGTTTGGCTTTGTCGGCTCAAAGGGAAATTCAA ATAGCGTCCCCACTCTCACGTGCGCCGCCTCGAGCGAGAAGGACGA GCTGTGA (SEQ ID NO: 152) |
| 2053 | BAASS:P26222 | MANKHLSLSLFLVLLG LSASLASGQNDSPFYV NPNMSSAEWVRNNPND PRTPVIRDRIASVPQG TWFAHHNPGQITGQVD ALMSAAQAAGKIPILV VYNAPGRDCGNHSSGG APSHSAYRSWIDEFAA GLKNRPAYIIVEPDLI SLMSSCMQHVQQEVLE TMAYAGKALKAGSSQA RIYFDAGHSAWHSPAQ MASWLQQADISNSAHG IATNTSNYRWTADEVA YAKAVLSAIGNPSLRA VIDTSRNGNGPAGNEW CDPSGRAIGTPSTTNT | ATGGCGAACAAACATTTGTCCCTCTCCCTCTTCCTCGTCCTCCTTG GCCTGTCGGCCAGCTTGGCCTCCGGGCAAAACGATAGTCCATTCTA CGTGAACCCGAATATGTCATCAGCTGAGTGGGTGCGTAACAACCCC AATGACCCTCGCACACCAGTCATTAGGGATCGTATTGCCTCGGTGC CCCAAGGAACGTGGTTCGCCCACCATAACCCTGGCCAGATTACAGG GCAAGTTGATGCTCTGATGTCCGCCGCTCAAGCCGCGGGTAAGATC CCTATTCTCGTGGTGTACAACGCACCAGGACGCGACTGCGGGAATC ATAGTTCGGGTGGGGCTCCTTCCCACAGCGCTTATCGGTCTTGGAT CGACGAGTTTGCTGCTGGCCTCAAGAACCGTCCCGCTTACATCATT GTGGAGCCTGACCTGATAAGCCTTATGTCGTCGTGTATGCAGCACG TTCAACAGGAGGTGCTCGAGACTATGGCCTACGCAGGGAAGGCCTT GAAGGCCGGCTCATCCCAGGCCCGTATCTATTTCGACGCGGGGCAT TCGGCGTGGCATTCACCAGCGCAGATGGCTTCTTGGCTCCAGCAGG CTGATATCTCAAACTCTGCACATGGTATCGCCACGAATACTTCTAA CTACCGTTGGACCGCTGATGAAGTCGCGTACGCCAAGGCCGTGCTG TCCGCCATAGGAAATCCCTCCCTCAGAGCCGTCATAGATACGTCCC GCAACGGAAATGGCCCTGCTGGAAATGAGTGGTGCGACCCAAGCGG |

TABLE 1-continued

Sequences of CWDEs and their fusions in vectors

| pAG vector | Sequence annotation | Protein sequence | Nucleotide sequence |
|---|---|---|---|
| | | GDPMIDAFLWIKLPGE ADGCIAGAGQFVPQAA YEMAIAAGGTNPNPNP NPTPTPTPTPTPPPGS SGACTATYTIANEWND GFQATVTVTANQNITG WTVTWTFTDGQTITNA WNADVSTSGSSVTARN VGHNGTLSQGASTEFG FVGSKGNSNSVPTLTC AAS* (SEQ ID NO: 81) | ACGCGCTATCGGAACCCCGAGTACCACAAATACTGGCGACCCAATG ATCGATGCTTTCCTCTGGATTAAGCTTCCGGGAGAAGCAGACGGTT GCATCGCCGGAGCTGGCCAATTCGTTCCACAAGCAGCATACGAGAT GGCTATTGCGGCGGGTGGTACGAATCCTAATCCCAACCCCAACCCT ACGCCAACGCCCACACCGACTCCCACTCCACCTCCGGGGAGCAGCG GCGCCTGCACAGCCACCTATACAATCGCAAACGAATGGAATGATGG CTTCCAAGCGACGGTGACGGTGACCGCGAACCAGAACATCACTGGG TGGACTGTCACTTGGACTTTCACGGATGGACAGACTATTACTAACG CCTGGAATGCTGACGTTTCGACGTCAGGTTCGTCTGTGACGGCGCG CAACGTCGGGCATAATGGTACTCTCTCCCAGGGCGCCAGCACAGAG TTTGGCTTTGTCGGCTCAAAGGGAAATTCAAATAGCGTCCCCACTC TCACGTGCGCCGCCTCGTGA (SEQ ID NO: 153) |
| 2054 | BAASS:P26222:SEKDEL | MANKHLSLSLFLVLLG LSASLASGQNDSPFYV NPNMSSAEWVRNNPND PRTPVIRDRIASVPQG TWFAHHNPGQITGQVD ALMSAAQAAGKIPILV VYNAPGRDCGNHSSGG APSHSAYRSWIDEFAA GLKNRPAYIIVEPDLI SLMSSCMQHVQQEVLE TMAYAGKALKAGSSQA RIYFDAGHSAWHSPAQ MASWLQQADISNSAHG IATNTSNYRWTADEVA YAKAVLSAIGNPSLRA VIDTSRNGNGPAGNEW CDPSGRAIGTPSTTNT GDPMIDAFLWIKLPGE ADGCIAGAGQFVPQAA YEMAIAAGGTNPNPNP NPTPTPTPTPTPPPGS SGACTATYTIANEWND GFQATVTVTANQNITG WTVTWTFTDGQTITNA WNADVSTSGSSVTARN VGHNGTLSQGASTEFG FVGSKGNSNSVPTLTC AASSEKDEL* (SEQ ID NO: 82) | ATGGCGAACAAACATTTGTCCCTCTCCCTCTTCCTCGTCCTCCTTG GCCTGTCGGCCAGCTTGGCCTCCGGGCAAAACGATAGTCCATTCTA CGTGAACCCGAATATGTCATCAGCTGAGTGGGTGCGTAACAACCCC AATGACCCTCGCACACCAGTCATTAGGGATCGTATTGCCTCGGTGC CCCAAGGAACGTGGTTCGCCCACCATAACCCTGGCCAGATTACAGG GCAAGTTGATGCTCTGATGTCCGCCGCTCAAGCCGCGGGTAAGATC CCTATTCTCGTGGTGTACAACGCACCAGGACGCGACTGCGGGAATC ATAGTTCGGTGGGGCTCCTTCCCACAGCGCTTATCGGTCTTGGAT CGACGAGTTTGCTGCTGGCCTCAAGAACCGTCCCGCTTACATCATT GTGGAGCCTGACCTGATAAGCCTTATGTCGTCGTGTATGCAGCACG TTCAACAGGAGGTGCTCGAGACTATGGCCTACGCAGGGAAGGCCTT GAAGGCCGGCTCATCCCAGGCCCGTATCTATTTCGACGCGGGGCAT TCGGCGTGGCATTCACCAGCGCAGATGGCTTCTTGGCTCCAGCAGG CTGATATCTCAAACTCTGCACATGGTATCGCCACGAATACTTCTAA CTACCGTTGGACCGCTGATGAAGTCGCGTACGCCAAGGCCGTGCTG TCCGCCATAGGAAATCCCTCCCTCAGAGCCGTCATAGATACGTCCC GCAACGGAAATGGCCCTGCTGGAAATGAGTGGTGCGACCCAAGCGG ACGCGCTATCGGAACCCCGAGTACCACAAATACTGGCGACCCAATG ATCGATGCTTTCCTCTGGATTAAGCTTCCGGGAGAAGCAGACGGTT GCATCGCCGGAGCTGGCCAATTCGTTCCACAAGCAGCATACGAGAT GGCTATTGCGGCGGGTGGTACGAATCCTAATCCCAACCCCAACCCT ACGCCAACGCCCACACCGACTCCCACTCCACCTCCGGGGAGCAGCG GCGCCTGCACAGCCACCTATACAATCGCAAACGAATGGAATGATGG CTTCCAAGCGACGGTGACGGTGACCGCGAACCAGAACATCACTGGG TGGACTGTCACTTGGACTTTCACGGATGGACAGACTATTACTAACG CCTGGAATGCTGACGTTTCGACGTCAGGTTCGTCTGTGACGGCGCG CAACGTCGGGCATAATGGTACTCTCTCCCAGGGCGCCAGCACAGAG TTTGGCTTTGTCGGCTCAAAGGGAAATTCAAATAGCGTCCCCACTC TCACGTGCGCCGCCTCGAGCGAGAAGGACGAGCTGTGA (SEQ ID NO: 154) |
| 2055 | HvAleSP:P26222 | MAHARVLLLALAVLAT AAVAVASSSSFADSNP IRPVTDRAASTNDSPF YVNPNMSSAEWVRNNP NDPRTPVIRDRIASVP QGTWFAHHNPGQITGQ VDALMSAAQAAGKIPI LVVYNAPGRDCGNHSS GGAPSHSAYRSWIDEF AAGLKNRPAYIIVEPD LISLMSSCMQHVQQEV LETMAYAGKALKAGSS QARIYFDAGHSAWHSP AQMASWLQQADISNSA HGIATNTSNYRWTADE VAYAKAVLSAIGNPSL RAVIDTSRNGNGPAGN EWCDPSGRAIGTPSTT NTGDPMIDAFLWIKLP GEADGCIAGAGQFVPQ AAYEMAIAAGGTNPNP NPNPTPTPTPTPTPPP GSSGACTATYTIANEW NDGFQATVTVTANQNI TGWTVTWTFTDGQTIT NAWNADVSTSGSSVTA RNVGHNGTLSQGASTE FGFVGSKGNSNSVPTL TCAAS* (SEQ ID NO: 83) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCAACGATAGT CCATTCTACGTGAACCCGAATATGTCATCAGCTGAGTGGGTGCGTA ACAACCCCAATGACCCTCGCACACCAGTCATTAGGGATCGTATTGC CTCGGTGCCCCAAGGAACGTGGTTCGCCCACCATAACCCTGGCCAG ATTACAGGGCAAGTTGATGCTCTGATGTCCGCCGCTCAAGCCGCGG GTAAGATCCCTATTCTCGTGGTGTACAACGCACCAGGACGCGACTG CGGGAATCATAGTTCGGTGGGGCTCCTTCCCACAGCGCTTATCGG TCTTGGATCGACGAGTTTGCTGCTGGCCTCAAGAACCGTCCCGCTT ACATCATTGTGGAGCCTGACCTGATAAGCCTTATGTCGTCGTGTAT GCAGCACGTTCAACAGGAGGTGCTCGAGACTATGGCCTACGCAGGG AAGGCCTTGAAGGCCGGCTCATCCCAGGCCCGTATCTATTTCGACG CGGGGCATTCGGCGTGGCATTCACCAGCGCAGATGGCTTCTTGGCT CCAGCAGGCTGATATCTCAAACTCTGCACATGGTATCGCCACGAAT ACTTCTAACTACCGTTGGACCGCTGATGAAGTCGCGTACGCCAAGG CCGTGCTGTCCGCCATAGGAAATCCCTCCCTCAGAGCCGTCATAGA TACGTCCCGCAACGGAAATGGCCCTGCTGGAAATGAGTGGTGCGAC CCAAGCGGACGCGCTATCGGAACCCCGAGTACCACAAATACTGGCG ACCCAATGATCGATGCTTTCCTCTGGATTAAGCTTCCGGGAGAAGC AGACGGTTGCATCGCCGGAGCTGGCCAATTCGTTCCACAAGCAGCA TACGAGATGGCTATTGCGGCGGGTGGTACGAATCCTAATCCCAACC CCAACCCTACGCCAACGCCCACACCGACTCCCACTCCACCTCCGGG GAGCAGCGGCGCCTGCACAGCCACCTATACAATCGCAAACGAATGG AATGATGGCTTCCAAGCGACGGTGACGGTGACCGCGAACCAGAACA TCACTGGGTGGACTGTCACTTGGACTTTCACGGATGGACAGACTAT TACTAACGCCTGGAATGCTGACGTTTCGACGTCAGGTTCGTCTGTG ACGGCGCGCAACGTCGGGCATAATGGTACTCTCTCCCAGGGCGCCA GCACAGAGTTTGGCTTTGTCGGCTCAAAGGGAAATTCAAATAGCGT CCCCACTCTCACGTGCGCCGCCTCGTGA (SEQ ID NO: 155) |

TABLE 1-continued

Sequences of CWDEs and their fusions in vectors

| pAG vector | Sequence annotation | Protein sequence | Nucleotide sequence |
|---|---|---|---|
| 2056 | HvAleSP:P26222: SEKDEL | MAHARVLLLALAVLAT AAVAVASSSSFADSNP IRPVTDRAASTNDSPF YVNPNMSSAEWVRNNP NDPRTPVIRDRIASVP QGTWFAHHNPGQITGQ VDALMSAAQAAGKIPI LVVYNAPGRDCGNHSS GGAPSHSAYRSWIDEF AAGLKNRPAYIIVEPD LISLMSSCMQHVQQEV LETMAYAGKLALKAGSS QARIYFDAGHSAWHSP AQMASWLQQADISNSA HGIATNTSNYRWTADE VAYAKAVLSAIGNPSL RAVIDTSRNGNGPAGN EWCDPSGRAIGTPSTT NTGDPMIDAFLWIKLP GEADGCIAGAGQFVPQ AAYEMAIAAGGTNPNP NPNPTPTPTPTPTPPP GSSGDCTATYTIANEW NDGFQATVTVTANQNI TGWTVTWTFTDGQTIT NAWNADVSTSGSSVTA RNVGHNGTLSQGASTE FGFVGSKGNSNSVPTL TCAASSEKDEL* (SEQ ID NO: 84) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCGCCTCCACCAACGATAGT CCATTCTACGTGAACCCGAATATGTCATCAGCTGAGTGGGTGCGTA ACAACCCCAATGACCCTCGCACACCAGTCATTAGGGATCGTATTGC CTCGGTGCCCCAAGGAACGTGGTTCGCCCACCATAACCCTGGCCAG ATTACAGGGCAAGTTGATGCTCTGATGTCCGCCGCTCAAGCCGCGG GTAAGATCCCTATTCTCGTGGTGTACAACGCACCAGGACGCGACTG CGGGAATCATAGTTCGGGTGGGCTCCTTCCCACAGCGCTTATCGG TCTTGGATCGACGAGTTTGCTGCTGGCCTCAAGAACCGTCCCGCTT ACATCATTGTGGAGCCTGACCTGATAAGCCTTATGTCGTCGTGTAT GCAGCACGTTCAACAGGAGGTGCTCGAGACTATGGCCTACGCAGGG AAGGCCTTGAAGGCCGGCTCATCCCAGGCCCGTATCTATTTCGACG CGGGGCATTCGGCGTGGCATTCACCAGCGCAGATGGCTTCTTGGCT CCAGCAGGCTGATATCTCAAACTCTGCACATGGTATCGCCACGAAT ACTTCTAACTACCGTTGGACCGCTGATGAAGTCGCGTACGCCAAGG CCGTGCTGTCCGCCATAGGAAATCCCTCCCTCAGAGCCGTCATAGA TACGTCCCGCAACGGAAATGGCCCTGCTGGAAATGAGTGGTGCGAC CCAAGCGGACGCGCTATCGGAACCCCGAGTACCACAAATACTGGCG ACCCAATGATCGATGCTTTCCTCTGGATTAAGCTTCCGGGAGAAGC AGACGGTTGCATCGCCGGAGCTGGCCAATTCGTTCCACAAGCAGCA TACGAGATGGCTATTGCGGCGGGTGGTACGAATCCTAATCCCAACC CCAACCCTACGCCAACGCCCACACCGACTCCCACTCCACCTCCGGG GAGCAGCGGCGCCTGCACAGCCACCTATACAATCGCAAACGAATGG AATGATGGCTTCCAAGCGACGGTGACGGTGACCGCGAACCAGAACA TCACTGGGTGGACTGTCACTTGGACTTTCACGGATGGACAGACTAT TACTAACGCCTGGAATGCTGACGTTTCGACGTCAGGTTCGTCTGTG ACGCGCGCAACGTCGGGCATAATGGTACTCTCTCCCAGGGCGCCA GCACAGAGTTTGGCTTTGTCGGCTCAAAGGGAAATTCAAATAGCGT CCCCACTCTCACGTGCGCCGCCTCGAGCGAGAAGGACGAGCTGTGA (SEQ ID NO: 156) |
| 2057 | BAASS:P77853:SEKDEL | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GTYDIYRTTRVNQPSI VGTATFDQYWSVRTSK RTSGTVTVTDHFRAWA NRGLNLGTIDQITLCV EGYQSSGSANITQNTF SQGSSSGSSGGSSGST TTTRIECENMSLSGPY VSRITNPFNGIALYAN GDTARATVNFPASRNY NFRLRGCGNNNNLARV DLRIDGRTVGTFYYQG TYPWEAPIDNVYVSAG SHTVEITVTADNGTWD VYADYLVIQSEKDEL* (SEQ ID NO: 85) | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGACCTACGACATCTATAGGACGACAC GCGTCAACCAGCCTTCCATTGTGGGGACAGCCACGTTCGATCAGTA CTGGAGCGTGCGCACCTCTAAGCGCACCAGTGGCACCGTGACCGTG ACCGATCACTTCCGCGCCTGGGCGAACCGGGGCCTGAACCTCGGCA CAATAGACCAAATTACATTGTGCGTGGAGGGTTACCAAAGCTCTGG ATCAGCCAACATCACCCAGAACACCTTCTCTCAGGGCTCTTCTTCC GGCAGTTCGGGTGGCTCATCCGGCTCCACAACGACTACTCGCATCG AGTGTGAGAACATGTCCTTGTCCGGACCCTACGTTAGCAGGATCAC CAATCCCTTTAATGGTATTGCGCTGTACGCCAACGGAGACACAGCC CGCGCTACCGTTAACTTCCCCGCAAGTCGCAACTACAATTTCCGCC TGCGGGGTTGCGGCAACAACAATAATCTTGCCCGTGTGGACCTGAG GATCGACGGACGGACCGTCGGGACCTTTTATTACCAGGGCACATAC CCCTGGGAGGCCCCAATTGACAATGTTTATGTCAGTGCGGGGAGTC ATACAGTCGAAATCACTGTTACTGCGGATAACGGCACATGGGACGT GTATGCCGACTACCTGGTGATACAGAGCGAGAAGGACGAGCTGTGA (SEQ ID NO: 157) |
| 2058 | PR1a:P77853:SEKDEL | MGFVLFSQLPSFLLVS TLLLFLVISHSCRAQQ TSITLTSNASGTFDGY YYELWKDTGNTTMTVY TQGRFSCQWSNINNAL FRTGKKYNQNWQSLGT IRITYSATYNPNGNSY LCIYGWSTNPLVEFYI VESWGNWRPPGATSLG QVTIDGGTYDIYRTTR VNQPSIVGTATFDQYW SVRTSKRTSGTVTVTD HFRAWANRGLNLGTID QITLCVEGYQSSGSAN ITQNTFSQGSSSGSSG GSSGSTTTRIECENM | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GCAAACAAGCATTACTCTGACATCCAACGCATCCGGTACGTTTGAC GGTTACTATTACGAACTCTGGAAGGATACTGGCAATACAACAATGA CGGTCTACACTCAAGGTCGCTTTTCCTGCCAGTGGTCGAACATCAA TAACGCGTTGTTTAGGACCGGGAAGAAATACAACCAGAATTGGCAG TCTCTTGGCACAATCCGGATCACGTACTCTGCGACTTACAACCCAA ACGGGAACTCCTACTTGTGTATCTATGGCTGGTCTACCAACCCATT GGTCGAGTTCTACATCGTTGAGTCCTGGGGGAACTGGAGACCGCCT GGTGCCACGTCCCTGGGCCAAGTGACAATCGATGGCGGGACCTACG ACATCTATAGGACGACACGCGTCAACCAGCCGTCAATTGTGGGGAC AGCCACGTTCGATCAGTACTGGAGCGTGCGCACCTCTAAGCGGACT TCAGGAACAGTGACCGTGACCGATCACTTCCGCGCCTGGGCGAACC GGGGCCTGAACCTCGGCACAATAGACCAAATTACATTGTGCGTGGA GGGTTACCAAAGCTCTGGATCAGCCAACATCACCCAGAACACCTTC TCTCAGGGCTCTTCTTCCGGCAGTTCGGGTGGCTCATCCGGCTCCA |

TABLE 1-continued

Sequences of CWDEs and their fusions in vectors

| pAG vector | Sequence annotation | Protein sequence | Nucleotide sequence |
|---|---|---|---|
| | | SLSGPYVSRITNPFNG IALYANGDTARATVNF PASRNYNFRLRGCGNN NNLARVDLRIDGRTVG TFYYQGTYPWEAPIDN VYVSAGSHTVEITVTA DNGTWDVYADYLVIQS EKDEL* (SEQ ID NO: 86) | CAACGACTACTCGCATCGAGTGTGAGAACATGTCCTTGTCCGGACC CTACGTTAGCAGGATCACCAATCCCTTTAATGGTATTGCGCTGTAC GCCAACGGAGACACAGCCCGCGCTACCGTTAACTTCCCCGCAAGTC GCAACTACAATTTCCGCTGCGGGGTTGCGGCAACAACAATAATCT TGCCCGTGTGGACCTGAGGATCGACGGACGGACCGTCGGGACCTTT TATTACCAGGGCACATACCCCTGGGAGGCCCCAATTGACAATGTTT ATGTCAGTGCGGGAGTCATACAGTCGAAATCACTGTTACTGCGGA TAACGGCACATGGGACGTGTATGCCGACTACCTGGTGATACAGAGC GAGAAGGACGAGCTGTGA (SEQ ID NO: 158) |
| 2059 | 043097 | MFPAGNATELEKRQTT PNSEGWHDGYYYSWWS DGGAQATYTNLEGGTY EISWGDGGNLVGGKGW NPGLNARAIHFEGVYQ PNGNSYLAVYGWTRNP LVEYYIVENFGTYDPS SGATDLGTVECDGSIY RLGKTTRVNAPSIDGT QTFDQYWSVRQDKRTS GTVQTGCHFDAWARAG LNVNGDHYYQIVATEG YFSSGYARITVADVG* (SEQ ID NO: 87) | ATGTTCCCAGCTGGAAACGCAACGGAATTGGAGAAAAGACAAACCA CCCCTAACTCTGAGGGCTGGCATGACGGATACTACTACTCTTGGTG GAGCGATGGTGGTGCACAGGCCACCTATACAAACCTCGAAGGCGGC ACTTATGAGATTTCATGGGGTGACGGTGGCAACCTTGTCGGCGGAA AGGGGTGGAACCCCGGACTTAACGCCAGGGCAATCCACTTCGAAGG GGTGTACCAGCCCAATGGCAACTCATACCTGGCCGTCTACGGGTGG ACGCGCAATCCGCTGGTTGAGTACTATATCGTGGAGAATTTCGGAA CTTATGACCCTAGCTCCGGTGCCACGGACCTCGGGACAGTCGAGTG TGACGGAAGCATCTACAGGCTGGGTAAAACTACCCGCGTTAATGCT CCATCGATCGACGGCACGCAAACATTTGATCAATACTGGTCCGTGC GGCAGGATAAGAGGACAAGCGGCACAGTTCAGACGGGTTGCCACTT TGATGCCTGGGCAAGAGCGGGGCTCAATGTGAATGGGGACCACTAC TATCAGATTGTGGCGACCGAGGGCTATTTCTCCAGTGGCTATGCGC GTATAACCGTCGCTGATGTTGGATGA (SEQ ID NO: 159) |
| 2060 | PR1a:043097 | MGFVLFSQLPSFLLVS TLLLFLVISHSCRAFP AGNATELEKRQTTPNS EGWHDGYYYSWWSDGG AQATYTNLEGGTYEIS WGDGGNLVGGKGWNPG LNARAIHFEGVYQPNG NSYLAVYGWTRNPLVE YYIVENFGTYDPSSGA TDLGTVECDGSIYRLG KTTRVNAPSIDGTQTF DQYWSVRQDKRTSGTV QTGCHFDAWARAGLNV NGDHYYQIVATEGYFS SGYARITVADVG* (SEQ ID NO: 88) | ATGGGCTTCGTGCTCTTCTCCCAGCTGCCTTCCTTCCTTCTTGTCT CCACCCTGCTCTTGTTCCTCGTGATCTCCCACTCCTGCCGCGCCTT CCCAGCTGGAAACGCAACGGAATTGGAGAAAAGACAAACCACCCCT AACTCTGAGGGCTGGCATGACGGATACTACTACTCTTGGTGGAGCG ATGGTGGTGCACAGGCCACCTATACAAACCTCGAAGGCGGCACTTA TGAGATTTCATGGGGTGACGGTGGCAACCTTGTCGGCGGAAAGGGG TGGAACCCCGGACTTAACGCCAGGGCAATCCACTTCGAAGGGGTGT ACCAGCCCAATGGCAACTCATACCTGGCCGTCTACGGGTGGACGCG CAATCCGCTGGTTGAGTACTATATCGTGGAGAATTTCGGAACTTAT GACCCTAGCTCCGGTGCCACGGACCTCGGGACAGTCGAGTGTGACG GAAGCATCTACAGGCTGGGTAAAACTACCCGCGTTAATGCTCCATC GATCGACGGCACGCAAACATTTGATCAATACTGGTCCGTGCGGCAG GATAAGAGGACAAGCGGCACAGTTCAGACGGGTTGCCACTTTGATG CCTGGGCAAGAGCGGGGCTCAATGTGAATGGGGACCACTACTATCA GATTGTGGCGACCGAGGGCTATTTCTCCAGTGGCTATGCGCGTATA ACCGTCGCTGATGTTGGATGA (SEQ ID NO: 160) |
| 2061 | PR1a:043097:SEKDEL | MGFVLFSQLPSFLLVS TLLLFLVISHSCRAFP AGNATELEKRQTTPNS EGWHDGYYYSWWSDGG AQATYTNLEGGTYEIS WGDGGNLVGGKGWNPG LNARAIHFEGVYQPNG NSYLAVYGWTRNPLVE YYIVENFGTYDPSSGA TDLGTVECDGSIYRLG KTTRVNAPSIDGTQTF DQYWSVRQDKRTSGTV QTGCHFDAWARAGLNV NGDHYYQIVATEGYFS SGYARITVADVGSEKD EL* (SEQ ID NO: 89) | ATGGGCTTCGTGCTCTTCTCCCAGCTGCCTTCCTTCCTTCTTGTCT CCACCCTGCTCTTGTTCCTCGTGATCTCCCACTCCTGCCGCGCCTT CCCAGCTGGAAACGCAACGGAATTGGAGAAAAGACAAACCACCCCT AACTCTGAGGGCTGGCATGACGGATACTACTACTCTTGGTGGAGCG ATGGTGGTGCACAGGCCACCTATACAAACCTCGAAGGCGGCACTTA TGAGATTTCATGGGGTGACGGTGGCAACCTTGTCGGCGGAAAGGGG TGGAACCCCGGACTTAACGCCAGGGCAATCCACTTCGAAGGGGTGT ACCAGCCCAATGGCAACTCATACCTGGCCGTCTACGGGTGGACGCG CAATCCGCTGGTTGAGTACTATATCGTGGAGAATTTCGGAACTTAT GACCCTAGCTCCGGTGCCACGGACCTCGGGACAGTCGAGTGTGACG GAAGCATCTACAGGCTGGGTAAAACTACCCGCGTTAATGCTCCATC GATCGACGGCACGCAAACATTTGATCAATACTGGTCCGTGCGGCAG GATAAGAGGACAAGCGGCACAGTTCAGACGGGTTGCCACTTTGATG CCTGGGCAAGAGCGGGGCTCAATGTGAATGGGGACCACTACTATCA GATTGTGGCGACCGAGGGCTATTTCTCCAGTGGCTATGCGCGTATA ACCGTCGCTGATGTTGGAAGCGAGAAGGACGAGCTGTGA (SEQ ID NO: 161) |
| 2062 | BAASS:043097 | MANKHLSLSLFLVLLG LSASLASGQVFPAGNA TELEKRQTTPNSEGWH DGYYYSWWSDGGAQAT YTNLEGGTYEISWGDG GNLVGGKGWNPGLNAR AIHFEGVYQPNGNSYL AVYGWTRNPLVEYYIV ENFGTYDPSSGATDLG TVECDGSIYRLGKTTR VNAPSIDGTQTFDQYW SVRQDKRTSGTVQTGC | ATGGCGAACAAACATTTGTCCCTCTCCCTCTTCCTCGTCCTCCTTG GCCTGTCGGCCAGCTTGGCCTCCGGGCAAGTCTTCCCAGCTGGAAA CGCAACGGAATTGGAGAAAAGACAAACCACCCCTAACTCTGAGGGC TGGCATGACGGATACTACTACTCTTGGTGGAGCGATGGTGGTGCAC AGGCCACCTATACAAACCTCGAAGGCGGCACTTATGAGATTTCATG GGGTGACGGTGGCAACCTTGTCGGCGGAAAGGGGTGGAACCCCGGA CTTAACGCCAGGGCAATCCACTTCGAAGGGGTGTACCAGCCCAATG GCAACTCATACCTGGCCGTCTACGGGTGGACGCGCAATCCGCTGGT TGAGTACTATATCGTGGAGAATTTCGGAACTTATGACCCTAGCTCC GGTGCCACGGACCTCGGGACAGTCGAGTGTGACGGAAGCATCTACA GGCTGGGTAAAACTACCCGCGTTAATGCTCCATCGATCGACGGCAC GCAAACATTTGATCAATACTGGTCCGTGCGGCAGGATAAGAGGACA |

TABLE 1-continued

Sequences of CWDEs and their fusions in vectors

| pAG vector | Sequence annotation | Protein sequence | Nucleotide sequence |
|---|---|---|---|
| | | HFDAWARAGLNVNGDH YYQIVATEGYFSSGYA RITVADVG* (SEQ ID NO: 90) | AGCGGCACAGTTCAGACGGGTTGCCACTTTGATGCCTGGCAAGAG CGGGGCTCAATGTGAATGGGGACCACTACTATCAGATTGTGGCGAC CGAGGGCTATTTCTCCAGTGGCTATGCGCGTATAACCGTCGCTGAT GTTGGATGA (SEQ ID NO: 162) |
| 2063 | BAASS:O43097:SEKDEL | MANKHLSLSLFLVLLG LSASLASGQVFPAGNA TELEKRQTTPNSEGWH DGYYYSWWSDGGAQAT YTNLEGGTYEISWGDG GNLVGGKGWNPGLNAR AIHFEGVYQPNGNSYL AVYGWTRNPLVEYYIV ENFGTYDPSSGATDLG TVECDGSIYRLGKTTR VNAPSIDGTQTFDQYW SVRQDKRTSGTVQTGC HFDAWARAGLNVNGDH YYQIVATEGYFSSGYA RITVADVGSEKDEL* (SEQ ID NO: 91) | ATGGCGAACAAACATTTGTCCCTCTCCCTCTTCCTCGTCCTCCTTG GCCTGTCGGCCAGCTTGGCCTCCGGGCAAGTCTTCCCAGCTGGAAA CGCAACGGAATTGGAGAAAAGACAAACCACCCCTAACTCTGAGGGC TGGCATGACGGATACTACTACTCTTGGTGGAGCGATGGTGGTGCAC AGGCCACCTATACAAACCTCGAAGGCGGCACTTATGAGATTTCATG GGGTGACGGTGGCAACCTTGTCGGCGGAAAGGGGTGGAACCCCGGA CTTAACGCCAGGGCAATCCACTTCGAAGGGGTGTACCAGCCCAATG GCAACTCATACCTGGCCGTCTACGGGTGGACGCGCAATCCGCTGGT TGAGTACTATATCGTGGAGAATTTCGGAACTTATGACCCTAGCTCC GGTGCCACGGACCTCGGACAGTCGAGTGTGACGGAAGCATCTACA GGCTGGGTAAAACTACCCGCGTTAATGCTCCATCGATCGACGGCAC GCAAACATTTGATCAATACTGGTCCGTGCGGCAGGATAAGAGGACA AGCGGCACAGTTCAGACGGGTTGCCACTTTGATGCCTGGCAAGAG CGGGGCTCAATGTGAATGGGGACCACTACTATCAGATTGTGGCGAC CGAGGGCTATTTCTCCAGTGGCTATGCGCGTATAACCGTCGCTGAT GTTGGAAGCGAGAAGGACGAGCTGTGA (SEQ ID NO: 163) |
| 2064 | HvAleSP:O43097 | MAHARVLLLALAVLAT AAVAVASSSSFADSNP IRPVTDRAASTFPAGN ATELEKRQTTPNSEGW HDGYYYSWWSDGGAQA TYTNLEGGTYEISWGD GGNLVGGKGWNPGLNA RAIHFEGVYQPNGNSY LAVYGWTRNPLVEYYI VENFGTYDPSSGATDL GTVECDGSIYRLGKTT RVNAPSIDGTQTFDQY WSVRQDKRTSGTVQTG CHFDAWARAGLNVNGD HYYQIVATEGYFSSGY ARITVADVG* (SEQ ID NO: 92) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCTTCCCAGCT GGAAACGCAACGGAATTGGAGAAAAGACAAACCACCCCTAACTCTG AGGGCTGGCATGACGGATACTACTACTCTTGGTGGAGCGATGGTGG TGCACAGGCCACCTATACAAACCTCGAAGGCGGCACTTATGAGATT TCATGGGGTGACGGTGGCAACCTTGTCGGCGGAAAGGGGTGGAACC CCGGACTTAACGCCAGGGCAATCCACTTCGAAGGGGTGTACCAGCC CAATGGCAACTCATACCTGGCCGTCTACGGGTGGACGCGCAATCCG CTGGTTGAGTACTATATCGTGGAGAATTTCGGAACTTATGACCCTA GCTCCGGTGCCACGGACCTCGGACAGTCGAGTGTGACGGAAGCAT CTACAGGCTGGGTAAAACTACCCGCGTTAATGCTCCATCGATCGAC GGCACGCAAACATTTGATCAATACTGGTCCGTGCGGCAGGATAAGA GGACAAGCGGCACAGTTCAGACGGGTTGCCACTTTGATGCCTGGGC AAGAGCGGGGCTCAATGTGAATGGGGACCACTACTATCAGATTGTG GCGACCGAGGGCTATTTCTCCAGTGGCTATGCGCGTATAACCGTCG CTGATGTTGGATGA (SEQ ID NO: 164) |
| 2065 | HvAleSP:O43097: SEKDEL | MAHARVLLLALAVLAT AAVAVASSSSFADSNP IRPVTDRAASTFPAGN ATELEKRQTTPNSEGW HDGYYYSWWSDGGAQA TYTNLEGGTYEISWGD GGNLVGGKGWNPGLNA RAIHFEGVYQPNGNSY LAVYGWTRNPLVEYYI VENFGTYDPSSGATDL GTVECDGSIYRLGKTT RVNAPSIDGTQTFDQY WSVRQDKRTSGTVQTG CHFDAWARAGLNVNGD HYYQIVATEGYFSSGY ARITVADVGSEKDEL* (SEQ ID NO: 93) | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCTTCCCAGCT GGAAACGCAACGGAATTGGAGAAAAGACAAACCACCCCTAACTCTG AGGGCTGGCATGACGGATACTACTACTCTTGGTGGAGCGATGGTGG TGCACAGGCCACCTATACAAACCTCGAAGGCGGCACTTATGAGATT TCATGGGGTGACGGTGGCAACCTTGTCGGCGGAAAGGGGTGGAACC CCGGACTTAACGCCAGGGCAATCCACTTCGAAGGGGTGTACCAGCC CAATGGCAACTCATACCTGGCCGTCTACGGGTGGACGCGCAATCCG CTGGTTGAGTACTATATCGTGGAGAATTTCGGAACTTATGACCCTA GCTCCGGTGCCACGGACCTCGGACAGTCGAGTGTGACGGAAGCAT CTACAGGCTGGGTAAAACTACCCGCGTTAATGCTCCATCGATCGAC GGCACGCAAACATTTGATCAATACTGGTCCGTGCGGCAGGATAAGA GGACAAGCGGCACAGTTCAGACGGGTTGCCACTTTGATGCCTGGGC AAGAGCGGGGCTCAATGTGAATGGGGACCACTACTATCAGATTGTG GCGACCGAGGGCTATTTCTCCAGTGGCTATGCGCGTATAACCGTCG CTGATGTTGGAAGCGAGAAGGACGAGCTGTGA (SEQ ID NO: 165) |
| 2066 | BAASS:P77853S158-2 | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GTYDIYRTTRVNQPCL AEGSLVLDAATGQRVP IEKVRPGMEVFSLGPD YRLYRVPVLEVLESGV REVVRLRTRSGRTLVL TPDHPLLTPEGWKPLC DLPLGTPIAVPAELPV | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGACCTACGACATCTATAGGACGACAC GCGTCAACCAGCCTTGCCTGGCCGAGGGCTCGCTCGTCTTGGACGC GGCTACCGGCCAGAGGGTCCCTATCGAAAAGGTGCGTCCGGGGATG GAAGTTTTCTCTTGGGACCTGATTACAGACTGTATCGGGTGCCCG TTTTGGAGGTCCTTGAGAGCGGGGTTAGGGAAGTTGTGCGCCTCAG AACTCGGTCAGGGAGAACGCTGGTGTTGACACCAGATCACCCGCTT TTGACCCCCGAAGGTTGGAAACCTCTTTGTGACCTCCCGCTTGGAA |

TABLE 1-continued

Sequences of CWDEs and their fusions in vectors

| pAG vector | Sequence annotation | Protein sequence | Nucleotide sequence |
|---|---|---|---|
| | | AGHLAPPEERVTLLAL LLGDGNTKLPGRRGTR PNAFFYSKDPELLAAY RRCAEALGAKVKAYVH PTTGVVTLATLAPRPG AQDPVKRLVVEAGMVA KAEEKRVPEEVFRYRR EALALFLGRLFSTDGS VEKKRISYSSASLGLA QDDAHLLLRLGITSQL RSRGPRAHEVLISGRE DILRFAELIGPYLLGA KRERLAALEAEARRRL PGQGWHLRLVLPAVAY RVSEAKRRSGFSWSEA GRRVAVAGSCLSSGLN LKLPRRYLSRHRLSLL GEAFADPGLEALAEGQ VLWDPIVAVEPAGKAR TFDLRVPPFANFVSED LVVHNSIVGTATFDQY WSVRTSKRTSGTVTVT DHFRAWANRGLNLGTI DQITLCVEGYQSSGSA NITQNTFSQGSSSGSS GGSSGSTTTTRIECEN MSLSGPYVSRITNPFN GIALYANGDTARATVN FPASRNYNFRLRGCGN NNNLARVDLRIDGRTV GTFYYQGTYPWEAPID NVYVSAGSHTVEITVT ADNGTWDVYADYLVIQ* (SEQ ID NO: 94) | CTCCAATTGCAGTCCCCGCAGAACTGCCTGTGGCGGGCCACTTGGC CCCACCTGAAGAACGTGTTACGCTCCTGGCTCTTCTGTTGGGGGAT GGGAACACAAAGCTGCCGGGTCGGAGAGGTACACGTCCTAATGCCT TCTTCTACAGCAAAGACCCCGAATTGCTCGCGGCTTATCGCCGGTG TGCAGAAGCCTTGGGTGCAAAGGTGAAAGCATACGTCCACCCGACT ACGGGGGTGGTTACACTCGCAACCCTCGCTCCACGTCCTGGAGCTC AAGATCCTGTCAAACGCCTCGTTGTCGAGGCGGGAATGGTTGCTAA AGCCGAAGAGAAGAGGGTCCCGGAGGAGGTGTTTCGTTACCGGCGT GAGGCGTTGGCCCTTTTCTTGGGCCGTTTGTTCTCGACAGACGGCT CTGTTGAAAAGAAGAGGATCTCTTATTCAAGTGCCAGTTTGGGACT GGCCCAGGATGACGCACATCTCTTGCTGCGCCTTGGAATTACATCT CAACTCCGTTCGAGAGGGCCACGGGCTCACGAGGTTCTTATATCGG GCCGCGAGGATATTTTGCGGTTTGCTGAACTTATCGGACCCTACCT CTTGGGGGCAAGAGGGAGAGACTTGCAGCGCTGGAAGCTGAGGCC CGCAGGCGTTTGCCTGGACAGGGATGGCACTTGCGGCTTGTTCTTC CTGCCGTGGCGTACAGAGTGAGCGAGGCTAAAAGGCGCTCGGGATT TTCGTGGAGTGAAGCCGGTCGGCGCGTCGCAGTTGCGGGATCGTGT TTGTCATCTGGACTCAACCTCAAATTGCCCAGACGCTACCTTTCTC GGCACCGGTTGTCGCTGCTCGGTGAGGCTTTTGCCGACCCTGGGCT GGAAGCGCTCGGAAGGCCAAGTGCTCTGGGACCCTATTGTTGCT GTCGAACCGGCCGGTAAGGCGAGAACATTCGACTTGCGCGTTCCAC CCTTTGCAAACTTCGTGAGCGAGGACCTGGTGGTGCATAACTCCAT TGTGGGACAGCCACGTTCGATCAGTACTGGAGCGTGCGCACCTCT AAGCGGATTCAGGAACAGTGACCGTGACCGATCACTTCCGCGCCT GGGCGAACCGGGCCTGAACCTCGGCACAATAGACCAAATTACATT GTGCGTGGAGGGTTACCAAAGCTCTGGATCAGCCAACATCACCCAG AACACCTTCTCTCAGGGCTCTTCTTCCGGCAGTTCGGGTGGCTCAT CCGGCTCCACAACGACTACTCGCATCGAGTGTGAGAACATGTCCTT GTCCGGACCCTACGTTAGCAGGATCACCAATCCCTTTAATGGTATT GCGCTGTACGCCAACGGAGACACAGCCCGCGCTACCGTTAACTTCC CCGCAAGTCGCAACTACAATTTCCGCCTGCGGGGTTGCGGCAACAA CAATAATCTTGCCCGTGTGGACCTGAGGGATCGACGGACGGACCGTC GGGACCTTTTATTACCAGGGCACATACCCCTGGGAGGCCCCAATTG ACAATGTTTATGTCAGTGCGGGGAGTCATACAGTCGAAATCACTGT TACTGCGGATAACGGCACATGGGACGTGTATGCCGACTACCTGGTG ATACAGTGA (SEQ ID NO: 166) |
| 2067 | BAASS:P77853S158-19 | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GTYDIYRTTRVNQPCL AEGSLVLDAATGQRVP IEKVRPGMEVFSLGPD YRLYRVPVLEVLESGV GEVVRLRTRSGRTLVL TPDHPLLTPEGWKPLC DLPLGTPIAVPAELPV AGHLAPPEERVTLLAL LLGDGNTKLSGRRGTR PIAFFYSKDPELLAAY RRCAEALGAKVKAYVH PTTGVVTLATLAPRPG AQDPVKRLVVEAGMVA KAEEKRVPEEVFRYRR EALALFLGRLFSTDGS VEKKRISYSSASLGLA QDVAHLLLRLGITSQL RSRGPRAHEVLISGRE DILRFAELIGPYLLGA KRERLAALEAEARRRL PGQGWHLRLVLPAVAY RVSEAKRRSGFSWSEA GRRVAVAGSCLSSGLN LKLPRRYLSRHRLSLL GEAFADPGLEALAEGQ VLWDPIVAVEPAGKAR TFDLRVPPFANFVSED LVVHNSIVGTATFDQY WSVRTSKRTSGTVTVT | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATGATGGCGGGACCTACGACATCTATAGGACGACAC GCGTCAACCAGCCTTGCCTGGCCGAGGGCTCGCTCGTCTTGGACGC GGCTACCGGGCAGAGGGTCCCTATCGAAAAGGTGCGTCCGGGGATG GAAGTTTTCTCCTTGGGACCTGATTACAGACTGTATCGGGTGCCCG TTTTGGAGGTCCTTGAGAGCGGGGTTGGGGAAGTTGTGCGCGTCAG AACTCGGTCAGGGAGAACGCTGGTGTTGACACAGATCACCCGCTT TTGACCCCCGAAGGTTGGAAACCTGTTTGTGACCTCCCGCTTGGAA CTCCAATTGCAGTCCCCGCAGAACTGCCTGTGGCGGGCCACTTGGC CCCACCTGAAGAACGTGTTACGCTCCTGGCTCTTCTGTTGGGGGAT GGGAACACAAAGCTGTCGGGTCGGAGAGGTACACGTCCTATTGCCT TCTTCTACAGCAAAGACCCCGAATTGCTCGCGGCTTATCGCCGGTG TGCAGAAGCCTTGGGTGCAAAGGTGAAAGCATACGTCCACCCGACT ACGGGGGTGGTTACACTCGCAACCCTCGCTCCACGTCCTGGAGCTC AAGATCCTGTCAAACGCCTCGTTGTCGAGGCGGGAATGGTTGCTAA AGCCGAAGAGAAGAGGGTCCCGGAGGAGGTGTTTCGTTACCGGCGT GAGGCGTTGGCCCTTTTCTTGGGCCGTTTGTTCTCGACAGACGGCT CTGTTGAAAAGAAGAGGATCTCTTATTCAAGTGCCAGTTTGGGACT GGCCCAGGATGTCGCACATCTCTTGCTGCGCCTTGGAATTACATCT CAACTCCGTTCGAGAGGGCCACGGGCTCACGAGGTTCTTATATCGG GCCGCGAGGATATTTTGCGGTTTGCTGAACTTATCGGACCCTACCT CTTGGGGGCAAGAGGGAGAGACTTGCAGCGCTGGAAGCTGAGGCC CGCAGGCGTTTGCCTGGACAGGGATGGCACTTGCGGCTTGTTCTTC CTGCCGTGGCGTACAGAGTGAGCGAGGCTAAAAGGCGCTCGGGATT TTCGTGGAGTGAAGCCGGTCGGCGCGTCGCAGTTGCGGGATCGTGT TTGTCATCTGGACTCAACCTCAAATTGCCCAGACGCTACCTTTCTC GGCACCGGTTGTCGCTGCTCGGTGAGGCTTTTGCCGACCCTGGGCT GGAAGCGCTCGGAAGGCCAAGTGCTCTGGGACCCTATTGTTGCT GTCGAACCGGCCGGTAAGGCGAGAACATTCGACTTGCGCGTTCCAC CCTTTGCAAACTTCGTGAGCGAGGACCTGGTGGTGCATAACTCCAT |

TABLE 1-continued

Sequences of CWDEs and their fusions in vectors

| pAG vector | Sequence annotation | Protein sequence | Nucleotide sequence |
|---|---|---|---|
| | | DHFRAWANRGLNLGTI DQITLCVEGYQSSGSA NITQNTFSQGSSSGSS GGSSGSTTTTRIECEN MSLSGPYVSRITNPFN GIALYANGDTARATVN FPASRNYNPRLRGCGN NNNLARVDLRIDGRTV GTFYYQGTYPWEAPID NVYVSAGSHTVEITVT ADNGTWDVYADYLVIQ * (SEQ ID NO: 95) | TGTGGGGACAGCCACGTTCGATCAGTACTGGAGCGTGCGCACCTCT AAGCGGACTTCAGGAACAGTGACCGTGACCGATCACTTCCGCGCCT GGGCGAACCGGGGCCTGAACCTCGGCACAATAGACCAAATTACATT GTGCGTGGAGGGTTACCAAAGCTCTGGATCAGCCAACATCACCCAG AACACCTTCTCTCAGGGCTCTTCTTCCGGCAGTTCGGTGGCTCAT CCCGGCTCCACAACGACTACTCGCATCGAGTGTGAGAACATGTCCTT GTCCGGACCCTACGTTAGCAGGATCACCAATCCCTTTAATGGTATT GCGCTGTACGCCAACGGAGACACAGCCCGCGCTACCGTTAACTTCC CCGCAAGTCGCAACTACAATTTCCGCCTGCGGGGTTGCGGCAACAA CAATAATCTTGCCCGTGTGGACCTGAGGATCGACGGACGGACCGTC GGGACCTTTTATTACCAGGGCACATACCCCTGGGAGGCCCCAATTG ACAATGTTTATGTCAGTGCGGGGAGTCATACAGTCGAAATCACTGT TACTGCGGATAACGGCACATGGGACGTGTATGCCGACTACCTGGTG ATACAGTGA (SEQ ID NO: 167) |
| 2068 | BAASS:P77853T134-1 | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGACLAEGSLVLD AATGQRVPIEKVRPGM EVFSLGPDYRLYRVPV LEVLESGVREVVRLRT RSGRTLVLTPDHPLLT PEGWKPLCDLPLGTPI AVPAELPVACHLAPPE ERVTLLALLLGDGNTK PSGRRGTRPNAFFYSK DPELLAAYRRCAEALG AKVKAYVHPTTGVVTL ATLAPRPGAQDPVKRL VVEAGMVAKAEEKRVP EEVFRYRREALALFLG RLFSTDGSVEKKRISY SSASLGLAQDVAHLLL RLGITSQLRSRGPRAH EVLISGREDILRFAEL IGPYLLGAKRERLAAL EAEARRRLPGQGWHLR LVLPAVAYRVSEAKRR SGFSWSEAGRRVAVAG SCLSSGLNLKLPRRYL SRHRLSLLGEAFADPG LEALAEGQVLWDPIVA VEPAGKARTFDLRVPP FANFVSEDLVVHNTSP LGQVTIDGGTYDIYRT TRVNQPSIVGTATFDQ YWSVRTSKRTSGTVTV TDHFRAWANRGLNLGT IDQITLCVEGYQSSGS ANITQNTFSQGSSSGS SGGSSGSTTTTRIECE NMSLSGPYVSRITNPF NGIALYANGDTARATV NFPASRNYNPRLRGCG NNNNLARVDLRIDGRT VGTFYYQGTYPWEAPI DNVYVSAGSHTVEITV TADNGTWDVYADYLVI Q* (SEQ ID NO: 96) | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCTGCCTGGCCGAG GCTCGCTCGTCTTGGACGCGGCTACCGGGCAGAGGGTCCCTATCG AAAAGGTGCGTCCGGGGATGGAAGTTTTCTCCTTGGGACCTGATTA CAGACTGTATCGGGTGCCCGTTTTGGAGGTCCTTGAGAGCGGGGTT AGGGAAGTTGTGCGCCTCAGAACTCGGTCAGGGAGAACGCTGGTGT TGACACCAGATCACCCGCTTTTGACCCCCGAAGGTTGGAAACCTCT TGTGACCTCCCGCTTGGAACTCCAATTGCAGTCCCGCAGAACTG CCTGTGGCGTGCCACTTGGCCCCACCTGAAGAACGTGTTACGCTCC TGGCTCTTCTGTTGGGGGATGGAACACAAAGCCGTCGGGTCGGAG AGGTACACGTCCTAATGCCTTCTTCTACAGCAAAGACCCCGAATTG CTCGCGGCTTATCGCCGGTGTGCAGAAGCCTTGGGTGCAAAGGTGA AAGCATACGTCCACCCGACTACGGGGGTGGTTACACTCGCAACCCT CGCTCCACGTCCTGGAGCTCAAGATCCTGTCAAACGCCTCGTTGTC GAGGCGGGAATGGTTGCTAAAGCCGAAGAGAAGAGGGTCCCGGAGG AGGTGTTTCGTTACCGGCGTGAGGCGTTGGCCCTTTTCTTGGGCCG TTTGTTTCTCGACAGACGGCTCTGTTGAAAAGAAGAGGATCTCTTAT TCAAGTGCCAGTTTGGGACTGGCCCAGGATGTCGCACATCTCTTGC TGCGCCTTGGAATTACATCTCAACTCCGTTCGAGAGGGCCACGGGC TCACGAGGTTCTTATATCGGGCCGCGAGGATATTTTGCGGTTTGCT GAACTTATCGGACCCTACCTCTTGGGGGCCAAGAGGGAGAGACTTG CAGCGCTGGAAGCTGAGGCCCGCAGGCGTTTGCCTGGACAGGGATG GCACTTGCGGCTTGTTCTTCCTGCCGTGGCGTACAGAGTGAGCGAG GCTAAAAGGCGCTCGGGATTTTCGTGGAGTGAAGCCGGTCGGCGCG TCGCAGTTGCGGGATCGTGTTTGTCATCTGGACTCAACCTCAAATT GCCCAGACGCTACCTTTCTCGGCACCGGTTGTCGCTGCTCGGTGAG GCTTTTGCCGACCCTGGGCTGGAAGCGCTCGCGGAAGGCCAAGTGC TCTGGGACCCTATTGTTGCTGTCGAACCGGCCGGTAAGGCGAGAAC ATTCGACTTGCGCGTTCCACCCTTTGCAAACTTCGTGAGCGAGGAC CTGGTGGTGCATAACACGTCCCCCTTGGGCCAAGTGACAATCGATG GCGGGACCTACGACATCTATAGGACGACACGCGTCAACCAGCCTTC CATTGTGGGGACAGCCACGTTCGATCAGTACTGGAGCGTGCGCACC TCTAAGCGGACTTCAGGAACAGTGACCGTGACCGATCACTTCCGCG CCCTGGGCGAACCGGGGCCTGAACCTCGGCACAATAGACCAAATTAC ATTGTGCGTGGAGGGTTACCAAAGCTCTTGGATCAGCCAACATCACC CAGAACACCTTCTCTCAGGGCTCTTCTTCCGGCAGTTCGGTGGCT CATCCGGCTCCACAACGACTACTCGCATCGAGTGTGAGAACATGTC CTTGTCCGGACCCTACGTTAGCAGGATCACCAATCCCTTTAATGGT ATTGCGCTGTACGCCAACGGAGACACAGCCCGCGCTACCGTTAACT TCCCCGCAAGTCGCAACTACAATTTCCGCCTGCGGGGTTGCGGCAA CAACAATAATCTTGCCCGTGTGGACCTGAGGATCGACGGACGGACC GTCGGGACCTTTTATTACCAGGGCACATACCCCTGGGAGGCCCCAA TTGACAATGTTTATGTCAGTGCGGGGAGTCATACAGTCGAAATCAC TGTTACTGCGGATAACGGCACATGGGACGTGTATGCCGACTACCTG GTGATACAGTGA (SEQ ID NO: 168) |
| 2069 | 068438 | MLEDKSPKLPDYKNDL LYERTFDEGLCFPWHT CEDSGGKCDFAVVDVP GEPGNKAFRLTVIDKG QNKWSVQMRHRGITLE QGHTYTVRFTIWSDKS CRVYAKIGQMGEPYTE | ATGCTGGAGGACAAGTCTCCCAAACTGCCTGATTATAAGAACGACC TTCTGTACGAACGCACATTCGACGAGGGGCTCTGCTTCCCGTGGCA CACGTGCGAAGATTCAGGAGGGAAATGCGATTTTGCCGTGGTCGAC GTTCCAGGCGAGCCTGGGAACAAGGCGTTCAGGCTCACTGTTATCG ATAAGGGTCAGAACAAGTGGTCGGTCCAAATGAGACACCGGGGTAT CACGTTGGAGCAGGGGCACACATACACCGTTCGGTTTACTATCTGG AGCGACAAGAGCTGCCGCGTGTATGCCAAAATCGGCCAAATGGGTG |

TABLE 1-continued

Sequences of CWDEs and their fusions in vectors

| pAG vector | Sequence annotation | Protein sequence | Nucleotide sequence |
|---|---|---|---|
| | | YWNNNWNPFNLTPGQK LTVEQNFTMNYPTDDT CEFTFHLGGELAAGTP YYVYLDDVSLYDPRFV KPVEYVLPQPDVRVNQ VGYLPFAKKYATVVSS STSPLKWQLLNSANQV VLEGNTIPKGLDKDSQ DYVHWIDFSNFKTEGK GYYFKLPTVNSDTNYS HPFDISADIYSKMKFD ALAFFYHKRSGIPIEM PYAGGEQWTRPAGHIG VAPNKGDTNVPTWPQD DEYAGRPQKYYTKDVT GGWYDAGDHGKYVVNG GIAVWTLMNMYERAKI RGIANQGAYKDGGMNI PERNNGYPDILDEARW EIEFFKKMQVTEKEDP SIAGMVHHKIHDFRWT ALGMLPHEDPQPRYLR PVSTAATLNFAATLAQ SARLWKDYDPTFAADC LEKAEIAWQAALKHPD IYAEYTPGSGGPGGGP YNDDYVGDEFYWAACE LYVTTGKDEYKNYLMN SPHYLEMPAKMGENGG ANGEDNGLWGCFTWGT TQGLGTITLALVENGL PSADIQKARNNIAKAA DKWLENIEEQGYRLPI KQAEDERGGYPWGSNS FILNQMIVMGYAYDFT GNSKYLDGMQDGMSYL LGRNGLDQSYVTGYGE RPLQNPHDRFWTPQTS KKFPAPPPGIIAGGPN SRFEDPTITAAVKKDT PPQKCYIDHTDSWSTN EITINWNAPFAWVTAY LDEIDLITPPGGVDPE EPEVIYGDCNGDGKVN STDAVALKRYILRSGI SINTDNADVNADGRVN STDLAILKRYILKEID VLPHK* (SEQ ID NO: 97) | AACCCTACACGGAGTACTGGAACAATAACTGGAATCCGTTCAACCT CACTCCGGGGCAGAAATTGACGGTGGAACAGAACTTTACTATGAAT TATCCCACGGACGACACGTGTGAGTTTACCTTCCACTTGGGAGGGG AACTGGCAGCCGGGACCCCTTACTACGTGTACCTCGACGACGTTTC TCTTTACGATCCCCGCTTTGTCAAGCCAGTGGAATACGTCCTGCCT CAACCGGATGTCAGGGTTAATCAAGTTGGATACCTCCCTTTTGCTA AGAAATATGCTACTGTCGTGTCATCGAGCACGTCCCCATTGAAGTG GCAACTTCTGAATAGTGCAAACCAAGTTGTCTTGGAGGGCAATACA ATCCCCAAGGGACTGGACAAAGATTCACAAGACTACGTTCATTGGA TCGATTTCTCGAACTTTAAGACCGAAGGCAAGGGGTACTATTTCAA GTTGCCCACTGTGAACTCCGATACTAACTACTCCCACCCGTTTGAT ATTTCTGCAGATATCTATTCAAAGATGAAGTTCGACGCGCTCGCTT TCTTTTACCATAAAAGGTCGGGAATACCAATCGAGATGCCCTACGC CGGGGGAGAGCAGTGGACAAGGCCCGCAGGGCACATTGGTGTCGCG CCGAACAAGGGCGACACGAATGTGCCAACTTGGCCCCAGGATGACG AATATGCTGGACGCCCCCAGAAATACTATACGAAAGACGTGACCGG CGGGTGGTACGATGCCGGTGACCACGGCAAGTACGTCGTGAACGGG GGTATCGCAGTTTGGACCCTTATGAATATGTACGAGAGAGCAAAGA TTAGAGGAATCGCTAACCAGGGTGCCTACAAAGATGGAGGAATGAA TATCCCGGAAAGGAATAACGGCTATCCTGATATTCTGGACGAGGCC AGATGGGAGATCGAATTTTTTAAGAAGATGCAAGTCACTGAGAAAG AAGATCCGTCGATTGCAGGTATGGTGCACCACAAGATCCACGATTT CAGGTGGACGGCGCTCGGAATGTTGCCTCACGAGGACCCCCAGCCA CGCTACCTTCGGCCCGTCAGCACAGCGGCAACCCTGAATTTCGCAG CGACCCTCGCTCAGTCTGCCAGATTGTGGAAGGATTACGACCCGAC TTTTGCAGCGGACTGCCTTGAGAAAGCTGAAATTGCCTGGCAAGCA GCACTCAAACACCCGGACATCTACGCTGAGTACACGCCAGGAAGCG GTGGGCCGGGTGGAGGTCCTTATAATGACGATTATGTCGGGGACGA GTTCTACTGGGCCGCTTGTGAACTCTATGTGACAACCGGTAAGGAT GAGTACAAGAATTACTTGATGAATAGTCCGCACTATCTGGAAATGC CAGCGAAGATGGGCGAGAACGGAGGGGCTAACGGCGAGGACAACGG TCTCTGGGGCTGCTTTACTTGGGGAACGACACAGGGGTTGGGTACA ATTACCCTTGCCCTCGTTGAAAACGGCCTCCCTTCGGCGGATATTC AAAAGGCCCGCAACAATATCGCTAAAGCCGCAGATAAGTGGCTTGA GAATATTGAAGAACAAGGTTACCGCCTGCCTATCAAACAAGCGGAG GATGAACGGGCGGATACCCGTGGGGTAGTAATTCTTTCATTCTCA ACCAGATGATCGTCATGGGCTACGCTTACGACTTCACGGGAAACAG CAAGTATCTTGACGGGATGCAGGACGGCATGTCCTACCTGCTCGGT AGAAACGGACTTGATCAATCGTACGTTACTGGGTACGGGGAGAGGC CACTTCAGAACCCCCACGACCGCTTTTGGACCCCTCAAACTTCGAA GAAATTCCCGGCCCCACCCCCTGGTATTATCCAGGCGGGCCGAAT AGCCGGTTTGAAGATCCAACGATCACTGCAGCGGTTAAGAAGGATA CACCCCCGCAGAAGTGCTATATTGACCACACCGATTCCTGGTCTAC TAACGAGATCACGATTAATTGGAACGCCCCCTTCGCGTGGGTCACA GCGTATCTGGACGAAATTGACTTGATTACCCCACCCGGCGGAGTGG ACCCTGAAGAGCCGGAAGTTATCTACGGTGATTGTAACGGCGACGG AAAGGTTAATTCGACCGATGCTGTGGCCCTTAAAAGGTATATCCTC CGCAGCGGTATCTCGATCAACACGGACAACGCGGACGTTAATGCAG ATGGTCGCGTGAATAGCACTGACCTCGCTATTTTGAAGCGCTATAT TTTGAAGGAGATCGATGTTCTTCCTCACAAGTGA (SEQ ID NO: 169) |
| 2070 | PR1a:068438 | MGFVLFSQLPSFLLVS TLLLFLVISHSCRAQN LEDKSPKLPDYKNDLL YERTFDEGLCFPWHTC EDSGGKCDFAVVDVPG EPGNKAFRLTVIDKGQ NKWSVQMRHRGITLEQ GHTYTVRFTIWSDKSC RVYAKIGQMGEPYTEY WNNNWNPFNLTPGQKL TVEQNFTMNYPTDDTC EFTFHLGGELAAGTPY YVYLDDVSLYDPRFVK PVEYVLPQPDVRVNQV GYLPFAKKYATVVSSS TSPLKWQLLNSANQVV LEGNTIPKGLDKDSQD YVHWIDFSNFKTEGKG YYFKLPTVNSDTNYSH PFDISADIYSKMKFDA LAFFYHKRSGIPIEMP YAGGEQWTRPAGHIGV APNKGDTNVPTWPQDD | ATGGGCTTCGTGCTCTTCTCCCAGCTGCCTTCCTTCCTTCTTGTCT CCACCCTGCTCTTGTTCCTCGTGATCTCCCACTCCTGCCGCGCCCA GAACCTGGAGGACAAGTCTCCCAAACTGCCTGATTATAAGAACGAC CTTCTGTACGAACGCACATTCGACGAGGGCTCTGCTTCCCGTGGC ACACGTGCTCCGAAGATTCAGGAGGGAAATGCGATTTTGCCGTGGTCGA CGTTCCAGGCGAGCCTGGGAACAAGGCGTTCAGGCTCACTGTTATC GATAAGGGTCAGAACAAGTGGTCGGTCCAAATGAGACACCGGGGTA TCACGTTGGAGCAGGGGCACACATACACCGTTCGGTTTACTATCTG GAGCGACAAGAGCTGCCGCGTGTATGCCAAATCGGCCAAATGGGT GAACCCTACACGGAGTACTGGAACAATAACTGGAATCCGTTCAACC TCACTCCGGGGCAGAAATTGACGGTGGAACAGAACTTTACTATGAA TTATCCCACGGACGACACGTGTGAGTTTACCTTCCACTTGGGAGGG GAACTGGCAGCCGGGACCCCTTACTACGTGTACCTCGACGACGTTT CTCTTTACGATCCCCGCTTTGTCAAGCCAGTGGAATACGTCCTGCC TCAACCGGATGTCAGGGTTAATCAAGTTGGATACCTCCCTTTTGCT AAGAAATATGCTACTGTCGTGTCATCGAGCACGTCCCCATTGAAGT GGCAACTTCTGAATAGTGCAAACCAAGTTGTCTTGGAGGGCAATAC ATCCCCAAGGGACTGGACAAAGATTCACAAGACTACGTTCATTGG ATCGATTTCTCGAACTTTAAGACCGAAGGCAAGGGGTACTATTTCA AGTTGCCCACTGTGAACTCCGATACTAACTACTCCCACCCGTTTGA TATTTCTGCAGATATCTATTCAAAGATGAAGTTCGACGCGCTCGCT TTCTTTTACCATAAAAGGTCGGGAATACCAATCGAGATGCCCTACG CCGGGGGAGAGCAGTGGACAAGGCCCGCAGGGCACATTGGTGTCGC |

TABLE 1-continued

Sequences of CWDEs and their fusions in vectors

| pAG vector annotation | Sequence Protein sequence | Nucleotide sequence |
|---|---|---|
| | EYAGRPQKYYTKDVTG<br>GWYDAGDHGKYVVNGG<br>IAVWTLMNMYERAKIR<br>GIANQGAYKDGGMNIP<br>ERNNGYPDILDEARWE<br>IEFFKKMQVTEKEDPS<br>IAGMVHHKIHDFRWTA<br>LGMLPHEDPQPRYLRP<br>VSTAATLNFAATLAQS<br>ARLWKDYDPTFAADCL<br>EKAEIAWQAALKHPDI<br>YAEYTPGSGGPGGGPY<br>NDDYVGDEFYWAACEL<br>YVTTGKDEYKNYLMNS<br>PHYLEMPAKMGENGGA<br>NGEDNGLWGCFTWGTT<br>QGLGTITLALVENGLP<br>SADIQKARNNIAKAAD<br>KWLENIEEQGYRLPIK<br>QAEDERGGYPWGSNSF<br>ILNQMIVMGYAYDFTG<br>NSKYLDGMQDGMSYLL<br>GRNGLDQSYVTGYGER<br>PLQNPHDRFWTPQTSK<br>KFPAPPPGIIAGGPNS<br>RFEDPTITAAVKKDTP<br>PQKCYIDHTDSWSTNE<br>ITINWNAPPAWVTAYL<br>DEIDLITPPGGVDPEE<br>PEVIYGDCNGDGKVNS<br>TDAVALKRYILRSGIS<br>INTDNADVNADGRVNS<br>TDLAILKRYILKEIDV<br>LPHK* (SEQ ID NO: 98) | GCCGAACAAGGGCGACACGAATGTGCCAACTTGGCCCCAGGATGAC<br>GAATATGCTGGACGCCCCCAGAAATACTATACGAAAGACGTGACCG<br>GCGGGTGGTACGATGCCGGTGACCACGGCAAGTACGTCGTGAACGG<br>GGGTATCGCAGTTTGGACCCTTATGAATATGTACGAGAGAGCAAAG<br>ATTAGAGGAATCGCTAACCAGGGTGCCTACAAAGATGGAGGAATGA<br>ATATCCCGGAAAGGAATAACGGCTATCCTGATATTCTGGACGAGGC<br>CAGATGGGAGATCGAATTTTTTAAGAAGATGCAAGTCACTGAGAAA<br>GAAGATCCGTCGATTGCAGGTATGGTGCACCACAAGATCCACGATT<br>TCAGGTGGACGGCGCTCGGAATGTTGCCTCACGAGGACCCCCAGCC<br>ACGCTACCTTCGGCCCGTCAGCACAGCGGCAACCCTGAATTTCGCA<br>GCGACCCTCGCTCAGTCTGCCAGATTGTGGAAGGATTACGACCCGA<br>CTTTTGCAGCGGACTGCCTTGAGAAAGCTGAAATTGCCTGGCAAGC<br>AGCACTCAAACACCCGGACATCTACGCTGAGTACACGCCAGGAAGC<br>GGTGGGCCGGGTGGAGGTCCTTATAATGACGATTATGTCGGGGACG<br>AGTTCTACTGGGCCGCTTGTGAACTCTATGTGACAACCGGTAAGGA<br>TGAGTACAAGAATTACTTGATGAATAGTCCGCACTATCTGGAAATG<br>CCAGCGAAGATGGGCGAGAACGGAGGGGCTAACGGCGAGGACAACG<br>GTCTCTGGGGCTGCTTTACTTGGGGAACGACACAGGGGTTGGGTAC<br>AATTACCCTTGCCCTCGTTGAAAACGGCCTCCCTTCGGCGGATATT<br>CAAAAGGCCCGCAACAATATCGCTAAGACGCAGATAAGTGGCTTG<br>AGAATATTGAAGAACAAGGTTACCGCCTGCCTATCAAACAAGCGGA<br>GGATGAACGGGCGGATACCCGTGGGGTAGTAATTCTTTCATTCTC<br>AACCAGATGATCGTCATGGGCTACGCTTACGACTTCACGGGAAACA<br>GCAAGTACTTGACGGGATGCAGGACGGCATGTCCTACCTGCTCGG<br>TAGAAACGGACTTGATCAATCGTACGTTACTGGGTACGGGGAGAGG<br>CCACTTCAGAACCCCCACGACCGCTTTTGGACCCCTCAAACTTCGA<br>AGAAATTCCCGGCCCCACCCCCTGGTATTATCGCAGGCGGGCCGAA<br>TAGCCGGTTTGAAGATCCAACATCACTGCAGCGGTTAAGAAGGAT<br>ACACCCCCGCAGAAGTGCTATATTGACCACACCGATTCCTGGTCTA<br>CTAACGAGATCACGATTAATTGGAACGCCCCCTTCGCGTGGGTCAC<br>AGCGTATCTGGACGAAATTGACTTGATTACCCCACCCGGCGGAGTG<br>GACCCTGAAGAGCCGGAAGTTATCTACGGTGATTGTAACGGCGACG<br>GAAAGGTTAATTCGACCGATGCTGTGGCCCTTAAAAGGTATATCCT<br>CCGCAGCGGTATCTCGATCAACACGGACAACGCGGACGTTAATGCA<br>GATGGTCGCGTGAATAGCACTGACCTCGCTATTTTGAAGCGCTATA<br>TTTTGAAGGAGATCGATGTTCTTCCTCACAAGTGA (SEQ ID NO: 170) |
| 2071 PR1a:068438:SEKDEL | MGFVLFSQLPSFLLVS<br>TLLLFLVISHSCRAQN<br>LEDKSPKLPDYKNDLL<br>YERTFDEGLCFPWHTC<br>EDSGGKCDFAVVDVPG<br>EPGNKAFRLTVIDKGQ<br>NKWSVQMRHRGITLEQ<br>GHTYTVRFTIWSDKSC<br>RVYAKIGQMGEPYTEY<br>WNNNWNPFNLTPGQKL<br>TVEQNFTMNYPTDDTC<br>EFTFHLGGELAAGTPY<br>YVYLDDVSLYDPRFVK<br>PVEYVLPQPDVRVNQV<br>GYLPFAKKYATVVSSS<br>TSPLKWQLLNSANQVV<br>LEGNTIPKGLDKDSQD<br>YVHWIDFSNFKTEGKG<br>YYFKLPTVNSDTNYSH<br>PFDISADIYSKMKFDA<br>LAFFYHKRSGIPIEMP<br>YAGGEQWTRPAGHIGV<br>APNKGDTNVPTWPQDD<br>EYAGRPQKYYTKDVTG<br>GWYDAGDHGKYVVNGG<br>IAVWTLMNMYERAKIR<br>GIANQGAYKDGGMNIP<br>ERNNGYPDILDEARWE<br>IEFFKKMQVTEKEDPS<br>IAGMVHHKIHDFRWTA<br>LGMLPHEDPQPRYLRP<br>VSTAATLNFAATLAQS<br>ARLWKDYDPTFAADCL<br>EKAEIAWQAALKHPDI<br>YAEYTPGSGGPGGGPY<br>NDDYVGDEFYWAACEL<br>YVTTGKDEYKNYLMNS | ATGGGCTTCGTGCTCTTCTCCCAGCTGCCTTCCTTCCTTCTTGTCT<br>CCACCCTGCTCTTGTTCCTCGTGATCTCCCACTCCTGCCGCGCCCA<br>GAACCTGGAGGACAAGTCTCCCAAACTGCCTGATTATAAGAACGAC<br>CTTCTGTACGAACGCACATTCGACGAGGGGCTCTGCTTCCCGTGGC<br>ACACGTGCGAAGATTCAGGAGGGAAATGCGATTTTGCCGTGGTCGA<br>CGTTCCAGGCGAGCCTGGGAACAAGGCGTTCAGGCTCACTGTTATC<br>GATAAGGGTCAGAACAAGTGGTCGGTCCAAATGAGACACCGGGGTA<br>TCACGTTGGAGCAGGGGCACACATACACCGTTCGGTTTACTATCTG<br>GAGCGACAAGAGCTGCCGCGTGTATGCCAAAATCGGCCAAATGGGT<br>GAACCCTACACGGAGTACTGGAACAATAACTGGAATCCGTTCAACC<br>TCACTCCGGGGCAGAAATTGACGGTGGAACAGAACTTTACTATGAA<br>TTATCCCACGGACGACACGTGTGAGTTTACCTTCCACTTGGGAGGG<br>GAACTGGCAGCCGGGACCCCTTACTACGTGTACCTCGACGACGTTT<br>CTCTTTACGATCCCCGCTTTGTCAAGCCAGTGGAATACGTCCTGCC<br>TCAACCGGATGTCAGGGTTAATCAAGTTGGATACCTCCCTTTTGCT<br>AAGAAATATGCTACTGTCGTGTCATCGAGCACGTCCCCATTGAAGT<br>GGCAACTTCTGAATAGTGCAAACCAAGTTGTCTTGGAGGGCAATAC<br>AATCCCCAAGGGACTGGACAAAGATTCACAAGACTACGTTCATTGG<br>ATCGATTTCTCGAACTTTAAGACCGAAGGCAAGGGGTACTATTTCA<br>AGTTGCCCACTGTGAACTCCGATACTAACTACTCCCACCCGTTTGA<br>TATTTCTGCAGATATCTATTCAAAGATGAAGTTCGACGCGCTCGCT<br>TTCTTTTACCATAAAAGGTCGGGAATACCAATCGAGATGCCCTACG<br>CCGGGGAGAGCAGTGGACAAGGCCCGCAGGGCACATTGGTGTCGC<br>GCCGAACAAGGGCGACACGAATGTGCCAACTTGGCCCCAGGATGAC<br>GAATATGCTGGACGCCCCCAGAAATACTATACGAAAGACGTGACCG<br>GCGGGTGGTACGATGCCGGTGACCACGGCAAGTACGTCGTGAACGG<br>GGGTATCGCAGTTTGGACCCTTATGAATATGTACGAGAGAGCAAAG<br>ATTAGAGGAATCGCTAACCAGGGTGCCTACAAAGATGGAGGAATGA<br>ATATCCCGGAAAGGAATAACGGCTATCCTGATATTCTGGACGAGGC<br>CAGATGGGAGATCGAATTTTTTAAGAAGATGCAAGTCACTGAGAAA<br>GAAGATCCGTCGATTGCAGGTATGGTGCACCACAAGATCCACGATT<br>TCAGGTGGACGGCGCTCGGAATGTTGCCTCACGAGGACCCCCAGCC<br>ACGCTACCTTCGGCCCGTCAGCACAGCGGCAACCCTGAATTTCGCA<br>GCGACCCTCGCTCAGTCTGCCAGATTGTGGAAGGATTACGACCCGA<br>CTTTTGCAGCGGACTGCCTTGAGAAAGCTGAAATTGCCTGGCAAGC<br>AGCACTCAAACACCCGGACATCTACGCTGAGTACACGCCAGGAAGC<br>GGTGGGCCGGGTGGAGGTCCTTATAATGACGATTATGTCGGGGACG |

TABLE 1-continued

Sequences of CWDEs and their fusions in vectors

| pAG vector | Sequence annotation | Protein sequence | Nucleotide sequence |
|---|---|---|---|
| | | PHYLEMPAKMGENGGA NGEDNGLWGCFTWGTT QGLGTITLALVENGLP SADIQKARNNIAKAAD KWLENIEEQGYRLPIK QAEDERGGYPWGSNSF ILNQMIVMGYAYDFTG NSKYLDGMQDGMSYLL GRNGLDQSYVTGYGER PLQNPHDRFWTPQTSK KFPAPPPGIIAGGPNS RFEDPTITAAVKKDTP PQKCYIDHTDSWSTNE ITINWNAPFAWVTAYL DEIDLITPPGGVDPEE PEVIYGDCNGDGKVNS TDAVALKRYILRSGIS INTDNADVNADGRVNS TDLAILKRYILKEIDV LPHKSEKDEL* (SEQ ID NO: 99) | AGTTCTACTGGGCCGCTTGTGAACTCTATGTGACAACCGGTAAGGA TGAGTACAAGAATTACTTGATGAATAGTCCGCACTATCTGGAAATG CCAGCGAAGATGGGCGAGAACGGAGGGGCTAACGGCGAGGACAACG GTCTCTGGGGCTGCTTTACTTGGGGAACGACACAGGGGTTGGGTAC AATTACCCTTGCCCTCGTTGAAAACGGCCTCCCTTCGGCGGATATT CAAAAGGCCCGCAACAATATCGCTAAAGCCGCAGATAAGTGGCTTG AGAATATTGAAGAACAAGGTTACCGCCTGCCTATCAAACAAGCGGA GGATGAACGGGGCGGATACCCGTGGGGTAGTAATTCTTTCATTCTC AACCAGATGATCGTCATGGGCTACGCTTACGACTTCACGGGAAACA GCAAGTATCTTGACGGGATGCAGGACGGCATGTCCTACCTGCTCGG TAGAAACGGACTTGATCAATCGTACGTTACTGGGTACGGGGAGAGG CCACTTCAGAACCCCCACGACCGCTTTTGGACCCCTCAAACTTCGA AGAAATTCCCGGCCCCACCCCCTGGTATTATCGCAGGCGGGCCGAA TAGCCGGTTTGAAGATCCAACGATCACTGCAGCGGTTAAGAAGGAT ACACCCCGCAGAAGTGCTATATTGACCACACCGATTCCTGGTCTA CTAACGAGATCACGATTAATTGGAACGCCCCCTTCGCGTGGGTCAC AGCGTATCTGGACGAAATTGACTTGATTACCCCACCCGGCGGAGTG GACCCTGAAGAGCCGGAAGTTATCTACGGTGATTGTAACGGCACG GAAAGGTTAATTCGACCGATGCTGTGGCCCTTAAAAGGTATATCCT CCGCAGCGGTATCTCGATCAACACGGACAACGCGGACGTTAATGCA GATGGTCGCGTGAATAGCACTGACCTCGCTATTTTGAAGCGCTATA TTTTGAAGGAGATCGATGTTCTTCCTCACAAGAGCGAGAAGGACGA GCTGTGA (SEQ ID NO: 171) |
| 2072 | BAASS:068438 | MANKHLSLSLFLVLLG LSASLASGQVLEDKSP KLPDYKNDLLYERTFD EGLCFPWHTCEDSGGK CDFAVVDVPGEPGNKA FRLTVIDKGQNKWSVQ MRHRGITLEQGHTYTV RFTIWSDKSCRVYAKI GQMGEPYTEYWNNNWN PFNLTPGQKLTVEQNF TMNYPTDDTCEFTPHL GGELAAGTPYYVYLDD VSLYDPRFVKPVEYVL PQPDVRVNQVGYLPFA KKYATVVSSSTSPLKW QLLNSANQVVLEGNTI PKGLDKDSQDYVHWID FSNPFKTEGKGYYFKLP TVNSDTNYSHPFDISA DIYSKMKFDALAFFYH KRSGIPIEMPYAGGEQ WTRPAGHIGVAPNKGD TNVPTWPQDDEYAGRP QKYYTKDVTGGWYDAG DHGKYVVNGGIAVWTL MNMYERAKIRGIANQG AYKDGGMNIPERNNGY PDILDEARWEIEFFKK MQVTEKEDPSIAGMVH HKIHDFRWTALGMLPH EDPQPRYLRPVSTAAT LNFAATLAQSARLWKD YDPTFAADCLEKAEIA WQAALKHPDIYAEYTP GSGGPGGGPYNDDYVG DEFYWAACELYVTTGK DEYKNYLMNSPHYLEM PAKMGENGGANGEDNG LWGCFTWGTTQGLGTI TLALVENGLPSADIQK ARNNIAKAADKWLENI EEQGYRLPIKQAEDER GGYPWGSNSFILNQMI VMGYAYDFTGNSKYLD GMQDGMSYLLGRNGLD QSYVTGYGERPLQNPH DRFWTPQTSKKFPAPP PGIIAGGPNSRFEDPT ITAAVKKDTPPQKCYI DHTDSWSTNEITINWN APFAWVTAYLDEIDLI | ATGGCGAACAAACATTTGTCCCTCTCCCTCTTCCTCGTCCTCCTTG GCCTGTCGGCCAGCTTGGCCTCCGGGCAAGTCCTGGAGGACAAGTC TCCCAAACTGCCTGATTATAAGAACGACCTTCTGTACGAACGCACA TTCGACGAGGGGCTCTGCTTCCCGTGGCACACGTGCGAAGATTCAG GAGGGAAATGCGATTTTGCCGTGGTCGACGTTCCAGGCGAGCCTGG GAACAAGGCGTTCAGGCTCACTGTTATCGATAAGGGTCAGAACAAG TGGTCGGTCCAAATGAGACACCGGGGTATCACGTTGGAGCAGGGGC ACACATACACCGTTCGGTTTACTATCTGGAGCGACAAGAGCTGCCG CGTGTATGCCAAAATCGGCCAAATGGGTGAACCCTACACGGAGTAC TGGAACAATAACTGGAATCCGTTCAACCTCACTCCGGGGCAGAAAT TGACGGTGGAACAGAACTTTACTATGAATTATCCCACGGACGACAC GTGTGAGTTTACCTTCCACTTGGGAGGGGAACTGGCAGCCGGGACC CCTTACTACGTGTACCTCGACGACGTTTCTCTTTACGATCCCCGCT TTGTCAAGCCAGTGGAATACGTCCTGCCTCAACCGGATGTCAGGGT TAATCAAGTTGGATACCTCCCTTTTGCTAAGAAATATGCTACTGTC GTGTCATCGAGCACGTCCCCATTGAAGTGGCAACTTCTGAATAGTG CAAACCAAGTTGTCTTGGAGGGCAATACAATCCCCAAGGGACTGGA CAAAGATTCACAAGACTACGTTCATTGGATCGATTTCTCGAACTTT AAGACCGAAGGCAAGGGGTACTATTTCAAGTTGCCCACTGTGAACT CCGATACTAACTACTCCCACCCGTTTGATATTTCTGCAGATATCTA TTCAAAGATGAAGTTCGACGCGCTCGCTTTCTTTTACCATAAAAGG TCGGGAATACCAATCGAGATGCCCTACGCCGGGGGAGAGCAGTGGA CAAGGCCCGCAGGGCACATTGGTGTCGCGCCGAACAAGGGCGACAC GAATGTGCCAACTTGGCCCCAGGATGACGAATATGCTGGACGCCCC CAGAAATACTATACGAAAGACGTGACCGGCGGTGGATACGATGCCG GTGACCACGGCAAGTACGTCGTGAACGGGGGTATCGCAGTTTGGAC CCTTATGAATATGTACGAGAGCAAAGATTAGAGGAATCGCTAAC CAGGGTGCCTACAAAGATGGAGGAATGAATATCCCGGAAAGGAATA ACGGCTATCCTGATATTCTGGACGAGGCCAGATGGGAGATCGAATT TTTTAAGAAGATGCAAGTCACTGAGAAAGAAGATCCGTCGATTGCA GGTATGGTCACCACAAGATCCACGATTTCAGGTGGACGGCGCTCG GAATGTTGCCTCACGAGGACCCCCAGCCACGCTACCTTCGGCCCGT CAGCACAGCGGCAACCCTGAATTTCGCAGCGACCCTCGCTCAGTCT GCCAGATTGTGGAAGGATTACGACCCGACTTTTGACGGACTGCC TTGAGAAAGCTGAAATTGCCTGGCAAGCAGCACTCAAACACCCGGA CATCTACGCTGAGTACACGCCAGGAAGCGGTGGGCCGGGTGGAGGT CCTTATAATGACGATTATGTCGGGGACGAGTTCTACTGGGCCGCTT GTGAACTCTATGTGACAACCGGTAAGGAGTACAAGAATTACTT GATGAATAGTCCGCACTATCTGGAAATGCCAGCGAAGATGGGCGAG AACGGAGGGGCTAACGGCGAGGACAACGGTCTCTGGGGCTGCTTTA CTTGGGGAACGACACAGGGGTTGGGTACAATTACCCTTGCCCTCGT TGAAAACGGCCTCCCTTCGGCGGATATTCAAAAGGCCCGCAACAAT ATCGCTAAAGCCGCAGATAAGTGGCTTGAGAATATTGAAGAACAAG GTTACCGCCTGCCTATCAAACAAGCGGAGGATGAACGGGGCGGATA CCCGTGGGGTAGTAATTCTTTCATTCTCAACCAGATGATCGTCATG GGCTACGCTTACGACTTCACGGGAAACAGCAAGTATCTTGACGGGA TGCAGGACGGCATGTCCTACCTGCTCGGTAGAAACGGACTTGATCA ATCGTACGTTACTGGGTACGGGGAGAGGCCACTTCAGAACCCCCAC GACCGCTTTGGACCCCTCAAACTTCGAAGAAATTCCCGGCCCCAC CCCCTGGTATTATCGCAGGCGGGCCGAATAGCCGGTTTGAAGATCC AACGATCACTGCAGCGGTTAAGAAGGATACACCCCGCAGAAGTGC |

TABLE 1-continued

Sequences of CWDEs and their fusions in vectors

| pAG vector | Sequence annotation | Protein sequence | Nucleotide sequence |
|---|---|---|---|
| | | TPPGGVDPEEPEVIYG DCNGDGKVNSTDAVAL KRYILRSGISINTDNA DVNADGRVNSTDLAIL KRYILKEIDVLPHK* (SEQ ID NO: 100) | TATATTGACCACACCGATTCCTGGTCTACTAACGAGATCACGATTA ATTGGAACGCCCCCTTCGCGTGGGTCACAGCGTATCTGGACGAAAT TGACTTGATTACCCCACCCGGCGGAGTGGACCCTGAAGAGCCGGAA GTTATCTACGGTGATTGTAACGGCGACGGAAAGGTTAATTCGACCG ATGCTGTGGCCCTTAAAAGGTATATCCTCCGCAGCGGTATCTCGAT CAACACGGACAACGCGGACGTTAATGCAGATGGTCGCGTGAATAGC ACTGACCTCGCTATTTTGAAGCGCTATATTTTGAAGGAGATCGATG TTCTTCCTCACAAGTGA (SEQ ID NO: 172) |
| 2073 | BAASS:068438:SEKDEL | MANKHLSLSLFLVLLG LSASLASGQVLEDKSP KLPDYKNDLLYERTFD EGLCFPWHTCEDSGGK CDFAVVDVPGEPGNKA FRLTVIDKGQNKWSVQ MRHRGITLEQGHTYTV RFTIWSDKSCRVYAKI GQMGEPYTEYWNNNWN PFNLTPGQKLTVEQNF TMNYPTDDTCEFTFHL GGELAAGTPYYVYLDD VSLYDPRFVKPVEYVL PQPDVRVNQVGYLPFA KKYATVVSSSTSPLKW QLLNSANQVVLEGNTI PKGLDKDSQDYVHWID FSNFKTEGKGYYFKLP TVNSDTNYSHPFDISA DIYSKMKFDALAFFYH KRSGIPIEMPYAGGEQ WTRPAGHIGVAPNKGD TNVPTWPQDDEYAGRP QKYYTKDVTGGWYDAG DHGKYVVNGGIAVWTL MNMYERAKIRGIANQG AYKDGGMNIPERNNGY PDILDEARWEIEFFKK MQVTEKEDPSIAGMVH HKIHDFRWTALGMLPH EDPQPRYLRPVSTAAT LNFAATLAQSARLWKD YDPTFAADCLEKAEIA WQAALKHPDIYAEYTP GSGGPGGGPYNDDYVG DEFYWAACELYVTTGK DEYKNYLMNSPHYLEM PAKMGENGGANGEDNG LWGCFTWGTTQGLGTI TLALVENGLPSADIQK ARNNIAKAADKWLENI EEQGYRLPIKQAEDER GGYPWGSNSFILNQMI VMGYAYDFTGNSKYLD GMQDGMSYLLGRNGLD QSYVTGYGERPLQNPH DRFWTPQTSKKFPAPP PGIIAGGPNSRFEDPT ITAAVKKDTPPQKCYI DHTDSWSTNEITINWN APFAWVTAYLDEIDLI TPPGGVDPEEPEVIYG DCNGDGKVNSTDAVAL KRYILRSGISINTDNA DVNADGRVNSTDLAIL KRYILKEIDVLPHKSE KDEL* (SEQ ID NO: 101) | ATGGCGAACAAACATTTGTCCCTCTCCCTCTTCCTCGTCCTCCTTG GCCTGTCGGCCAGCTTGGCCTCCGGGCAAGTCCTGGAGGACAAGTC TCCCAAACTGCCTGATTATAAGAACGACCTTCTGTACGAACGCACA TTCGACGAGGGGCTCTGCTTCCCGTGGCACACGTGCGAAGATTCAG GAGGGAAATGCGATTTTGCCGTGGTCGACGTTCCAGGCGAGCCTGG GAACAAGGCGTTCAGGCTCACTGTTATCGATAAGGGTCAGAACAAG TGGTCGGTCCAAATGAGACACCGGGGTATCACGTTGGAGCAGGGGC ACACATACACCGTTCGGTTTACTATCTGGAGCGACAAGAGCTGCCG CGTGTATGCCAAAATCGGCCAAATGGGTGAACCCTACACGGAGTAC TGGAACAATAACTGGAATCCGTTCAACCTCACTCCGGGGCAGAAAT TGACGGTGGAACAGAACTTTACTATGAATTATCCCACGGACGACAC GTGTGAGTTTACCTTCCACTTGGGAGGGGAACTGGCAGCCGGGACC CCTTACTACGTGTACCTCGACGACGTTTCTCTTTACGATCCCCGCT TTGTCAAGCCAGTGGAATACGTCCTGCCTCAACCGGATGTCAGGGT TAATCAAGTTGGATACCTCCCTTTTGCTAAGAAATATGCTACTGTC GTGTCATCGAGCACGTCCCCATTGAAGTGGCAACTTCTGAATAGTG CAAACCAAGTTGTCTTGGAGGGCAATACAATCCCCAAGGGACTGGA CAAAGATTCACAAGACTACGTTCATTGGATCGATTTCTCGAACTTT AAGACCGAAGGCAAGGGGTACTATTTCAAGTTGCCCACTGTGAACT CCGATACTAACTACTCCCACCCGTTTGATATTTCTGCAGATATCTA TTCAAAGATGAAGTTCGACGCGCTCGCTTTCTTTTACCATAAAAGG TCGGGAATACCAATCGAGATGCCCTACGCCGGGGGAGAGCAGTGGA CAAGGCCCGCCAGGGCACATTGGTGTCGCGCCGAACAAGGGCGACAC GAATGTGCCAACTTGGCCCCAGGATGACGAATATGCTGGACGCCCC CAGAAATACTATACGAAAGACGTGACCGGCGGTGGTACGATGGCCG GTGACCACGGCAAGTACGTCGTGAACGGGGGTATCGCAGTTTGGAC CCTTATGAATATGTACGAGAGAGCAAAGATTAGAGGAATCGCTAAC CAGGGTGCCTACAAAGATGGAGGAATGAATATCCCGGAAAGGAATA ACGGCTATCCTGATATTCTGGACGAGGCCAGATGGGAGATCGAATT TTTTAAGAAGATGCAAGTCACTGAGAAAGAAGATCCGTCGATTGCA GGTATGGTGCACCACAAGATCCACGATTTCAGGTGGACGGCGCTCG GAATGTTGCCTCACGAGGACCCCCAGCCACGCTACCTTCGGCCCGT CAGCACAGCGGCAACCCTGAATTTCGCAGCGACCCTCGCTCAGTCT GCCAGATTGTGGAAGGATTACGACCCGACTTTTGCAGCGGACTGCC TTGAGAAAGCTGAAATTGCCTGGCAAGCAGCACTCAAACACCCGGA CATCTACGCTGAGTACAGCGCCAGGAAGCGGTTGGCCGGGTGGAGGT CCTTATAATGACGATTATGTCGGGGACGAGTTCTACTGGGCCGCTT GTGAACTCTATGTGACAACCGGTAAGGATGAGTACAAGAATTACTT GATGAATAGTCCGCACTATCTGGAAATGCCAGCGAAGATGGGCGAG AACGGAGGGGCTAACGGCAGGACAACGGTCTCTGGGGCTGCTTTA CTTGGGGAACGACACAGGGGTTGGGTACAATTACCCTTGCCCTCGT TGAAAACGGCCTCCCTTCGGCGGATATTCAAAAGGCCCGCAACAAT ATCGCTAAAGCCGCAGATAAGTGGCTTGAGAATATTGAAGAACAAG GTTACCGCCTGCCTATCAAACAAGCGGAGGATGAACGGGGCGGATA CCCGTGGGGTAGTAATTCTTTCATTCTCAACCAGATGATCGTCATG GGCTACGCTTACGACTTCACGGGAAACAGCAAGTATCTTGACGGGA TGCAGGACGGCATGTCCTACCTGCTCGGTAGAAACGGACTTGATCA ATCGTACGTTACTGGGTACGGGGAGAGGCCACTTCAGAACCCCCAC GACCGCTTTTGGACCCCTCAAACTTCGAAGAAATTCCCGGCCCCAC CCCTGGTATTATCGCAGGCGGGCCGAATAGCCGGTTTGAAGATCCC AACGATCACTGCAGCGGTTAAGAAGGATACACCCCCGCAGAAGTGC TATATTGACCACACCGATTCCTGGTCTACTAACGAGATCACGATTA ATTGGAACGCCCCCTTCGCGTGGGTCACAGCGTATCTGGACGAAAT TGACTTGATTACCCCACCCGGCGGAGTGGACCCTGAAGAGCCGGAA GTTATCTACGGTGATTGTAACGGCGACGGAAAGGTTAATTCGACCG ATGCTGTGGCCCTTAAAAGGTATATCCTCCGCAGCGGTATCTCGAT CAACACGGACAACGCGGACGTTAATGCAGATGGTCGCGTGAATAGC ACTGACCTCGCTATTTTGAAGCGCTATATTTTGAAGGAGATCGATG TTCTTCCTCACAAGAGCGAGAAGGACGAGCTGTGA (SEQ ID NO: 173) |
| 2074 | HvAleSP:068438 | MAHARVLLLALAVLAT AAVAVASSSSFADSNP IRPVTDRAASTLEDKS PKLPDYKNDLLYERTF DEGLCFPWHTCEDSGG | ATGGCCCACGCCCGCGTCCTCCTCCTGGCGCTCGCCGTCCTGGCCA CCGCCGCCGTCGCCGTCGCCTCCTCCTCCTTCGCCGACTCCAA CCCGATCCGCCCGGTGACCGACCGCGCCGCCTCCACCCTGGAGGAC AAGTCTCCCAAACTGCCTGATTATAAGAACGACCTTCTGTACGAAC GCACATTCGACGAGGGGCTCTGCTTCCCGTGGCACACGTGCGAAGA |

TABLE 1-continued

Sequences of CWDEs and their fusions in vectors

| pAG vector | Sequence annotation | Protein sequence | Nucleotide sequence |
|---|---|---|---|
| | | KCDFAVVDVPGEPGNK<br>AFRLTVIDKGQNKWSV<br>QMRHRGITLEQGHTYT<br>VRFTIWSDKSCRVYAK<br>IGQMGEPYTEYWNNNW<br>NPFNLTPGQKLTVEQN<br>FTMNYPTDDTCEFTFH<br>LGGELAAGTPYYVYLD<br>DVSLYDPRFVKPVEYV<br>LPQPDVRVNQVGYLPF<br>AKKYATVVSSSTSPLK<br>WQLLNSANQVVLEGNT<br>IPKGLDKDSQDYVHWI<br>DFSNFKTEGKGYYFKL<br>PTVNSDTNYSHPFDIS<br>ADIYSKMKFDALAFFY<br>HKRSGIPIEMPYAGGE<br>QWTRPAGHIGVAPNKG<br>DTNVPTWPQDDEYAGR<br>PQKYYTKDVTGGWYDA<br>GDHGKYVVNGGIAVWT<br>LMNMYERAKIRGIANQ<br>GAYKDGGMNIPERNNG<br>YPDILDEARWEIEFFK<br>KMQVTEKEDPSIAGMV<br>HHKIHDFRWTALGMLP<br>HEDPQPRYLRPVSTAA<br>TLNFPAATLAQSARLWK<br>DYDPTFAADCLEKAEI<br>AWQAALKHPDIYAEYT<br>PGSGGPGGGPYNDDYV<br>GDEFYWAACELYVTTG<br>KDEYKNYLMNSPHYLE<br>MPAKMGENGGANGEDN<br>GLWGCFTWGTTQGLGT<br>ITLALVENGLPSADIQ<br>KARNNIAKAADKWLEN<br>IEEQGYRLPIKQAEDE<br>RGGYPWGSNSFILNQM<br>IVMGYAYDFTGNSKYL<br>DGMQDGMSYLLGRNGL<br>DQSYVTGYGERPLQNP<br>HDRFWTPQTSKKFPAP<br>PPGIIAGGPNSRFEDP<br>TITAAVKKDTPPQKCY<br>IDHTDSWSTNEITINW<br>NAPFAWVTAYLDEIDL<br>ITPPGGVDPEEPEVIY<br>GDCNGDGKVNSTDAVA<br>LKRYILRSGISINTDN<br>ADVNADGRVNSTDLAI<br>LKRYILKEIDVLPHK*<br>(SEQ ID NO: 102) | TTCAGGAGGGAAATGCGATTTTGCCGTGGTCGACGTTCCAGGCGAG<br>CCTGGGAACAAGGCGTTCAGGCTCACTGTTATCGATAAGGGTCAGA<br>ACAAGTGGTCGGTCCAAATGAGACACCGGGGTATCACGTTGGAGCA<br>GGGGCACACATACACCGTTCGGTTTACTATCTGGAGCGACAAGAGC<br>TGCCGCGTGTATGCCAAAATCGGCCAAATGGGTGAACCCTACACGG<br>AGTACTGGAACAATAACTGGAATCCGTTCAACCTCACTCCGGGGCA<br>GAAATTGACGGTGGAACAGAACTTTACTATGAATTATCCCACGGAC<br>GACACGTGTGAGTTTACCTTCCACTTGGGAGGGGAACTGGCAGCCG<br>GGACCCCTTACTACGTGTACCTCGACGACGTTTCTCTTTACGATCC<br>CCGCTTTGTCAAGCCAGTGGAATACGTCCTGCCTCAACCGGATGTC<br>AGGGTTAATCAAGTTGGATACCTCCCTTTTGCTAAGAAATATGCTA<br>CTGTCGTGTCATCGAGCACGTCCCCATTGAAGTGGCAACTTCTGAA<br>TAGTGCAAACCAAGTTGTCTTGGAGGGCAATACAATCCCCAAGGGA<br>CTGGACAAAGATTCACAAGACTACGTTCATTGGATCGATTTCTCGA<br>ACTTTAAGACCGAAGGCAAGGGGTACTATTTCAAGTTGCCCACTGT<br>GAACTCCGATACTAACTACTCCCACCCGTTTGATATTTCTGCAGAT<br>ATCTATTCAAAGATGAAGTTCGACGCGCTCGCTTTCTTTTACCATA<br>AAAGGTCGGAATACCAATCGAGATGCCCTACGCCGGGGGAGAGCA<br>GTGGACAAGGCCCGCAGGGCACATTGGTGTCGCGCCGAACAAGGGC<br>GACACGAATGTGCCAACTTGGCCCCAGGATGACGAATATGCTGGAC<br>GCCCCCAGAAATACTATACGAAAGACGTGACCGGCGGGTGGTACGA<br>TGCCGGTGACCACGGCAAGTACGTCGTGAACGGGGGTATCGCAGTT<br>TGGACCCTTATGAATATGTACGAGAGAGCAAAGATTAGAGGAATCG<br>CTAACCAGGGTGCCTACAAAGATGGAGGAATGAATATCCCGGAAAG<br>GAATAACGGCTATCCTGATATTCTGGACGAGGCCAGATGGGAGATC<br>GAATTTTTTAAGAAGATGCAAGTCACTGAGAAAGAAGATCCGTCGA<br>TTGCAGGTATGGTGCACCACAAGATCCACGATTTCAGGTGGACGGC<br>GCTCGGAATGTTGCCTCACGAGGACCCCCAGCCACGCTACCTTCGG<br>CCCGTCAGCACAGCGGCAACCCTGAATTTCGCAGCGACCCTCGCTC<br>AGTCTGCCAGATTGTGGAAGGATTACGACCCGACTTTTGCAGCGGA<br>CTGCCTTGAGAAAGCTGAAATTGCCTGGCAAGCAGCACTCAAACAC<br>CCGGACATCTACGCTGAGTACACGCCAGGAAGCGGTGGGCCGGGTG<br>GAGGTCCTTATAATGACGATTATGTCGGGGACGAGTTCTACTGGGC<br>CGCTTGTGAACTCTATGTGACAACCGGTAAGGATGAGTACAAGAAT<br>TACTTGATGAATAGTCCGCACTATCTGGAAATGCCAGCGAAGATGG<br>GCGAGAACGGAGGGGCTAACGGCGAGGACAACGGTCTCTGGGGCTG<br>CTTTACTTGGGGAACGACACAGGGGTTGGGTACAATTACCCTTGCC<br>CTCGTTGAAAACGGCCTCCCTTCGGCGGATATTCAAAAGGCCCGCA<br>ACAATATCGCTAAAGCCGCAGATAAGTGGCTTGAGAATATTGAAGA<br>ACAAGGTTACCGCCTGCCTATCAAACAAGCGGAGGATGAACGGGGC<br>GGATACCCGTGGGGTAGTAATTCTTTCATTCTCAACCAGATGATCG<br>TCATGGGCTACGCTTACGACTTCACGGGGAAACAGCAAGTATCTTGA<br>CGGGATGCAGGACGGCATGTCCTACCTGCTCGGTAGAAACGGACTT<br>GATCAATCGTACGTTACTGGGTACGGGGAGAGGCCACTTCAGAACC<br>CCCACGACCGCTTTTGACCCCTCAAACTTCGAAGAAATTCCCGGC<br>CCCACCCCCTGGTATTATCGCAGGCGGGCCGAATAGCCGGTTTGAA<br>GATCAACGATCACTGCAGCGGTTAAGAAGGATACACCCCGCAGA<br>AGTGCTATATTGACCACACCGATTCCTGGTCTACTAACGAGATCAC<br>GATTAATTGGAACGCCCCCTTCGCTGGGTCACAGCGTATCTGGAC<br>GAAATTGACTTGATTACCCCACCCGGCGGAGTGGACCCTGAAGAGC<br>CGGAAGTTATCTACGGTGATTGTAACGGCGACGGAAAGGTTAATTC<br>GACCGATGCTGTGGCCCTTAAAAGGTATATCCTCCGCAGCGGTATC<br>TCGATCAACACGGACAACGCGGACGTTAATGCAGATGGTCGCGTGA<br>ATAGCACTGACCTCGCTATTTTGAAGCGCTATATTTTGAAGGAGAT<br>CGATGTTCTTCCTCACAAGTGA (SEQ ID NO: 174) |
| 2075 | HvAleSP:O68438:<br>SEKDEL | MAHARVLLLALAVLAT<br>AAVAVASSSSFADSNP<br>IRPVTDRAASTLEDKS<br>PKLPDYKNDLLYERTF<br>DEGLCFPWHTCEDSGG<br>KCDFAVVDVPGEPGNK<br>AFRLTVIDKGQNKWSV<br>QMRHRGITLEQGHTYT<br>VRFTIWSDKSCRVYAK<br>IGQMGEPYTEYWNNNW<br>NPFNLTPGQKLTVEQN<br>FTMNYPTDDTCEFTFH<br>LGGELAAGTPYYVYLD<br>DVSLYDPRFVKPVEYV<br>LPQPDVRVNQVGYLPF<br>AKKYATVVSSSTSPLK<br>WQLLNSANQVVLEGNT<br>IPKGLDKDSQDYVHWI<br>DFSNFKTEGKGYYFKL | ATGGCCCACGCCCGCGTCCTCCTCCTGGCGCTCGCCGTCCTGGCCA<br>CCGCCGCCGTCGCCGTCGCCTCCTCCTCCTTCGCCGACTCCAA<br>CCCGATCCGCCCGGTGACCGACCGCGCCGCCTCCACCCTGGAGGAC<br>AAGTCTCCCAAACTGCCTGATTATAAGAACGACCTTCTGTACGAAC<br>GCACATTCGACGAGGGGCTCTGCTTCCCGTGGCACACGTGCGAAGA<br>TTCAGGAGGGAAATGCGATTTTGCCGTGGTCGACGTTCCAGGCGAG<br>CCTGGGAACAAGGCGTTCAGGCTCACTGTTATCGATAAGGGTCAGA<br>ACAAGTGGTCGGTCCAAATGAGACACCGGGGTATCACGTTGGAGCA<br>GGGGCACACATACACCGTTCGGTTTACTATCTGGAGCGACAAGAGC<br>TGCCGCGTGTATGCCAAAATCGGCCAAATGGGTGAACCCTACACGG<br>AGTACTGGAACAATAACTGGAATCCGTTCAACCTCACTCCGGGGCA<br>GAAATTGACGGTGGAACAGAACTTTACTATGAATTATCCCACGGAC<br>GACACGTGTGAGTTTACCTTCCACTTGGGAGGGGAACTGGCAGCCG<br>GGACCCCTTACTACGTGTACCTCGACGACGTTTCTCTTTACGATCC<br>CCGCTTTGTCAAGCCAGTGGAATACGTCCTGCCTCAACCGGATGTC<br>AGGGTTAATCAAGTTGGATACCTCCCTTTTGCTAAGAAATATGCTA<br>CTGTCGTGTCATCGAGCACGTCCCCATTGAAGTGGCAACTTCTGAA<br>TAGTGCAAACCAAGTTGTCTTGGAGGGCAATACAATCCCCAAGGGA<br>CTGGACAAAGATTCACAAGACTACGTTCATTGGATCGATTTCTCGA |

TABLE 1-continued

Sequences of CWDEs and their fusions in vectors

| pAG vector | Sequence annotation | Protein sequence | Nucleotide sequence |
|---|---|---|---|
| | | PTVNSDTNYSHPFDIS ADIYSKMKFDALAFFY HKRSGIPIEMPYAGGE QWTRPAGHIGVAPNKG DTNVPTWPQDDEYAGR PQKYYTKDVTGGWYDA GDHGKYVVNGGIAVWT LMNMYERAKIRGIANQ GAYKDGGMNIPERNNG YPDILDEARWEIEFFK KMQVTEKEDPSIAGMV HHKIHDFRWTALGMLP HEDPQPRYLRPVSTAA TLNFAATLAQSARLWK DYDPTFAADCLEKAEI AWQAALKHPDIYAEYT PGSGGPGGGPYNDDYV GDEFYWAACELYVTTG KDEYKNYLMNSPHYLE MPAKMGENGGANGEDN GLWGCFTWGTTQGLGT ITLALVENGLPSADIQ KARNNIAKAADKWLEN IEEQGYRLPIKQAEDE RGGYPWGSNSFILNQM IVMGYAYDPTGNSKYL DGMQDGMSYLLGRNGL DQSYVTGYGERPLQNP HDRFWTPQTSKKFPAP PPGIIAGGPNSRFEDP TITAAVKKDTPPQKCY IDHTDSWSTNEITINW NAPPAWVTAYLDEIDL ITPPGGVDPEEPEVIY GDCNGDGKVNSTDAVA LKRYILRSGISINTDN ADVNADGRVNSTDLAI LKRYILKEIDVLPHKS EKDEL* (SEQ ID NO: 103) | ACTTTAAGACCGAAGGCAAGGGGTACTATTTCAAGTTGCCCCACTGT GAACTCCGATACTAACTACTCCCACCCGTTTGATATTTCTGCAGAT ATCTATTCAAAGATGAAGTTCGACGCGCTCGCTTTCTTTTACCATA AAAGGTCGGGAATACCAATCGAGATGCCCTACGCCGGGGGAGAGCA GTGGACAAGGCCCGCAGGGCACATTGGTGTCGCGCCGAACAAGGGC GACACGAATGTGCCAACTTGGCCCCAGGATGACGAATATGCTGGAC GCCCCAGAAATACTATACGAAAGACGTGACCGGCGGGTGGTACGA TGCCGGTGACCACGGCAAGTACGTCGTGAACGGGGGTATCGCAGTT TGGACCCTTATGAATATGTACGAGAGAGCAAAGATTAGAGGAATCG CTAACCAGGGTGCCTACAAAGATGGAGGAATGAATATCCCGGAAAG GAATAACGGCTATCCTGATATTCTGGACGAGGCCAGATGGGAGATC GAATTTTTTAAGAAGATGCAAGTCACTGAGAAAGAAGATCCGTCGA TTGCAGGTATGGTGCACCACAAGATCCACGATTTCAGGTGGACGGC GCTCGGAATGTTGCCTCACGAGGACCCCCAGCCACGCTACCTTCGG CCCGTCAGCACAGCGGCAACCCTGAATTTCGCAGCGACCCTCGCTC AGTCTGCCAGATTGTGGAAGGATTACGACCCGACTTTTGCAGCGGA CTGCCTTGAGAAAGCTGAAATTGCCTGGCAAGCAGCACTCAAACAC CCGGACATCTACGCTGAGTACACGCCAGGAAGCGGTGGGCCGGGTG GAGGTCCTTATAATGACGATTATGTCGGGGACGAGTTCTACTGGGC CGCTTGTGAACTCTATGTGACAACCGGTAAGGATGAGTACAAGAAT TACTTGATGAATAGTCCGCACTATCTGGAAATGCCAGCGAAGATGG GCGAGAACGGAGGGGCTAACGGCGAGGACAACGGTCTCTGGGGCTG CTTTACTTGGGGAACGACACAGGGGTTGGGTACAATTACCCTTGCC CTCGTTGAAAACGGCCTCCCTTCGGCGGATATTCAAAAGGCCCGCA ACAATATCGCTAAAGCCGCAGATAAGTGGCTTGAGAATATTGAAGA ACAAGGTTACGCCTGCCTATCAAACAAGCGGAGGATGAACGGGGC GGATACCCGTGGGGTAGTAATTCTTTCATTCTCAACCAGATGATCG TCATGGGCTACGCTTACGACTTCACGGGAAACAGCAAGTATCTTGA CGGGATGCAGGACGGCATGTCCTACCTGCTCGGTAGAAACGGACTT GATCAATCGTACGTTACTGGGTACGGGGAGAGGCCACTTCAGAACC CCCACGACCGCTTTTGGACCCCTCAAACTTCGAAGAAATTCCCGGC CCCACCCCCTGGTATTATCGCAGGCGGGCCGAATAGCCGGTTTGAA GATCCAACGATCACTGCAGCGGTTAAGAAGGATACACCCCCGCAGA AGTGCTATATTGACCACACCGATTCCTGGTCTACTAACGAGATCAC GATTAATTGGAACGCCCCCTTCGCGTGGGTCACAGCGTATCTGGAC GAAATTGACTTGATTACCCCACCCGGCGGAGTGGACCCTGAAGAGC CGGAAGTTATCTACGGTGATTGTAACGGCGACGGAAAGGTTAATTC GACCGATGCTGTGGCCCTTAAAAGGTATATCCTCCGCAGCGGTATC TCGATCAACACGGACAACGCGGACGTTAATGCAGATGGTCGCGTGA ATAGCACTGACCTCGCTATTTTGAAGCGCTATATTTTGAAGGAGAT CGATGTTCTTCCTCACAAGAGCGAGAAGGACGAGCTGTGA (SEQ ID NO: 175) |
| 2076 | P77853S158-2 | MQTSITLTSNASGTFD GYYYELWKDTGNTTMT VYTQGRFSCQWSNINN ALFRTGKKYNQNWQSL GTIRITYSATYNPNGN SYLCIYGWSTNPLVEF YIVESWGNWRPPGATS LGQVTIDGGTYDIYRT TRVNQPCLAEGSLVLD AATGQRVPIEKVRPGM EVFSLGPDYRLYRVPV LEVLESGVREVVRLRT RSGRTLVLTPDHPLLT PEGWKPLCDLPLGTPI AVPAELPVAGHLAPPE ERVTLLALLLGDGNTK LPGRRGTRPNAFFYSK DPELLAAYRRCAEALG AKVKAYVHPTTGVVTL ATLAPRPGAQDPVKRL VVEAGMVAKAEEKRVP EEVFRYRREALALFLG RLFSTDGSVEKKRISY SSASLGLAQDDAHLLL RLGITSQLRSRGPRAH EVLISGREDILRFAEL IGPYLLGAKRERLAAL EAEARRRLPGQGWHLR LVLPAVAYRVSEAKRR SGFSWSEAGRRVAVAG SCLSSGLNLKLPRRYL SRHRLSLLGEAFADPG | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGCTTTTCCTGCCAGTGGTCGAACATC AATAACGCGTTGTTTAGGACCGGGAAGAAATACAACCAGAATTGGC AGTCTCTTGGCACAATCCGGATCACGTACTCTGCGACTTACAACCC AAACGGGAACTCCTACTTGTGTATCTATGGCTGGTCTACCAACCCA TTGGTCGAGTTCTACATCGTTGAGTCCTGGGGGAACTGGAGACCGC CTGGTGCCACGTCCCTGGGCCAAGTGACAATCGATGGCGGGACCTA CGACATCTATAGGACGACACGCGTCAACCAGCCTTGCCTGGCCGAG GGCTCGCTCGTCTTGGACGCGGCTACCGGGCAGAGGGTCCCTATCG AAAAGGTGCGTCCGGGGATGGAAGTTTTCTCCTTGGGACCTGATTA CAGACTGTATCGGGTGCCCGTTTTGGAGGTCCTTGAGAGCGGGGTT AGGGAAGTTGTGCGCCTCAGAACTCGGTCAGGGAGAACGCTGGTGT TGACACCAGATCACCCGCTTTTGACCCCCGAAGGTTGGAAACCTCT TGTGACCTCCCGCTTGGAACTCCAATTGCAGTCCCCGCAGAACTG CCTGTGGCGGGCCACTTGGCCCCACCTGAAGAACGTGTTACGCTCC TGGCTCTTCTGTTGGGGGATGGGAACACAAAGCTGCCGGGTCGGAG AGGTACACGTCCTAATGCCTTCTTCTACAGCAAAGACCCCGAATTG CTCGCGGCTTATCGCCGGTGTGCAGAAGCCTTGGGTGCAAAGGTGA AAGCATACGTCCACCCGACTACGGGGGTGGTTACACTCGCAACCCT CGCTCCACGTCCTGGAGCTCAAGATCCTGTCAAACGCCTCGTTGTC GAGGCGGGAATGGTTGCTAAAGCCGAAGAGAAGAGGGTCCCGGAGG AGGTGTTTCGTTACCGGCGTGAGGCGTTGGCCCTTTTCTTGGGCCG TTTGTTCTCGACAGACGGCTCTGTTGAAAAGAAGAGGATCTCTTAT TCAAGTGCCAGTTTGGGACTGGCCCAGGATGACGCACATCTCTTGC TGCGCCTTGGAATTACATCTCAACTCCGTTCGAGAGGGCCACGGGC TCACGAGGTTCTTATATCGGGCCGCAGGATATTTTGCGGTTTGCT GAACTTATCGGACCCTACCTCTTGGGGGCCAAGAGGGAGAGACTTG CAGCGCTGGAAGCTGAGGCCCGCAGGCGTTTGCCTGGACAGGGATG GCACTTGCGGCTTGTTCTTCCTGCCGTGGCGTACAGAGTGAGCGAG GCTAAAAGGCGCTCGGGATTTTCGTGGAGTGAAGCCGGTCGGCGCG TCGCAGTTGCGGGATCGTGTTTGTCATCTGGACTCAACCTCAAATT |

TABLE 1-continued

Sequences of CWDEs and their fusions in vectors

| pAG vector | Sequence annotation | Protein sequence | Nucleotide sequence |
|---|---|---|---|
| | | LEALAEGQVLWDPIVA VEPAGKARTFDLRVPP FANFVSEDLVVHNSIV GTATFDQYWSVRTSKR TSGTVTVTDHFRAWAN RGLNLGTIDQITLCVE GYQSSGSANITQNTFS QGSSSGSSGGSSGSTT TTRIECENMSLSGPYV SRITNPFNGIALYANG DTARATVNFPASRNYN FRLRGCGNNNLARVD LRIDGRTVGTFYYQGT YPWEAPIDNVYVSAGS HTVEITVTADNGTWDV YADYLVIQ* (SEQ ID NO: 104) | GCCCAGACGCTACCTTTCTCGGCACCGGTTGTCGCTGCTCGGTGAG GCTTTTGCCGACCCTGGGCTGGAAGCGCTCGCGGAAGGCCAAGTGC TCTGGGACCCTATTGTTGCTGTCGAACCGGCCGGTAAGGCGAGAAC ATTCGACTTGCGCGTTCCACCCTTTGCAAACTTCGTGAGCGAGGAC CTGGTGGTGCATAACTCCATTGTGGGGACAGCCACGTTCGATCAGT ACTGGAGCGTGCGCACCTCTAAGCGGACTTCAGGAACAGTGACCGT GACCGATCACTTCCGCGCCTGGGCGAACCGGGGCCTGAACCTCGGC ACAATAGACCAAATTACATTGTGCGTGGAGGGTTACCAAAGCTCTG GATCAGCCAACATCACCCAGAACACCTTCTCTCAGGGCTCTTCTTC CGGCAGTTCGGGTGGCTCATCCGGCTCCACAACGACTACTCGCATC GAGTGTGAGAACATGTCCTTGTCCGGACCCTACGTTAGCAGGATCA CCAATCCCTTTAATGGTATTGCGCTGTACGCCAACGGAGACACAGC CCGCGCTACCGTTAACTTCCCCGCAAGTCGCAACTACAATTTCCGC CTGCGGGTTGCGGCAACAACAATAATCTTGCCCGTGTGGACCTGA GGATCGACGGACGGACCGTCGGGACCTTTTATTACCAGGGCACATA CCCCTGGGAGGCCCCAATTGACAATGTTTATGTCAGTGCGGGGAGT CATACAGTCGAAATCACTGTTACTGCGGATAACGGCACATGGGACG TGTATGCCGACTACCTGGTGATACAGTGA (SEQ ID NO: 176) |
| 2077 | P77853S158-19 | MQTSITLTSNASGTFD GYYYELWKDTGNTTMT VYTQGRFSCQWSNINN ALFRTGKKYNQNWQSL GTIRITYSATYNPNGN SYLCIYGWSTNPLVEF YIVESWGNWRPPGATS LGQVTIDGGTYDIYRT TRVNQPCLAEGSLVLD AATGQRVPIEKVRPGM EVFSLGPDYRLYRVPV LEVLESGVGEVVRLRT RSGRTLVLTPDHPLLT PEGWKPLCDLPLGTPI AVPAELPVAGHLAPPE ERVTLLALLLGDGNTK LSGRRGTRPIAFFYSK DPELLAAYRRCAEALG AKVKAYVHPTTGVVTL ATLAPRPGAQDPVKRL VVEAGMVAKAEEKRVP EEVFRYRREALALFLG RLFSTDGSVEKKRISY SSASLGLAQDVAHLLL RLGITSQLRSRGPRAH EVLISGREDILRFAEL IGPYLLGAKRERLAAL EAEARRRLPGQGWHLR LVLPAVAYRVSEAKRR SGFSWSEAGRRVAVAG SCLSSGLNLKLPRRYL SRHRLSLLGEAFADPG LEALAEGQVLWDPIVA VEPAGKARTFDLRVPP FANFVSEDLVVHNSIV GTATFDQYWSVRTSKR TSGTVTVTDHFRAWAN RGLNLGTIDQITLCVE GYQSSGSANITQNTFS QGSSSGSSGGSSGSTT TTRIECENMSLSGPYV SRITNPFNGIALYANG DTARATVNFPASRNYN FRLRGCGNNNLARVD LRIDGRTVGTFYYQGT YPWEAPIDNVYVSAGS HTVEITVTADNGTWDV YADYLVIQ* (SEQ ID NO: 105) | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGCTTTTCCTGCCAGTGGTCGAACATC AATAACGCGTTGTTTAGGACCGGGAAGAAATACAACCAGAATTGGC AGTCTCTTGGCACAATCCGGATCACGTACTCTGCGACTTACAACCC AAACGGGAACTCCTACTTGTGTATCTATGGCTGGTCTACCAACCCA TTGGTCGAGTTCTACATCGTTGAGTCCTGGGGGAACTGGAGACCGC CTGGTGCCACGTCCCTGGGCCAAGTGACAATCGATGGCGGGACCTA CGACATCTATAGGACGACACGCGTCAACCAGCCTTGCCTGGCCGAG GCTCGCTCGTCTTGGACGCGGCTACCGGGCAGAGGGTCCCTATCG AAAAGGTGCGTCCGGGGATGGAAGTTTTCTCCTTGGGACCTGATTA CAGACTGTATCGGGTGCCCGTTTTGGAGGTCTTGAGAGCGGGGTT GGGGAAGTTGTGCGCCTCAGAACTCGGTCAGGGAGAACGCTGGTGT TGACACCAGATCACCCGCTTTTGACCCCGAAGGTTGGAAACCTCT TTGTGACCTCCCGCTTGGAACTCCAATTGCAGTCCCGCAGAACTG CCTGTGGCGGGCCACTTGGCCCCACCTGAAGAACGTGTTACGCTCC TGGCTCTTCTGTTGGGGGATGGGAACACAAAGCTGTCGGGTCGGAG AGGTACACGTCCTATTGCCTTCTTCTACAGCAAAGACCCCGAATTG CTCGCGGCTTATCGCCGGTGTGCAGAAGCTTGGGTGCAAAGGTGA AAGCATACGTCCACCCGACTACGGGGTGGTTACACTCGCAACCCT CGCTCCACGTCCTGGAGTCAAGATCCTGTCAAACGCCTCGTTGTC GAGGCGGGAATGGTTGCTAAAGCCGAAGAGAAGAGGGTCCCGGAGG AGGTGTTCCGTTACCGGCGTGAGGCGTTGGCCCTTTTCTTGGGCCG TTTGTTCTCGACAGACGGCTCTGTTGAAAAGAAGAGGATCTCTTAT TCAAGTGCCAGTTTGGGACTGGCCCAGGATGTCGCACATCTCTTGC TGCGCCTTGGAATTACATCTCAACTCCGTTCGAGAGGGCCACGGGC TCACGAGGTTCTTATATCGGGCCGCGAGGATATTTTGCGGTTTGCT GAACTTATCGGACCCTACCTCTTGGGGGCCAAGAGGGAGAGACTTG CAGCGCTGGAAGCTGAGGCCCGCAGGCGTTTGCCTGGACAGGGATG GCACTTGCGGCTTGTTCTTCCTGCCGTGGCGTACAGAGTGAGCGAG GCTAAAAGGCGCTCGGGATTTTCGTGGAGTGAAGCCGGTCGGCGCG TCGCAGTTGCGGGATCGTGTTTGTCATCTGGACTCAACCTCAAATT GCCCAGACGCTACCTTTCTCGGCACCGGTTGTCGCTGCTCGGTGAG GCTTTTGCCGACCCTGGGCTGGAAGCGCTCGCGGAAGGCCAAGTGC TCTGGGACCCTATTGTTGCTGTCGAACCGGCCGGTAAGGCGAGAAC ATTCGACTTGCGCGTTCCACCCTTTGCAAACTTCGTGAGCGAGGAC CTGGTGGTGCATAACTCCATTGTGGGGACAGCCACGTTCGATCAGT ACTGGAGCGTGCGCACCTCTAAGCGGACTTCAGGAACAGTGACCGT GACCGATCACTTCCGCGCCTGGGCGAACCGGGGCCTGAACCTCGGC ACAATAGACCAAATTACATTGTGCGTGGAGGGTTACCAAAGCTCTG GATCAGCCAACATCACCCAGAACACCTTCTCTCAGGGCTCTTCTTC CGGCAGTTCGGGTGGCTCATCCGGCTCCACAACGACTACTCGCATC GAGTGTGAGAACATGTCCTTGTCCGGACCCTACGTTAGCAGGATCA CCAATCCCTTTAATGGTATTGCGCTGTACGCCAACGGAGACACAGC CCGCGCTACCGTTAACTTCCCCGCAAGTCGCAACTACAATTTCCGC CTGCGGGTTGCGGCAACAACAATAATCTTGCCCGTGTGGACCTGA GGATCGACGGACGGACCGTCGGGACCTTTTATTACCAGGGCACATA CCCCTGGGAGGCCCCAATTGACAATGTTTATGTCAGTGCGGGGAGT CATACAGTCGAAATCACTGTTACTGCGGATAACGGCACATGGGACG TGTATGCCGACTACCTGGTGATACAGTGA (SEQ ID NO: 177) |
| 2078 | P77853T134-1 | MQTSITLTSNASGTFD GYYYELWKDTGNTTMT VYTQGRFSCQWSNINN | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGCTTTTCCTGCCAGTGGTCGAACATC |

TABLE 1-continued

Sequences of CWDEs and their fusions in vectors

| pAG vector | Sequence annotation | Protein sequence | Nucleotide sequence |
|---|---|---|---|
| | | ALFRTGKKYNQNWQSL GTIRITYSATYNPNGN SYLCIYGWSTNPLVEF YIVESWGNWRPPGACL AEGSLVLDAATGQRVP IEKVRPGMEVFSLGPD YRLYRVPVLEVLESGV REVVRLRTRSGRTLVL TPDHPLLTPEGWKPLC DLPLGTPIAVPAELPV ACHLAPPEERVTLLAL LLGDGNTKPSGRRGTR PNAFFYSKDPELLAAY RRCAEALGAKVKAYVH PTTGVVTLATLAPRPG AQDPVKRLVVEAGMVA KAEEKRVPEEVFRYRR EALALFLGRLFSTDGS VEKKRISYSSASLGLA QDVAHLLLRLGITSQL RSRGPRAHEVLISGRE DILRFAELIGPYLLGA KRERLAALEAEARRRL PGGQWHLRLVLPAVAY RVSEAKRRSGESWSEA GRRVAVAGSCLSSGLN LKLPRRYLSRHRLSLL GEAFADPGLEALAEGQ VLWDPIVAVEPAGKAR TFDLRVPPFANFVSED LVVHNTSPLGQVTIDG GTYDIYRTTRVNQPSI VGTATFDQYWSVRTSK RTSGTVTVTDHFRAWA NRGLNLGTIDQITLCV EGYQSSGSANITQNTF SQGSSSGSSGGSSGST TTTRIECENMSLSGPY VSRITNPFNGIALYAN GDTARATVNFPASRNY NFRLRGCGNNNNLARV DLRIDGRTVGTFYYQG TYPWEAPIDNVYVSAG SHTVEITVTADNGTWD VYADYLVIQ* (SEQ ID NO: 106) | AATAACGCGTTGTTTAGGACCGGGAAGAAATACAACCAGAATTGGC AGTCTCTTGGCACAATCCGGATCACGTACTCTGCGACTTACAACCC AAACGGGAACTCCTACTTGTGTATCTATGGCTGGTCTACCAACCCA TTGGTCGAGTTCTACATCGTTGAGTCCTGGGGGAACTGGAGACCGC CTGGTGCCTGCCTGGCCGAGGGCTCGCTCGTCTTGGACGCGGCTAC CGGGCAGAGGGTCCCTATCGAAAAGGTGCGTCCGGGGATGGAAGTT TTCTCCTTGGGACCTGATTACAGACTGTATCGGGTGCCCGTTTTGG AGGTCCTTGAGAGCGGGGTTAGGGAAGTTGTGCGCCTCAGAACTCG GTCAGGGAGAACGCTGGTGTTGACACCAGATCACCCGCTTTTGACC CCCGAAGGTTGGAAACCTCTTTGTGACCTCCCGCTTGGAACTCCAA TTGCAGTCCCCGCAGAACTGCCTGTGGCGTGCCACTTGGCCCCACC TGAAGAACGTGTTACGCTCCTGGCTCTTCTGTTGGGGGATGGGAAC ACAAAGCCGTCGGGTCGGAGAGGTACACGTCCTAATGCCTTCTTCT ACAGCAAAGACCCCGAATTGCTCGCGGCTTATCGCCGGTGTGCAGA AGCCTTGGGTGCAAAGGTGAAAGCATACGTCCACCCGACTACGGGG GTGGTTACACTCGCAACCCTCGCTCCACGTCCTGGAGCTCAAGATC CTGTCAAACGCCTCGTTGTCGAGGCGGGAATGGTTGCTAAAGCCGA AGAGAAGAGGGTCCCGGAGGAGGTGTTTCGTTACCGGCGTGAGGCG TTGGCCCTTTTCTTGGGCCGTTTGTTCTCGACAGACGGCTCTGTTG AAAAGAAGAGGATCTCTTATTCAAGTGCCAGTTTGGGACTGGCCCA GGATGTCGCACATCTCTTGCTGCGCCTTGGAATTACATCTCAACTC CGTTCGAGAGGGCCACGGGCTCACGAGGTTCTTATATCGGGCCGCG AGGATATTTTGCGGTTTGCTGAACTTATCGGACCCTACCTCTTGGG GGCCAAGAGGGAGAGACTTGCAGCGCTGGAAGCTGAGGCCCGCAGG CGTTTGCCTGGACAGGGATGGCACTTGCGGCTTGTTCTTCCTGCCG TGGCGTACAGAGTGAGCGAGGCTAAAAGGCGCTCGGGATTTTCGTG GAGTGAAGCCGGTCGGCGCGTCGCAGTTGCGGGATCGTGTTTGTCA TCTGGACTCAACCTCAAATTGCCCAGACGCTACCTTTCTCGGCACC GGTTGTCGCTGCTCGGTGAGGCTTTTGCCGACCCTGGGCTGGAAGC GCTCGCGGAAGGCCAAGTGCTCTGGGACCCTATTGTTGCTGTCGAA CCGGCCGGTAAGGCGAGAACATTCGACTTGCGCGTTCCACCCTTTG CAAACTTCGTGAGCGAGGACCTGGTGGTGCATAACACGTCCCCCTT GGGCCAAGTGACAATCGATGGCGGGACCTACGACATCTATAGGACG ACACGCGTCAACCAGCCTTCCATTGTGGGGACAGCCACGTTCGATC AGTACTGGAGCGTGCGCACCTCTAAGCGGACTTCAGGAACAGTGAC CGTGACCGATCACTTCCGCGCCTGGGCGAACCGGGGCCTGAACCTC GGCACAATAGACCAAATTACATTGTGCGTGGAGGGTTACCAAAGCT CTGGATCAGCCAACATCACCCAGAACACCTTCTCTCAGGGCTCTTC TTCCGGCAGTTCGGGTGGCTCATCCGGCTCCACAACGACTACTCGC ATCGAGTGTGAGAACATGTCCTTGTCCGGACCCTACGTTAGCAGGA TCACCAATCCCTTTAATGGTATTGCGCTGTACGCCAACGGAGACAC AGCCCGCGCTACCGTTAACTTCCCCGCAAGTCGCAACTACAATTTC CGCCTGCGGGGTTGCGGCAACAACAATAATCTTGCCCGTGTGGACC TGAGGATCGACGGACGGACCGTCGGGACCTTTTATTACCAGGGCAC ATACCCCTGGGAGGCCCCAATTGACAATGTTTATGTCAGTGCGGGG AGTCATACAGTCGAAATCACTGTTACTGCGGATAACGGACACATGGG ACGTGTATGCCGACTACCTGGTGATACAGTGA (SEQ ID NO: 178) |
| 2079 | BAASS:P77853S158- 2:SEKDEL | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GTYDIYRTTRVNQPCL AEGSLVLDAATGQRVP IEKVRPGMEVFSLGPD YRLYRVPVLEVLESGV REVVRLRTRSGRTLVL TPDHPLLTPEGWKPLC DLPLGTPIAVPAELPV AGHLAPPEERVTLLAL LLGDGNTKLPGRRGTR PNAFFYSKDPELLAAY RRCAEALGAKVKAYVH PTTGVVTLATLAPRPG AQDPVKRLVVEAGMVA KAEEKRVPEEVFRYRR EALALFLGRLFSTDGS VEKKRISYSSASLGLA QDDAHLLLRLGITSQL | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGACCTACGACATCTATAGGACGACAC GCGTCAACCAGCCTTGCCTGGCCGAGGGCTCGCTCGTCTTGGACGC GGCTACCGGGCAGAGGGTCCCTATCGAAAAGGTGCGTCCGGGGATG GAAGTTTTCTCCTTGGGACCTGATTACAGACTGTATCGGGTGCCCG TTTTGGAGGTCCTTGAGAGCGGGGTTAGGGAAGTTGTGCGCCTCAG AACTCGGTCAGGGAGAACGCTGGTGTTGACACCAGATCACCCGCTT TTGACCCCCGAAGGTTGGAAACCTCTTTGTGACCTCCCGCTTGGAA CTCCAATTGCAGTCCCCGCAGAACTGCCTGTGGCGGGCCACTTGGC CCCACCTGAAGAACGTGTTACGCTCCTGGCTCTTCTGTTGGGGGAT GGGAACACAAAGCTGCCGGGTCGGAGAGGTACACGTCCTAATGCCT TCTTCTACAGCAAAGACCCCGAATTGCTCGCGGCTTATCGCCGGTG TGCAGAAGCCTTGGGTGCAAAGGTGAAAGCATACGTCCACCCGACT ACGGGGGTGGTTACACTCGCAACCCTCGCTCCACGTCCTGGAGCTC AAGATCCTGTCAAACGCCTCGTTGTCGAGGCGGGAATGGTTGCTAA AGCCGAAGAGAAGAGGGTCCCGGAGGAGGTGTTTCGTTACCGGCGT GAGGCGTTGGCCCTTTTCTTGGGCCGTTTGTTCTCGACAGACGGCT CTGTTGAAAAGAAGAGGATCTCTTATTCAAGTGCCAGTTTGGGACT |

TABLE 1-continued

Sequences of CWDEs and their fusions in vectors

| pAG vector | Sequence annotation | Protein sequence | Nucleotide sequence |
|---|---|---|---|
| | | RSRGPRAHEVLISGRE DILRFAELIGPYLLGA KRERLAALEAEARRRL PGQGWHLRLVLPAVAY RVSEAKRRSGFSWSEA GRRVAVAGSCLSSGLN LKLPRRYLSRHRLSLL GEAFADPGLEALAEGQ VLWDPIVAVEPAGKAR TFDLRVPPFANFVSED LVVHNSIVGTATFDQY WSVRTSKRTSGTVTVT DHFRAWANRGLNLGTI DQITLCVEGYQSSGSA NITQNTFSQGSSSGSS GGSSGSTTTTRIECEN MSLSGPYVSRITNPFN GIALYANGDTARATVN FPASRNYNFRLRGCGN NNNLARVDLRIDGRTV GTFYYQGTYPWEAPID NVYVSAGSHTVEITVT ADNGTWDVYADYLVIQ SEKDEL* (SEQ ID NO: 107) | GGCCCAGGATGACGCACATCTCTTGCTGCGCCTTGGAATTACATCT CAACTCCGTTCGAGAGGGCCACGGGCTCACGAGGTTCTTATATCGG GCCGCGAGGATATTTTGCGGTTTGCTGAACTTATCGGACCCTACCT CTTGGGGGCCAAGAGGGAGAGACTTGCAGCGCTGGAAGCTGAGGCC CGCAGGCGTTTGCCTGGACAGGGATGGCACTTGCGGCTTGTTCTTC CTGCCGTGGCGTACAGAGTGAGCGAGGCTAAAAGGCGCTCGGGATT TTCGTGGAGTGAAGCCGGTCGGCGCGTCGCAGTTGCGGGATCGTGT TGTCATCTGGACTCAACCTCAAATTGCCCAGACGCTACCTTTCTC GGCACCGGTTGTCGCTGCTCGGTGAGGCTTTTGCCGACCCTGGGCT GGAAGCGCTCGCGGAAGGCCAAGTGCTCTGGGACCCTATTGTTGCT GTCGAACCGGCCGGTAAGGCGAGAACATTCGACTTGCGCGTTCCAC CCTTTGCAAACTTCGTGAGCGAGGACCTGGTGGTGCATAACTCCAT TGTGGGACAGCCACGTTCGATCAGTACTGGAGCGTGCGCACCTCT AAGCGGACTTCAGGAACAGTGACCGTGACCGATCACTTCCGCGCCT GGGCGAACCGGGGCCTGAACCTCGGCACAATAGACCAAATTACATT GTGCGTGGAGGGTTACCAAAGCTCTGGATCAGCCAACATCACCCAG AACACCTTCTCTCAGGGCTCTTCTTCCGGCAGTTCGGGTGGCTCAT CCGGCTCCACAACGACTACTCGCATCGAGTGTGAGAACATGTCCTT GTCCGGACCCTACGTTAGCAGGATCACCAATCCCTTTAATGGTATT GCGCTGTACGCCAACGGAGACACAGCCCGCGCTACCGTTAACTTCC CCGCAAGTCGCAACTACAATTTCCGCCTGCGGGGTTGCGGCAACAA CAATAATCTTGCCCGTGTGGACCTGAGGATCGACGGACGGACCGTC GGGACCTTTTATTACCAGGGCACATACCCCTGGGAGGCCCCAATTG ACAATGTTTATGTCAGTGCGGGAGTCATACAGTCGAAATCACTGT TACTGCGGATAACGGCACATGGGACGTGTATGCCGACTACCTGGTG ATACAGAGCGAGAAGGACGAGCTGTGA (SEQ ID NO: 179) |
| 2080 | BAASS:P77853S158-19:SEKDEL | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GTYDIYRTTRVNQPCL AEGSLVLDAATGQRVP IEKVRPGMEVFSLGPD YRLYRVPVLEVLESGV GEVVRLRTRSGRTLVL TPDHPLLTPEGWKPLC DLPLGTPIAVPAELPV AGHLAPPEERVTLLAL LLGDGNTKLSGRRGTR PIAFFYSKDPELLAAY RRCAEALGAKVKAYVH PTTGVVTLATLAPRPG AQDPVKRLVVEAGMVA KAEEKRVPEEVFRYRR EALALFLGRLFSTDGS VEKKRISYSSASLGLA QDVAHLLLRLGITSQL RSRGPRAHEVLISGRE DILRFAELIGPYLLGA KRERLAALEAEARRRL PGQGWHLRLVLPAVAY RVSEAKRRSGFSWSEA GRRVAVAGSCLSSGLN LKLPRRYLSRHRLSLL GEAFADPGLEALAEGQ VLWDPIVAVEPAGKAR TFDLRVPPFANFVSED LVVHNSIVGTATFDQY WSVRTSKRTSGTVTVT DHFRAWANRGLNLGTI DQITLCVEGYQSSGSA NITQNTFSQGSSSGSS GGSSGSTTTTRIECEN MSLSGPYVSRITNPFN GIALYANGDTARATVN FPASRNYNFRLRGCGN NNNLARVDLRIDGRTV GTFYYQGTYPWEAPID NVYVSAGSHTVEITVT | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGACCTACGACATCTATAGGACGACAC GCGTCAACCAGCCTTGCCTGGCCGAGGGCTCGCTCGTCTTGGACGC GGCTACCGGGCAGAGGGTCCCTATCGAAAAGGTGCGTCCGGGGATG GAAGTTTTCTCCTTGGGACCTGATTACAGACTGTATCGGGTGCCCG TTTTGGAGGTCCTTGAGAGCGGGGTTGGGGAGTTGTGCGCCTCAG AACTCGGTCAGGGAGAACGCTGGTGTTGACACCAGATCACCCGCTT TTGACCCCCGAAGGTTGGAAACCTCTTTGTGACCTCCCGCTTGGAA CTCCAATTGCAGTCCCCGCAGAACTGCCTGTGGCGGGCCACTTGGC CCCACCTGAAGAACGTGTTACGCTCCTGGCTCTTCTTGTTGGGGGAT GGGAACACAAAGCTGTCGGGTCGGAGAGGTACACGTCCTATTGCCT TCTTCTACAGCAAAGACCCCGAATTGCTCGCGGCTTATCGCCGGTG TGCAGAAGCCTTGGGTGCAAAGGTGAAAGCATACGTCCACCCGACT ACGGGGGTGGTTACACTCGCAACCCTCGCTCCACGTCCTGGAGCTC AAGATCCTGTCAAACGCCTCGTTGTCGAGGCGGGAATGGTTGCTAA AGCCGAAGAGAAGAGGGTCCCGGAGGAGGTGTTTCGTTACCGGCGT GAGGCGTTGGCCCTTTTCTTGGGCCGTTTGTTCTCGACAGACGGCT CTGTTGAAAAGAAGAGGATCTCTTATTCAAGTGCCAGTTTGGGACT GGCCCAGGATGTCGCACATCTCTTGCTGCGCCTTGGAATTACATCT CAACTCCGTTCGAGAGGGCCACGGGCTCACGAGGTTCTTATATCGG GCCGCGAGGATATTTTGCGGTTTGCTGAACTTATCGGACCCTACCT CTTGGGGGCCAAGAGGGAGAGACTTGCAGCGCTGGAAGCTGAGGCC CGCAGGCGTTTGCCTGGACAGGGATGGCACTTGCGGCTTGTTCTTC CTGCCGTGGCGTACAGAGTGAGCGAGGCTAAAAGGCGCTCGGGATT TTCGTGGAGTGAAGCCGGTCGGCGCGTCGCAGTTGCGGGATCGTGT TGTCATCTGGACTCAACCTCAAATTGCCCAGACGCTACCTTTCTC GGCACCGGTTGTCGCTGCTCGGTGAGGCTTTTGCCGACCCTGGGCT GGAAGCGCTCGCGGAAGGCCAAGTGCTCTGGGACCCTATTGTTGCT GTCGAACCGGCCGGTAAGGCGAGAACATTCGACTTGCGCGTTCCAC CCTTTGCAAACTTCGTGAGCGAGGACCTGGTGGTGCATAACTCCAT TGTGGGACAGCCACGTTCGATCAGTACTGGAGCGTGCGCACCTCT AAGCGGACTTCAGGAACAGTGACCGTGACCGATCACTTCCGCGCCT GGGCGAACCGGGGCCTGAACCTCGGCACAATAGACCAAATTACATT GTGCGTGGAGGGTTACCAAAGCTCTGGATCAGCCAACATCACCCAG AACACCTTCTCTCAGGGCTCTTCTTCCGGCAGTTCGGGTGGCTCAT CCGGCTCCACAACGACTACTCGCATCGAGTGTGAGAACATGTCCTT GTCCGGACCCTACGTTAGCAGGATCACCAATCCCTTTAATGGTATT GCGCTGTACGCCAACGGAGACACAGCCCGCGCTACCGTTAACTTCC CCGCAAGTCGCAACTACAATTTCCGCCTGCGGGGTTGCGGCAACAA CAATAATCTTGCCCGTGTGGACCTGAGGATCGACGGACGGACCGTC |

TABLE 1-continued

Sequences of CWDEs and their fusions in vectors

| pAG vector | Sequence annotation | Protein sequence | Nucleotide sequence |
|---|---|---|---|
| | | ADNGTWDVYADYLVIQ SEKDEL* (SEQ ID NO: 108) | GGGACCTTTTATTACCAGGGCACATACCCCTGGGAGGCCCCAATTG ACAATGTTTATGTCAGTGCGGGGAGTCATACAGTCGAAATCACTGT TACTGCGGATAACGGCACATGGGACGTGTATGCCGACTACCTGGTG ATACAGAGCGAGAAGGACGAGCTGTGA (SEQ ID NO: 180) |
| 2081 | BAASS:P77853T143-1:SEKDEL | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGACLAEGSLVLD AATGQRVPIEKVRPGM EVFSLGPDYRLYRVPV LEVLESGVREVVRLRT RSGRTLVLTPDHPLLT PEGWKPLCDLPLGTPI AVPAELPVACHLAPPE ERVTLLALLLGDGNTK PSGRRGTRPNAFFYSK DPELLAAYRRCAEALG AKVKAYVHPTTGVVTL ATLAPRPGAQDPVKRL VVEAGMVAKAEEKRVP EEVFRYRREALALFLG RLFSTDGSVEKKRISY SSASLGLAQDVAHLLL RLGITSQLRSRGPRAH EVLISGREDILRFAEL IGPYLLGAKRERLAAL EAEARRRLPGQGWHLR LVLPAVAYRVSEAKRR SGFSWSEAGRRVAVAG SCLSSGLNLKLPRRYL SRHRLSLLGEAFADPG LEALAEGQVLWDPIVA VEPAGKARTFDLRVPP FANFVSEDLVVHNTSP LGQVTIDGGTYDIYRT TRVNQPSIVGTATFDQ YWSVRTSKRTSGTVTV TDHFRAWANRGLNLGT IDQITLCVEGYQSSGS ANITQNTFSQGSSSGS SGGSSGSTTTTRIECE NMSLSGPYVSRITNPF NGIALYANGDTARATV NFPASRNYNFRLRGCG NNNNLARVDLRIDGRT VGTFYYQGTYPWEAPI DNVYVSAGSHTVEITV TADNGTWDVYADYLVI QSEKDEL* (SEQ ID NO: 109) | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCTGCCTGGCCGAG GGCTCGCTCGTCTTGGACGCGGCTACCGGGCAGAGGGTCCCTATCG AAAAGGTGCGTCCGGGGATGGAGGTTTTCTCCTTGGGACCTGATTA CAGACTGTATCGGGTGCCCGTTTTGGAGGTCCTTGAGAGCGGGGTT AGGGAAGTTGTGCGCCTCAGAACTCGGTCAGGGAGAACGCTGGTGT TGACACCAGATCACCCGCTTTTGACCCCCGAAGGTTGGAAACCTCT TTGTGACCTCCCGCTTGGAACTCCAATTGCAGTCCCCGCAGAACTG CCTGTGGCGTGCCACTTGGCCCCCACCTGAAGAACGTGTTACGCTC CTGGCTCTTCTGTTGGGGGATGGGAACACAAAGCCGTCGGGTCGGAG AGGTACACGTCCTAATGCCTTCTTCTACAGCAAAGACCCCGAATTG CTCGCGGCTTATCGCCGGTGTGCAGAGGCTTGGGTGCAAAGGTGA AAGCATACGTCCACCCGACTACGGGGTGGTTACACTCGCAACCCT CGTCCACGTCCTGGAGCTCAAGATCCTGTCAAACGCCTCGTTGTC GAGGCGGGAATGGTTGCTAAAGCCGAAGAGAAGAGGGTCCCGGAGG AGGTGTTTCGTTACCGGCGTGAGGCGTTGGCCCTTTTCTTGGGCCG TTTGTTCTCGACAGACGGCTCTGTTGAAAAGAAGAGGATCTCTTAT TCAAGTGCCAGTTTGGGACTGGCCCAGGATGTCGCACATCTCTTGC TGCGCCTTGGAATTACATCTCAACTCCGTTCGAGAGGGCCACGGGC TCACGAGGTTCTTTATATCGGGCCGCGAGGATATTTTGCGGTTTGCT GAACTTATCGGACCCTACCTCTTGGGGGCCAAGAGGGAGAGACTTG CAGCGCTGGAAGCTGAGGCCCGCAGGCGTTTGCCTGGACAGGGATG GCACTTGCGGCTTGTTCTTCCTGCCGTGGCGTACAGAGTGAGCGAG GCTAAAAGGCGCTCGGGATTTTCGTGGAGTGAAGCCGGTCGGCGCG TCGCAGTTGCGGGATCGTGTTTGTCATCTGACTCAACCTCAAATT GCCCAGACGCTACCTTTCTCGGCACCGGTTGTCGCTGCTCGGTGAG GCTTTTGCCGACCCTGGGCTGGAAGCGCTCGCGGAAGGCCAAGTGC TCTGGGACCCTATTGTTGCTGTCGAACCGGCCGGTAAGGCGAGAAC ATTCGACTTGCGCGTTCCACCCTTGGAACTTCGTGAGCGAGGAC CTGGTGGTCATAAACACGTCCCCCTTGGGCCAAGTGACAATCGATG GCGGGACCTACGACATCTATAGGACGACACGCGTCAACCAGCCTTC CATTGTGGGACAGCCACGTTCGATCAGTACTGGAGCGTGCGCACC TCTAAGCGGACTTCAGGAACAGTGACCGTGACCGATCACTTCCGCG CCTGGGCGAACCGGGGCCTGAACCTCGGCACAATAGACCAAATTAC ATTGTGCGTGGAGGGTTACCAAAGCTCTGGATCAGCCAACATCACC CAGAACACCTTCTCTCAGGGCTCTTCTTCCGGCAGTTCGGGTGGCT CATCCGGCTCCACAACGACTACTCGCATCGAGTGTGAGAACATGTC CTTGTCCGGACCCTACGTTAGCAGGATCACCAATCCCTTTAATGGT ATTGCGCTGTACGCCAACGGAGACACAGCCCGCGCTACCGTTAACT TCCCCGCAAGTCGCAACTACAATTTCCGCCTGCGGGGTTGCGGCAA CAACAATAATCTTGCCCGTGTGGACCTGAGGATCGACGGACGGACC GTCGGGACCTTTTATTACCAGGGCACATACCCCTGGGAGGCCCCAA TTGACAATGTTTATGTCAGTGCGGGGAGTCATACAGTCGAAATCAC TGTTACTGCGGATAACGGCACATGGGACGTGTATGCCGACTACCTG GTGATACAGAGCGAGAAGGACGAGCTGTGA (SEQ ID NO: 181) |
| 2082 | GluB4SP:O43097 | MATIAFSRLSIYFCVL LLCHGSMAFPAGNATE LEKRQTTPNSEGWHDG YYYSWWSDGGAQATYT NLEGGTYEISWGDGGN LVGGKGWNPGLNARAI HFEGVYQPNGNSYLAV YGWTRNPLVEYYIVEN FGTYDPSSGATDLGTV ECDGSIYRLGKTTRVN APSIDGTQTFDQYWSV RQDKRTSGTVQTGCHF DAWARAGLNVNGDHYY QIVATEGYFSSGYARI TVADVG* (SEQ ID NO: 110) | ATGGCCACCATCGCTTTCTCCCGCTTGTCCATCTACTTCTGCGTGC TTCTCCTGTGCCACGGCTCCATGGCCTTCCCAGCTGGAAACGCAAC GGAATTGGAGAAAAGACAAACCACCCCTAACTCTGAGGGCTGGCAT GACGGATACTACTACTCTTGGTGGAGCGATGGTGGTGCACAGGCCA CCTATACAAACCTCGAAGGCGGCACTTATGAGATTCATGGGGTGA CGGTGGCAACCTTGTCGGCGGAAAGGGTGGAACCCCGGACTTAAC GCCAGGGCAATCCACTTCGAAGGGTGTACCAGCCCAATGGCAACT CATACCTGGCCGTCTACGGGTGGACGCGCAATCCGCTGGTTGAGTA CTATATCGTGGAGAATTTCGGAACTTATGACCCTAGCTCCGGTGCC ACGGACCTCGGGACAGTCGAGTGTGACGGAAGCATCTACAGGCTGG GTAAAACTACCCGCGTTAATGCTCCATCGATCGACGGCACACAAAC ACAGTTCAGACGGGTTGCCACTTTGATGCCTGGGCAAGAGCGGGGC TCAATGTGAATGGGACCACTACTATCAGATTGTGGCGACCGAGGG CTATTTCTCCAGTGGCTATGCGCGTATAACCGTCGCTGATGTTGGA TGA (SEQ ID NO: 182) |

TABLE 1-continued

Sequences of CWDEs and their fusions in vectors

| pAG vector | Sequence annotation | Protein sequence | Nucleotide sequence |
|---|---|---|---|
| 2083 | GluB4SP:O43097: SEKDEL | MATIAFSRLSIYFCVL LLCHGSMAFPAGNATE LEKRQTTPNSEGWHDG YYYSWWSDGGAQATYT NLEGGTYEISWGDGGN LVGGKGWNPGLNARAI HFEGVYQPNGNSYLAV YGWTRNPLVEYYIVEN FGTYDPSSGATDLGTV ECDGSIYRLGKTTRVN APSIDGTQTFDQYWSV RQDKRTSGTVQTGCHF DAWARAGLNVNGDHYY QIVATEGYFSSGYARI TVADVGSEKDEL* (SEQ ID NO: 111) | ATGGCCACCATCGCTTTCTCCCGCTTGTCCATCTACTTCTGCGTGC TTCTCCTGTGCCACGGCTCCATGGCCTTCCCAGCTGGAAACGCAAC GGAATTGGAGAAAAGACAAACCACCCCTAACTCTGAGGGCTGGCAT GACGGATACTACTACTCTTGGTGGAGCGATGGTGGTGCACAGGCCA CCTATACAAACCTCGAAGGCGGCACTTATGAGATTTCATGGGGTGA CGGTGGCAACCTTGTCGGCGGAAAGGGGTGGAACCCCGGACTTAAC GCCAGGGCAATCCACTTCGAAGGGGTGTACCAGCCCAATGGCAACT CATACCTGGCCGTCTACGGGTGGACGCGCAATCCGCTGGTTGAGTA CTATATCGTGGAGAATTTCGGAACTTATGACCCTAGCTCCGGTGCC ACGGACCTCGGGACAGTCGAGTGTGACGGAAGCATCTACAGGCTGG GTAAAACTACCCGCGTTAATGCTCCATCGATCGACGGCACGCAAAC ATTTGATCAATACTGGTCCGTGCGGCAGGATAAGAGGACAAGCGGC ACAGTTCAGACGGGTTGCCACTTTGATGCCTGGGCAAGAGCGGGGC TCAATGTGAATGGGACCACTACTATCAGATTGTGGCGACCGAGGG CTATTTCTCCAGTGGCTATGCGCGTATAACCGTCGCTGATGTTGGA AGCGAGAAGGACGAGCTGTGA (SEQ ID NO: 183) |
| 2084 | GluB4SP:NtEGm | MATIAFSRLSIYFCVL LLCHGSMAAYDYKQVL RDSLLFYEAQRSGRLP ADQKVTWRKDSALNDQ GDQGQDLTGGYFDAGD FVKFGFPMAYTATVLA WGLIDFEAGYSSAGAL DDGRKAVKWATDYFIK AHTSQNEFYGQVGQGD ADHAFWGRPEDMTMAR PAYKIDTSRPGSDLAG ETAAALAAASIVFRNV DGTYSNNLLTHARQLF DFANNYRGKYSDSITD ARNFYASADYRDELVW AAAWLYRATNDNTYLN TAESLYDEFGLQNWGG GLNWDSKVSGVQVLLA KLTNKQAYKDTVQSYV NYLINNQQKTPKGLLY IDMWGTLRHAANAAFI MLEAAELGLSASSYRQ FAQTQIDYALGDGGRS FVCGFGSNPPTRPHHR SSSCPPAPATCDWNTF NSPDPNYHVLSGALVG GPDQNDNYVDDRSDYV HNEVATDYNAGFQSAL AALVALGY* (SEQ ID NO: 112) | ATGGCCACCATCGCTTTCTCCCGCTTGTCCATCTACTTCTGCGTGC TTCTCCTGTGCCACGGCTCCATGGCCGCTTACGACTACAAGCAGGT GTTGCGGGACTCGCTACTATTCTATGAGGCCCAGAGATCCGGCCGG CTCCCAGCCGACCAGAAGGTCACGTGGAGGAAGGATAGCGCGCTGA ATGACCAGGGTGACCAGGGACAAGACTTGACCGGCGGCTACTTTGA CGCTGGGGACTTCGTCAAGTTCGGGTTCCCCATGGCTTATACCGCA ACCGTGCTGGCATGGGGCCTCATAGATTTTGAGGCCGGCTACAGCA GTGCCGGGGCCTTGGATGATGGACGGAAGGCTGTCAAATGGGCCAC CGACTATTTCATAAAGGCCCACACAAGTCAAAATGAGTTCTATGGT CAGGTCGGCCAGGGTGACGCCGATCACGCTTTCTGGGGAAGACCAG AGGATATGACGATGGCGCGCCGGGCGTACAAGATAGACACCTCAAG GCCTGGCTCTGATCTGGCAGGCGAGACAGCGGCTGCTCTTGCCGCT GCTTCAATCGTGTTCCGGAACGTCGATGGCACTTACTCAAATAACC TGTTAACACACGCTCGCCAGCTATTCGACTTCGCGAACAACTACCG GGGAAAGTATAGTGACTCTATTACTGACGCAAGAAATTTCTACGCA AGCGCAGACTACAGAGACGAGTTGGTTTGGGCTGCTGCGTGGTTAT ACAGAGCGACCAACGACAACACCTACCTCAACACTGCTGAGTCACT GTACGATGAGTTTGGGCTACAGAACTGGGGGGGGGGCCTGAACTGG GATAGCAAGGTGTCTGGCGTGCAGGTGTTGTTGGCCAAGCTTACCA ATAAGCAGGCCTACAAGGACACGGTGCAGTCTTACGTCAATTACCT AATTAATAACCAGCAGAAGACTCCCAAGGGCCTCCTCTACATCGAC ATGTGGGGCACCCTTCGCCACGCTGCCAACGCCGCATTCATCATGC TCGAAGCCGCCGAGCTGGGCCTTGTCCGCCTCCTCTTATAGACAGTT CGCGCAAACGCAAATCGACTACGCCCTGGGCGATGGTGGCCGCTCC TTTGTGTGCGGGTTCGGGAGTAATCCTCCTACGAGACCGCACCACA GATCCTCGTCGTGCCCGCCAGCTCCCGCTACTTGCGACTGGAATAC ATTCAACTCACCTGACCCAAACTACCACGTCCTCTCTGGGGCCCTA GTGGGCGGACCTGATCAGAATGACAACTACGTCGATGACCGTTCAG ACTATGTTCACAACGAAGTCGCCACTGATTACAACGCGGGTTTCCA GTCCGCGTTAGCTGCTTTGGTGGCCCTTGGTTACTGA (SEQ ID NO: 184) |
| 2085 | P77853T145-307 | MQTSITLTSNASGTFD GYYYELWKDTGNTTMT VYTQGRFSCQWSNINN ALFRTGKKYNQNWQSL GTIRITYSATYNPNGN SYLCIYGWSTNPLVEF YIVESWGNWRPPGATS LGQVTIDGGSVTGDTE IIVKRNGRIEFVPIEK LFERVDYRIGEKEYCI LEDVEALTLDNRDKLI WKKVPYVMRHRAKKKV YRIWITNSWYIDVTED HSLIVAEDGLKEARPM EIEGKSLIATKDDLSG VEYIKPHAIEEISYNG YVYDIEVEGTHRFFAN GILVHNTYDIYRTTRV NQPSIVGTATFDQYWS VRTSKRTSGTVTVTDH FRAWANRGLNLGTIDQ ITLCVEGYQSSGSANI TQNTFSQGSSSGSSGG SSGSTTTTRIECENMS LSGPYVSRITNPFNGI | ATGCAAACAAGCATTACTCTGACATCCAACGCATCCGGTACGTTTG ACGGTTACTATTACGAACTCTGGAAGGATACTGGCAATACAACAAT GACGGTCTACACTCAAGGTCGTTTTCCTGCCAGTGGTCGAACATC AATAACGCGTTGTTTAGGACCGGGAAGAAATACAACCAGAATTGGC AGTCTCTTGGCACAATCCGGATCACGTACTCTGCGACTTACAACCC AAACGGGAACTCCTACTTGTGTATCTATGGCTGGTCTACCAACCCA TTGGTCGAGTTCTACATCGTTGAGTCCTGGGGGAACTGGAGACCGC CTGGTGCCACGTCCCTGGGCCAAGTGACAATCGATGGCGGGAGCGT TACTGGAGACACCGAAATTATCGTCAAGAGAAATGGTAGGATCGAA TTTGTCCCGATCGAGAAGCTCTTTGAGAGAGTGGACTATAGAATAG GCGAGAAAGAATACTGCATCCTTGAGGACGTTGAGGCGCTGACTCT TGACAACAGAGACAAACTTATTTGGAAGAAGGTGCCCTACGTCATG CGTCACAGGGCAAAGAAAAAGGTCTACCGTATCTGGATTACTAATT CATGGTACATAGACGTTACAGAGGACCACTCCCTGATTGTGGCTGA GGACGGGCTGAAGGAGGCCCGCCCATGGAAATTGAGGGCAAGTCT CTGATTGCAACTAAAGATGATCTCTCTGGCGTTGAGTACATCAAGC CTCACGCTATTGAGGAGATTAGTTACAACGGTTACGTGTACGATAT CGAAGTGGAGGGTACTCATAGATTCTTCGCTAATGGGATACTGGTG CATAACACCTACGACATCTATAGGACGACACGCGTCAACCAGCCTT CCATTGTGGGGACAGCCACGTTCGATCAGTACTGGAGCGTGCACA CTCAAGCGGACTTCAGGAACAGTGACCGTGACCGATCACTTCCGC GCTGGGCGAACCGGGGCCTGAACCTCGGCACAATAGACCAAATTA CATTGTGCGTGGAGGGTTACCAAAGCTCTGGATCAGCCAACATCAC CCAGAACACCTTCTCTCAGGGGCTCTTCTTCCGGCAGTTCGGGTGGC TCATCCGGCTCCACAACGACTACTCGCATCGAGTGTGAGAACATGT |

TABLE 1-continued

Sequences of CWDEs and their fusions in vectors

| pAG vector | Sequence annotation | Protein sequence | Nucleotide sequence |
|---|---|---|---|
| | | ALYANGDTARATVNFP ASRNYNFRLRGCGNNN NLARVDLRIDGRTVGT FYYQGTYPWEAPIDNV YVSAGSHTVEITVTAD NGTWDVYADYLVIQ* (SEQ ID NO: 113) | CCTTGTCCGGACCCTACGTTAGCAGGATCACCAATCCCTTTAATGG TATTGCGCTGTACGCCAACGGAGACACAGCCCGCGCTACCGTTAAC TTCCCCGCAAGTCGCAACTACAATTTCCGCCTGCGGGGTTGCGGCA ACAACAATAATCTTGCCCGTGTGGACCTGAGGATCGACGGACGGAC CGTCGGGACCTTTTATTACCAGGGCACATACCCCTGGGAGGCCCCA ATTGACAATGTTTATGTCAGTGCGGGGAGTCATACAGTCGAAATCA CTGTTACTGCGGATAACGGCACATGGGACGTGTATGCCGACTACCT GGTGATACAGTGA (SEQ ID NO: 185) |
| 2086 | BAASS:P77853T145-307 | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GSVTGDTEIIVKRNGR IEFVPIEKLFERVDYR IGEKEYCILEDVEALT LDNRDKLIWKKVPYVM RHRAKKKVYRIWITNS WYIDVTEDHSLIVAED GLKEARPMEIEGKSLI ATKDDLSGVEYIKPHA IEEISYNGYVYDIEVE GTHRFFANGILVHNTY DIYRTTRVNQPSIVGT ATFDQYWSVRTSKRTS GTVTVTDHFRAWANRG LNLGTIDQITLCVEGY QSSGSANITQNTFSQG SSSGSSGGSSGSTTTT RIECENMSLSGPYVSR ITNPFNGIALYANGDT ARATVNFPASRNYNFR LRGCGNNNNLARVDLR IDGRTVGTFYYQGTYP WEAPIDNVYVSAGSHT VEITVTADNGTWDVYA DYLVIQ* (SEQ ID NO: 114) | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGAGCGTTACTGGAGACACCGAAATTA TCGTCAAGAGAAATGGTAGGATCGAATTTGTCCCGATCGAGAAGCT CTTTGAGAGAGTGGACTATAGAATAGGCGAGAAAGAATACTGCATC CTTGAGGACGTTGAGGCGCTGACTCTTGACAACAGAGACAAACTTA TTTGGAAGAAGGTGCCCTACGTCATGCGTCACAGGGCAAAGAAAAA GGTCTACCGTATCTGGATTACTAATTCATGGTACATAGACGTTACA GAGGACCACTCCCTGATTGTGGCTGAGGACGGGCTGAAGGAGGCCC GCCCCATGGAAATTGAGGGCAAGTCTCTGATTGCAACTAAAGATGA TCTCTCTGGCGTTGAGTACATCAAGCCTCACGCTATTGAGGAGATT AGTTACAACGGTTACGTGTACGATATCGAAGTGGAGGGTACTCATA GATTCTTCGCTAATGGGATACTGGTGCATAACACCTACGACATCTA TAGGACGACACGCGTCAACCAGCCTTCCATTGTGGGGACAGCCACG TTCGATCAGTACTGGAGCGTGCGCACCTCTAAGCGGACTTCAGGAA CAGTGACCGTGACCGATCACTTCCGCGCCTGGGCGAACCGGGGCCT GAACCTCGGCACAATAGACCAAATTACATTGTGCGTGGAGGGTTAC CAAAGCTCTGGATCAGCCAACATCACCCAGAACACCTTCTCTCAGG GCTCTTCTTCCGGCAGTTCGGGTGGCTCATCCGGCTCCACAACGAC TACTCGCATCGAGTGTGAGAACATGTCCTTGTCCGGACCCTACGTT AGCAGGATCACCAATCCCTTTAATGGTATTGCGCTGTACGCCAACG GAGACACAGCCCGCGCTACCGTTAACTTCCCCGCAAGTCGCAACTA CAATTTCCGCCTGCGGGGTTGCGGCAACAACAATAATCTTGCCCGT GTGGACCTGAGGATCGACGGACGGACCGTCGGGACCTTTTATTACC AGGGCACATACCCCTGGGAGGCCCCAATTGACAATGTTTATGTCAG TGCGGGGAGTCATACAGTCGAAATCACTGTTACTGCGGATAACGGC ACATGGGACGTGTATGCCGACTACCTGGTGATACAGTGA (SEQ ID NO: 186) |
| 2087 | BAASS:P77853T145-307:SEKDEL | MANKHLSLSLFLVLLG LSASLASGQQTSITLT SNASGTFDGYYYELWK DTGNTTMTVYTQGRFS CQWSNINNALFRTGKK YNQNWQSLGTIRITYS ATYNPNGNSYLCIYGW STNPLVEFYIVESWGN WRPPGATSLGQVTIDG GSVTGDTEIIVKRNGR IEFVPIEKLFERVDYR IGEKEYCILEDVEALT LDNRDKLIWKKVPYVM RHRAKKKVYRIWITNS WYIDVTEDHSLIVAED GLKEARPMEIEGKSLI ATKDDLSGVEYIKPHA IEEISYNGYVYDIEVE GTHRFFANGILVHNTY DIYRTTRVNQPSIVGT ATFDQYWSVRTSKRTS GTVTVTDHFRAWANRG LNLGTIDQITLCVEGY QSSGSANITQNTFSQG SSSGSSGGSSGSTTTT RIECENMSLSGPYVSR ITNPFNGIALYANGDT ARATVNFPASRNYNFR LRGCGNNNNLARVDLR IDGRTVGTFYYQGTYP | ATGGCGAACAAACATTTGTCCCTCTCCCTCTTCCTCGTCCTCCTTG GCCTGTCGGCCAGCTTGGCCTCCGGGCAACAAACAAGCATTACTCT GACATCCAACGCATCCGGTACGTTTGACGGTTACTATTACGAACTC TGGAAGGATACTGGCAATACAACAATGACGGTCTACACTCAAGGTC GCTTTTCCTGCCAGTGGTCGAACATCAATAACGCGTTGTTTAGGAC CGGGAAGAAATACAACCAGAATTGGCAGTCTCTTGGCACAATCCGG ATCACGTACTCTGCGACTTACAACCCAAACGGGAACTCCTACTTGT GTATCTATGGCTGGTCTACCAACCCATTGGTCGAGTTCTACATCGT TGAGTCCTGGGGGAACTGGAGACCGCCTGGTGCCACGTCCCTGGGC CAAGTGACAATCGATGGCGGGAGCGTTACTGGAGACACCGAAATTA TCGTCAAGAGAAATGGTAGGATCGAATTTGTCCCGATCGAGAAGCT CTTTGAGAGAGTGGACTATAGAATAGGCGAGAAAGAATACTGCATC CTTGAGGACGTTGAGGCGCTGACTCTTGACAACAGAGACAAACTTA TTTGGAAGAAGGTGCCCTACGTCATGCGTCACAGGGCAAAGAAAAA GGTCTACCGTATCTGGATTACTAATTCATGGTACATAGACGTTACA GAGGACCACTCCCTGATTGTGGCTGAGGACGGGCTGAAGGAGGCCC GCCCCATGGAAATTGAGGGCAAGTCTCTGATTGCAACTAAAGATGA TCTCTCTGGCGTTGAGTACATCAAGCCTCACGCTATTGAGGAGATT AGTTACAACGGTTACGTGTACGATATCGAAGTGGAGGGTACTCATA GATTCTTCGCTAATGGGATACTGGTGCATAACACCTACGACATCTA TAGGACGACACGCGTCAACCAGCCTTCCATTGTGGGGACAGCCACG TTCGATCAGTACTGGAGCGTGCGCACCTCTAAGCGGACTTCAGGAA CAGTGACCGTGACCGATCACTTCCGCGCCTGGGCGAACCGGGGCCT GAACCTCGGCACAATAGACCAAATTACATTGTGCGTGGAGGGTTAC CAAAGCTCTGGATCAGCCAACATCACCCAGAACACCTTCTCTCAGG GCTCTTCTTCCGGCAGTTCGGGTGGCTCATCCGGCTCCACAACGAC TACTCGCATCGAGTGTGAGAACATGTCCTTGTCCGGACCCTACGTT AGCAGGATCACCAATCCCTTTAATGGTATTGCGCTGTACGCCAACG GAGACACAGCCCGCGCTACCGTTAACTTCCCCGCAAGTCGCAACTA CAATTTCCGCCTGCGGGGTTGCGGCAACAACAATAATCTTGCCCGT |

TABLE 1-continued

Sequences of CWDEs and their fusions in vectors

| pAG Sequence vector annotation | Protein sequence | Nucleotide sequence |
|---|---|---|
| | WEAPIDNVYVSAGSHT VEITVTADNGTWDVYA DYLVIQSEKDEL* (SEQ ID NO: 115) | GTGGACCTGAGGATCGACGGACGGACCGTCGGGACCTTTTATTACC AGGGCACATACCCCTGGGAGGCCCCAATTGACAATGTTTATGTCAG TGCGGGGAGTCATACAGTCGAAATCACTGTTACTGCGGATAACGGC ACATGGGACGTGTATGCCGACTACCTGGTGATACAGAGCGAGAAGG ACGAGCTGTGA (SEQ ID NO: 187) |

Example 6—Plant Transformation

Maize Transformation

Agrobacterium-mediated transformation of immature maize embryos was performed as described in Negrotto et al., (2000) Plant Cell Reports 19: 798-803, which is incorporated herein by reference as if fully set forth. Transformation plasmids and selectable marker genes used for transformation were cloned into a pAG-series vector suitable for monocot transformation as described above. The vectors utilized for this example contained the phosphomannose isomerase (PMI) gene (Negrotto et at (2000) Plant Cell Reports 19: 798-803) as a selectable marker, but other markers could be used in the same capacity.

Transformation Vector and Agrobacterium Strains

Agrobacterium tumefaciens transformation vectors were constructed using standard molecular techniques known in the art, as described above. The plasmids were introduced into Agrobacterium strains LBA4404+pSB1 (Ishida et al. (1996) Nature Biotechnology 14:745-750, which is incorporated herein by reference as if fully set forth).

Overnight cultures of the Agrobacterium strain containing the plasmid were grown for two days on plates with solid YP medium for 2 to 4 days at 28° C. containing 100 mg/L spectinomycin and 10 mg/L tetracycline.

Agrobacterium was re-suspended in LS-inf media supplemented with 100 mM acetosyringone (As) (LSAs medium) (Negrotto et al., (2000) Plant Cell Rep 19: 798-803, which is incorporated herein by reference as if fully set forth) until the Agrobacterium cells were uniformly dispersed in the suspension. The Agrobacterium suspension was then diluted to an $OD_{660}$ in the range of 0.5 to 0.8 and vortexed for about 15 seconds.

Infection and Co-Cultivation of Maize Immature Embryos

Maize (Zea maize cultivars HiII, A188 or B73) stock plants were grown in a greenhouse under 16 hours of daylight at 28° C. Immature ears were collected 7 to 15 days after pollination and sterilized by immersing in 20% chlorine bleach (available under the registered trademark CHLOROX®) for 15-20 minutes. Sterilized ears were then rinsed thoroughly with sterile water.

Immature zygotic embryos were isolated from the kernels and collected into a sterile eppendorf tube containing liquid LS-inf+100 p1M As (LSAs) media. Embryos were vortexed for 5 seconds and rinsed once with fresh infection medium. Infection media was removed, Agrobacterium solution was added and embryos were vortexed for 30 seconds and allowed to settle with the bacteria for about 5 minutes.

After inoculation, immature embryos were then transferred scutellum side up to LSAs medium and cultured in the dark for two to three days at 22 C.

Recovery, Selection of Transformed Maize Embryogenic Tissue and Plant Regeneration After co-cultivation, immature embryos were transferred onto LSDc medium supplemented with 200 mg/l of timentine and 1.6 mg/l silver nitrate (Negrotto et al. 2000). The plates were incubated for 5 to 15 days at 28° C. in the dark.

Embryos producing embryogenic callus were transferred to LSD1M0. 5S medium (LSDc with 5 mg/l Dicamba, 10 g/l mannose, 5 g/l sucrose). The cultures were selected on this medium for 6 weeks with 3 week subculture intervals. Surviving cultures were transferred either to LSD1M0.5S medium to be bulked-up or to Reg1 medium (as described in Negrotto et al., 2000). Following culturing in the light (16 hour light/8 hour dark regiment), green tissues were then transferred to Reg2 medium without growth regulators (as described in Negrotto et al., 2000) and incubated for 1-2 weeks. Well-developed seedlings with leaves and roots were transferred to Reg3 medium (as described in Negrotto et al., 2000) and grown in the light.

Leaves were sampled for PCR analysis to identify transgenic plants containing the selectable marker gene according to Negrotto et al. (2000), and gene of interest. PCR positive and rooted plants were rinsed with water to wash off the agar medium, and transplanted to soil and grown in the greenhouse for seeds.

Switchgrass Transformation

Media used in developing the Agrobacterium-mediated transformation protocol, employed to transform switchgrass plants, were prepared using standard methods known to one of ordinary skill in the art. The following media were used in the Examples described herein.

Somatic Embryo Induction Medium (SEI)

SEI medium was prepared using 4.3 g of MS basal salt mixture, B5 vitamins (100 mg of myo-Inositol, 1 mg of nicotinic acid, 1 mg of pyridoxine HCl and 10 mg of thiamine HCl), 30 g sucrose, 5 mg 2,4-D and 10 mg BAP, 1.2 g/l Gelrite (Sigma, St. Louis, Mo., USA). These reagents were mixed in sterile water, which was taken up to a final volume of 1 L. The pH was adjusted to 5.8 prior to autoclaving.

Regeneration Medium

Regeneration medium was prepared using 4.3 g of MS basal salt mixture, MS vitamins (100 mg of myo-Inositol, 1 mg of nicotinic acid, 1 mg of pyridoxine HCl and 10 mg of thiamine HCl), 30 g sucrose, and 1.2 g Gelrite (Sigma, St. Louis, Mo., USA). These reagents were mixed in sterile water and taken up to a final volume of 1 L. The pH was adjusted to 5.8 prior to autoclaving.

Inoculation Medium (SW-1)

SW-1 medium was prepared using 4.3 g MS salts, B5 vitamins (100 mg of myo-Inositol, 1 mg of nicotinic acid, 1 mg of pyridoxine HCl and 10 mg of thiamine HCl), 68.5 g sucrose, 36 g glucose, and 1 g casamino acids. These reagents were mixed in sterile water and taken up to a final volume of 1 L. The pH was adjusted to 5.8 prior to autoclaving.

Co-Cultivation Medium (SW-2)

SW-2 medium was prepared using 4.3 g MS salts, B5 vitamins (100 mg of myo-Inositol, 1 mg of nicotinic acid, 1 mg of pyridoxine HCl and 10 mg of thiamine HCl), 0.7 g L-proline, 10 mg BAP, 5 mg 2,4-D, 0.5 g MES, 20 g sucrose, 10 g glucose and 1.2 g Gelrite. These reagents were mixed in sterile water and taken up to a final volume of 1 L. The pH was adjusted to 5.8 prior to autoclaving.

Resting Medium (SW-3)

SW-3 medium was prepared using 4.3 g MS salts, B5 vitamins (100 mg of myo-Inositol, 1 mg of nicotinic acid, 1 mg of pyridoxine HCl and 10 mg of thiamine HCl), 10 mg BAP, 5 mg 2,4-D, 30 g sucrose and 1.2 g Gelrite. These reagents were mixed in sterile water and taken up to a final volume of 1 L. The pH was adjusted to 5.8 prior to autoclaving.

Selection Medium 1 (S1)

51 medium was prepared using 4.3 g MS salts, B5 vitamins (100 mg of myo-Inositol, 1 mg of nicotinic acid, 1 mg of pyridoxine HCl and 10 mg of thiamine HCl), 10 mg BAP, 5 mg 2,4-D, 5 g sucrose, 10 g mannose and 1.2 g Gelrite. These reagents were mixed in sterile water and taken up to a final volume of 1 L. The pH was adjusted to 5.8 prior to autoclaving. Regeneration medium (R1). R1 medium was prepared using 4.3 g MS salts, B5 vitamins (100 mg of myo-Inositol, 1 mg of nicotinic acid, 1 mg of pyridoxine HCl and 10 mg of thiamine HCl), 30 g sucrose and 1.2 g Gelrite. These reagents were mixed in sterile water and taken up to a final volume of 1 L. The pH was adjusted to 5.8 prior to autoclaving.

Initiation of Embryogenic Callus Cultures

Mature switchgrass seeds (*Panicum virgatum*, cv. Alamo) were prepared for transformation by removing their seed coat using sand paper. With the seed coat removed, individual seeds were selected for sterilization. Switchgrass seeds were sterilized by immersing in 20% chlorine bleach (available under the registered trademark CHLOROX®) for 5-10 minutes. Sterilized seeds were then rinsed thoroughly with sterile water. Sterile seeds were placed onto somatic embryo induction medium (SEI) and were incubated at 28° C. in the dark for about 3-4 weeks. Resulting embryogenic callus clusters were transferred to fresh SEI medium and cultured for additional 6 weeks with 3 weeks subculture intervals at 28° C. in the dark.

Transformation Vector and *Agrobacterium* Strains

*Agrobacterium tumefaciens* transformation vectors were constructed as described above using standard molecular techniques known in the art. The plasmids were introduced into *Agrobacterium* strains LBA4404+pSB1 (Ishida et al. (1996) Nature Biotechnology 14:745-750).

Overnight cultures of the *Agrobacterium* strain containing the plasmid were grown for two days on plates with YP medium containing 100 mg/L spectinomycin and 10 mg/L tetracycline.

Preparation of *Agrobacterium* for Transformation

*Agrobacterium* culture was initiated weekly from a glycerol stock stored at −80° C., on YP semi-solid medium containing appropriate antibiotics and grown at 28° C. in an incubator.

The *Agrobacterium* was streaked onto fresh YP medium containing appropriate antibiotics the day before the inoculation and was grown in a 28° C. incubator. For plant transformation use, the *Agrobacterium* was collected from the plate using a disposable plastic inoculation loop and suspended in liquid inoculation medium, such as SW1, in a sterile 15 ml disposable polypropylene centrifugation tube. *Agrobacterium* was resuspended in the tube by vortexing for about 3 to 5 minutes until the *Agrobacterium* cells were uniformly dispersed in the suspension. The *Agrobacterium* suspension was then diluted to an $OD_{660}$ in the range of 0.5 to 0.8 and vortexed for about 15 seconds.

Infection and Co-Cultivation of Switchgrass Embryogenic Callus Cultures

The switchgrass type II repetitive somatic embryogenic callus clusters, 2 mm to 3 mm in diameter, were infected with *Agrobacterium* by mixing the explants with bacterial suspension as prepared above, and vortexed for 30 sec. The mixture was incubated with the prepared explants for about 3 to 15 minutes at room temperature.

Following infection, the *Agrobacterium* suspension explants were placed on co-cultivation medium (SW-2) in 100×15 mm Petri plates and were incubated for 2 to 3 days at 22° C. in the dark.

Regeneration and Selection of Transgenic Plants

After co-cultivation, the explants were transferred onto recovery medium with antibiotics to kill *Agrobacterium* or to inhibit *Agrobacterium* growth, without selection agent, such as recovery medium (SW3) supplemented with 200 mg/L timentin. The plates were incubated for 5 to 15 days at 28° C. in the dark. The explants were then transferred to S1 solid medium (10 g/L mannose and 5 g/l sucrose) supplemented with antibiotics for about 14 to 21 days. The explants were then transferred to fresh S1 medium (10 g/L mannose and 5 g/l sucrose) for about 14 to 21 days. Resistant clones were transferred to embryo differentiation medium R1 (5 g/l mannose and 10 g/l sucrose) and were incubated at 28° C. in the dark for about 2 to 3 weeks.

Differentiating plant tissues were transferred to fresh embryo differentiation medium R1 (5 g/l mannose and 10 g/l sucrose) and were incubated at 26° C. in the light for about 2 to 3 weeks.

Well-developed seedlings with leaves and roots were transferred to rooting medium. Leaves were sampled for PCR analysis to identify transgenic plants containing the selectable marker gene according to Negrotto et al. (2000), and gene of interest. PCR positive and rooted plants were rinsed with water to wash off the agar medium, and transplanted to soil and grown in the greenhouse for seeds.

Sorghum Somatic Embryogenic Culture Transformation

Materials and Methods

Media used in the *Agrobacterium*-mediated transformation protocol employed to develop transformed *sorghum* plants were prepared using standard methods known to one of ordinary skill in the art. The following media were used in the Examples described herein.

Somatic Embryo Induction Medium (SGWT-SEI)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 30 g sucrose, 1.5 mg 2,4-D, and 8 g Agar (Sigma, St. Louis, Mo., USA) were combined in sterile water. The final volume of the mixture was taken up to 1 L using sterile water. The pH was adjusted to 5.8 prior to autoclaving.

Regeneration Medium (SGWT-R)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 30 g sucrose, 1.0 mg IAA, 0.5 mg kinetin and 2.4 g Gelrite (Sigma, St. Louis, Mo., USA) were combined in sterile water. The final volume of the mixture was taken up to 1 L using sterile water. The pH was adjusted to 5.8 prior to autoclaving.

Inoculation Medium (SGI-1)

4.3 g MS salts, B5 vitamins (100 mg of myo-Inositol, 1 mg of nicotinic acid, 1 mg of pyridoxine HCl and 10 mg of thiamine HCl), 68.5 g sucrose, 36 g glucose, 1.0 g casamino acids, and 1.5 mg 2,4-D were combined in sterile water. The mixture was taken up to a final volume of 1 L using sterile water. The pH was adjusted to 5.2 prior to autoclaving.

Co-Cultivation Medium (SGC-2)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 20 g sucrose, 10 g glucose, 0.5 g MES, 1.5 mg 2,4-D, 40 mg acetosyringone, and 8 g agar were combined in sterile water. The mixture was taken up to a final volume of 1 L using sterile water. The pH was adjusted to 5.8.

Somatic Embryo Induction Medium (SGCI-3)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 30 g sucrose, 1.5 mg 2,4-D, and 8 g agar (Sigma, St. Louis, Mo., USA) were combined in sterile water. The mixture was taken up to a final volume of 1 L using sterile water. The pH was adjusted to 5.8. After autoclaving timentin was added to the final concentration of 200 mg/l.

Selection Medium 1 (SGS1-4)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 5 g sucrose, 10 g mannose, 1.5 mg 2,4-D, and 8 g agar (Sigma, St. Louis, Mo., USA) were combined in sterile water. The mixture was taken up to a final volume of 1 L using sterile water. The pH was adjusted to 5.8. After autoclaving timentin was added to the final concentration of 200 mg/l.

Selection Medium 2 (SGS2-5)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 5 g sucrose, 9.0 g mannose, 1.5 mg 2,4-D, and 8 g agar (Sigma, St. Louis, Mo., USA) were combined in sterile water. The mixture was taken up to a final volume of 1 L using sterile water. The pH was adjusted to 5.8. After autoclaving timentin was added to the final concentration of 200 mg/l.

Regeneration Medium (SGR1-6)

4.3 g of MS basal salt mixture, B5 vitamins (100 mg of myo-Inositol, 1 mg of nicotinic acid, 1 mg of pyridoxine HCl and 10 mg of thiamine HCl), 1.2 g $KH_2PO_4$, 2.0 g L-proline, 0.9 g L-asparagine, 20 g sucrose, 5.0 g mannose, 1.0 mg IAA, 0.5 mg kinetin and 2.4 g Gelrite (Sigma, St. Louis, Mo., USA) were combined in sterile water. The mixture was taken up to a final volume of 1 L using sterile water. After autoclaving timentin was added to the final concentration of 200 mg/l.

Initiation of Somatic Embryogenic Cultures from Immature Zygotic Embryos

Sorghum (Sorghum bicolor (L.) Moench) immature caryopses were sterilized by immersing in 20% chlorine bleach (CHLOROX®) for 20 minutes. Sterilized caryopses were then rinsed thoroughly with sterile water.

Immature embryos were isolated from caryopses and were placed onto somatic embryo induction medium (SGWT-SEI). Plates were incubated at 26 to 28° C. in the dark for about 2 to 4 weeks. The resulting somatic embryogenic clusters were used for transformation experiments or transferred to fresh SEI medium and cultured for additional 3 to 6 weeks with 3 weeks subculture intervals at 28° C. in the dark prior to use in transformation experiments.

Transformation Vector and *Agrobacterium* Strains

*Agrobacterium tumefaciens* transformation vectors were constructed as described above using standard molecular techniques known in the art. The plasmids were introduced into *Agrobacterium* strains LBA4404+pSB1 (Ishida et al. (1996) Nature Biotechnology 14:745-750).

Overnight cultures of the *Agrobacterium* strain containing the plasmid were grown for two days on plates with YP medium containing 100 mg/L spectinomycin and 10 mg/L tetracycline.

Preparation of *Agrobacterium* for Transformation

*Agrobacterium* culture was initiated weekly from glycerol stocks, stored at −80° C., onto YP semi-solid medium containing appropriate antibiotics and grown at 28° C. in an incubator.

The *Agrobacterium* was streaked onto fresh YP medium containing appropriate antibiotics the day before the inoculation and was grown in a 28° C. incubator. For plant transformation use, the *Agrobacterium* was collected from the plate using a disposable plastic inoculation loop and suspended in liquid inoculation medium, such as SW1, in a sterile 15 ml disposable polypropylene centrifugation tube. *Agrobacterium* was resuspended in the tube by vortexing for about 3 to 5 minutes until the *Agrobacterium* cells were uniformly dispersed in the suspension. The *Agrobacterium* suspension was then diluted to an OD660 of 0.5 to 0.8 and vortexed for about 15 seconds.

Infection and Co-Cultivation of *Sorghum* Somatic Embryogenic Cultures

The *sorghum* somatic embryogenic clusters were infected with *Agrobacterium* by mixing the explants with bacterial suspension prepared as described above, and vortexed for 30 sec. The mixture was incubated with the prepared explants for about 3 to 15 minutes at room temperature.

Following infection, the *Agrobacterium* suspension explants were placed on co-cultivation medium (SGC-2) in 100×15 mm Petri plates and were incubated for 2 to 3 days at 22° C. in the dark.

Regeneration and Selection of Transgenic Plants

After co-cultivation, the explants were transferred onto recovery medium with antibiotics to kill *Agrobacterium*, or to inhibit *Agrobacterium* growth, without a plant selection agent, such as recovery medium (SGCI-3) supplemented with 200 mg/L timentin. The plates were incubated for 5 to 15 days at 28° C. in the dark.

The explants were then transferred to SGS1-4 solid medium (10 g/L mannose and 5 g/l sucrose) supplemented with antibiotics for about 14 to 21 days.

The explants were then transferred to fresh SGS2-5 medium (10 g/L mannose and 5 g/l sucrose) for about 14 to 21 days.

Resistant clones were transferred to embryo differentiation medium SGR1-6 (5 g/l mannose and 10 g/l sucrose) and were incubated at 28° C. in the dark for about 2 to 3 weeks.

Differentiating plant tissues were transferred to fresh embryo differentiation medium R1 (5 g/l mannose and 10 g/l sucrose) and were incubated at 26° C. in the light for about 2 to 3 weeks.

Well developed seedlings with leaves and roots were transferred to rooting medium.

Leaves were sampled for PCR analysis to identify transgenic plants containing the selectable marker gene according to Negrotto et al. (2000), and gene of interest. PCR positive and rooted plants were rinsed with water to wash off the agar medium, and transplanted to soil and grown in the greenhouse for seeds.

Example 7—Analysis of Transgenic Plants

Microbial Production of Enzymes

As part of the analysis of transgenic plants, microbial production can be utilized to generate enzyme standards. Although the microbially produced enzymes may have different glycosylation patterns, or other post-translational modifications, than the protein expressed in plants, the microbial protein is an acceptable standard for generating antibodies, for assay measurements, and for western blots.

Example 8—Production of Xylanases Using *P. pastoris*

Genes encoding enzymes of interest were cloned into expression vectors and transformed into suitable expression hosts. Pichai *pastoris* expression was performed in YPD media at 30° C. and 300 rpm. Culture supernatants were harvested after three to five days of expression corresponding to the time point of highest enzyme activity per ml of clarified supernatant. The supernatant was concentrated by tangential flow filtration with a 10 kDa MWCO membrane and exhaustively buffered exchanged with appropriate reaction buffer.

The amount of enzyme present in the concentrated culture supernatants was determined by treating a 10 µl sample with PNGaseF (NEB) according to the manufacture's protocol to remove N-linked glycans from the target protein. The sample was serially diluted and 10 µl of each dilution was fractionated by SDS-PAGE and stained with Simply Blue Safe stain (Invitrogen) according to the manufacture's guidelines. The concentration of the sample was designated as the highest dilution factor in which the target protein was still detectable after staining.

Rabbit Antiserum Generation

Antibodies that cross react with specific proteins were generated by New England Peptide. Proteins of interest were expressed in *Pichia pastoris*. The resulting culture supernatant was concentrated by tangential flow filtration using a 10 kDa MWCO filter (Millipore) and in some case further purified by column chromatography. The sample concentrate was further polished using centricon filtration device with a 10 kDa MWCO (Millipore) then fractionated by SDS-PAGE. The protein band corresponding to the predicted molecular weight of the target protein was excised from the gel using a razor blade and sent to New England Peptide for anti-sera generation. Upon receipt, the specificity of each antiserum was validated by Western Blot, aliquoted and stored at 4° C. or −20° C. Western Blot analysis was performed under standard conditions known in the art.

Example 9—Determination of Xylanase Activity by Reducing Sugar Measurement

Xylanase activity was determined using birch wood xylan as a substrate and measuring the production of reducing sugar ends with the Nelson-Somogyi reducing sugar microassay (Green et al. 1989, Adaptation of the Nelson-Somogyi reducing-sugar assay to a microassay using microtiter plates, Anal Biochem. 1989 Nov. 1; 182(2):197-9, which is incorporated by reference herein as if fully set forth). A 2% (w/v) substrate solution was prepared by dissolving birchwood xylan (Sigma) in boiling water. 0.02% azide (final concentration) was added as a preservative. Reagents for the Nelson-Somogyi reducing sugar assay were prepared as previously described (Green et al. 1989). Protein concentrations were determined using the BCA protein assay kit (Thermo Scientific) or represented as a dilution factor as described above.

Assays consisted of 250 µl of 2% birchwood xylan, 250 µl buffer, and varying volumes of xylanase preparation (or xylanase standards used to generate a standard curve) in a total reaction volume of one milliliter. Assays were conducted at 60° C. for 20 minutes then placed on ice to stop the reaction. From each reaction, 50 µl of each reaction were assayed for the presence of reducing sugars using the Nelson-Somogyi reducing sugar assay as previously described. Xylanase activity units were determined from results corresponding to the linear range of the analysis. The specific activity of the enzyme preparations was calculated by the following equation: Specific Activity=(mM reducing ends produced)/(dilution factor concentration).

Figure 7:
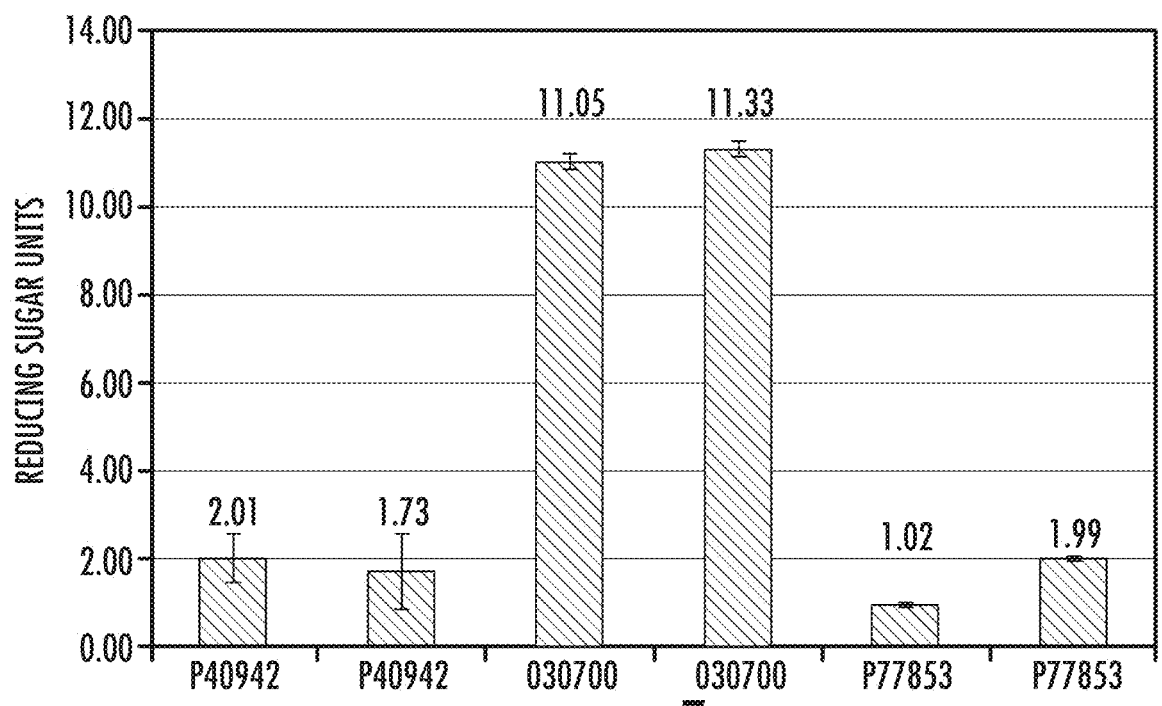
FIG. 7 illustrates the specific activity of three xylanases with accession numbers P40942, P77853 and O30700.

Referring to FIG. 7, the specific activity of three xylanases with accession numbers P40942, P77853 and O30700 was identified. As shown, the specific activity of O30700 is 5 times that of P40942 and P77853 when birchwood xylan is used as a substrate.

Example 10—Analysis of Transgenic Plant Material

Transgenic plants were assayed to determine the levels of accumulated active enzyme. For these assays, samples of liquid nitrogen frozen leaf tissue were ground in a mortar and pestle and the grindate collected. 10 mg of frozen leaf grindate was distributed into each well of a microtiter. To each well 200 µl of 100 mM buffer was added and the reactions mixed by pipetting. The plates were sealed and placed into a shaking incubator (200 rpm) at 55° C. for 16 hours. Post incubation, each reaction was applied to a Multiscreen HTS filterplate with a 1.2 µm glass fiber filter (Millipore, Billerica Mass.) and filtered by centrifugation at 500×g for 3 minutes. Enzyme activity was assessed by assaying 50 µl of the resulting filtrate using the Nelson-Somogyi reducing sugar assay as previously described. Extracted protein was determined using the BCA protein assay kit (Thermo). Levels of activity were presented as mM reducing sugar ends produced per mg of extracted protein.

Figure 8:
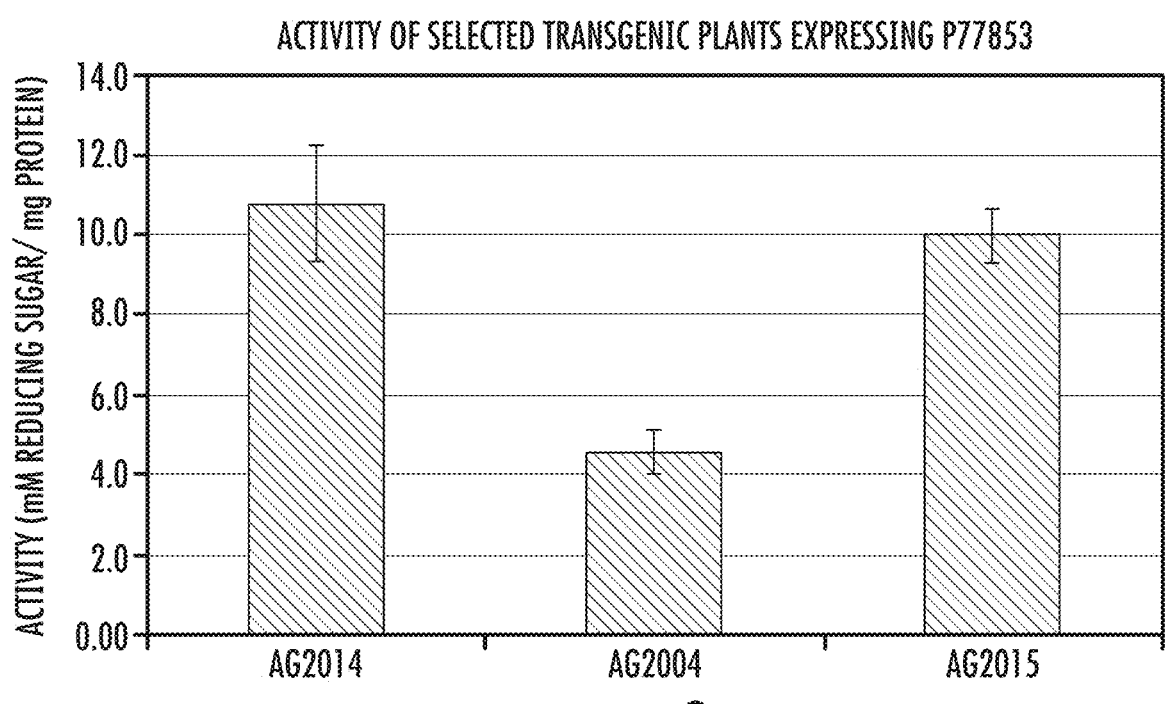
FIG. 8 illustrates the activity of various transgenic plant samples expressing Xylanase P77853.

Referring to FIG. 8, the activity of various transgenic plant samples expressing Xylanase P77853 is shown. The samples labeled AG2014 and AG2015 were transformed with the plasmids pAG2014 and pAG2015, respectively, and AG2004 is a control. The production of reducing sugars in transgenic plant samples as compared to the wildtype sample indicated the accumulation of active xylanase in transgenic plant tissue.

Example 11—Determination of Activity Against pNP-Conjugated Glycosides

In order to characterize the enzymatic range of activities of particular xylanases several assays were performed using p-nitrophenol (pNP)-conjugated glycosides. One molar stocks of the substrates were made in dimethylsulfoxide. Reactions consisted of 5 mM (final concentration) substrate, 100 mM buffer in 50 µl and 1-10 µl of enzyme preparation. Reactions were prepared then incubated at 60° C. for one hour. The reactions were stopped and developed upon addition of 100 µl of 0.1M carbonate buffer pH 10.5. Hydrolysis of the substrate, which was indicated by the formation of pNP, was detected as an increase of absorbance at 400 nm.

Polysaccharide endohydrolysis substrates was also determined using AZCL conjugated substrates supplies (Megazyme) and used according to the manufacture's standard protocol. Briefly, 250 µl of a specific buffer was mixed with 100 µl of enzyme preparation and 150 µl of water. The reaction was placed in a water bath incubator set at the desired temperature (usually between 37° C. and 70° C.) for five minutes after which one tablet of either xylazyme AX or cellazyme C was added. The reaction were incubated for 10 minutes then removed from the incubator and stopped with 10 ml of 2% (w/v) Tris Base (Sigma®). Endohydrolysis of the polyscaahride substrate was indicated by the release of soluble blue dye. The amount of released dye was quantified by measuring absorbance of the reaction supernatant at 590 nm. Controls for these reactions include protein extracts from the *P. pastoris* or *E. coli* wild type strain and recombinant enzyme producing strain.

Table 1, below, demonstrates the detected activities of several xylanases. As indicated endo-xylanase activity was detected for the P77853, O30700 and P40942 samples. Cellobiohydrolase and β-glucosidase activities were detected in samples contain P40942 indicating that this enzyme is capable of endohydrolysis of xylan and exohydrolysis of cellulose and cellobiose.

TABLE 1

| Sample | Xylanase | β-xylo-sidase | Cellulase | Cellobio-hydrolase | β-gluco-sidase |
|---|---|---|---|---|---|
| P77853 | + | − | − | − | − |
| O30700 | + | − | − | − | − |
| P40942 | + | − | − | + | + |
| *P. pastoris* | − | − | − | − | − |
| *E. coli* | − | − | − | − | − |

Example 12—Determination of Thermal Stability

Figure 9:
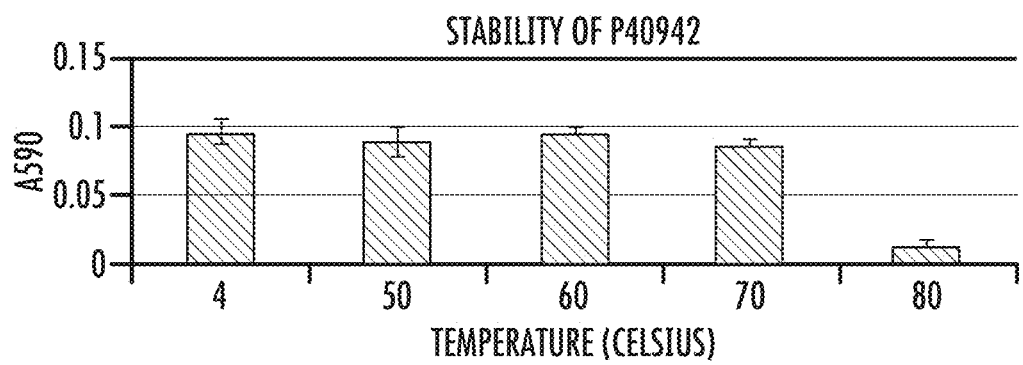
FIG. 9 illustrates thermal stability assays for O30700, P77853 and P40942.
Figure 9:
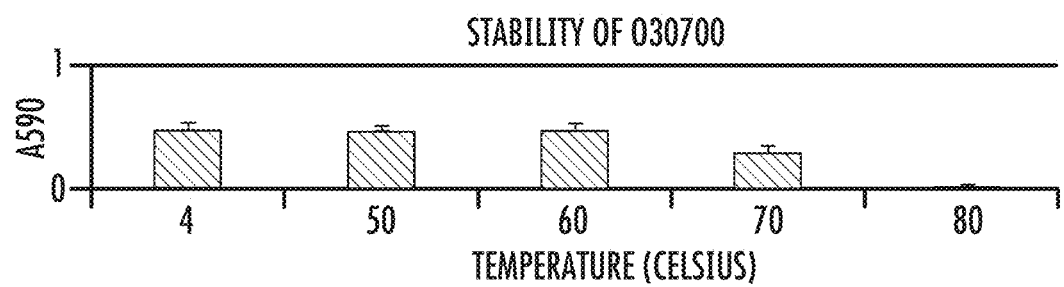
Figure 9:
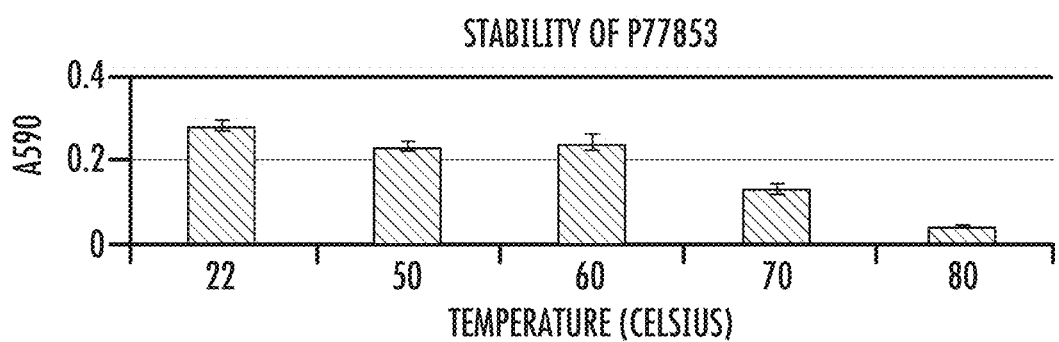

Thermal stability of enzymes was assessed by recovery of enzymatic activity after incubation at elevated temperatures. Briefly, preparations of xylanase P77, 030 or 040 were incubated at 4° C., 50° C., 60° C., 70° C. or 80° C. for one hour then assayed using the xylazyme AX substrate as described above. Referring to FIG. 9, xylanases O30700 and P77853 retain nearly 100% activity after one hour incubation at up to 60° C., but have reduced activity when exposed to 70° C. and 80° C. temperature treatments. Xylanase P40942 retains nearly 100% activity after one hour at temperatures up to 70° C., while at 80° C. its activity was reduced relative to exposure at the lower temperatures tested.

The thermal stability of the enzyme is one characteristic that may impact its utility in different applications. For example, in processing lignocellulosic bioimass; e.g., that derived from corn (stover), switchgrass, *miscanthus, sorghum*, or sugarcane, if the transgenic biomass material is to be treated at 70° C. for one hour, P40942 may be a better enzyme to deliver xylanase activity than O30700 or P77853 because of its increased stability at that temperature. In contrast, if transgenic grain; e.g., from transgenic corn or *sorghum*, is going to be used in formulating an animal feed ration, where the feed is ground and mixed at a temperature of 50° C., then any of these enzymes may be sufficiently thermal stable. However, these uses of particular enzymes do not preclude other uses of the same particular enzymes.

Example 13—Materials and Methods for Evaluating Transgenic Plants and their Pretreatment and Enzymatic Hydrolysis Processes Various process configurations may be used to process biomass and certain plant tissues. One process configuration is referred to as a macro-scale process, which can be scaled up, and is described directly below. Another process configuration is referred to as a micro-scale process, which can be used for plant evaluation, and is detailed below, following the description of a macro-scale process.

Example 13a—Macro-Scale Process

Figure 10:
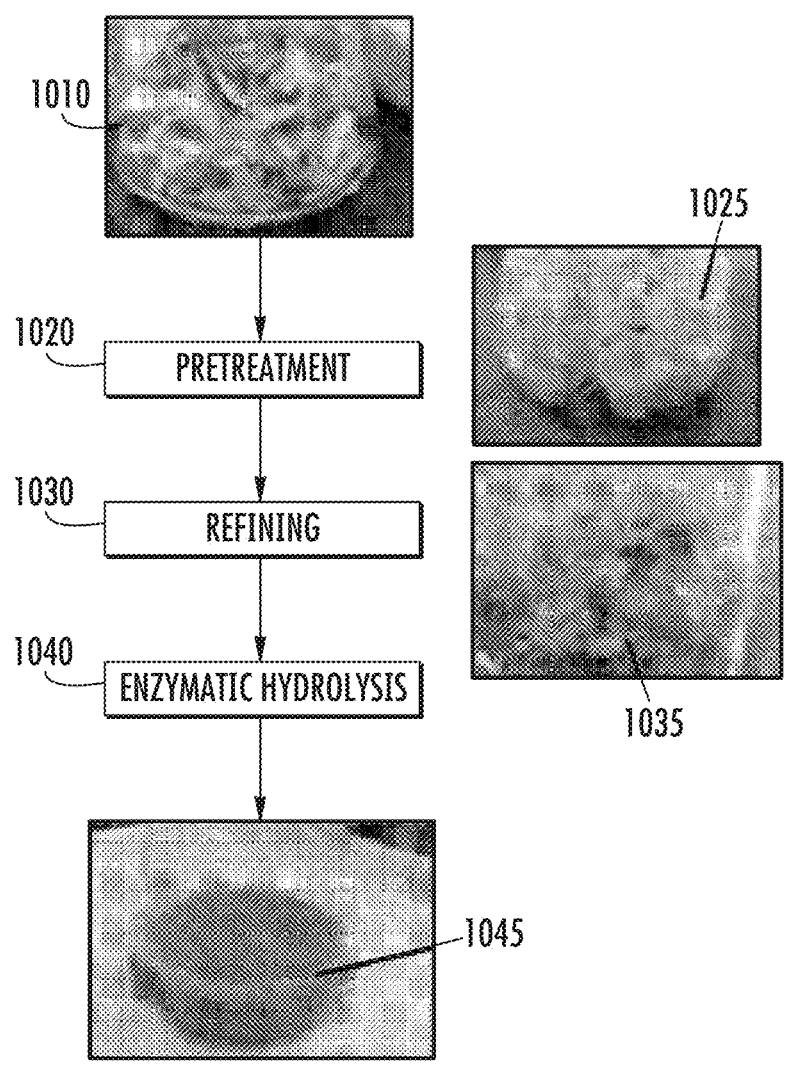
FIG. 10 illustrates a process flow diagram for a macro-scale process.

Macro-scale sequential low temperature chemi-mechanical pretreatment (CMPT) and one-stage enzymatic hydrolysis:

Referring to FIG. 10, biomass conversion to fermentable sugars by a macro-scale process method was used with several feedstocks. FIG. 10 illustrates the process flow diagram for the macro-scale process.

Biomass Substrate Preparation:

Corn stover was transformed with the noted plasmid containing either a β-glucosidase, endoglucanase, cellobiohydrolase, FAE, or xylanase, or combination of enzymes. The vector used may be any vector encoding a CWDE or derivative thereof, including any one or more of the vectors disclosed herein. In this example, the vector was pAG2015, pAG2042, and pAG2063. The stover was dried in an air-circulator at 37° C. for about 2 weeks. The dried corn stover 1010 was cut to 1.0-1.5 inch long.

Pretreatment:

The cut dried corn stover 1010 was pretreated at step 1020 by using either pure water or a combination of 8%-38% (wt./wt. on corn stover) ammonium bisulfite and 4%-19% (wt./wt. on corn stover) ammonium carbonate (pH 7.6-8.5). The biomass was added to a flask with pretreatment solution at a liquid-to-solid (L/S) ratio of 8. The mixture was shaken at temperatures of 40° C.-90° C. for four to 19 hours. The pretreated material was filtered using VWR grade 415 filter paper, and the material 1025 was collected for further analysis.

Refining:

The pretreated biomass was refined at step 1030 in a blend with DI water at 40° C.-90° C. After blending, the biomass was filtered using VWR grade 415 filter paper. The refined biomass (pulp) that did not pass through was washed with DI water at 40° C.-90° C. DI water. The pulp 1035 was stored at 4° C. for moisture balance and further enzymatic hydrolysis.

Enzymes:

Accellerase™ 1000 enzyme (Genencor International, Rochester, N.Y.), was used. The endoglucanase activity was 2500 CMC U/g (minimum). The beta-glucosidase activity was 400 pNPG U/g (minimum). The appearance was brown liquid. The pH was 4.8-5.2.

Alternatively, a cocktail of enzymes were used, which contained: Endoglucanase (C8546), β-glucosidase (49291), and xylanase (X2753) all purchased from Sigma (St. Louis, Mo.), and a cellobiohydrolase (E-CBHI) that was purchased from Megazyme (Wicklow, Ireland).

Enzymatic Hydrolysis:

The NREL standard protocol (LAP-009) was followed. At step 1040, the pretreated and refined stover was hydrolyzed in 0.1 M sodium citrate (pH 5.0) at a biomass solid content of 6.0% at an enzyme loading of 0.2-0.4 ml per g corn stover to release sugar 1045. The reaction occurred in a 250 mL erhlenmeyer flask at 250 rpm for 0-48 hr period at 45° C.-55° C. Depending upon the enzyme mixture and enzyme expressed in the plant, the pH was varied from 5 to 9. The preferred pH for these enzyme mixtures was usually 5.

Tetracycline or an equivalent antibiotic may optionally be added to the hydrolysis to prevent the growth of any potential microbial contamination.

Analysis of Fermentable Sugars:

The hydrolysate samples were heated at 95° C. for 20 min and then centrifuged at 9,000×g, following which the supernatants were clarified by passage through 0.20 μm PVDF filters (Cat.#: 09-910-13, Fisher Scientific, Pittsburgh, Pa.). Monosaccharide and disaccharide concentrations were determined by high performance liquid chromatography (HPLC), using a Shimadzu LC-20 AD binary pump with LC solutions software (Shimadzu, Kyoto, Japan). Sugar concentrations were determined using an Aminex HPX-87P sugar column (Bio-Rad Laboratories, Hercules, Calif.) operating at 0.6 ml/min and 85° C. with degassed water as the mobile phase. Peak areas for all samples, analyzed with an RI detector (RID LOAD), were integrated and the values were compared to standard curves for quantification.

Results of Macro-Scale Processing

1—Corn Stover from Wild Type AxB Plants.

For corn stover, the theoretical yield of sugar is 33.5% (wt/wt) glucose and 16.3% (wt/wt) xylose.

Pretreatment: conducted as described above with either 8% ammonium bisulfate and 4% ammonium carbonate or 38% ammonium bisulfate, 19% ammonium carbonate at a temperature of 70° C. for 4 hrs.

Enzyme hydrolysis: conducted as described above for 24 or 48 hrs.

The results are presented in Table 2, below. 54.5% (24 hours) and 62.3% (48 hours) glucose recovery yields as well as 20% (24 hours) and 27.5% (48 hours) of xylose recovery yields can be achieved in one-day and two-day enzymatic hydrolysis from diluted chemical pretreatment. The results demonstrate the efficiency of low temperature CMPT on enzymatic hydrolysis.

TABLE 2

Glucose and xylose yields from enzymatic hydrolysis of pretreated corn stover (A × B)

| Pretreatment | 8% Bisulfite, 4% Carbonate | | 38% Bisulfite, 19% Carbonate | |
|---|---|---|---|---|
| Enzymatic hydrolysis time (hrs) | 24 | 48 | 24 | 48 |
| Glucose (g/100 g stover) | 18.292 | 21.056 | 23.995 | 24.300 |
| Xylose (g/100 g stover) | 3.285 | 4.483 | 5.637 | 5.836 |

2—Stover.

Oven-dried, wild type AxB corn stover was tested and compared against a mixture of stover from nine pAG2015 transgenic corn plants (referred to in this example as "2015M").

Pretreatment: conducted as described above with 16% ammonium bisulfate and 8% ammonium carbonate (pH 7.6) at 70° C. for 4 hrs.

Enzyme hydrolysis: conducted as described above for 0 or 24 hrs.

The results are presented in Table 3, below. Better hydrolysis performance in terms of sugar yields were observed from the pAG2015 transgenic corn plants than wild-type AxB plants.

TABLE 3

Glucose and xylose yields from enzymatic hydrolysis of pretreated corn stover (A × B and 2015M).

| Plant source | 2015M | | Wild type A × B | |
|---|---|---|---|---|
| Enzymatic Hydrolysis (hrs) | 0 | 24 | 0 | 24 |
| Glucose (g/100 g stover) | 2.171 | 18.332 | 2.232 | 14.771 |
| Xylose (g/100 g stover) | 0.390 | 3.797 | 0.380 | 3.303 |

Figure 11:
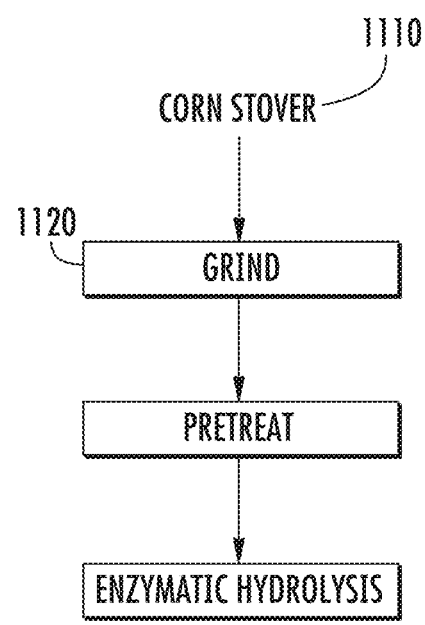
FIG. 11 illustrates a process flow diagram for a micro-scale process.

Example 13b—Micro-Scale Process: Simplified Low Temperature Chemi-Mechanical Pretreatment (CMPT) and Enzymatic Hydrolysis Referring to FIG. 11, a micro-scale saccharification method was used to screen several biomass feedstocks for conversion to fermentable sugars using either a one-stage or two-stage enzymatic hydrolysis.

Biomass Substrate Preparation:

Corn stover 1110 from corn transformed with the desired vector containing either a beta-glucosidase, endoglucanase, cellobiohydrolase, FAE, or xylanase, or combination of enzymes was obtained. The stover was dried in an air-circulator at 37° C. for about 2 weeks. After drying, the corn stover was cut to 1.0-1.5 inch long. The stover was milled at step 1120 using UDY mill (Model 014, UDY Corporation, Fort Collins, Co) with a screen of 0.5 mm.

Pretreatment:

The milled corn stover was pretreated at step 1130 by using either pure water or chemicals. The biomass was added to 2-mL tubes with pretreatment solution at a liquid-to-solid ratio of 10. 20 mg of biomass could be utilized. The mixture was shaken at temperature of 40° C.-90° C. for 15-19 hrs. The pre-treated material was subject to enzymatic hydrolysis without inter-stage washing.

Enzymes:

Endoglucanase (C8546), beta-glucosidase (49291), and xylanase (X2753) were all purchased from Sigma® (St. Louis, Mo.). The cellobiohydrolase (E-CBHI) was purchased from Megazyme® (Wicklow, Ireland).

Enzymatic Hydrolysis:

The process is based on the NREL standard protocol (LAP-009).

One-Stage Hydrolysis:

The milled, pretreated stover was suspended at a 2% (w/v) glucan loading in polybuffer (50 mM Na citrate, 20 mM K-phosphate, dibasic, 17 mM arginine, 40 mM glycine, 25 mM EPPS, 20 mM HEPES, 0.02% sodium azide) with pH values ranging from 3.5 to 5.0. The pH used was based on final pH of the suspended pretreated stover. The cocktail enzyme loading was based on experiments using 10 mg stover and are given in Table 4, below. Analysis was done on the biomass without any added enzymes (no-cocktail), and with the cocktail missing the xylanse, endoglucanase, or other enzymes that were expressed in the plant (cocktail minus xylanase or endoglucanase depending on the enzyme expressed in plants), in the hydrolysis. This was done to evaluate the effect of the in planta expressed enzymes on hydrolysis. Samples were hydrolyzed at 40° C. or 50° C. for 48-96 hrs at 200 rpm (1 mL reaction volume).

Tetracycline or an equivalent antibiotic may optionally be added to the hydrolysis to prevent the growth of any potential microbial contamination.

TABLE 4

| Enzyme loading for a full cocktail | |
| --- | --- |
| Enzyme | Enzyme loading per 10 mg stover |
| endoglucanase | 0.5 µM |
| cellobiohydrolase | 0.1 µM |
| β-glycosidase | 0.01 µM |
| endoxylanase | 0.3 µM |

Two-Stage Hydrolysis:

The first-stage enzymatic hydrolysis was named depending on the enzymes expressed in plant (for example, "xylanase hydrolysis" or "glucanase hydrolysis"). The second-stage enzymatic hydrolysis that followed was named "enzyme cocktail hydrolysis."

For the first-stage, milled, pretreated stover was suspended at a 3% (w/v) glucan loading in polybuffer with pH's ranging from 5.0 to 8.4. The pH used was based on the optimal pH for the plant expressed enzyme. This hydrolysis was conducted at 55° C., 300 rpm for 24-48 hrs.

For the enzyme cocktail hydrolysis, the pH was adjusted to 5.0 using concentrated HCl as needed. Then cocktail enzymes were added to samples as noted in one-stage enzymatic hydrolysis, resulting in samples with no cocktail, the full cocktail, and the cocktail minus xylanase or endoglucanase. Polybuffer pH 5.0 was added for a final solid content of 2%. Samples were hydrolyzed at 50° C. at 200 rpm for 48-96 hrs.

Tetracycline or an equivalent antibiotic may optionally be added to the hydrolysis to prevent the growth of any potential microbial contamination.

Analysis of Fermentable Sugar:

The hydrolysate samples were incubated at 95° C. for 20 min and then centrifuged at 9,000×g, following which the supernatants were clarified by passage through 0.20 µm PVDF filters. Monosaccharide and disaccharide concentrations were determined by high performance liquid chromatography (HPLC), using a Shimadzu LC-20 AD binary pump with LC solutions software (Shimadzu, Kyoto, Japan). Sugar concentrations were determined using an Aminex HPX-87P sugar column (Bio-Rad Laboratories, Hercules, Calif.) operating at 0.6 ml/min and 85° C. with degassed water as the mobile phase. Peak areas for all samples, analyzed with an RI detector (RID LOAD), were integrated and the values were compared to standard curves for quantification.

Results of Micro-Scale Processing

1—One-Stage Enzymatic Hydrolysis, pAG2015.

Plant stover analyzed: a transgenic corn plant designated 2015.05 (made by transforming corn with pAG2015, which expresses a xylanase) was used to provide stover. Control plant: a transgenic corn plant designated 2004.8.4 (a T1 generation plant, descended from a parent that was made by transforming corn with pAG2004, which does not encode a xylanase enzyme) was used to provide control stover. Theoretical sugar yield: 2015.05: 33.35% glucose, 18.69% xylose; 2004.8.4: 2015.05: 34.68% glucose, 20.6% xylose.

Pretreatment: conducted as described above with 1:19 (v/v) 15% NH$_4$OH, 20% NH$_4$Cl at 40° C. or 60° C. for 15 hrs, 300 rpm.

One-stage enzymatic hydrolysis: As described above with 0.02% sodium azide at 50° C. for 48 hours, 250 rpm.

Figure 12:
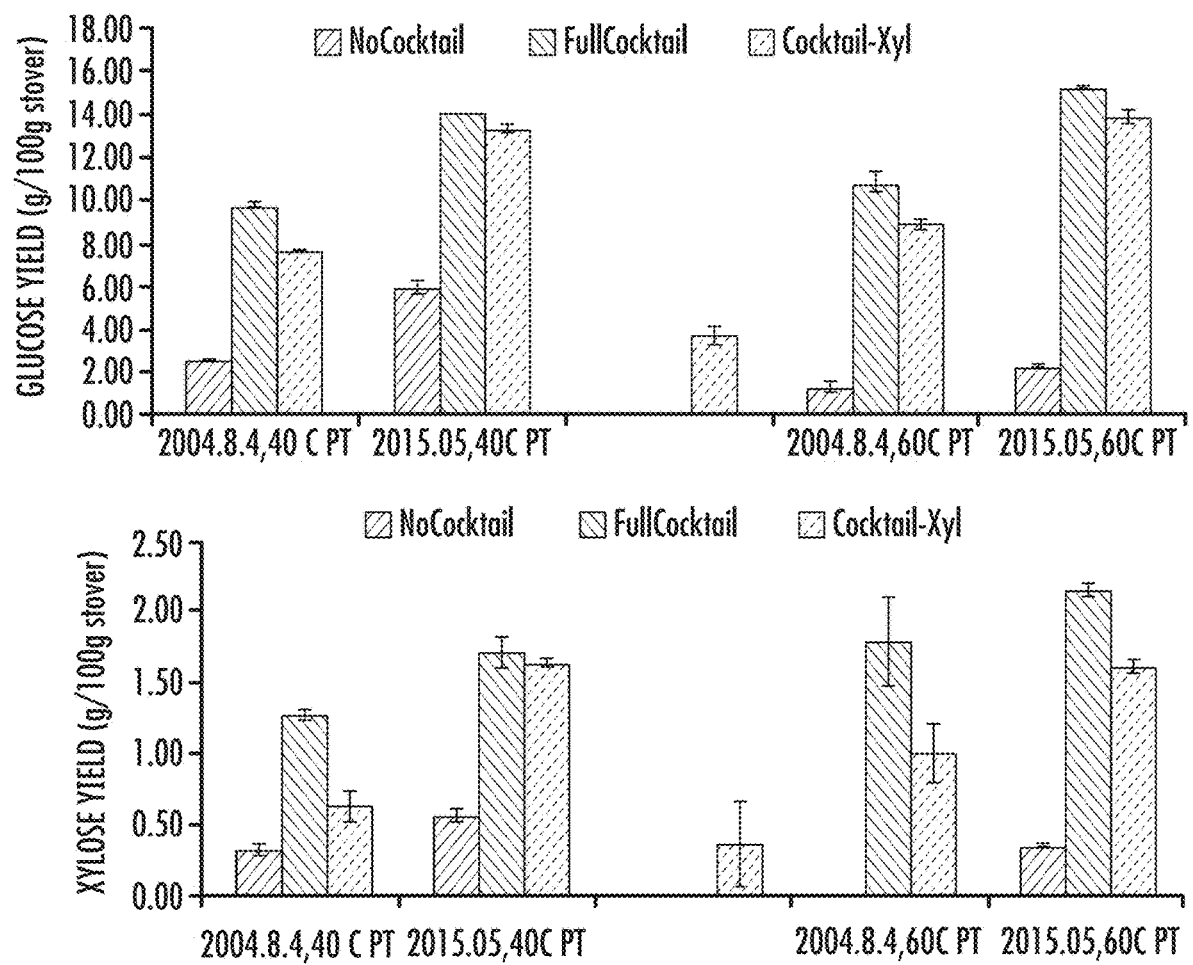
FIG. 12 illustrates glucose and xylose yields (percentage on biomass weight) from enzymatic hydrolysis of pretreated corn stover (2015.05 and 2004.8.4).

FIG. 12 illustrates the glucose and xylose yield (percentage on biomass weight) from enzymatic hydrolysis of pretreated corn stover (2015.05 and 2004.8.4). As shown in FIG. 12, 2015.05 shows better hydrolysis performance from both overall hydrolysis yield and based on the effect of the in planta xylanase on hydrolysis (as shown by the "Cocktail-Xyl" treatment). In FIG. 12, the following labels are used: 40 C PT: pretreatment done at 40° C.; 60 C PT: pretreatment at 60° C. "Cocktail-Xyl" denotes the one-stage enzymatic hydrolysis that was conducted without xylanase in the external enzyme cocktail. Each labeled sample in FIG. 12 shows the results for no cocktail, full cocktail and cocktail-Xyl from left to right.

2—One-Stage Enzymatic Hydrolysis, pAG2063

Plant stover analyzed: transgenic plants designated 2063.13 and 2063.17 (made by transforming corn with pAG2063, which expresses a xylanase) were used to provide stover. Control plant designated 2004.8.4 (a transgenic plant made by transforming corn with pAG2004; no xylanase enzyme expressed) was used to provide control stover.

Pretreatment: conducted as described above with 1:19 (v/v) 15% NH$_4$OH, 20% NH$_4$Cl, at either 40° C. or 60° C. for 15 hrs, 300 rpm.

One-stage enzymatic hydrolysis: conducted as described above with 1.0 mg/ml tetracycline at 50° C. for 48 hours, 250 rpm.

Figure 13:
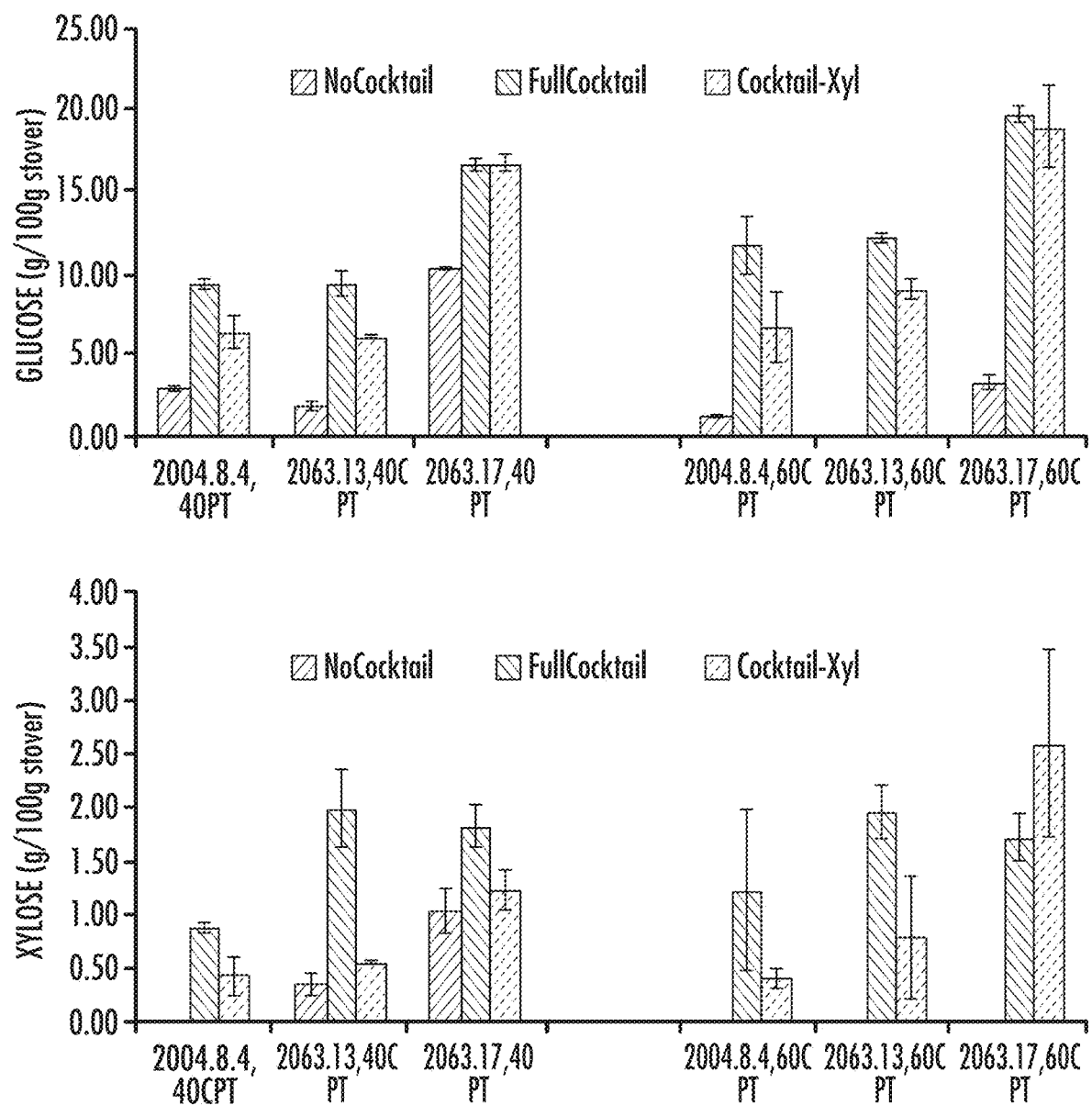
FIG. 13 illustrates glucose and xylose yields (percentage on biomass weight) from enzymatic hydrolysis of pretreated corn stover (2004.8.4, 2063.13, and 2063.17).

FIG. 13 illustrates the glucose and xylose yield (percentage on biomass weight) from enzymatic hydrolysis of pretreated corn stover (2004.8.4, 2063.13, and 2063.17). As shown in FIG. 13, transgenic plant 2063.17 shows better hydrolysis performance than control plant and 2063.13 from both overall hydrolysis yield and based on the effect of in planta xylanase on hydrolysis (as shown by the "Cocktail-Xyl" treatment). In FIG. 13, the following labels were used: 40 C PT: pretreatment done at 40° C.; 60 C PT: pretreatment at 60° C. "Cocktail-Xyl" denotes the one-stage enzymatic hydrolysis that was conducted without xylanase being included in the external enzyme cocktail. Each labeled sample in FIG. 13 shows the results for cocktail-Xyl and full cocktail from right to left. Samples where only two bars are visible show only the cocktail-Xyl and full cocktail results. Samples where three bars are visible show the no cocktail results to the left of the full cocktail results.

3—Two-Stage Enzymatic Hydrolysis, pAG2014.

Plant stover analyzed: transgenic plant 2015.05 was used to provide stover; and control plant 2004.8.4 was used to provide control stover. As used herein, a T0 plant is the $1^{st}$ generation; and a T1 plant is the $2^{nd}$ generation, created from the T0 plant seeds.

Pretreatment: conducted as described with DI water at 55° C. for 16 hrs, 300 rpm.

First-stage enzymatic hydrolysis (Xylanase hydrolysis): conducted as described previously at 55° C., for 24 hrs with 0.02% sodium azide, 250 rpm.

Second-stage hydrolysis (enzyme cocktail hydrolysis): conducted as described at 50° C. using cocktail for 48 hrs.

Figure 14:
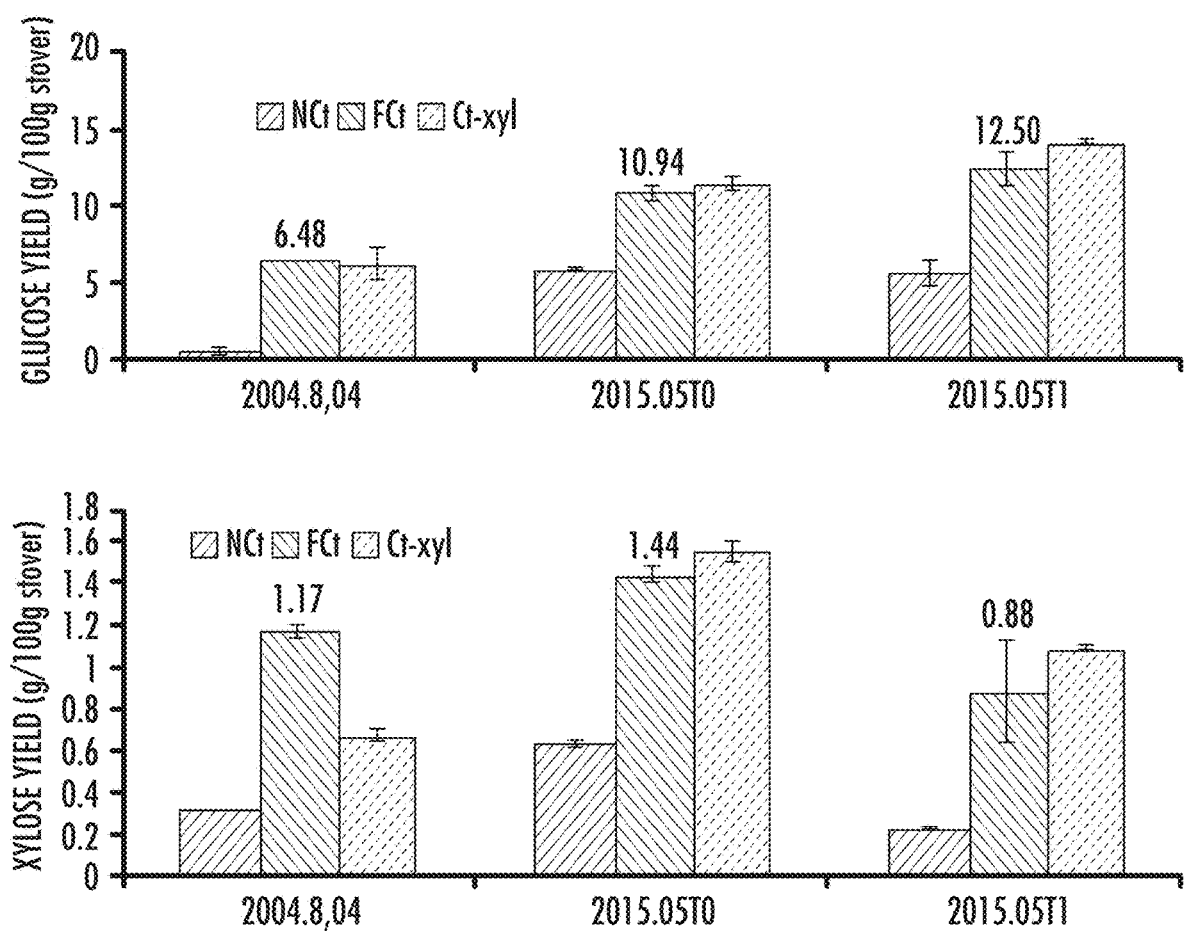
FIG. 14 illustrates glucose and xylose yields (percentage on biomass weight) from enzymatic hydrolysis of pretreated corn stover (2015.05 and 2004.8.4).

FIG. 14 illustrates glucose and xylose yields (percentage on biomass weight) from enzymatic hydrolysis of pretreated corn stover (2015.05 and 2004.8.4). T0 and T1 2015.05 plants both show better hydrolysis performance from both overall hydrolysis yield and based on the effect of the in planta xylanase on hydrolysis (See FIG. 14, "Ct-xyl" treatment). In FIG. 14, the following labels were used: "N Ct": No Cocktail, "F Ct": Full Cocktail, "Ct-xyl": Cocktail minus xylanase. Each labeled sample in FIG. 14 shows the results for no cocktail, full cocktail and cocktail-Xyl from left to right.

4—Two-Stage Enzymatic Hydrolysis, pAG2063.

Plant stover analyzed: A transgenic plant designated 2063.17 (made by transforming corn with pAG2063) was used to provide stover. A control plant designated 2004.8.4 (made by transforming core with pAG2004) was used to provide control stover.

Pretreatment: conducted as described with DI water at 55° C. for 16 hrs, 300 rpm.

First-stage enzymatic hydrolysis (Xylanase hydrolysis): conducted as described previously at 55° C., for 24 hrs with 0.02% sodium azide, 250 rpm.

Second-stage hydrolysis (enzyme cocktail hydrolysis): conducted as described at 50° C. using cocktail for 96 hrs.

Figure 15:
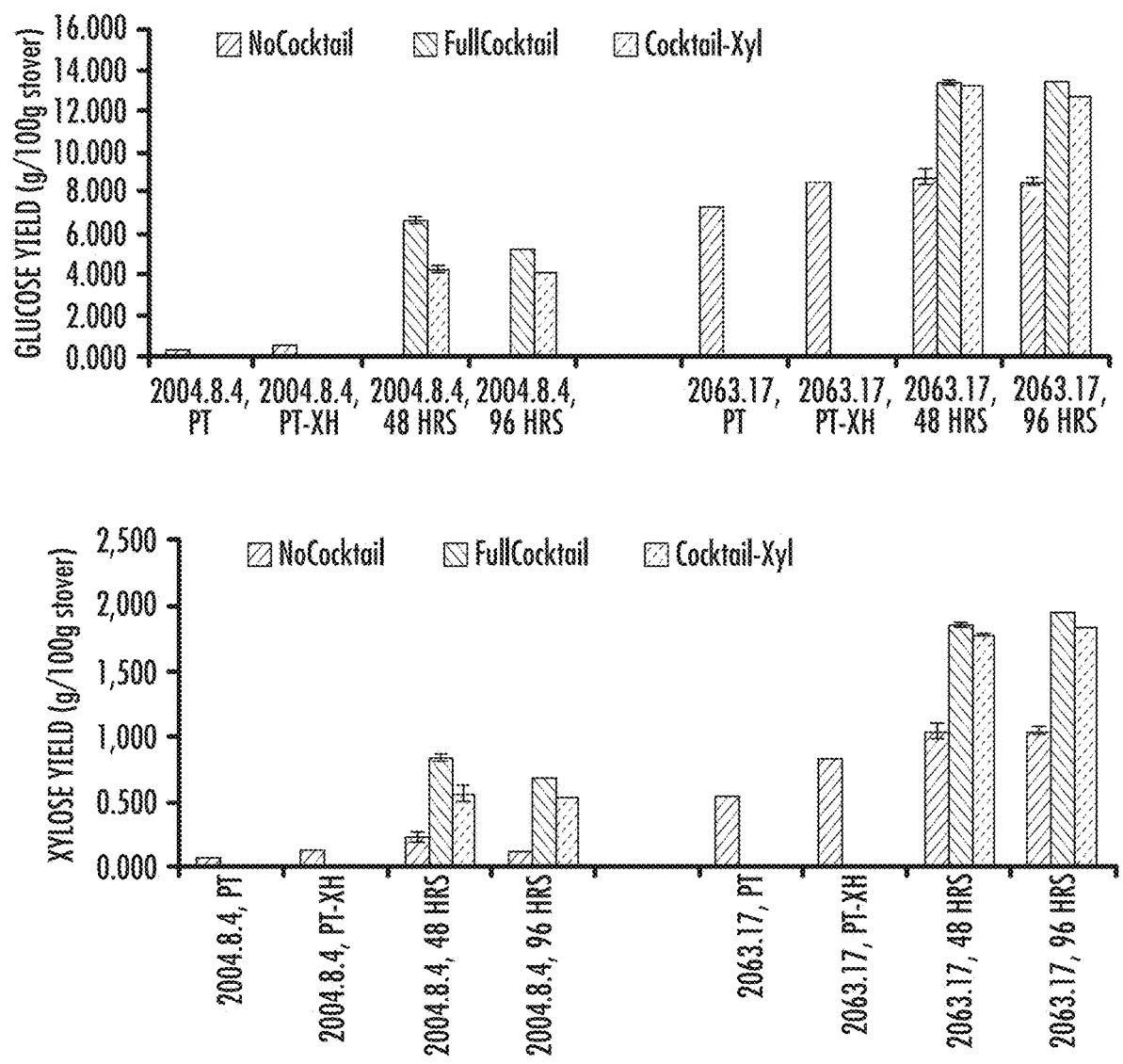
FIG. 15 illustrates glucose and xylose yields (percentage on biomass weight) from enzymatic hydrolysis of pretreated corn stover (2064.17 and 2004.8.4).

FIG. 15 illustrates glucose and xylose yields (percentage on biomass weight) from enzymatic hydrolysis of pretreated corn stover (2064.17 and 2004.8.4). As shown in FIG. 15, both glucose and xylose yields for 2063.17 are consistently higher than for 2004.8.4 through the course of pretreatment, $1^{st}$-stage xylanase hydrolysis, and $2^{nd}$ stage enzyme cocktail hydrolysis. Xylose yield for 2063.17 increases through the courses, indicating a positive effect of in planta xylanase on xylan hydrolysis.

In FIG. 15, the following labels were used: PT: levels after pretreatment; PT-XH: levels after xylanase hydrolysis, 48 hrs: levels after 48 hrs of stage two; 96 hrs: levels after 96 hrs of stage two. "Cocktail-Xyl" denotes the one-stage enzymatic hydrolysis that was conducted without xylanase being included in the external enzyme cocktail. The 2004.8.4, PT2004.8.4 PT-XH, 2063.17 and PT2063.17 PT-XH samples show only no cocktail results. The remaining samples show the results for no cocktail, full cocktail and cocktail minus xylanase from left to right.

5—One-Stage Enzymatic Hydrolysis, pAG2042.

Plant stover analyzed: Transgenic plants designated 2042.2, 2042.3, and 2042.6 (made by transforming corn with pAG2042) were used to provide stover. Control corn plant 2004.8.4 was used to provide control stover.

Pretreatment: conducted as described above with 0.3 M ammonium bisulfite/0.34 M ammonium carbonate at temperatures of either 40° C. or 60° C. for 19 hrs, 300 rpm.

One-stage enzymatic hydrolysis: conducted as described above with 1.0 mg/ml tetracycline at 50° C. for 48 hours, 250 rpm.

Figure 16:
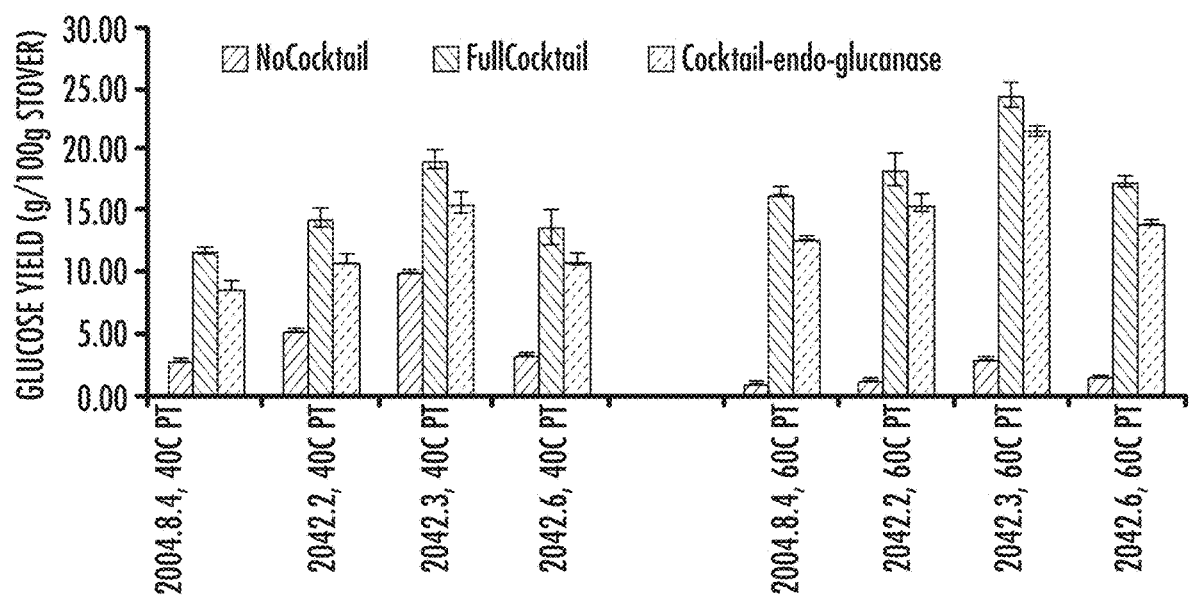
FIG. 16 illustrates glucose yield (percentage on biomass weight) from enzymatic hydrolysis of pretreated corn stover (2042.02, 2042.03, 2042.06 and 2004.8.4).

FIG. 16 illustrates the glucose yield (percentage on biomass weight) from enzymatic hydrolysis of pretreated corn stover (2042.02, 2042.03, 2042.06 and 2004.8.4). As shown in FIG. 16, the glucose yield from 2042.3 is significantly higher than the glucose yield from the other two transgenic plants (2042.2 and 2042.6) as well as control plant (2004.8.4). In FIG. 16, the following labels were used: 40 C PT: pretreatment done at 40° C.; 60 C PT: pretreatment at 60° C. Each labeled sample in FIG. 16 shows the results for no cocktail, full cocktail and cocktail minus endo-glucanase from left to right.

Example 14—Determination of Reducing Sugar Release with Transgenic Plant Material Referring to FIG. 8, transgenic plants were assayed to determine the levels of accumulated active enzyme. For these assays, samples of liquid nitrogen frozen leaf tissue were ground with a mortar and pestle and the resulting ground samples were collected. 10 mg of frozen leaf grindate was measured and deposited into a well of a microtiter. To each well, 200 µl of 100 mM sodium phosphate buffer (pH 6.5) was added and the reactions mixed by pipetting. The plates were sealed with foil and placed into a shaking incubator (200 rpm) at 55° C. for 16 hours. Post incubation, each reaction was applied to a Multiscreen HTS filterplate with a 1.2 µm glass fiber filter (Millipore, Billerica Mass.) and filtered by centrifugation at 500×g for 3 minutes. Enzyme activity was assessed by assaying 50 µl of the resulting filtrate using the Nelson-Somogyi reducing sugar assay as previously described. Extracted protein was determined using the BCA protein assay kit (Thermo Scientific). Levels of activity were presented as mM reducing sugar ends produced per mg of extracted protein. The production of reducing sugars in transgenic plant samples (AG2014 and AG2015) as compared to the non-xylanase expressing transgenic control plant sample (AG2004) indicated the accumulation of active xylanase in transgenic plant tissue.

Example 15—Detection of Autolysis Activity in Transgenic Corn Stover

Ten milligrams (+1-1 mg) of ground sample was applied to a 1.5 ml microfuge tube. The ground sample was resuspended in 1 ml of 100 mM sodium phosphate buffer containing 40 µg tetracycline and 30 µg of cycloheximide. The reactions were incubated for 64 hours at 60° C. with end-over-end mixing (18 rpm). The reaction supernatant was collected and assayed for the presence of reducing sugars using the Nelson-Somogyi reducing sugar assay. The results from this assay were reported as mM xylose equivalent reducing ends produced/mg stover by comparison to a xylose standard curve.

Example 16—Transgenic Plants and Transgenic Plants Expressing Cell Wall Degrading Enzymes In general, for each transformation vector, at least 20 events were made. In some case many more (up to 90) transgenic events were made and all events were used to evaluate the effect of the transformation process and gene expression.

Transgenic Plants Constructed Using pAG3000 and pAG3001

Figure 17A:
FIG. 17A illustrates a transgenic plant made with pAG3000.
Figure 17B:
FIG. 17B illustrates a transgenic plant made with pAG3001.

Referring to FIGS. 17A and 17B, T0 plants were regenerated from the transformation protocol described above using pAG3000 and pAG3001. The plant transformation vectors, pAG3000 and pAG3001 were described above. These vectors have the rice actin 1 promoter driving the *E. coli* gene for phosphomannose isomerase (PMI), which can be used for selecting transgenic plants or other purposes. The difference between pAG3000 and pAG3001 lies in the junction between the rice actin 1 promoter and the PMI gene. In pAG3000 a partial eukaryotic translation initiation site consensus was used, while in pAG3001, the complete eukaryotic translation initiation site was used. Maize embryos were transformed with pAG3000 and pAG3001 as described above.

Transgenic plants expressing pAG3000 and pAG3001 were regenerated as described above. Based on experimental results and following the procedures above, transgenic plants having pAG3000 and pAG3001 were selected at an average rate of 22.6% and 12.3%, respectively in maize. In other species, transformation efficiency (as defined by the number of transgenic plants divided by the number targets for transformation, where no more than one transgenic event can be generated per target) is not easily calculated because target calli are not readily enumerated as discrete targets. The maximum efficiency observed in any single experiment was 28% for pAG3000 and 14% for pAG3001. Based on these data, using the partial eukaryotic translation initiation site consensus sequence provided increased transformation efficiency compared to the complete eukaryotic translation initiation sequence. Although the rice actin 1 promoter is considered a relatively strong constitutive promoter, the transformation efficiencies obtained by linking it to PMI were unknown and it was uncertain how much better they could be improved relative to the CMPS:PMI construct obtained originally. Based on these results, the average transformation selection efficiency using CMPS:PMI was 1.5%, with a maximum of 14%, but efficiencies of 0%, 2%, 3%, 6%, 7%, 13%, and 14% were observed in individual experiments. Ranges in transformation efficiency can be impacted by the quality of the transformation target material, but these averages and ranges help define what could be expected from transformation using these constructs. Based on these results, linking PMI to the rice actin 1 promoter improved PMI transformation efficiency using the procedures described above. Furthermore, using the junction between the rice actin 1 promoter and PMI in pAG3000, improved the average transformation efficiency above the level of improvement when using the junction employed in pAG3001.

As shown in FIGS. 17A and 17B, transgenic plants with pAG3000 (FIG. 17A) and pAG3001 (FIG. 17B) are phenotypically normal for transgenic plants at this stage of development. The transgenic nature of these plants was verified using PCR.

Example 17—Transgenic Plants Constructed Using pAG2004 and pAG2005

Figure 18A:
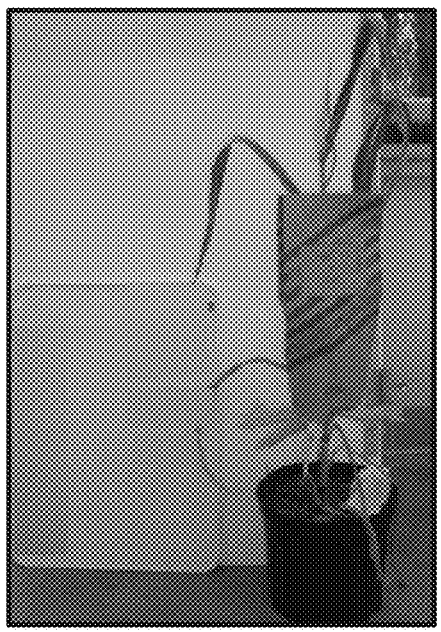
FIG. 18A illustrates a transgenic plant made with pAG2004.
Figure 18B:
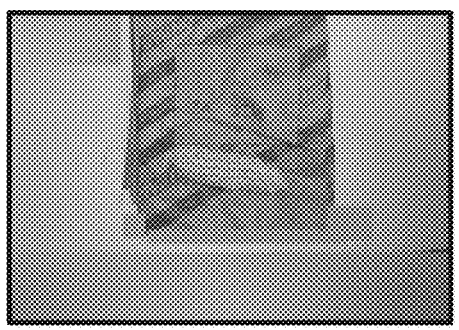
FIG. 18B illustrates a cob from a transgenic plant made with pAG2004.
Figure 18C:
FIG. 18C illustrates a cob from a transgenic plant made with pAG2004.
Figure 19A:
FIG. 19A illustrates a transgenic plant made with pAG2005.
Figure 19B:
FIG. 19B illustrates a transgenic plant made with pAG2005.

Referring to FIGS. 18A, 18B, 18C, 19A and 19B, corn was transformed with the plant transformation vectors, pAG2004 (FIGS. 18A, 18B and 18C) and pAG2005 FIGS. 19A and 19B). These vectors have the rice ubiquitin 3 promoter driving the E. coli gene for phosphomannose isomerase (PMI), which can be used for selecting transgenic plants or other purposes. The difference between pAG2004 and pAG2005 is that pAG2005 contains an additional, empty expression cassette that other genes of interest can be cloned into. In terms of selecting transgenic events, pAG2004 and pAG2005 have the identical rice ubiquitin 3 promoter and PMI selection cassette. These two vectors combined to give an average transformation efficiency of 20%. In individual experiments, these vectors provided transformation efficiencies of 0%, 4%, 7%, 10%, 11%, 12%, 13%, 14%, 15%, 17%, 18%, 24%, 28%, 29%, 30%, 31%, 32%, 40%, 50%, 53%, and 64%. Ranges in transformation efficiency can be impacted by the quality of the transformation target material, but these averages and ranges could be expected from transformation using these constructs.

The rice ubiquitin 3 promoter fused to PMI significantly increased transformation efficiencies that were observed relative to CMPS:PMI, using the method described above. Furthermore, the average transformation efficiency was greater than that using pAG3001, and similar to the efficiency observed using pAG3000. Because the maximum efficiencies obtained using pAG2004 and pAG2005 were greater than those obtained using pAG3000, the pAG2004 and pAG2005 selection cassettes were used for further development of transgenic plants, as described above.

FIGS. 18A, 18B, 18C, 19A and 19B illustrate T0 plants regenerated from the transformation protocol described above. FIG. 18A shows that a nearly senescent pAG2004 transgenic plant is phenotypically normal. FIGS. 18B and 18C show that cobs from a pAG2004 transgenic plant are also phenotypically normal. FIGS. 19A and 19B show that pAG2005 transgenic plants are phenotypically normal. The transgenic nature of these plants was verified using PCR.

Figure 20:
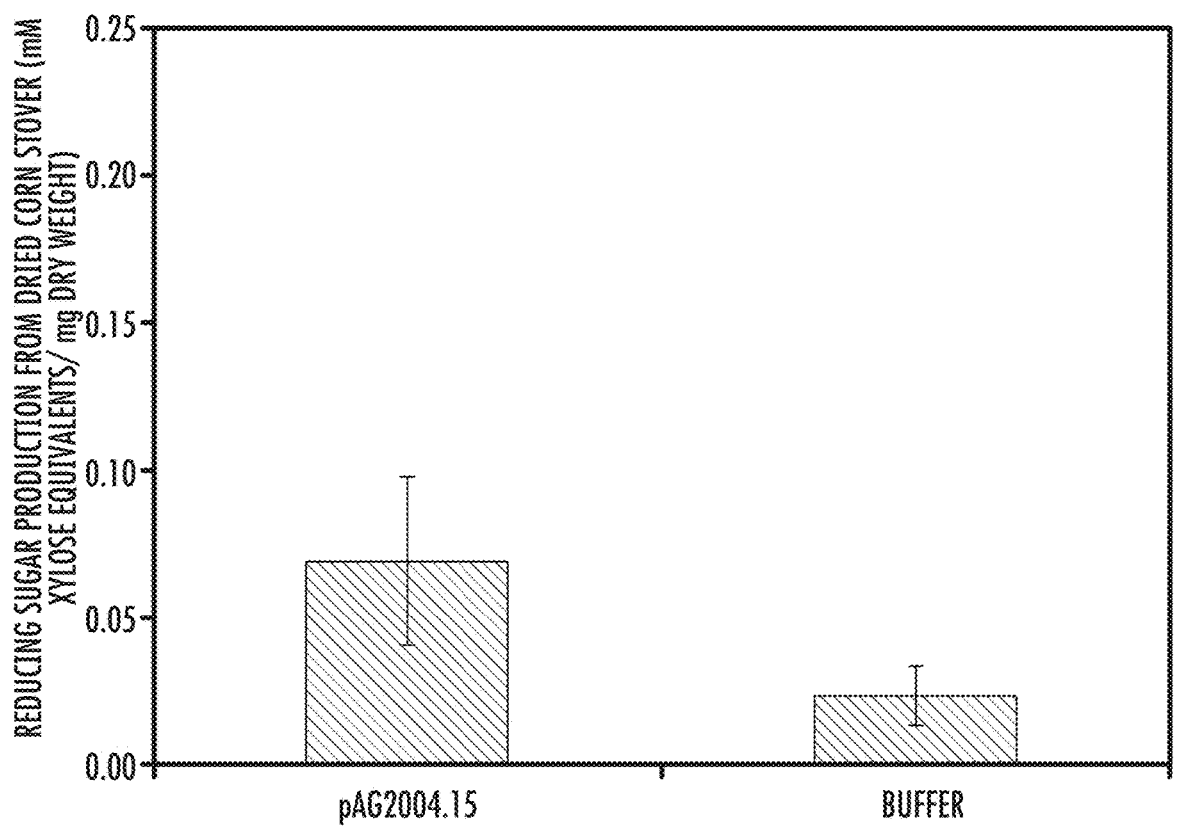
FIG. 20 illustrates measurement of reducing sugars from transgenic plant event #15 transformed with pAG2004.

FIG. 20 illustrates measurement of reducing sugars from transgenic plant event #15 transformed with pAG2004. In FIG. 20, the buffer sample represents the background of the assay, where 1 mg of buffer was used in the measurement. Because pAG2004 does not express a cell wall degrading enzyme, its reducing sugar measurement represents a negative control to compare other plants against and is also representative of wild-type, non-transgenic plants.

Example 18—Transgenic Plants Constructed Using pAG2016

The transformation vector pAG2016 was used in transformation to regenerate transgenic plants. This transformation vector was derived from pAG2005 and contains an expression cassette for the production of beta-glucoronidase (GUS). In this expression cassette, GUS is fused to the maize codon optimized PR1a signal peptide, which directs GUS to the apoplast intercellular space. The transformation efficiency of this vector has an average of 16%, and was in the expected range for the PMI selection cassette used.

Figure 21A:
FIG. 21A illustrates a transgenic plant made with pAG2016.
Figure 21B:
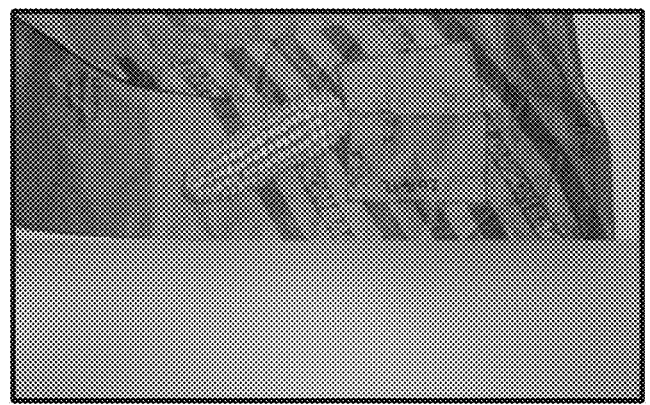
FIG. 21B illustrates a cob from a transgenic plant made with pAG2016.

Referring to FIGS. 21A and 21B, T0 pAG2016 transgenic plants and cobs are phenotypically normal. The plants were regenerated from the transformation protocol described above. The transgenic nature of these plants was verified using PCR. These plants demonstrate that a transgene can be effectively expressed from the expression cassette contained within pAG2005. The transgenic plants also demonstrate that the PR1a signal peptide, which was fused to GUS in pAG2016, did not interfere dramatically with transformation efficiency or the phenotype of the transgenic plant.

Example 19—Transgenic Plants Constructed Using pAG2014, pAG2015, pAG2020, pAG2025

The transformation vectors pAG2014, pAG2015, pAG2020, pAG2025 were used in transformation to regenerate transgenic plants. Transformation vectors pAG2014, pAG2015, and pAG2020 were derived from pAG2005 and each contains an expression cassette for the production of a xylanase (accession number P77853). In pAG2014, the P77853 gene is fused to the barley alpha amylase signal sequence (BAASS; SEQ ID NO: 8) for cell wall targeting. In pAG2015, the P77853 gene is not fused to any signal peptide and therefore should accumulate in the cytoplasm of cells. In pAG2020, P77853 is fused to the PR1a signal peptide for targeting of the enzyme to the apoplast. In contrast, pAG2025 was derived from pAG2012, which uses the rice glutelin GluB-4 promoter and GluB-4 signal sequence to direct seed tissue specific expression of P77853. The average transformation efficiency for pAG2014 was 30%, for pAG2015 it was 34%, for pAG2020 it was 24%, and for pAG2025 it was 10%. All of these efficiencies were within the expected range of transformation efficiency when using the rice ubiquitin 3 promoter and PMI selection cassette.

Activity measurements were made from transgenic events generated using methods described above. The following figures show the results of the activity measurements.

Figure 22:
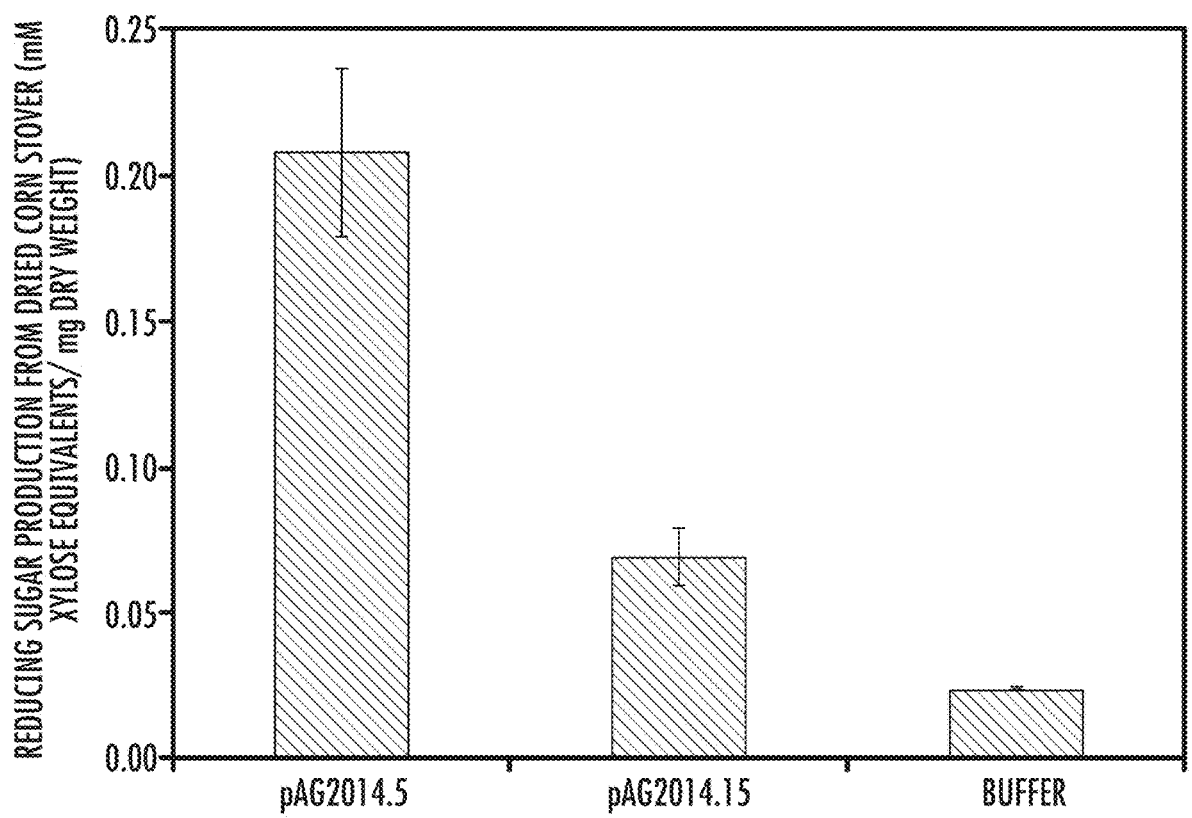
FIG. 22 illustrates reducing sugar measurements from transgenic plants.

Referring to FIG. 22, reducing sugar measurements were made for transgenic plants. FIG. 22 shows the reducing sugar production of transgenic plants having pAG2014 (left sample) or pAG2004 (middle samples), and a buffer control (right sample). Transgenic plant event #5 (left sample) made with pAG2014, which expresses the P77853 xylanase produces significantly more reducing sugars when incubated at 60° C. than plants made with pAG2004.

Figure 23:
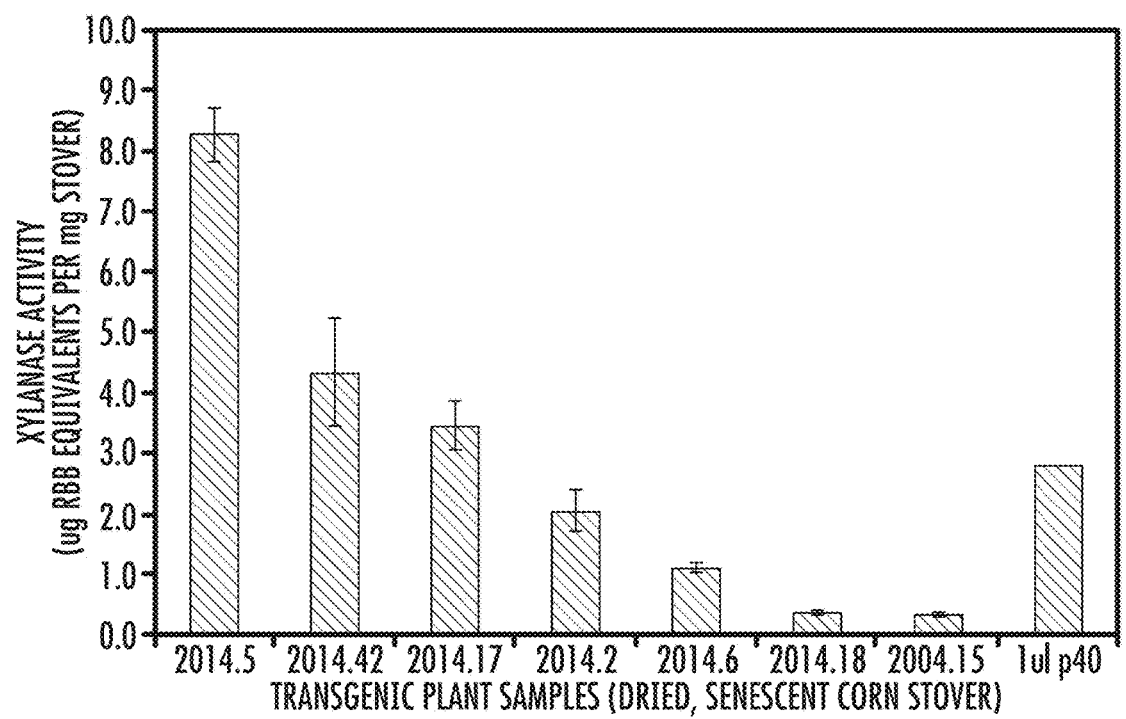
FIG. 23 illustrates enzyme activity measurements from dried, senescent corn stover samples.

Referring to FIG. 23, enzyme activity measurements were made from dried, senescent corn stover samples. The first six samples from the left in FIG. 23 are different transgenic plants having pAG2014. The seventh sample is a negative control from a transgenic plant having pAG2004. Transgenic plants made with pAG2014 were allowed to senesce, and were then dried down in an incubator to bone dry levels. The level of dry may be less than 1% moisture. The stover samples were milled and assayed as described above. As shown, the enzyme activity is stable even through the senescence, drying, and milling processes. A range of activities was obtained in this data, from low levels (close to the non-xylanase expressing control (2004.15)) up to over 8 µg RBB equivalents/mg stover.

Figure 24:
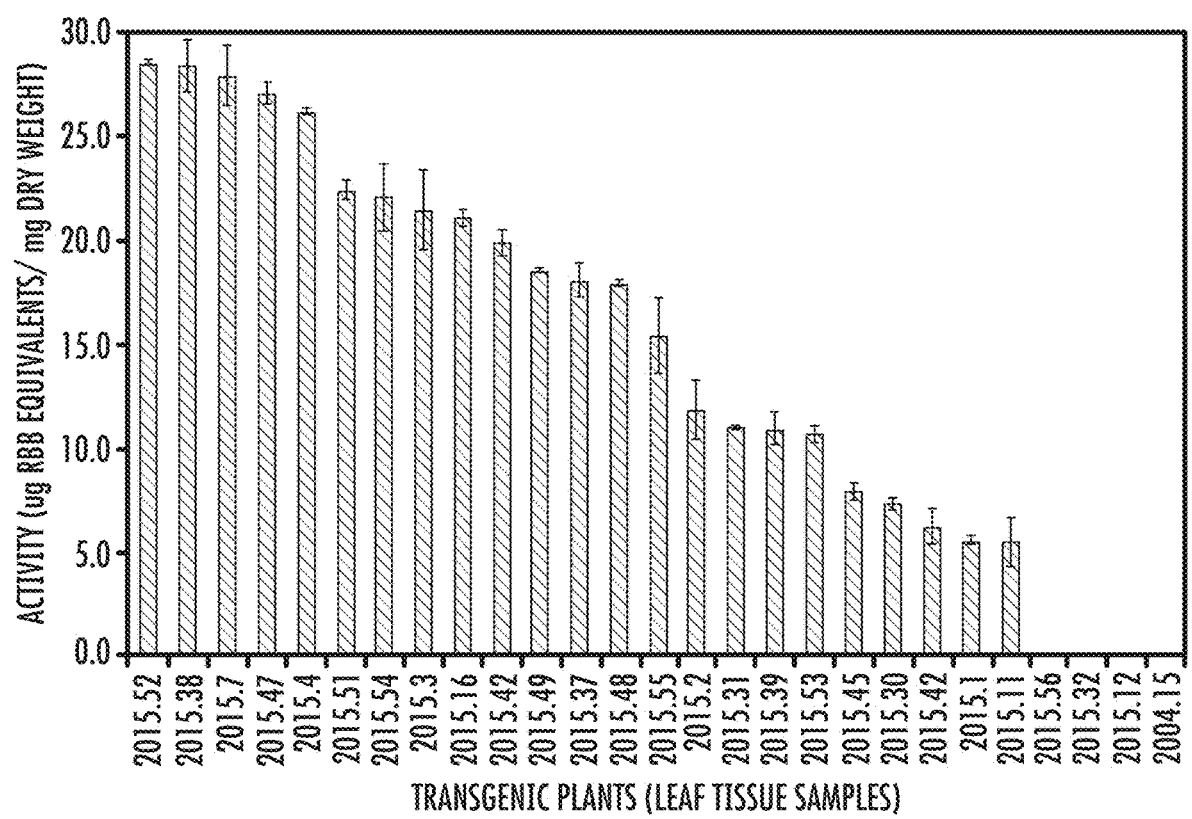
FIG. 24 illustrates enzyme activity measurements from leaf tissue samples of transgenic plants made with pAG2015, pAG2014, or pAG2004.

Referring to FIG. 24, enzyme activity measurements were made from leaf tissue samples of transgenic plants made with pAG2015, pAG2014, or pAG2004. A samples for pAG2014 is shown seventh from the right. A sample for pAG2004 is shown last. All other samples are different transgenic events for pAG2015 plants. As seen, a range of activity levels are obtained because gene insertion into the plant genome is highly variable and significantly affects expression properties. In general, a maximum activity level may be achieved for a given vector, and any activity below that level is also possible.

As shown in FIG. 24, pAG2015 (cytoplasmic P77853) and pAG2014 (BAASS:P77853) provide significant activity levels. Activity from pAG2015 is significant when expressed in plants and sampled from green tissues, and from senescent corn stover, however, thus assays have shown that pAG2014 provides a greater level of reducing sugar production when assayed from senescent corn stover. In contrast, pAG2025 provides no activity in green tissues tested (data not shown in FIG. 24), as would be expected given the seed specific nature of the pAG2025 transgene expression cassette.

Figure 25A:
FIG. 25A illustrates a transgenic plant made with pAG2014.
Figure 25B:
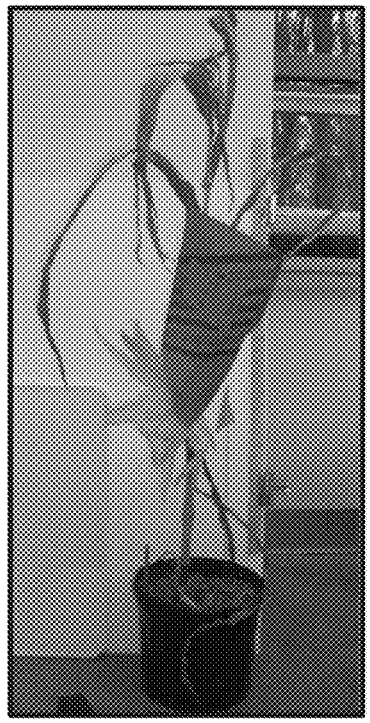
FIG. 25B illustrates a transgenic plant made with pAG2014.
Figure 25C:
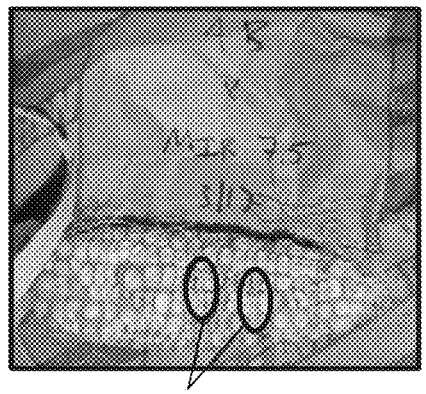
FIG. 25C illustrates a cob from a transgenic plant made with pAG2014.
Figure 26A:
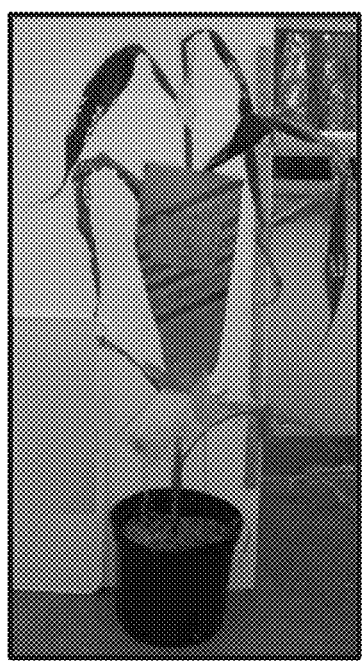
FIG. 26A illustrates a transgenic plant made with pAG2015.
Figure 26B:
FIG. 26B illustrates a transgenic plant made with pAG2015.
Figure 26C:
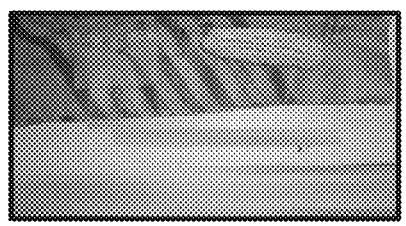
FIG. 26C illustrates a cob from a transgenic plant made with pAG2015.
Figure 26D:
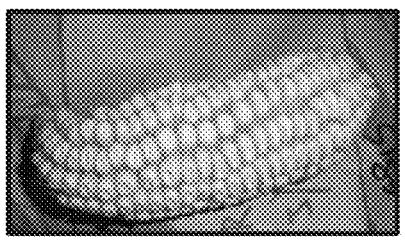
FIG. 26D illustrates a cob from a transgenic plant made with pAG2015.

FIGS. 25A and 25B illustrate transgenic plants made with pAG2014, FIG. 25C illustrates a cob from a transgenic plant made with the pAG2014. FIGS. 26A and 26B illustrate transgenic plants made with pAG2015, and FIGS. 26C and 26D illustrate cobs from transgenic plants made with pAG2015. FIGS. 27A and 27B illustrate transgenic plants made with pAG2020, and FIG. 27C illustrate a cob from a transgenic plant made with pAG2020. Referring to FIGS. 28A, 28B, and 28C, transgenic plants made with pAG2025 are illustrated. These plants demonstrate that the P77853 xylanase can be effectively expressed from the expression cassette contained within pAG2005. The transgenic plants also demonstrate that the BAASS [SEQ ID NO: 8] and PR1a [SEQ ID NO: 6] signal peptides, which are fused to P77853 in pAG2014 and pAG2020, respectively, do not interfere with transformation efficiency, but do impact phenotype relative to cytoplasmic accumulation. The phenotypes of these plants were very interesting and unanticipated. No known work has shown the expression of xylanase enzymes in corn, switchgrass, sorghum, or sugarcane. Based on the results herein, xylanase enzymes impart specific phenotypes, but they were highly dependent upon the specific enzyme, signal peptide, and promoter used, as well as the presence of the ER retention signal, SEKDEL [SEQ ID NO: 12].

The P77853 xylanase is interesting because transgenic maize plants made using pAG2014, pAG2015, pAG2020 and pAG2025 all had normal growth phenotypes, but some had different seed phenotypes. That the plants develop normally is somewhat surprising because xylanase hydrolyzes xylan in the hemicellulose component of plant cell walls Referring to FIGS. 25A, 25B and 25C, for pAG2014 (BAASS:P77853), severely shriveled kernels were observed in many of the transgenic events. These plants had normal growth and development, but a segregating shriveled seed phenotype was observed in multiple plants. See shriveled seeds 2510 in FIG. 25C. Shriveled seeds were randomly selected along with normal seeds and tested for increases in xylanase activity (indicating presence of the P77853 enzyme). Of the seeds tested, all shriveled seeds had a significant increase in xylanase activity, while the normal seeds had undetectable xylanase activity, as did seeds from a wild-type plant. In addition, twelve shriveled seeds were selected from a random cob and planted alongside 12 normal looking seeds. Of the seeds planted, only one of the 12 shriveled seeds germinated (it was tested by PCR and shown to have the P77853 gene), while nine of the 12 normal seeds germinated. Of the nine normal seeds that germinated, eight did not have the P77853 gene, while one did have the P77853, as determined by PCR. This suggests that P77853, when expressed as a fusion with the BAASS signal sequence, results in seeds that have reduced fertility relative to the non-transgenic seeds and that the level of infertility may be dependent upon the level of P77853 expression. While shriveled seeds and infertility would be a significant commercial detriment in corn, it could be advantageous in switchgrass, sorghum, miscanthus, and sugarcane, where plant sterility may be beneficial from the perspective of regulatory approval. Furthermore, perennial crops like switchgrass and sugarcane can be clonally produced via tissue culture using methods known in the art, and vegetatively expanded. In these crops decreased fertility may be less of an issue and could be advantageous for gene confinement. Thus, while the adverse seed phenotype of P77853 in corn and other grain crops is detrimental, in forage, sugar, and non-grain crops used as animal feedstocks or fermentation feedstocks, P77853 may provide significant benefits for fiber digestion, hydrolysis, and decreased fertility. Transgenic switchgrass events made using pAG2014 were phenotypically normal.

Referring to FIGS. 26A, 26B, 26C and 26D, for pAG2015, which did not have a signal peptide and therefore accumulated P77853 in the cytoplasm of plant cells, no adverse phenotype was observed. Some maize seeds from these plants were slightly more off color than the WT seeds, but no other abnormal phenotype has been observed thus far (See FIG. 26D). These plants do accumulate significant levels of xylanase activity, which is on average at least equal to, and in most events somewhat higher, than the xylanase activity detected in the pAG2014 events. That the two plants do not share the same seed phenotype is noteworthy and indicates that the BAASS [SEQ ID NO: 8] signal sequence for cell wall targeting, which was used in the pAG2014 vector, contributes to the seed phenotype observed in the pAG2014 events. Because these plants accumulate high levels of xylanase activity, they may be useful as a source of xylanase enzyme, as a feedstock that can auto-hydrolyze the hemicellulose components for use in industrial processes such as fermentation, as a forage animal feed or animal feed additive, and as a grain animal feed or feed additive. Unlike transgenic events made using pAG2014, those made using pAG2015 did not have an abnormal seed phenotype and may prove useful in grain crops such as corn, (grain) sorghum, wheat, barley, and others.

Referring to FIGS. 27A, 27B and 27C, for pAG2020 (PR1a:P77853) events, both the plants and cobs looked normal and did not have a significant observable phenotype. This is particularly surprising since PR1a targets the fused P77853 xylanase to the apoplast, where it would be anticipated to have an effect similar to that of the pAG2014 events. It is not known if the PR1a signal peptide causes lower expression, lower enzyme accumulation, or is less effective at targeting the P77853 protein, but the absence of a seed phenotype in these transgenic plants is surprising given the results obtained from pAG2014. Because these plants accumulate xylanase activity, they may be useful as a source of xylanase enzyme, as a feedstock that can autohydrolyze the hemicellulose components for use in industrial processes such as fermentation, as a forage animal feed or animal feed additive, and as a grain animal feed or feed additive. Unlike transgenic events made using pAG2014, those made using pAG2020 did not have an abnormal seed phenotype and may prove useful in grain crops such as corn, (grain) *sorghum*, wheat, barley, and others.

Referring to FIGS. 28A, 28B and 28C, For pAG2025 (GluB4:P77853) events, all plants looked phenotypically normal.

Example 20—Transgenic Plants Constructed Using pAG2017, pAG2019, and pAG2027

The transformation vectors pAG2017, pAG2019, and pAG2027 were used in transformation to regenerate transgenic plants. Transformation vectors pAG2017 and pAG2019 were derived from pAG2005, and each contains an expression cassette for the production of a xylanase (accession number P40942). Vector pAG2027 was derived from pAG2012 and expresses the P40942 xylanase from the GluB-4 promoter, which is expressed predominantly in the seed. In pAG2017, the P40942 xylanase is fused to the PR1a signal peptide for targeting of the enzyme to the apoplast. In pAG2019, the P40942 gene is fused to the barley alpha amylase signal sequence (BAASS; SEQ ID NO: 8) for cell wall targeting. The average transformation efficiency for pAG2017 was 16%, for pAG2019 it was 13%, and for pAG2027 it was 29%.

Figure 29A:
FIG. 29A illustrates a transgenic plant made with pAG2017.
Figure 29B:
FIG. 29B illustrates a transgenic plant made with pAG2017.
Figure 29C:
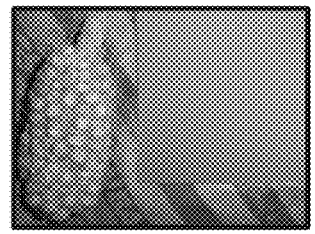
FIG. 29C illustrates a cob from a transgenic plant made with pAG2017.
Figure 29D:
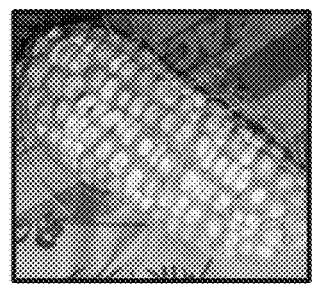
FIG. 29D illustrates a cob from a transgenic plant made with pAG2017.

In contrast to transgenic plants expressing P77853, which were all phenotypically normal except for the above described seed abnormalities, plants expressing the P40942 xylanase were severely stunted, except for those made from pAG2027. Referring to FIGS. 29A, 29B, 29C and 29D, plants transformed with pAG2017 (PR1a:P40942) are severely stunted and never grew to the same height as the wild-type plants, or plants transformed with pAG2020 (PR1a:P77853). FIG. 29A shows a stunted pAG2017 transgenic plant. FIG. 29B shows a stunted pAG2017 transgenic plant along side a wild type plant on the right. FIGS. 29C and 29D show cobs from a pAG2017 transgenic plant with partially shriveled seeds having abnormal coloration. The results with pAG2017 were unanticipated given that P77853 and P40942 have approximately the same specific activity when measured in vitro, on birchwood xylan (see above). P40942 also has some cellobiohydrolase (CBH) activity, so it is possible that this activity contributes to the observed phenotype, but other groups have expressed CBH enzymes in maize with apparently no growth phenotype observed. The significant growth phenotype difference between transgenic plants made with pAG2017 and pAG2020 is quite surprising and very unanticipated.

In addition to the growth phenotype in the pAG2017 plants, the seeds from these plants, or outcrosses of these plants on to AxB non-trangenic plants, also displayed a similar shriveled phenotype as observed in the seeds of transgenic plants made with pAG2014, as well as showing some discoloration of the seeds. Approximately 20 shriveled seeds were collected from the pAG2017 plants and all tested positive for xylanase activity, while plump seeds did not have detectable increases in xylanase activity as determined using the methods described above.

Figure 30A:
FIG. 30A illustrates a transgenic plant made with pAG2019.
Figure 30B:
FIG. 30B illustrates a transgenic plant made with pAG2019 in comparison to a wild type plant.

Referring to FIGS. 30A and 30B, transgenic plants made with pAG2019 (BAASS:P40942) also possessed a stunted growth phenotype, similar to transgenic plants made with pAG2017. This was surprising given that transgenic plants made with pAG2014 (BAASS:P77853) did not have a growth phenotype, yet the P40942 and P77853 xylanases have approximately the same specific activity, when measured on birchwood xylan. FIG. 30A shows a stunted transgenic plant made with pAG2019, and FIG. 30B shows a shows a stunted transgenic plant made with pAG2019 along side a wild type plant on the left.

Figure 31:
FIG. 31 illustrates a transgenic plants made with pAG2019 or pAG2027 in comparison to a wild type plant. The left three plants were made with pAG2019. The right three plants were made with pAG2027.

Referring to FIG. 31, transgenic plants made with pAG2027, which express P40942 from the rice GlutB promoter, are phenotypically normal with regards to growth. The left three plants in FIG. 31 were made with pAG2019. The right three plants were made with pAG2027. The result with pAG2027 was in contrast to transgenic plants made with pAG2017 and pAG2019, and is surprising because P40942 expressed from the rice ubiquitin promoter, using either PR1a or the BAASS signaling sequences, caused stunted growth. However, the result agrees with the observation that plants made with pAG2025 (rice ubiquitin 3 promoter driving P77853), are not stunted and grow normally. Given the differences in phenotypes observed between vectors expressing P77853 and P40942, it could not be predicted what the result with pAG2027 would be. Because the GlutB promoter primarily expresses the enzyme in the seed, it may be that none of the enzymes expressed from the GluB promoter will show a growth phenotype or phenotype associated with the green tissue, and only seed phenotypes, similar to those observed in plants made with pAG2014 and pAG2017.

Example 21—Transgenic Plants Constructed Using pAG2018 and pAG2026

The transformation vectors pAG2018 and pAG2026 were used in transformation to regenerate transgenic plants. Vector pAG2018 was derived from pAG2005 and contains an expression cassette for the production of a xylanase (accession number O30700), fused to the BAASS [SEQ ID NO: 8] signal sequence. Vector pAG2026 was derived from pAG2012 and expresses the O30700 xylanase from the GluB-4 promoter, which is expressed predominantly in the seed. The average transformation efficiency for pAG2018 was 13% and for pAG2026 it was 18%.

Figure 32A:
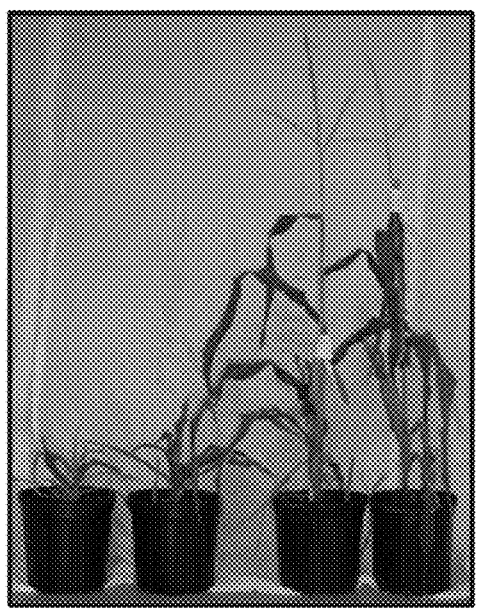
FIG. 32A illustrates two transgenic plants made with pAG2018 on the left and two non-hydrolase expressing plants on the right.
Figure 32B:
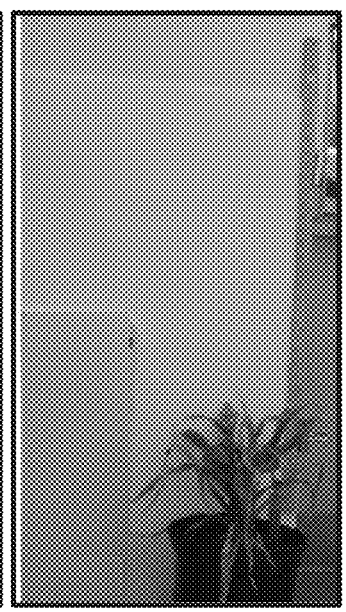
FIG. 32B illustrates a transgenic plant made with pAG2018.
Figure 32C:
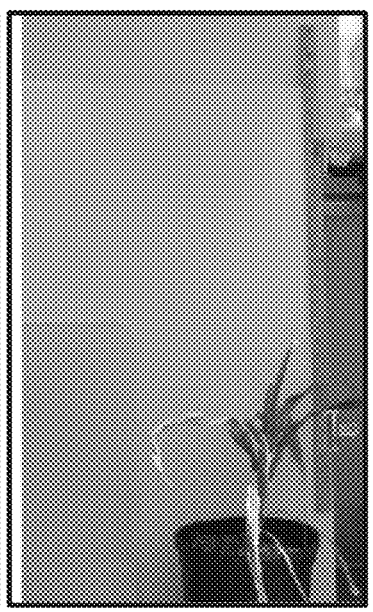
FIG. 32C illustrates a transgenic plant made with pAG2018.

As described above, transgenic plants expressing P77853 were all phenotypically normal except for the above described seed abnormalities. In contrast, referring to FIGS. 32A, 32B and 32C, transgenic plants made with pAG2018 and expressing the O30700 xylanase were severely stunted and never grew to the same height as the wild-type plants or plants transformed with pAG2014. FIG. 32A shows two transgenic plants made with pAG2018 on the left and two non-hydrolase expressing plants on the right. FIGS. 32B and 32C each show a transgenic plant made with pAG2018. These results were unanticipated given that P77853 and O30700 are both endo-xylanase enzymes, and in contrast to P40942, O30700 does not have any CBH activity. The growth phenotype observed with O30700 was very similar to the stunted growth observed in the pAG2017 and pAG2019 plants.

Figure 33A:
FIG. 33A illustrates a transgenic plant made with pAG2026.
Figure 33B:
FIG. 33B illustrates a transgenic plant made with pAG2026.
Figure 33C:
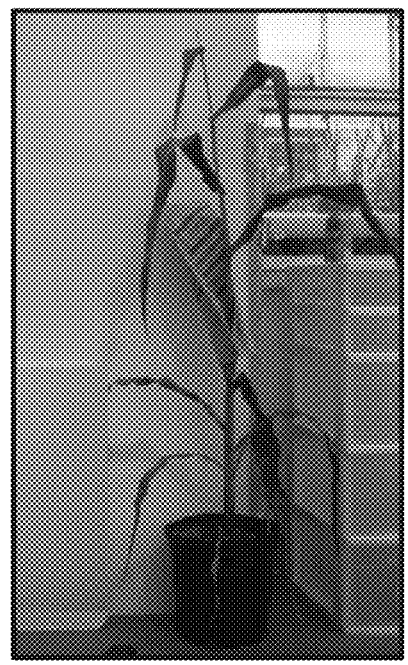
FIG. 33C illustrates a transgenic plant made with pAG2026.
Figure 34A:
FIG. 34A illustrates a transgenic plant made with pAG2021.
Figure 34B:
FIG. 34B illustrates a transgenic plant made with pAG2021.
Figure 34C:
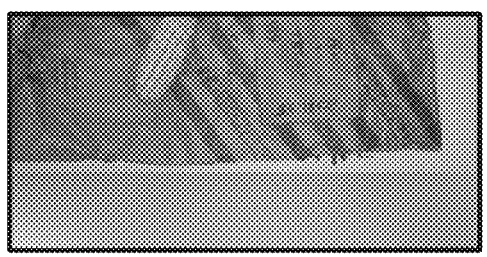
FIG. 34C illustrates a cob from a transgenic plant made with pAG2021.
Figure 34D:
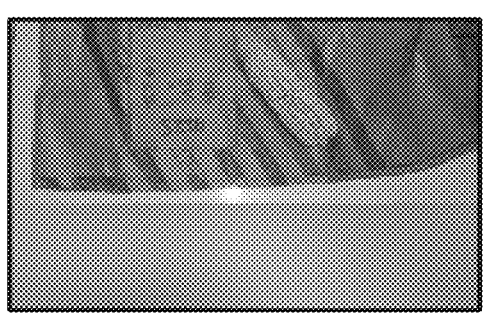
FIG. 34D illustrates a cob from a transgenic plant made with pAG2021.

In contrast to transgenic plants made with pAG2018 transgenic plants made with pAG2026, which express O30700 from the rice GlutB promoter, are phenotypically normal with regards to growth. See FIGS. 33A, 33B and 33C, which illustrate three different transgenic plants made with pAG2026. These results are surprising because O30700 expressed from the rice ubiquitin promoter and fused to the BAASS [SEQ ID NO: 8] signaling sequence caused stunted growth. In contrast, the result agrees with the observation that plants made with pAG2025 (rice ubiquitin 3 promoter driving P77853), are not stunted and grow normally, however, given the differences in phenotypes observed between vectors expressing P77853 and O30700, it could not be predicted what this result would be. Because the GlutB promoter primarily expresses the enzyme in the seed, it may be that none of the enzymes expressed from the GluB promoter will show a growth phenotype or phenotype associated with the green tissue, and only seed phenotypes similar to those observed in plants made with pAG2014 and pAG2017.

Example 22—Transgenic Plants Constructed Using pAG2021, pAG2023 (P77853m3), pAG2022, pAG2024

The transformation vectors pAG2021, pAG2023, pAG2022, and pAG2024 were used in transformation to regenerate transgenic plants. These vectors were all derived from pAG2005 and contain an expression cassette for the production of an intein-modified xylanase (referred to as P77853m3). In transformation vectors pAG2021 and pAG2022, the intein-modified P77853m3 protein was fused to the PR1a signal peptide, while in pAG2023 and pAG2024, P77853m3 was fused to the BAASS signal peptide [SEQ ID NO: 8]. Vectors pAG2022 and pAG2024 also have a SEKDEL endoplasmic reticulum retention sequence [SEQ ID NO: 12] appended to the P77853m3, whereas pAG2021 and pAG2023 lack the SEKDEL sequence [SEQ ID NO:12]. The average transformation efficiency for pAG2021 was 19%, for pAG2022 it was 21%, for pAG2023 it was 24%, and for pAG2024 it was 38%.

Figure 35A:
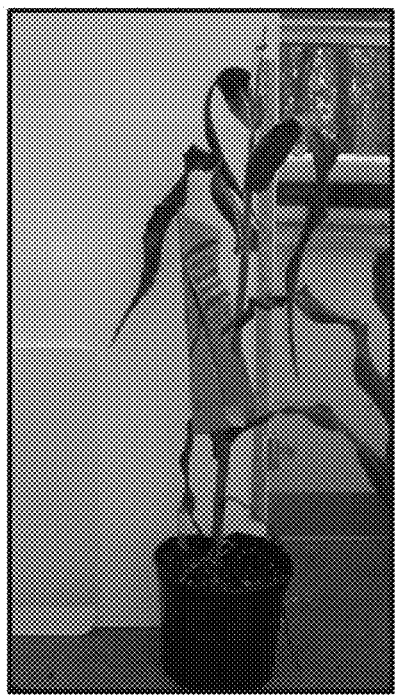
FIG. 35A illustrates a transgenic plant made with pAG2022.
Figure 35B:
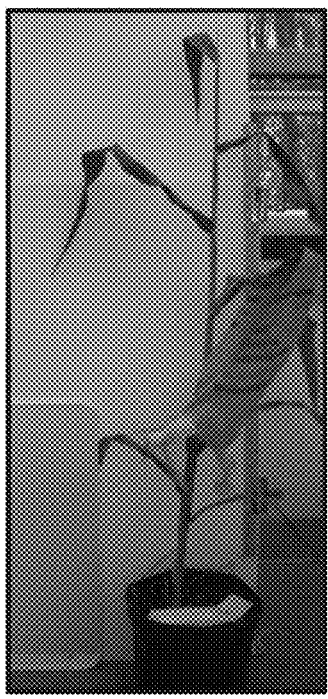
FIG. 35B illustrates a transgenic plant made with pAG2022.
Figure 35C:
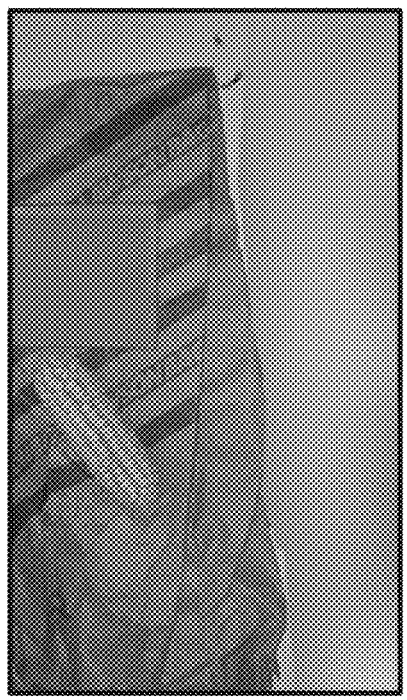
FIG. 35C illustrates a cob from a transgenic plant made with pAG2022.
Figure 36A:
FIG. 36A illustrates a transgenic plant made with pAG2023.
Figure 36B:
FIG. 36B illustrates a transgenic plant made with pAG2023.
Figure 36C:
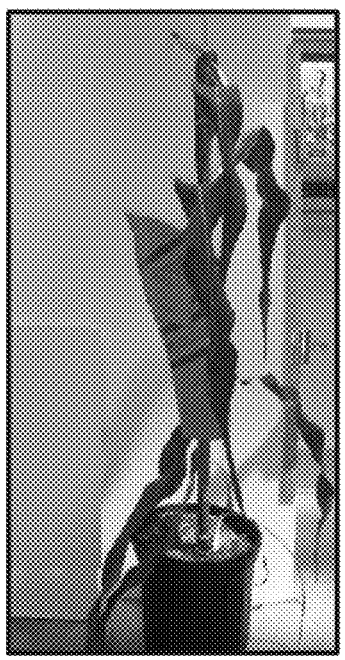
FIG. 36C illustrates a transgenic plant made with pAG2023.
Figure 37A:
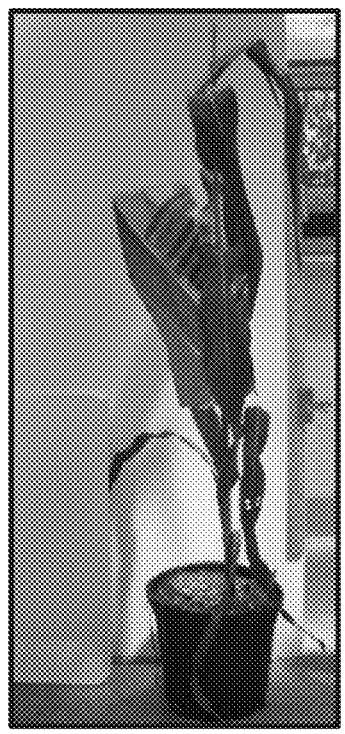
FIG. 37A illustrates a transgenic plant made with pAG2024.
Figure 37B:
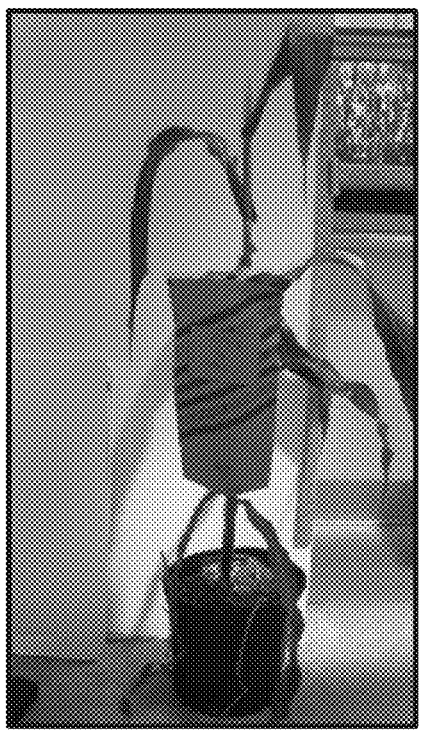
FIG. 37B illustrates a transgenic plant made with pAG2024.
Figure 37C:
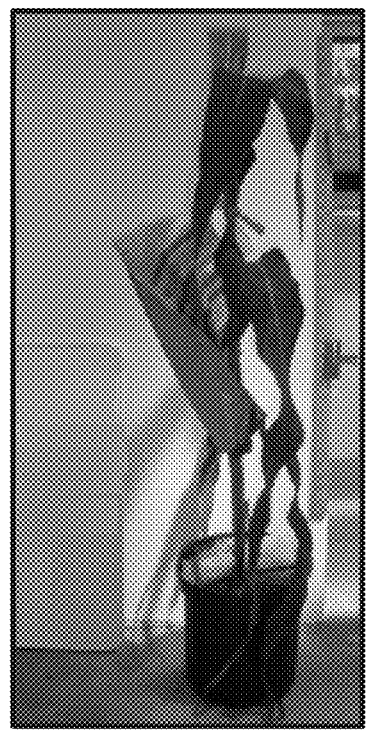
FIG. 37C illustrates a transgenic plant made with pAG2024.

None of the transgenic plants made with pAG2021, pAG2022, pAG2023, and pAG2024 have an abnormal phenotype. See FIGS. 34A, 34B, 34C and 34D for pAG2021 results. Transgenic plants made with pAG2021 grew normally, achieved normal height and had a normal seed set. See FIGS. 35A, 35B and 35C for pAG2022 results. Transgenic plants made with pAG2022 also grew normally, achieved normal height and had a normal seed set. See FIGS. 36A, 36B and 36C for pAG2023 results. These figures show that transgenic plants made with pAG2023 grew normally and achieved normal heights. See FIGS. 37A, 37B and 37C for pAG2024 results. These figures show that transgenic plants made with pAG2024 also grew normally and achieved normal heights. It is demonstrated herein that intein modification of a cell wall degrading enzyme can protect a plant from any phenotype that may be imparted by non-intein-modified enzyme. The cis-splicing intein (mini-Psp-pol M1L4 m3), designed to have temperature sensitive splicing activity, was used in this example. Because the plants were grown at non-splicing temperatures there was no observed activity and no associated growth or seed phenotypes. At some temperatures the intein may splice to some extent and reveal active enzyme. Because the plants have a normal phenotype, expression of intein-modified proteins is a way of providing an embedded cell wall degrading activity in plants that can be regained subsequently, but does not have a phenotypic effect on the plant.

Figure 38:
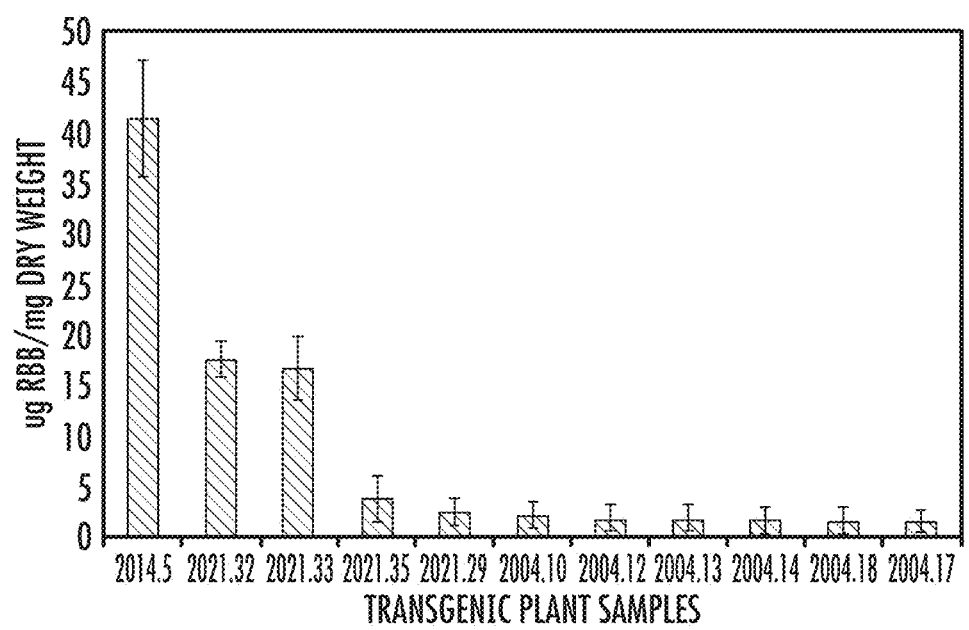
FIG. 38 illustrates activity data from some of the pAG2021 events, along with measurements from pAG2004 events (negative controls for xylanase activity) and a pAG20014 event (positive control for xylanase activity).

Referring to FIG. 38, enzyme activity of selected transgenic events was assayed. This figure highlights activity data from some of the pAG2021 events, along with measurements from pAG2004 events (negative controls for xylanase activity) and a pAG20014 event (positive control for xylanase activity). For this assay, samples of dried corn stover from senescent plants were assayed using the methods described above. Plant samples were labeled according to the vector number that was used to make them. Measurements for 2014.5 (transgenic maize event made with pAG2014 and labeled at 2014.5) represent the positive control for xylanase activity, while measurements for 2004.# (transgenic maize events made with pAG2004) represent xylanase negative control stover. As shown, two of the transgenic plants made with pAG2021 provide significant amounts of xylanase activity, but the plants were phenotypically normal, unlike the pAG2014 events, which showed a seed phenotype.

Embodiments herein include but are not limited to the plants described above and/or illustrated in the drawings or parts thereof, vectors encoding any amino acid sequence herein, vectors including any nucleic acid sequence herein, any amino acid sequence herein, any nucleic acid herein, any plant including a vector herein, any plant including a nucleic acid herein, any plant including an amino acid sequence herein, and any method of using any plant, plant part, vector, amino acid sequence or protein sequence herein.

The sequence of pAG2015 is:

(SEQ ID NO: 207)
aattcatactaaagcttgcatgcctgcaggtcgactctagtaacggccgc cagtgtgctggaattaattcggcttgtcgaccacccaacccatatcgac agaggatgtgaagaacaggtaaatcacgcagaagaacccatctctgatag cagctatcgattagaacaacgaatccatattgggtccgtgggaaatactt actgcacaggaaggggcgatctgacgaggcccgccaccggcctcgacc cgaggccgaggccgacgaagcgccggcgagtacggcgccgcggcggcctc tgcccgtgccctctgcgcgtgggagggagaggccgcggtggtggggcgc gcgcgcgcgcgcgcagctggtgcggcggcgcggggtcagccgccgag ccggcggcgacggaggagcagggcggcgtggacgcgaacttccgatcggt tggtcagagtgcgcgagttgggcttagccaattaggtctcaacaatctat tgggccgtaaaattcatgggccctggtttgtctaggcccaatatcccgtt catttcagcccacaaatatttccccagaggattattaaggcccacacgca gcttatagcagatcaagtacgatgtttcctgatcgttggatcggaaacgt acggtcttgatcaggcatgccgacttcgtcaaagagaggcggcatgacct gacgcggagttggttccgggcaccgtctggatggtcgtaccgggaccgga cacgtgtcgcgcctccaactacatggacacgtgtggtgctgccattgggc cgtacgcgtggcggtgaccgcaccggatgctgcctcgcaccgccttgccc acgctttatatagagaggttttctctccattaatcgcatagcgagtcgaa tcgaccgaaggggaggggagcgaagctttgcgttctctaatcgcctcgt -continued caaggtaactaatcaatcacctcgtcctaatcctcgaatctctcgtggtg
cccgtctaatctcgcgattttgatgctcgtggtggaaagcgtaggaggat
cccgtgcgagttagtctcaatctctcagggtttcgtgcgattttagggtg
atccacctcttaatcgagttacggtttcgtgcgattttagggtaatcctc
ttaatctctcattgatttagggtttcgtgagaatcgaggtagggatctgt
gttatttatatcgatctaatagatggattggttttgagattgttctgtca
gatggggattgtttcgatatattaccctaatgatgtgtcagatggggatt
gtttcgatatattaccctaatgatgtgtcagatggggattgtttcgatat
attaccctaatgatggataataagagtagttcacagttatgttttgatcc
tgccacatagtttgagttttgtgatcagatttagttttacttatttgtgc
ttagttcggatgggattgttctgatattgttccaatagatgaatagctcg
ttaggttaaaatctttaggttgagttaggcgacacatagtttatttcctc
tggatttggattggaattgtgttcttagttttttttcccctggatttggat
tggaattgtgtggagctgggttagagaattacatctgtatcgtacacc
tacttgaactgtagagcttgggttctaaggtcaatttaatctgtattgta
tctggctctttgcctagttgaactgtagtgctgatgttgtactgtgtttt
tttacccgttttatttgctttactcgtgcaaatcaaatctgtcagatgct
agaactaggtggctttattctgtgttcttacatagatctgttgtcctgta
gttacttatgtcagttttgttattatctgaagatattttggttgttgct
tgttgatgtggtgtgagctgtgagcagcgctcttatgattaatgatgctg
tccaattgtagtgtagtatgatgtgattgatatgttcatctatttttgagc
tgacagtaccgatatcgtaggatctggtgccaacttattctccagctgct
ttttttttacctatgttaattccaatcctttcttgcctcttccagatccag
ataatgcagaaactcattaactcagtgcaaaactatgcctggggcagcaa
aacgcgttgactgaactttatggtatggaaaatccgtccagccagccga
tggccgagctgtggatgggcgcacatccgaaaagcagttcacgagtgcag
aatgccgccggagatatcgtttcactgcgtgatgtgattgagagtgataa
atcgactctgctcggagaggccgttgccaaacgctttggcgaactgcctt
tcctgttcaaagtattatgcgcagcacagccactctccattcaggttcat
ccaaacaaacacaattctgaaatcggttttgccaaagaaaatgccgcagg
tatcccgatggatgccgccgagcgtaactataaagatcctaaccacaagc
cggagctggttttgcgctgacgcctttccttgcgatgaacgcgtttcgt
gaatttccgagattgtctccctactccagccggtcgcaggtgcacatcc
ggcgattgctcacttttttacaacagcctgatgccgaacgtttaagcgaac
tgttcgccagcctgttgaatatgcagggtgaagaaaatcccgcgcgctg
gcgattttaaaatcggccctcgatagccagcagggtgaaccgtggcaaac
gattcgtttaatttctgaattttacccggaagacagcggtctgttctccc
cgctattgctgaatgtggtgaaattgaaccctggcgaagcgatgttcctg
ttcgctgaaacaccgcacgcttacctgcaaggcgtggcgctggaagtgat
ggcaaactccgataacgtgctgcgtgcgggtctgacgcctaaatacattg ataattccggaactggttgccaatgtgaaattcgaagccaaaccggctaac
cagttgttgacccagccggtgaaacaaggtgcagaactggacttcccgat
tccagtggatgattttgccttctcgctgcatgaccttagtgataaagaaa
ccaccattagccagcagagtgccgccattttgttctgcgtcgaaggcgat
gcaacgttgtggaaaggttctcagcagttacagcttaaaccgggtgaatc
agcgtttattgccgccaacgaatcaccggtgactgtcaaaggccacggcc
gtttagcgcgtgtttacaacaagctgtaagagcttactgaaaaaattaac
atctcttgctaagctgggagctctagatccccgaatttccccgatcgttc
aaacatttggcaataaagtttcttaagattgaatcctgttgccggtcttg
cgatgattatcatataatttctgttgaattacgttaagcatgtaataatt
aacatgtaatgcatgacgttatttatgagatgggttttatgattagagt
cccgcaattatacatttaatacgcgatagaaaacaaaatatagcgcgcaa
actaggataaattatcgcgcgcggtgtcatctatgttactagatcgggaa
ttggcgagctcgaattaattcagtacattaaaaacgtccgcaatgtgtta
ttaagttgtctaagcgtcaatttgtttacaccacaatatatcctgccacc
agccagccaacagctccccgaccggcagctcggcacaaaatcaccactcg
atacaggcagcccatcagtccgggacggcgtcagcgggagagccgttgta
aggcggcagactttgctcatgttaccgatgctattcggaagaacggcaac
taagctgccgggtttgaaacacggatgatctcgcggagggtagcatgttg
attgtaacgatgacagagcgttgctgcctgtgatcaaatatcatctccct
cgcagagatccgaattatcagccttcttattcatttctcgcttaaccgtg
acaggctgtcgatcttgagaactatgccgacataataggaaatcgctgga
taaagccgctgaggaagctgagtggcgctatttcttagaagtgaacgtt
gacgatcgtcgaccgtaccccgatgaattaattcggacgtacgttctgaa
cacagctggatacttacttgggcgattgtcatacatgacatcaacaatgt
acccgtttgtgtaaccgtctcttggaggttcgtatgacactagtggttcc
cctcagcttgcgactagatgttgaggcctaacattttattagagagcagg
ctagttgcttagatacatgatcttcaggccgttatctgtcagggcaagcg
aaaaattggccatttatgacgaccaatgccccgcagaagctcccatctttg
ccgccatagacgccgcgccccctttgggggtgtagaacatccttttgcc
agatgtggaaaagaagttcgttgtcccattgttggcaatgacgtagtagc
cggcgaaagtgcgagacccatttcgcgctatatataagcctacgatttccg
ttgcgactattgtcgtaattggatgaactattatcgtagttgctctcaga
gttgtcgtaatttgatggactattgtcgtaattgcttatggagttgtcgt
agttgcttggagaaatgtcgtagttggatggggagtagtcatagggaaga
cgagcttcatccactaaaacaattggcaggtcagcaagtgcctgccccga
tgccatcgcaagtacgaggcttagaaccaccttcaacagatcgcgcatag
tcttccccagctctctaacgcttgagttaagccgcgccgcgaagcggcgt
cggcttgaacgaattgttagacattatttgccgactaccttggtgatctc
gcctttcacgtagtgaacaaattcttccaactgatctgcgcgcgaggcca
agcgatcttcttgtccaagataagcctgcctagcttcaagtatgacgggc tgatactgggccggcaggcgctccattgccagtcggcagcgacatcctt
cggcgcgattttgccggttactgcgctgtaccaaatgcgggacaacgtaa
gcactacatttcgctcatcgccagcccagtcgggcggcgagttccatagc
gttaaggtttcatttagcgcctcaaatagatcctgttcaggaacggatc
aaagagttcctccgccgctggacctaccaaggcaacgctatgttctcttg
cttttgtcagcaagatagccagatcaatgtcgatcgtggctggctcgaag
atacctgcaagaatgtcattgcgctgccattctccaaattgcagttcgcg
cttagctggataacgccacggaatgatgtcgtcgtgcacaacaatggtga
cttctacagcgcggagaatctcgctctctccaggggaagccgaagtttcc
aaaaggtcgttgatcaaagctcgccgcgttgtttcatcaagccttacgt
caccgtaaccagcaaatcaatatcactgtgtggcttcaggccgccatcca
ctgcggagccgtacaaatgtacggccagcaacgtcggttcgagatggcgc
tcgatgacgccaactacctctgatagttgagtcgatacttcggcgatcac
cgcttccctcatgatgtttaactcctgaattaagccgcgccgcgaagcgg
tgtcggcttgaatgaattgttaggcgtcatcctgtgctcccgagaaccag
taccagtacatcgctgtttcgttcgagacttgaggtctagttttatacgt
gaacaggtcaatgccgccgagagtaaagccacattttgcgtacaaattgc
aggcaggtacattgttcgtttgtgtctctaatcgtatgccaaggagctgt
ctgcttagtgcccacttttcgcaaattcgatgagactgtgcgcgactcc
tttgcctcggtgcgtgtgcgacacaacaatgtgttcgatagaggctagat
cgttccatgttgagttgagttcaatcttcccgacaagctcttggtcgatg
aatgcgccatagcaagcagagtcttcatcagagtcatcatccgagatgta
atccttccggtaggggctcacacttctggtagatagttcaaagccttggt
cggataggtgcacatcgaacacttcacgaacaatgaaatggttctcagca
tccaatgtttccgccacctgctcagggatcaccgaaatcttcatatgacg
cctaacgcctggcacagcggatcgcaaacctggcgcggcttttggcacaa
aaggcgtgacaggtttgcgaatccgttgctgccacttgttaaccccttttg
ccagatttggtaactataatttatgttagaggcgaagtcttgggtaaaaa
ctggcctaaaattgctgggattcaggaaagtaaacatcaccttccggc
tcgatgtctattgtagatatgtagtgtatctacttgatcggggatct
gctgcctcgcgcgtttcggtgatgacggtgaaaacctctgacacatgcag
ctcccggagacggtcacagcttgtctgtaagcggatgccgggagcagaca
agcccgtcagggcgcgtcagcgggtgttggcgggtgtcggggcgcagcca
tgacccagtcacgtagcgatagcggagtgtatactggcttaactatgcgg
catcagagcagattgtactgagagtgcaccatatgcggtgtgaaataccg
cacagatgcgtaaggagaaaataccgcatcaggcgctcttccgcttcctc
gctcactgactcgctgcgctcggtcgttcggctgcggcgagcggtatcag
ctcactcaaaggcggtaatacggttatccacagaatcaggggataacgca
ggaaagaacatgtgagcaaaaggccagcaaaaggccaggaaccgtaaaaa
ggccgcgttgctggcgttttccataggctccgcccccctgacgagcatc acaaaaatcgacgctcaagtcagaggtggcgaaacccgacaggactataa
agataccaggcgtttccccctggaagctccctcgtgcgctctcctgttcc
gaccctgccgcttaccggatacctgtccgcctttctcccttcgggaagcg
tggcgctttctcatagctcacgctgtaggtatctcagttcggtgtaggtc
gttcgctccaagctgggctgtgtgcacgaaccccccgttcagcccgaccg
ctgcgccttatccggtaactatcgtcttgagtccaacccggtaagacacg
acttatcgccactggcagcagccactggtaacaggattagcagagcgagg
tatgtaggcggtgctacagagttcttgaagtggtggcctaactacggcta
cactagaaggacagtatttggtatctgcgctctgctgaagccagttacct
tcggaaaaagagttggtagctcttgatccggcaaacaaaccaccgctggt
agcggtggtttttttgtttgcaagcagcagattacgcgcagaaaaaaagg
atctcaagaagatcctttgatcttttctacggggtctgacgctcagtgga
acgaaaactcacgttaagggattttggtcatgagattatcaaaaaggatc
ttcacctagatccttttaaattaaaaatgaagttttaaatcaatctaaag
tatatatgagtaaacttggtctgacagttaccaatgcttaatcagtgagg
cacctatctcagcgatctgtctatttcgttcatccatagttgcctgactc
cccgtcgtgtagataactacgatacgggagggcttaccatctggccccag
tgctgcaatgataccgcgagacccacgctcaccggctccagatttatcag
caataaaccagccagccggaagggccgagcgcagaagtggtcctgcaact
ttatccgcctccatccagtctattaattgttgccgggaagctagagtaag
tagttcgccagttaatagtttgcgcaacgttgttgccattgctgcagggg
ggggggggggggggttccattgttcattccacggacaaaaacagagaaag
gaaacgacagaggccaaaagctcgctttcagcacctgtcgtttcctttc
ttttcagagggtattttaaataaaaacattaagttatgacgaagaagaac
ggaaacgccttaaaccggaaaattttcataaatagcgaaaacccgcgagg
tcgccgccccgtaacctgtcggatcaccggaaaggacccgtaaagtgata
atgattatcatctacatatcacaacgtgcgtggaggccatcaaaccacgt
caaataatcaattatgacgcaggtatcgtattaattgatctgcatcaact
taacgtaaaaacaacttcagacaatacaaatcagcgacactgaatacggg
gcaacctcatgtcccccccccccccccctgcaggcatcgtggtgtcacg
ctcgtcgtttggtatggcttcattcagctccggttcccaacgatcaaggc
gagttacatgatcccccatgttgtgcaaaaaagcggttagctccttcggt
cctccgatcgttgtcagaagtaagttggccgcagtgttatcactcatggt
tatggcagcactgcataattctcttactgtcatgccatccgtaagatgct
tttctgtgactggtgagtactcaaccaagtcattctgagaatagtgtatg
cggcgaccgagttgctcttgcccggcgtcaacacgggataataccgcgcc
acatagcagaactttaaaagtgctcatcattggaaaacgttcttcgggc
gaaaactctcaaggatcttaccgctgttgagatccagttcgatgtaaccc
actcgtgcacccaactgatcttcagcatcttttactttcaccagcgtttc
tgggtgagcaaaaacaggaaggcaaaatgccgcaaaaaagggaataaggg
cgacacggaaatgttgaatactcatactcttccttttcaatattattga -continued

```
agcatttatcagggttattgtctcatgagcggatacatatttgaatgtat
ttagaaaaataaacaaatagggggttccgcgcacatttccccgaaaagtgc
cacctgacgtctaagaaaccattattatcatgacattaacctataaaaat
aggcgtatcacgaggcccttttcgtcttcaagaattggtcgacgatcttgc
tgcgttcggatattttcgtggagttcccgccacagacccggattgaaggc
gagatccagcaactcgcgccagatcatcctgtgacggaactttggcgcgt
gatgactggccaggacgtcggccgaaagagcgacaagcagatcacgcttt
tcgacagcgtcggatttgcgatcgaggattttcggcgctgcgctacgtc
cgcgaccgcgttgagggatcaagccacagcagcccactcgaccttctagc
cgacccagacgagccaagggatcttttttggaatgctgctccgtcgtcagg
ctttccgacgtttgggtggttgaacagaagtcattatcgcacggaatgcc
aagcactcccgaggggaaccctgtggttggcatgcacatacaaatggacg
aacggataaaccttttcacgccctttttaaatatccgattattctaataaa
cgctcttttctcttaggtttacccgccaatatatcctgtcaaacactgat
agtttaaactgaaggcgggaaacgacaacctgatcatgagcggagaatta
agggagtcacgttatgaccccgccgatgacgcgggacaagccgttttac
gtttggaactgacagaaccgcaacgttgaaggagccactcagcttaatta
agtctaactcgagttactggtacgtaccaaatccatggaatcaaggtacc
gtcgactctagtaacggccgccagtgtgctggaattaattcggcttgtcg
accacccaaccccatatcgacagaggatgtgaagaacaggtaaatcacgc
agaagaacccatctctgatagcagctatcgattagaacaacgaatccata
ttgggtccgtgggaaatacttactgcacaggaaggggcgatctgacgag
gccccgccaccggcctcgacccgaggccgaggccgacgaagcgccggcga
gtacggcgccgcggcggcctctgcccgtgccctctgcgcgtgggagggag
aggccgcggtggtggggcgcgcgcgcgcgcgcgcagctggtgcggcg
gcgcgggggtcagccgccgagccggcggcgacggaggagcagggcggcgt
ggacgcgaacttccgatcggttggtcagagtgcgcgagttgggcttagcc
aattaggtctcaacaatctattgggccgtaaaattcatgggccctggttt
gtctaggcccaatatcccgttcatttcagcccacaaatatttccccagag
gattattaaggcccacacgcagcttatagcagatcaagtacgatgtttcc
tgatcgttggatcggaaacgtacggtcttgatcaggcatgccgacttcgt
caaagagaggcggcatgacctgacgcggagttggttccgggcaccgtctg
gatggtcgtaccgggaccggacacgtgtcgcgcctccaactacatggaca
cgtgtggtgctgccattgggccgtacgcgtggcggtgaccgcaccggatg
ctgcctcgcaccgccttgcccacgctttatatagagaggttttctctcca
ttaatcgcatagcgagtcgaatcgaccgaaggggaggggggagcgaagctt
tgcgttctctaatcgcctcgtcaaggtaactaatcaatcacctcgtccta
atcctcgaatctctcgtggtgcccgtctaatctcgcgattttgatgctcg
tggtggaaagcgtaggaggatcccgtgcgagttagtctcaatctctcagg
gtttcgtgcgatttagggtgatccacctcttaatcgagttacggtttcg
tgcgatttagggtaatcctcttaatctctcattgatttagggtttcgtg
agaatcgaggtagggatctgtgttatttatatcgatctaatagatggatt
ggttttgagattgttctgtcagatggggattgtttcgatatattcccta
atgatgtgtcagatggggattgtttcgatatattccctaatgatgtgtc
agatggggattgtttcgatatattccctaatgatggataataagagtag
ttcacagttatgttttgatcctgccacatagtttgagttttgtgatcaga
tttagttttacttattttgtgcttagttcggatgggattgttctgatattg
ttccaatagatgaatagctcgttaggttaaaatctttaggttgagttagg
cgacacatagttttatttcctctggatttggattggaattgtgttcttagt
ttttttcccctggatttggattggaattgtgtggagctgggttagagaat
tacatctgtatcgtgtacacctacttgaactgtagagcttgggttctaag
gtcaatttaatctgtattgtatctggctattgcctagttgaactgtagtg
ctgatgttgtactgtgattttacccgttttatttgcttactcgtgcaa
atcaaatctgtcagatgctagaactaggtggcttttattctgtgttcttac
atagatctgttgtcctgtagttacttatgtcagttttgttattatctgaa
gatattttggttgttgcttgttgatgtggtgtgagctgtgagcagcgct
cttatgattaatgatgctgtccaattgtagtgtagtatgatgtgattgat
atgttcatctattttgagctgacagtaccgatatcgtaggatctggtgcc
aacttattctccagctgcttttttttacctatgttaattccaatcctttc
ttgcctcttccagatccagataatgcaaacaagcattactctgacatcca
acgcatccggtacgtttgacggttactattacgaactctggaaggatact
ggcaatacaacaatgacggtctacactcaaggtcgcttttcctgccagtg
gtcgaacatcaataacgcgttgtttaggaccgggaagaaatacaaccaga
attggcagtctcttggcacaatccggatcacgtactctgcgacttacaac
ccaaacgggaactcctacttgtgtatctatggctggtctaccaacccatt
ggtcgagttctacatcgttgagtcctgggggaactggagaccgcctggtg
ccacgtccctgggccaagtgacaatcgatggcgggacctacgacatctat
aggacgacacgcgtcaaccagccttccattgtggggacagccacgttcga
tcagtactggagcgtgcgcacctctaagcggacttcaggaacagtgaccg
tgaccgatcacttccgcgcctgggcgaaccggggcctgaacctcggcaca
atagaccaaattacattgtgcgtggagggttaccaaagctctggatcagc
caacatcacccagaacaccttctctcagggctcttcttccggcagttcgg
gtggctcatccggctccacaacgactactcgcatcgagtgtgagaacatg
tccttgtccggaccctacgttagcaggatcaccaatcccttaatggtat
tgcgctgtacgccaacggagacacagcccgcgctaccgttaacttcccg
caagtcgcaactacaatttccgcctgcgggggttgcggcaacaacaataat
cttgcccgtgtggacctgaggatcgacgacggaccgtcgggacctttta
ttaccagggcacatacccctgggaggccccaattgacaatgtttatgtca
gtgcggggagtcatacagtcgaaatcactgttactgcggataacggcaca
tgggacgtgtatgccgactacctggtgatacagtgacctaggtccccgaa
tttccccgatcgttcaaacatttggcaataaagtttcttaagattgaatc
```

-continued

```
ctgttgccggtcttgcgatgattatcatataatttctgttgaattacgtt aagcatgtaataattaacatgtaatgcatgacgttatttatgagatgggt ttttatgattagagtcccgcaattatacatttaatacgcgatagaaaaca aaatatagcgcgcaaactaggataaattatcgcgcgcggtgtcatctatg ttactagatcgggaattgg.
```

The references cited throughout this application, are incorporated for all purposes apparent herein and in the references themselves as if each reference was fully set forth. For the sake of presentation, specific ones of these references are cited at one or more particular location herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10988788B2). An electronic copy of the "Sequence Listing" will also be available from the USPTO upon request and payment of the fee set forth in 37 CFR 1.19(b)(3).

What is claimed is:

1. A transgenic plant comprising a nucleic acid that encodes a xylanase, wherein the transgenic plant is switchgrass, and the xylanase comprises consists of the amino acid of SEQ ID NO: 44.

2. The transgenic plant of claim 1, wherein the xylanase is expressed in a seed of the switchgrass.

3. The transgenic plant of claim 1, wherein the xylanase is expressed in a compartment of a plant cell of the switchgrass.

4. A method of processing plant biomass comprising:
mixing a plant or part thereof with liquid to form a mixture having a liquid to solid ratio selected from a value from 8 to 10, and maintaining the mixture at a temperature less than or equal to 100° C., wherein the liquid comprises water, ammonium bisulfite and ammonium carbonate; and adding at least one cell wall degrading enzyme to the mixture, wherein the plant is the transgenic plant of claim 1.

5. The method of claim 4 further comprising heating the mixture to maintain a temperature of 40° C. to 90° C.

6. The method of claim 4, wherein the ammonium bisulfite is at a concentration of 8% to 38% on a wt./wt. basis with the plant or part thereof.

7. The method of claim 4, wherein the liquid is at a pH of 7.6 to 8.5 and the ammonium carbonate is at a concentration of 4% to 19% on a wt./wt. basis with the plant or part thereof.

8. The method of claim 4, wherein the at least one cell wall degrading enzyme is selected from the group consisting of: an endoglucanase, a 6-glucosidase, a cellobiohydrolase, a xylanase, a cellulase, a glucosidase, a xylosidase, an arabinofuronosidase and a ferulic acid esterase.

9. The method of claim 8, wherein the at least one cell wall degrading enzyme comprises at least one of an endoglucanase, a B-glucosidase and a cellobiohydrolase.

10. The method of claim 8, wherein the at least one cell wall degrading enzyme comprises a xylanase.

* * * * *